(12) United States Patent
Griesgraber et al.

(10) Patent No.: US 7,943,609 B2
(45) Date of Patent: May 17, 2011

(54) CHIRAL FUSED [1,2]IMIDAZO[4,5-C] RING COMPOUNDS

(75) Inventors: George W. Griesgraber, Eagan, MN (US); Tushar A. Kshirsagar, Woodbury, MN (US); Azim A. Celebi, Kenilworth, NJ (US); Sarah J. Slania, Minneapolis, MN (US); Michael E. Danielson, Saint Paul, MN (US); Michael J. Rice, Oakdale, MN (US); Joshua R. Wurst, Saint Paul, MN (US)

(73) Assignee: 3M Innovative Proprerties Company, St. Paul, MN (US)

( * ) Notice: Subject to any disclaimer, the term of this patent is extended or adjusted under 35 U.S.C. 154(b) by 535 days.

(21) Appl. No.: 11/813,039

(22) PCT Filed: Dec. 29, 2005

(86) PCT No.: PCT/US2005/047258
§ 371 (c)(1),
(2), (4) Date: Jun. 28, 2007

(87) PCT Pub. No.: WO2006/074003
PCT Pub. Date: Jul. 13, 2006

(65) Prior Publication Data
US 2008/0269192 A1 Oct. 30, 2008

Related U.S. Application Data

(60) Provisional application No. 60/640,614, filed on Dec. 30, 2004, provisional application No. 60/697,257, filed on Jul. 7, 2005.

(51) Int. Cl.
*A61K 31/4745* (2006.01)
*C07D 487/22* (2006.01)
(52) U.S. Cl. ............ 514/229.5; 514/230.2; 544/99; 544/101
(58) Field of Classification Search ............ 544/99, 544/101; 514/229.5, 230.2
See application file for complete search history.

(56) References Cited

U.S. PATENT DOCUMENTS

| | | |
|---|---|---|
| 3,314,941 A | 4/1967 | Lundquist, Jr. et al. |
| 3,450,693 A | 6/1969 | Suzuki et al. |
| 3,670,086 A | 6/1972 | Pryor et al. |
| 3,692,907 A | 9/1972 | Fleming et al. |
| 3,891,660 A | 6/1975 | Denzel et al. |
| 3,899,508 A | 8/1975 | Wikel |
| 3,917,624 A | 11/1975 | Abu El-Haj et al. |
| 4,006,237 A | 2/1977 | Buckle et al. |
| 4,053,588 A | 10/1977 | Konig et al. |
| 4,381,344 A | 4/1983 | Rideout et al. |
| 4,552,874 A | 11/1985 | Mardin et al. |
| 4,563,525 A | 1/1986 | Campbell, Jr. |
| 4,593,821 A | 6/1986 | Brule |
| 4,668,686 A | 5/1987 | Meanwell et al. |
| 4,689,338 A | 8/1987 | Gerster |
| 4,690,930 A | 9/1987 | Takada et al. |
| 4,698,346 A | 10/1987 | Musser et al. |
| 4,698,348 A | 10/1987 | Gerster |
| 4,753,951 A | 6/1988 | Takada et al. |
| 4,758,574 A | 7/1988 | Robertson et al. |
| 4,774,339 A | 9/1988 | Haugland et al. |
| 4,775,674 A | 10/1988 | Meanwell et al. |
| 4,800,206 A | 1/1989 | Alig et al. |
| 4,826,830 A | 5/1989 | Han et al. |
| 4,837,378 A | 6/1989 | Borgman |
| 4,880,779 A | 11/1989 | Gallaher |
| 4,904,669 A | 2/1990 | Knoll et al. |
| 4,929,624 A | 5/1990 | Gerster et al. |
| 4,988,714 A | 1/1991 | Alig et al. |
| 4,988,815 A | 1/1991 | Andre et al. |
| 5,037,986 A | 8/1991 | Gerster |
| 5,175,296 A | 12/1992 | Gerster |
| 5,187,288 A | 2/1993 | Kang et al. |
| 5,225,183 A | 7/1993 | Purewal et al. |
| 5,238,944 A | 8/1993 | Wick et al. |
| 5,248,782 A | 9/1993 | Haugland et al. |
| 5,266,575 A | 11/1993 | Gerster et al. |
| 5,268,376 A | 12/1993 | Gester |
| 5,274,113 A | 12/1993 | Kang et al. |
| 5,346,905 A | 9/1994 | Gerster |
| 5,352,680 A | 10/1994 | Portoghese et al. |
| 5,352,784 A | 10/1994 | Nikolaides et al. |
| 5,367,076 A | 11/1994 | Gerster |
| 5,376,501 A | 12/1994 | Marien et al. |
| 5,378,848 A | 1/1995 | Takada et al. |
| 5,389,640 A | 2/1995 | Gerster et al. |

(Continued)

FOREIGN PATENT DOCUMENTS

AU 2004220534 A1 9/2004

(Continued)

OTHER PUBLICATIONS

Cecil Textbook of Medicine (20th Edition, vol. 2, 1996, pp. 1739-1747).*
Patrick et al., Paragraph 10.3: Drug optimization: strategies in drug design. An Introduction to Medicinal Chemistry. Oxford: Oxford University Press. Jan. 2005. 200-218.
Stanley et al., Imiquimod and the imidazoquinolones: mechanism of action and therapeutic potential. Clin Exp Dermatol. Oct. 2002;27(7):571-7. Review.
Supplemental European Search Report for EP 05855766.1 mailed Oct. 9, 2008.
International Search Report and Written Opinion for PCT/US2005/047258 mailed Sep. 24, 2007.
International Preliminary Report on Patentability for PCT/US2005/047258 mailed Oct. 25, 2007.

(Continued)

*Primary Examiner* — Kahsay T Habte
(74) *Attorney, Agent, or Firm* — Kathleen B. Gross

(57) ABSTRACT

Fused [1,2]imidazo[4,5-c] ring compounds (e.g., imidazo[4,5-c]quinolines, 6,7,8,9-tetrahydroimidazo[4,5-c]quinolines, imidazo[4,5-c]naphthyridines, and 6,7,8,9-tetrahydroimidazo[4,5-c]naphthyridines) with a —CH(—$X_1$—$R_1$)-group in the fused ring at the 1-position of the imidazo ring, pharmaceutical compositions containing the compounds, intermediates, methods of making the compounds, and methods of use of these compounds as immunomodulators, for inducing cytokine biosynthesis in animals and in the treatment of diseases including viral and neoplastic diseases, are disclosed.

15 Claims, No Drawings

U.S. PATENT DOCUMENTS

| | | |
|---|---|---|
| 5,395,937 A | 3/1995 | Nikolaides et al. |
| 5,444,065 A | 8/1995 | Nikolaides et al. |
| 5,446,153 A | 8/1995 | Lindstrom et al. |
| 5,446,160 A | 8/1995 | Stucky et al. |
| 5,482,936 A * | 1/1996 | Lindstrom .................... 514/183 |
| 5,494,916 A | 2/1996 | Lindstrom et al. |
| 5,500,228 A | 3/1996 | Lawter et al. |
| 5,525,612 A | 6/1996 | Gerster |
| 5,530,114 A | 6/1996 | Bennett et al. |
| 5,569,450 A | 10/1996 | Duan et al. |
| 5,571,819 A | 11/1996 | Sabb et al. |
| 5,578,727 A | 11/1996 | Andre et al. |
| 5,585,612 A | 12/1996 | Harp, Jr. |
| 5,602,256 A | 2/1997 | Andr e et al. |
| 5,605,899 A | 2/1997 | Gerster et al. |
| 5,612,377 A | 3/1997 | Crooks et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,731,193 A | 3/1998 | Mori et al. |
| 5,736,553 A | 4/1998 | Wick et al. |
| 5,741,908 A | 4/1998 | Gerster et al. |
| 5,741,909 A | 4/1998 | Gerster et al. |
| 5,750,134 A | 5/1998 | Scholz et al. |
| 5,756,747 A | 5/1998 | Gerster |
| 5,776,432 A | 7/1998 | Schultz et al. |
| 5,780,045 A | 7/1998 | McQuinn et al. |
| 5,837,809 A | 11/1998 | Grandy et al. |
| 5,840,744 A | 11/1998 | Borgman |
| 5,854,257 A | 12/1998 | Armitage et al. |
| 5,861,268 A | 1/1999 | Tang et al. |
| 5,886,006 A | 3/1999 | Nikolaides et al. |
| 5,939,047 A | 8/1999 | Jernberg |
| 5,939,090 A | 8/1999 | Beaurline et al. |
| 5,962,479 A | 10/1999 | Chen |
| 5,962,636 A | 10/1999 | Bachmaier et al. |
| 5,977,366 A | 11/1999 | Gerster et al. |
| 6,028,076 A | 2/2000 | Hirota et al. |
| 6,039,969 A | 3/2000 | Tomai et al. |
| 6,057,371 A | 5/2000 | Glennon |
| 6,069,140 A | 5/2000 | Sessler et al. |
| 6,069,149 A | 5/2000 | Nanba et al. |
| 6,071,949 A | 6/2000 | Mulshine et al. |
| 6,077,349 A | 6/2000 | Kikuchi |
| 6,083,505 A | 7/2000 | Miller et al. |
| 6,110,929 A | 8/2000 | Gerster et al. |
| 6,113,918 A | 9/2000 | Johnson et al. |
| 6,121,323 A | 9/2000 | Merrill |
| 6,123,957 A | 9/2000 | Jernberg |
| 6,126,938 A | 10/2000 | Guy et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,294,271 B1 | 9/2001 | Sumita et al. |
| 6,303,347 B1 | 10/2001 | Johnson et al. |
| 6,309,623 B1 | 10/2001 | Weers et al. |
| 6,315,985 B1 | 11/2001 | Wu et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,348,462 B1 | 2/2002 | Gerster et al. |
| 6,365,166 B2 | 4/2002 | Beaurline et al. |
| 6,376,501 B1 | 4/2002 | Isobe et al. |
| 6,376,669 B1 | 4/2002 | Rice et al. |
| 6,387,383 B1 | 5/2002 | Dow et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,485 B1 | 9/2002 | James et al. |
| 6,451,810 B1 | 9/2002 | Coleman et al. |
| 6,465,654 B2 | 10/2002 | Gerster et al. |
| 6,476,000 B1 | 11/2002 | Agrawal |
| 6,486,168 B1 | 11/2002 | Skwierczynski et al. |
| 6,486,186 B2 | 11/2002 | Fowler et al. |
| 6,511,485 B2 | 1/2003 | Hirt et al. |
| 6,514,985 B1 | 2/2003 | Gerster et al. |
| 6,518,239 B1 | 2/2003 | Kuo et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,582,957 B1 | 6/2003 | Turner, Jr. et al. |
| 6,610,319 B2 | 8/2003 | Tomai et al. |
| 6,627,638 B2 | 9/2003 | Gerster et al. |
| 6,627,639 B2 | 9/2003 | Stack et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,334 B2 | 1/2004 | Gerster et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Rice et al. |
| 6,780,873 B2 | 8/2004 | Crooks et al. |
| 6,784,188 B2 | 8/2004 | Crooks et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,855,217 B2 | 2/2005 | Suzuki |
| 6,855,350 B2 | 2/2005 | Lu |
| 6,878,719 B2 | 4/2005 | Lindstrom et al. |
| 6,888,000 B2 | 5/2005 | Crooks et al. |
| 6,894,060 B2 | 5/2005 | Slade |
| 6,894,165 B2 | 5/2005 | Gerster et al. |
| 6,897,221 B2 | 5/2005 | Crooks et al. |
| 6,900,016 B1 | 5/2005 | Venter et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,240 B2 | 9/2005 | Bauer et al. |
| 6,943,255 B2 | 9/2005 | Lindstrom et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,253 B2 | 7/2006 | Brunner et al. |
| 7,078,523 B2 | 7/2006 | Crooks et al. |

| Patent/Publication | Date | Inventor |
|---|---|---|
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,544,697 B2 | 6/2009 | Hays et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 2001/0046968 A1 | 11/2001 | Zagon et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2002/0137101 A1 | 9/2002 | Meyers |
| 2002/0173655 A1 | 11/2002 | Dellaria et al. |
| 2002/0193729 A1 | 12/2002 | Cormier et al. |
| 2003/0022302 A1 | 1/2003 | Lewis et al. |
| 2003/0044429 A1 | 3/2003 | Aderem et al. |
| 2003/0082108 A1 | 5/2003 | Mulshine et al. |
| 2003/0088102 A1 | 5/2003 | Matsubara et al. |
| 2003/0096835 A1 | 5/2003 | Crooks et al. |
| 2003/0096998 A1 | 5/2003 | Gerster et al. |
| 2003/0130299 A1 | 7/2003 | Crooks et al. |
| 2003/0133733 A1 | 7/2003 | Korhonen |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0144286 A1 | 7/2003 | Frenkel et al. |
| 2003/0158192 A1 | 8/2003 | Crooks et al. |
| 2003/0161797 A1 | 8/2003 | Miller et al. |
| 2003/0172391 A1 | 9/2003 | Turner et al. |
| 2003/0185835 A1 | 10/2003 | Braun |
| 2003/0187016 A1 | 10/2003 | Crooks et al. |
| 2003/0199461 A1 | 10/2003 | Averett et al. |
| 2003/0199538 A1 | 10/2003 | Skwierczynski et al. |
| 2003/0212092 A1 | 11/2003 | Heppner et al. |
| 2003/0216481 A1 | 11/2003 | Jia |
| 2003/0232074 A1 | 12/2003 | Lipford et al. |
| 2003/0232763 A1 | 12/2003 | Jia |
| 2003/0232852 A1 | 12/2003 | Lindstrom et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0067975 A1 | 4/2004 | Crooks et al. |
| 2004/0072858 A1 | 4/2004 | Charles et al. |
| 2004/0076633 A1 | 4/2004 | Thomsen et al. |
| 2004/0091491 A1 | 5/2004 | Kedl et al. |
| 2004/0092545 A1 | 5/2004 | Crooks et al. |
| 2004/0097542 A1 | 5/2004 | Crooks et al. |
| 2004/0106638 A1 | 6/2004 | Lindstrom |
| 2004/0132079 A1 | 7/2004 | Gupta et al. |
| 2004/0132748 A1 | 7/2004 | Isobe et al. |
| 2004/0132766 A1 | 7/2004 | Griesgraber |
| 2004/0141950 A1 | 7/2004 | Noelle et al. |
| 2004/0147543 A1 | 7/2004 | Hays et al. |
| 2004/0157874 A1 | 8/2004 | Crooks et al. |
| 2004/0162309 A1 | 8/2004 | Gorden et al. |
| 2004/0167157 A1 | 8/2004 | Masui et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Miller et al. |
| 2004/0181130 A1 | 9/2004 | Miller et al. |
| 2004/0181211 A1 | 9/2004 | Graham et al. |
| 2004/0191833 A1 | 9/2004 | Fink et al. |
| 2004/0192585 A1 | 9/2004 | Owens et al. |
| 2004/0197865 A1 | 10/2004 | Gupta et al. |
| 2004/0202720 A1 | 10/2004 | Wightman et al. |
| 2004/0204436 A1 | 10/2004 | Gerster et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0009858 A1 | 1/2005 | Martinez-Colon et al. |
| 2005/0032829 A1 | 2/2005 | Lindstrom et al. |
| 2005/0048072 A1 | 3/2005 | Kedl et al. |
| 2005/0054590 A1 | 3/2005 | Averett |
| 2005/0054640 A1 | 3/2005 | Griesgraber et al. |
| 2005/0054665 A1 | 3/2005 | Miller et al. |
| 2005/0059072 A1 | 3/2005 | Birmachu et al. |
| 2005/0070460 A1 | 3/2005 | Hammerbeck et al. |
| 2005/0085500 A1 | 4/2005 | Gutman et al. |
| 2005/0096259 A1 | 5/2005 | Tomai et al. |
| 2005/0119273 A1 | 6/2005 | Lipford et al. |
| 2005/0136065 A1 | 6/2005 | Valiante |
| 2005/0148620 A1 | 7/2005 | Crooks et al. |
| 2005/0158325 A1 | 7/2005 | Hammerbeck et al. |
| 2005/0165236 A1 | 7/2005 | Colombo et al. |
| 2005/0171072 A1 | 8/2005 | Tomai et al. |
| 2005/0226878 A1 | 10/2005 | Tomai et al. |
| 2005/0234088 A1 | 10/2005 | Griesgraber |
| 2005/0239733 A1 | 10/2005 | Jurk et al. |
| 2005/0239735 A1 | 10/2005 | Miller et al. |
| 2005/0245562 A1 | 11/2005 | Garcia-Echeverria et al. |
| 2005/0267145 A1 | 12/2005 | Merrill et al. |
| 2005/0281813 A1 | 12/2005 | Dedera et al. |
| 2006/0009482 A1 | 1/2006 | Tomai et al. |
| 2006/0100229 A1 | 5/2006 | Hays et al. |
| 2006/0106052 A1 | 5/2006 | Crooks et al. |
| 2006/0188913 A1 | 8/2006 | Krieg et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0155767 A1 | 7/2007 | Radmer et al. |
| 2007/0166384 A1 | 7/2007 | Zarraga |
| 2007/0167476 A1 | 7/2007 | Kshirsagar et al. |
| 2007/0208052 A1 | 9/2007 | Prince et al. |
| 2007/0213356 A1 | 9/2007 | Merrill et al. |
| 2007/0219196 A1 | 9/2007 | Krepski et al. |
| 2007/0219228 A1 | 9/2007 | Niwas et al. |
| 2007/0259881 A1 | 11/2007 | Dellaria et al. |
| 2007/0259907 A1 | 11/2007 | Prince |
| 2007/0287725 A1 | 12/2007 | Miser et al. |
| 2007/0292456 A1 | 12/2007 | Hammerbeck et al. |
| 2008/0015184 A1 | 1/2008 | Kshirsagar et al. |
| 2008/0070907 A1 | 3/2008 | Griesgraber et al. |
| 2008/0085895 A1 | 4/2008 | Griesgraber et al. |
| 2008/0114019 A1 | 5/2008 | Kshirsagar et al. |
| 2008/0119508 A1 | 5/2008 | Slade et al. |
| 2008/0207674 A1 | 8/2008 | Stoesz et al. |
| 2008/0306252 A1 | 12/2008 | Crooks et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0018122 A1 | 1/2009 | Lindstrom et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0042925 A1 | 2/2009 | Kshirsagar et al. |
| 2009/0062272 A1 | 3/2009 | Bonk et al. |
| 2009/0062328 A1 | 3/2009 | Kshirsagar et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0240055 A1 | 9/2009 | Krepski et al. |

| | | | |
|---|---|---|---|
| 2009/0253695 A1 | 10/2009 | Kshirsagar et al. | |
| 2009/0270443 A1 | 10/2009 | Stoermer et al. | |
| 2009/0318435 A1 | 12/2009 | Hays et al. | |
| 2010/0113565 A1 | 5/2010 | Gorden et al. | |
| 2010/0240693 A1 | 9/2010 | Lundquist, Jr. et al. | |

FOREIGN PATENT DOCUMENTS

| | | |
|---|---|---|
| AU | 2004229478 A1 | 10/2004 |
| AU | 2004264336 A1 | 2/2005 |
| AU | 2004268625 A1 | 3/2005 |
| AU | 2002239547 B2 | 11/2006 |
| CA | 2044087 A1 | 12/1991 |
| CA | 2158996 A1 | 10/1994 |
| CN | 1354663 A | 6/2002 |
| EP | 0 145 340 A2 | 6/1985 |
| EP | 0 223 420 A1 | 5/1987 |
| EP | 0 310 950 A1 | 4/1989 |
| EP | 0 385 630 A2 | 9/1990 |
| EP | 0 389 302 A1 | 9/1990 |
| EP | 0 394 026 A1 | 10/1990 |
| EP | 0 425 306 A2 | 5/1991 |
| EP | 0 510 260 A2 | 10/1992 |
| EP | 0 556 008 A1 | 8/1993 |
| EP | 0 645 389 A1 | 3/1995 |
| EP | 0 778 277 A1 | 6/1997 |
| EP | 0 894 797 A1 | 2/1999 |
| EP | 1 082 960 A2 | 3/2001 |
| EP | 1 097 709 A2 | 5/2001 |
| EP | 1 104 764 A1 | 6/2001 |
| EP | 1 145 340 A2 | 10/2001 |
| EP | 1 256 582 A1 | 11/2002 |
| EP | 1 341 791 A2 | 9/2003 |
| EP | 1 495 758 A2 | 1/2005 |
| HU | 34479 A2 | 3/1985 |
| HU | 210051 A2 | 6/1991 |
| HU | 218950 A2 | 9/1995 |
| IL | 73534 A | 12/1990 |
| JP | 53050197 A | 5/1978 |
| JP | 63010787 A | 1/1988 |
| JP | 1180156 A | 7/1989 |
| JP | 4066571 A | 3/1992 |
| JP | 4327587 A | 11/1992 |
| JP | 5286973 A | 11/1993 |
| JP | 9208584 A | 8/1997 |
| JP | 11222432 A | 8/1999 |
| JP | 2000247884 A | 9/2000 |
| NZ | 545412 A | 12/2008 |
| RU | 2076105 C1 | 3/1997 |
| RU | 2127273 C1 | 3/1999 |
| RU | 2221798 C2 | 1/2004 |
| WO | WO-91/06682 A1 | 5/1991 |
| WO | WO-92/06093 A1 | 4/1992 |
| WO | WO-92/15581 A1 | 9/1992 |
| WO | WO-92/15582 A1 | 9/1992 |
| WO | WO-93/05042 A1 | 3/1993 |
| WO | WO-93/09119 A1 | 5/1993 |
| WO | WO-93/20847 A1 | 10/1993 |
| WO | WO-94/10171 A1 | 5/1994 |
| WO | WO-95/02597 A1 | 1/1995 |
| WO | WO-95/02598 A1 | 1/1995 |
| WO | WO-96/11199 A1 | 4/1996 |
| WO | WO 96/21663 A1 | 7/1996 |
| WO | WO-97/48703 A1 | 12/1997 |
| WO | WO-97/48704 A1 | 12/1997 |
| WO | WO-98/17279 A1 | 4/1998 |
| WO | WO-98/30562 A1 | 7/1998 |
| WO | WO-98/48805 A1 | 11/1998 |
| WO | WO-98/50547 A2 | 11/1998 |
| WO | WO-98/54226 A1 | 12/1998 |
| WO | WO-99/18105 A1 | 4/1999 |
| WO | WO-99/29693 A1 | 6/1999 |
| WO | WO-00/06577 A1 | 2/2000 |
| WO | WO-00/09506 A1 | 2/2000 |
| WO | WO-00/19987 A1 | 4/2000 |
| WO | WO-00/40228 A2 | 7/2000 |
| WO | WO-00/47719 A2 | 8/2000 |
| WO | WO-00/75304 A1 | 12/2000 |
| WO | WO-00/76505 A1 | 12/2000 |
| WO | WO-00/76518 A1 | 12/2000 |
| WO | WO-00/76519 A1 | 12/2000 |
| WO | WO-01/34709 A1 | 5/2001 |
| WO | WO-01/51486 A2 | 7/2001 |
| WO | WO-01/55439 A1 | 8/2001 |
| WO | WO-01/58900 A1 | 8/2001 |
| WO | WO-01/74343 A2 | 10/2001 |
| WO | WO-01/74821 A1 | 10/2001 |
| WO | WO-02/07725 A1 | 1/2002 |
| WO | WO-02/22809 A2 | 3/2002 |
| WO | WO-02/24225 A1 | 3/2002 |
| WO | WO-02/36592 A1 | 5/2002 |
| WO | WO-02/46188 A2 | 6/2002 |
| WO | WO-02/46189 A2 | 6/2002 |
| WO | WO-02/46190 A2 | 6/2002 |
| WO | WO-02/46191 A2 | 6/2002 |
| WO | WO-02/46192 A2 | 6/2002 |
| WO | WO-02/46193 A2 | 6/2002 |
| WO | WO-02/46194 A2 | 6/2002 |
| WO | WO-02/46749 A2 | 6/2002 |
| WO | WO-02/085905 A1 | 10/2002 |
| WO | WO-02/102377 A1 | 12/2002 |
| WO | WO-03/008421 A1 | 1/2003 |
| WO | WO-03/009852 A1 | 2/2003 |
| WO | WO-03/020889 A2 | 3/2003 |
| WO | WO-03/043572 A2 | 5/2003 |
| WO | WO-03/045391 A1 | 6/2003 |
| WO | WO-03/045494 A2 | 6/2003 |
| WO | WO-03/045929 A1 | 6/2003 |
| WO | WO-03/050117 A1 | 6/2003 |
| WO | WO-03/050118 A1 | 6/2003 |
| WO | WO-03/050119 A2 | 6/2003 |
| WO | WO-03/050121 A1 | 6/2003 |
| WO | WO-03/077944 A1 | 9/2003 |
| WO | WO-03/080114 A2 | 10/2003 |
| WO | WO-03/086280 A2 | 10/2003 |
| WO | WO-03/086350 A1 | 10/2003 |
| WO | WO-03/089602 A2 | 10/2003 |
| WO | WO-03/097641 A2 | 11/2003 |
| WO | WO-03/101949 A2 | 12/2003 |
| WO | WO-03/103584 A2 | 12/2003 |
| WO | WO-2004/009593 A1 | 1/2004 |
| WO | WO-2004/028539 A2 | 4/2004 |
| WO | WO-2004/041285 A1 | 5/2004 |
| WO | WO-2004/043913 A2 | 5/2004 |
| WO | WO-2004/053057 A2 | 6/2004 |
| WO | WO-2004/053452 A2 | 6/2004 |
| WO | WO-2004/058759 A1 | 7/2004 |
| WO | WO-2004/071459 A2 | 8/2004 |
| WO | WO-2004/075865 A2 | 9/2004 |
| WO | WO-2004/080398 A2 | 9/2004 |
| WO | WO-2004/091500 A2 | 10/2004 |
| WO | WO-2004/096144 A2 | 11/2004 |
| WO | WO-2004/110991 A2 | 12/2004 |
| WO | WO-2004/110992 A2 | 12/2004 |
| WO | WO-2005/003064 A2 | 1/2005 |
| WO | WO-2005/003065 A2 | 1/2005 |
| WO | WO-2005/016273 A2 | 2/2005 |
| WO | WO-2005/016275 A2 | 2/2005 |
| WO | WO-2005/018551 A2 | 3/2005 |
| WO | WO-2005/018555 A2 | 3/2005 |
| WO | WO-2005/018556 A2 | 3/2005 |
| WO | WO-2005/020999 A1 | 3/2005 |
| WO | WO-2005/023190 A2 | 3/2005 |
| WO | WO-2005/025614 A3 | 3/2005 |
| WO | WO-2005/029037 A2 | 3/2005 |
| WO | WO-2005/032484 A3 | 4/2005 |
| WO | WO-2005/041891 A2 | 5/2005 |
| WO | WO-2005/048933 A2 | 6/2005 |
| WO | WO-2005/048945 A2 | 6/2005 |
| WO | WO-2005/049076 A1 | 6/2005 |
| WO | WO-2005/051317 A2 | 6/2005 |
| WO | WO-2005/051324 A2 | 6/2005 |
| WO | WO-2005/054237 A1 | 6/2005 |
| WO | WO-2005/054238 A1 | 6/2005 |
| WO | WO-2005/065678 A1 | 7/2005 |
| WO | WO-2005/066169 A2 | 7/2005 |
| WO | WO-2005/066170 A1 | 7/2005 |
| WO | WO-2005/066172 A1 | 7/2005 |
| WO | WO-2005/067500 A2 | 7/2005 |

| | | | |
|---|---|---|---|
| WO | WO-2005/076783 A2 | 8/2005 |
| WO | WO-2005/079195 A2 | 9/2005 |
| WO | WO-2005/094531 A2 | 10/2005 |
| WO | WO-2005/110013 A2 | 11/2005 |
| WO | WO-2005/123079 A2 | 12/2005 |
| WO | WO-2005/123080 A2 | 12/2005 |
| WO | WO-2006/004737 A2 | 1/2006 |
| WO | WO-2006/009826 A1 | 1/2006 |
| WO | WO-2006/009832 A1 | 1/2006 |
| WO | WO-2006/026760 A2 | 3/2006 |
| WO | WO-2006/028451 A1 | 3/2006 |
| WO | WO-2006/028545 A2 | 3/2006 |
| WO | WO-2006/028962 A2 | 3/2006 |
| WO | WO-2006/029115 A2 | 3/2006 |
| WO | WO-2006/031878 A2 | 3/2006 |
| WO | WO-2006/038923 A2 | 4/2006 |
| WO | WO-2006/063072 A2 | 6/2006 |
| WO | WO-2006/063152 A2 | 6/2006 |
| WO | WO-2006/065280 A2 | 6/2006 |
| WO | WO-2006/073940 A2 | 7/2006 |
| WO | WO-2006/074003 A2 | 7/2006 |
| WO | WO-2006/074045 A2 | 7/2006 |
| WO | WO-2006/083440 A2 | 8/2006 |
| WO | WO-2006/084251 A2 | 8/2006 |
| WO | WO-2006/086449 A2 | 8/2006 |
| WO | WO-2006/086633 A2 | 8/2006 |
| WO | WO-2006/086634 A2 | 8/2006 |
| WO | WO-2006/091394 A2 | 8/2006 |
| WO | WO-2006/091567 A2 | 8/2006 |
| WO | WO-2006/091568 A2 | 8/2006 |
| WO | WO-2006/091647 A2 | 8/2006 |
| WO | WO-2006/093514 A2 | 9/2006 |
| WO | WO-2006/098852 A2 | 9/2006 |
| WO | WO-2006/107753 A2 | 10/2006 |
| WO | WO-2006/107771 A2 | 10/2006 |
| WO | WO-2006/107851 A1 | 10/2006 |
| WO | WO-2006/107853 A2 | 10/2006 |
| WO | WO-2006/121528 A2 | 11/2006 |
| WO | WO-2006/122806 A2 | 11/2006 |
| WO | WO-2007/028129 A1 | 3/2007 |
| WO | WO-2007/030775 A2 | 3/2007 |
| WO | WO-2007/030777 A2 | 3/2007 |
| WO | WO-2007/035935 A1 | 3/2007 |
| WO | WO-2007/056112 A2 | 5/2007 |
| WO | WO-2007/062043 A1 | 5/2007 |
| WO | WO-2007/075468 A1 | 7/2007 |
| WO | WO-2007/079086 A1 | 7/2007 |
| WO | WO-2007/079146 A1 | 7/2007 |
| WO | WO-2007/079169 A2 | 7/2007 |
| WO | WO-2007/079171 A2 | 7/2007 |
| WO | WO-2007/079202 A2 | 7/2007 |
| WO | WO-2007/079203 A2 | 7/2007 |
| WO | WO-2007/092641 A2 | 8/2007 |
| WO | WO-2007/106852 A2 | 9/2007 |
| WO | WO-2007/106854 A2 | 9/2007 |
| WO | WO-2007/120121 A2 | 10/2007 |
| WO | WO-2007/143526 A2 | 12/2007 |
| WO | WO-2008/002646 A2 | 1/2008 |
| WO | WO-2008/008432 A2 | 1/2008 |
| WO | WO-2008/030511 A2 | 3/2008 |
| WO | WO-2008/036312 A1 | 3/2008 |
| WO | WO-2008/045543 A1 | 4/2008 |

OTHER PUBLICATIONS

[No Author Listed] "Aqueous cream." Wikipedia. Available at http://en.wikipedia.org/wiki/Aqueous_cream. Last accessed Sep. 15, 2010.
[No Author Listed] "Comparative Tests." Filed Apr. 8, 2005 during prosecution for EP 00938205.2, EP 00950215.4 and EP 00938211.0 in the name of 3M Innovative Properties Co.
[No Author Listed] Chemical Abstracts. 1964;61(1):6060g.
[No Author Listed] Encyclopedia of Pharmaceutical Technology. 2nd Ed. Marcel Dekker, Inc. 2002:856-60.
Agrawal et al., Synthetic agonists of Toll-like receptors 7, 8 and 9. Biochem Soc Trans. Dec. 2007;35(Pt 6):1461-7.
Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-24.

Akira et al., Recognition of pathogen-associated molecular patterns by TLR family. Immunol Lett. 2003;85:85-95.
Akira et al., Toll-like receptors: critical proteins linking innate and acquired immunity. Nature Immunol. 2001;2(8):675-80.
Alexopoulou et al., Recognition of double-stranded RNA and activation of NF-kappaB by Toll-like receptor 3. Nature. Oct. 18, 2001;413(6857):732-8.
Assuma et al., IL-1 and TNF Antagonists Inhibit the Inflammatory Response and Bone Loss in Experimental Periodontitis. J Immunol. 2000;160:403-09.
Au et al., Virus-mediated induction of interferon A gene requires cooperation between multiple binding factors in the interferon alpha promoter region. J Biol Chem. Nov. 15, 1993;268(32):24032-40.
Auerbach et al., Erythema nodosum following a jellyfish sting. J Emerg Med. Nov.-Dec. 1987;5(6):487-91.
Auwers, [Uber die Isomerie-Verhaltnisse in der Pyrazol-Reihe. Berichte. VI.] 1926;601-607. German.
Bachman et al., Synthesis of substituted quinolylamines. Derivatives of 4-amino-7-chloroquinoline. J Org Chem. 1950;15(6):1278-84.
Baffis et al., Use of interferon for prevention of hepatocellular carcinoma in cirrhotic patients with hepatitis B or hepatitis C virus infection. Ann Intern Med. Nov. 2, 1999;131(9):696-701.
Baker et al., Oral infection with Porphyromonas gingivalis and induced alveolar bone loss in immunocompetent and severe combined immunodeficient mice. Arch Oral Biol. Dec. 1994;39(12):1035-40.
Baldwin et al., Amino Acid Synthesis via Ring Opening of N-Sulphonyl Aziridine-2-Carboxylate Esters with Organometallic Reagents. Tetrahedron. 1993;49:6309-30.
Baranov et al., Imidazo[4-5c]quinolines. In Chemical Abstracts. 1976;85:637. Abstract 94362z.
Bártová et al., Th1 and Th2 cytokine profile in patients with early onset periodontitis and their healthy siblings. Mediators Inflamm. 2000;9(2):115-20.
Beck et al., Dental Infections and Atherosclerosis. Am Heart J. 1999;13:528-33.
Beckett et al., Configurational Studies in Synthetic Analgesics: the Synthesis of (-)-Methadone from D-(-)-Alanine. J Chem Soc. 1957;1:858-61.
Beilman et al., Experimental brown spider bite in the guinea pig: Results of treatment with dapsone or hyperbaric oxygen. J Wilderness Medicine. 1994;5:287-94.
Belikov, Abbreviated Guide to Synthetic and Natural Medications. Pharmaceutical Chemistry. Higher School. 1993;1:43-47. Russian.
Beltrami et al., Some Methylhydrazonium Salts; An Improved Synthesis of Tetramethylhydrazine. J Am Chem Soc. 1956;78:2467-68.
Berenyi et al., Ring transformation of condensed dihyrdo-astriazines. J Heterocyclic Chem. 1981;18:1537-40.
Bernstein et al., Daily or weekly therapy with resiquimod (R-848) reduces genital recurrences in herpes simplex virus-infected guinea pigs during and after treatment. J Infect Dis. Mar. 15, 2001;183(6):844-9. Epub Feb. 13, 2001.
Bertino et al., Principles of Cancer Therapy. Cecil Textbook of Medicine. Goldman et al., eds. 21th Ed. W.B. Saunders Company. 2000:1:1060-74.
Beutler et al., Tumor necrosis factor in the pathogenesis of infectious diseases. Crit Care Med. Oct. 1993;21(10 Suppl):S423-35.
Beutner et al., Therapeutic response of basal cell carcinoma to the immune response modifier imiquimod 5% cream. J Am Acad Dermatol. Dec. 1999;41(6):1002-7.
Beutner et al., Treatment of genital warts with an immune-response modifier (imiquimod). J Am Acad Dermatol. Feb. 1998;38(2 Pt 1):230-9.
Binder, Acute arthropod envenomation. Incidence, clinical features and management. Med Toxicol Adverse Drug Exp. May-Jun. 1989;4(3):163-73.
Bishop et al., Molecular mechanisms of B lymphocyte activation by the immune response. modifier R-848. J Immunol. Nov. 15, 2000;165(10):5552-7.
Bitterman-Deutsch et al., [Brown spider bite]. Harefuah. Sep. 1990;119(5-6):137-9. Hebrew.
Booth et al., Dapsone suppresses integrin-mediated neutrophil adherence function. J Invest Dermatol. Feb. 1992;98(2):135-40.

Borkan et al., An outbreak of venomous spider bites in a citrus grove. Am J Trop Med Hyg. Mar. 1995;52(3):228-30.

Bourke et al., The toll-like receptor repertoire of human B lymphocytes: inducible and selective expression of TLR9 and TLR10 in normal and transformed cells. Blood. Aug. 1, 2003;102(3):956-63. Epub Apr 10, 2003.

Brants, The Distribution of Tobacco Mosaic Virus (TMV) in Excised Tomato Roots Cultivated in Vitro. Tijdschr Plantenziekten, 1962;68:198-207.

Brassard et al., Interferon-α as an immunotherapeutic protein. J Leukoc Biol. Apr. 2002;71(4):565-81.

Breathnach, Azelaic acid: potential as a general antitumoural agent. Med Hypotheses. Mar. 1999;52(3):221-6.

Brennan et at, Automated bioassay of interferons in microtest plates. Biotechniques. Jun./Jul. 1983(1):78-82.

Broughton, Management of the brown recluse spider bite to the glans penis. Mil Med. Oct. 1996;161(10):627-9.

Buckle et al., 4-hydroxy-3-nitro-2-quinolones and related compounds as inhibitors of allergic reactions. J Med Chem. Jul. 1975;18(7):726-32.

Buisson et al., Preparation and use of (S)-O-acetyllactyl chloride (Mosandl's reagent) as a chiral derivatizing agent. Tetrahedron Assym. 1999;10:2997-3002.

Bulut et al., Cooperation of Toll-like receptor 2 and 6 for cellular activation by soluble tuberculosis factor and *Borrelia burgdorferi* outer surface protein A lipoprotein: role of Toll-interacting protein and IL-1 receptor signaling molecules in Toll-like receptor 2 signaling. J Immunol. Jul. 15, 2001;167(2):987-94.

Burleson, Chapter 14. Influenza Virus Host Resistance Model for Assessment of Immunostimulation, and Antiviral Compounds. Methods in Immunology. 1995;2:181-202.

Buschle et al., Interferon γ inhibits apoptotic cell death in B cell chronic lymphocytic leukemia. J Exp Med. Jan. 1, 1993;177(1):213-8.

Cai et al., Evaluation of trifluoroacetic acid as an ion-pair reagent in the separation of small ionizable molecules by reversed-phase liquid chromatography. Analytica Chmica Acta. 1999;399;249-258.

Cantell et al., IFN-γ Enhances Production of IFN-α in Human Macrophages but Not in Monocytes. J Interferon and Cytokine Res. 1996;16:461-63.

Carceller et al., Design, synthesis, and structure-activity relationship studies of novel 1-[(1-acyl-4-piperidyl)methyl]-1H-2-methylimidazo[4,5-c]pyridine derivatives as potent, orally active platelet-activating factor antagonists. J Med Chem. Jan. 19, 1996;39(2):487-93.

Carrigan et al., Synthesis and in vitro pharmacology of substituted quinoline-2,4-dicarboxylic acids as inhibitors of vesicular glutamate transport. J Med Chem. May 23, 2002;45(11):2260-76.

Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997;330(12):383-6.

Cheson et al, National Cancer Institute-sponsored Working Group guidelines for chronic lymphocytic leukemia: revised guidelines for diagnosis and treatment. Blood. Jun. 15, 1996;87(12):4990-7.

Chollet et al., Development of a topically active imiquimod formulation. Pharm Dev Technol. Jan. 1999;4(1):35-43.

Chuang et al., Toll-like receptor 9 mediates CpG-DNA signaling. J Leukoc Biol. Mar. 2002;71(3):538-44.

Claisen, [Uber α-Methyl-isoxazol.] Berichte. 1909;42:59-69. German.

Cohen et al., Cytokine function: a study in biologic diversity. Am J Clin Pathol. May 1996;105(5):589-98.

Cole et al., Brown recluse spider envenomation of the eyelid: an animal model. Ophthal Plast Reconstr Surg. Sep. 1995;11(3):153-64.

Colotta et al., Synthesis and structure-activity relationships of a new set of 2-arylpyrazolo[3,4-c]quinoline derivatives as adenosine receptor antagonists. J Med Chem. Aug. 10, 2000;43(16):3118-24.

Cristalli et al., Adenosine deaminase inhibitors: synthesis and structure-activity relationships of imidazole analogues of erythro-9-(2-hydroxy-3-nonyl)adenine. J Med Chem. Mar. 1991;34(3):1187-92.

Dai et al., Synthesis of a novel C2-symmetric thiourea and its application in the Pd-catalyzed cross-coupling reactions with arenediazonium salts under aerobic conditions. Org Lett. Jan. 22, 2004;6(2):221-4.

Davis, Current therapy for chronic hepatitis C. Gastroenterology. Feb. 2000;118(2 Suppl 1):S104-14.

Davis et al., Heterocyclic Syntheses with Malonyl Chloride. Part VI. 3-Substituted Pyridine Derivatives from α-Methylene-nitriles. J Chem Soc. 1962:3638-44.

Davis et al., Self-administered topical imiquimod treatment of vulvar intraepithelial neoplasia. A report of four cases. J Reprod Med. Aug. 2000;45(8):619-23.

De et al., Structure-activity relationships for antiplasmodial activity among 7-substituted 4-aminoquinolines. J Med Chem. Dec. 3, 1998;41(25):4918-26.

Debol et al., Anti-inflammatory action of dapsone: inhibition of neutrophil adherence is associated with inhibition of chemoattractant-induced signal transduction. J Leukoc Biol. Dec. 1997;62(6):827-36.

De Clerq, Synthetic interferon inducers. Top Curr Chem. 1974;52:173-208.

Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.

Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-68.

Delgado, Textbook of Organic Medicinal and Pharmaceutical Chemistry, Ninth Edition, Remers, ed., 1991:30-1.

Denzel et al. Imidazo [4,5-c]- and [4,5-b]pyridines. J. Heterocyclic Chem. 1977;14:813-821.

Diaz-Arrastia et al., Clinical and molecular responses in high-grade intraepithelial neoplasia treated with topical imiquimod 5%. Clin Cancer Res. Oct. 2001;7(10):3031-3.

Di Carlo et al., Neutrophils in anti-cancer immunological strategies: old players in new games. J Hematother Stem Cell Res. Dec. 2001;10(6):739-48.

Dicken et al., Reactions at High Pressures. [3 + 2] Dipolar Cycloaddition of Nitrones with Vinyl Ethers. J Org Chem. 1982;47:2047-51.

Dockrell et al., Imiquimod and resiquimod as novel immunomodulators. J Antimicrob Chemother. Dec. 2001;48(6):751-5.

Dorwald, "Preface." Side Reactions in Organic Synthesis. A Guide to Successful Synthesis Design. Wiley-VCH. 2005: IX.

Doyle et al., Toll-like receptor 3 mediates a more potent antiviral response than Toll-like receptor 4. J Immunol. Apr. 1, 2003;170(7):3565-71.

Drexler et al., Bryostatin 1 induces differentiation of B-chronic lymphocytic leukemia cells. Blood. Oct. 1989;74(5):1747-57.

Dzionek et al. BDCA-2, BDCA-3, and BDCA-4: three markers for distinct subsets of dendritic cells in human peripheral blood. J Immunol. Dec. 1, 2000;165(11):6037-46.

Edwards et al., Toll-like receptor expression in murine DC subsets: lack of TLR7 expression by CD8 alpha+ DC correlates with unresponsiveness to imidazoquinolines. Eur J Immunol. Apr. 2003;33(4):827-33.

Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-46.

Fecci et al., The history, evolution, and clinical use of dendritic cell-based immunization strategies in the therapy of brain tumors. J Neurooncol. Aug.-Sep. 2003;64(1-2):161-76.

Fitzgerald-Bocarsly et al., Virally-Responsive IFN-α Producing Cells in Human Blood and Tonsil Are CD11C/CD123+ Cells Identical to Precursors of Type Two Dendritic Cells (pDC2). J Interferon Cytokine Res. 1999;19(1):S117. Abstract P81.

Flo et al., Involvement of toll-like receptor (TLR) 2 and TLR4 in cell activation by mannuronic acid polymers. J Biol Chem. Sep 20, 2002;277(38):35489-95. Epub Jun. 27, 2002.

Fonteneau et al., Human Immunodeficiency Virus Type 1 Activates Plasmacytoid Dendritic Cells and Concomitantly Induces the Bystander Maturation of Myeloid Dendritic Cells. J Virol. 2004;78(10):5223-32.

Frankel et al., The Preparation of N-Disubstituted Formamides. Tetrahedron Lett. 1959;7:5-7.

Frantz et al., Toll4 (TLR4) expression in cardiac myocytes in normal and failing myocardium. J Clin Invest. Aug. 1999;104(3):271-80.

Fu et al., Regioselective Catalytic Hydrogenation of Polycyclic Aromatic Hydocarbons under Mild conditions. J Org Chem. 1980;45:2979-803.

Fuchsberger et al., Priming Interferon-α 1 or Interferon-α 2 Enhances the Production of Both Subtypes Simultaneously. J Interferon and Cytokine Res. 1995;15:637-39.

Galose, Dapsone (diaminodiphenylsulphone DDS). Clinical Toxicology Review. 1999:21(9). 3 pages.

Gendron, Loxosceles ignali Envenomation. Am J Emerg Med. Jan. 1990;8(1):51-4.

Genevois-Borella et al., Synthesis of 1-(3-R-Amino-4-Hydroxy Butyl)thymine Acyclonucleoside. Analogs as Potential Anti-AIDS Drugs. Tetrahedron Lett. 1990;31:4879-82.

Giannini et al., Influence of the Mucosal Epithelium Microenvironment on Langerhans Cells: Implications for the Development of Squamous Intraepithelial Lesions of the Cervix. Int J Cancer. 2002;97:654-59.

Gibson et al., Cellular requirements for cytokine production in response to the immunomodulators imiquimod and S-27609. J Interferon Cytokine Res. Jun. 1995;15(6):537-45.

Gibson et al., Plasmacytoid dendritic cells produce cytokines and mature in response to the TLR7 agonists, imiquimod and resiquimod. Cell Immunol. Jul.-Aug. 2002;218(1-2):74-86.

Gitelson et al., Chronic lymphocytic leukemia-reactive T cells during disease progression and after autologous tumor cell vaccines. Clin Cancer Res. May 2003;9(5):1656-65.

Gomez et al., Intradermal anti-loxosceles Fab fragments attenuate dermonecrotic arachnidism. Acad Emerg Med. 1999;6:1195-202.

Gorden et al., Synthetic TLR agonists reveal functional differences between human TLR7 and TLR8. J Immunol. Feb. 1, 2005;174(3):1259-68.

Gordon, Pattern recognition receptors: doubling up for the innate immune response. Cell. Dec. 27, 2002;111(7):927-30.

Gunning et al., Chemoprevention by lipoxygenase and leukotriene pathway inhibitors of vinyl carbamate-induced lung tumors in mice. Cancer Res. Aug. 1, 2002;62(15):4199-201.

Gürsel et al., Differential and competitive activation of human immune cells by distinct classes of CpG oligodeoxynucleotide. J Leukoc Biol. May 2002;71(5):813-20.

Hart, Napthyridines Hydroxynaphthyridies, Journal of Chemical Society, 1956; Part III:212-4.

Hartmann et al., Rational design of new CpG oligonucleotides that combine B cell activation with high IFN-alpha induction in plasmacytoid dendritic cells. Eur J Immunol. Jun. 2003;33(6):1633-41.

Hayashi Toll-like receptors stimulate human neutrophil function. Blood. Oct. 1, 2003;102(7):2660-69. Epub Jun. 26, 2003.

Hayes et at., Regulation of Interferon Production by Human Monocytes: Requirements for Priming for Lipopolysaccharide-Induced Production. J Leukocyte Biol. 1991;50:176-81.

Heil et al., Species-specific recognition of single-stranded RNA via toll-like receptor 7 and 8. Science. Mar. 5, 2004;303(5663):1526-9. Epub Feb. 19, 2004.

Heil et al., Synthetic immunostimulatory compounds activate immune cells via TLR7 and TLR8. 33th Annual Meeting of the Deutsche Gessellschaft Mr Immunologie, Marburg 2002. Abstract C.6.

Hemmi et al., Small anti-viral compounds activate immune cells via the TLR7 MyD88-dependent signaling pathway. Nat Immunol: Feb. 2002;3(2):196-200. Epub Jan. 22, 2002.

Hobbs et al., Comparison of hyperbaric oxygen and dapsone therapy for loxosceles envenomation. Acad Emerg Med. Aug. 1996;3(8):758-61.

Hoffman et al., Conformational requirements for histamine H2-receptor inhibitors: a structure-activity study of phenylene analogues related to cimetidine and tiotidine. J Med Chem. Feb. 1983;26(2):140-4.

Hofmanová et al., Lipoxygenase inhibitors induce arrest of tumor cells in S-phase of the cell cycle. Neoplasma. 2002;49(6):362-7.

Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.

Horng et al., The adaptor molecule TIRAP provides signaling specificity for Toll-like receptors. Nature. Nov. 21, 2002;420(6913):329-33.

Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-37.

Houben-Weyl, Quinoline and Isoquinoline. Methoden der Organischen Chemie. 1980:271-79. German.

Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. Apr. 1985;28(4):467-71.

Huppatz, Systemic fungicides. The synthesis of certain pyrazole analogues of carboxin. Aust J Chem. 1983;36:135-47.

Iino et al., Treatment of Chronic Hepatitis C With High-Dose Interferon α-2b. Multicenter Study. Dig Dis Sci. 1993;38(4):612-18.

Ito et al., Interferon-alpha and interleukin-12 are induced differentially by Toll-like receptor 7 ligands in human blood dendritic cell subsets. J Exp Med. Jun. 3, 2002;195(11):1507-12.

Iwashita et al., Syntheses of Isoretronecanol and Lupinine. J Org Chem. 1982;47:230-33.

Izumi et al., 1H-Imidazo[4,5-c]quinoline derivatives as novel potent TNF-alpha suppressors: synthesis and structure-activity relationship of 1-, 2-and 4-substituted 1H-imidazo[4,5-c]quinolines or 1H-imidazo[4,5-c]pyridines. Bioorg Med Chem. Jun. 12, 2003;11(12):2541-50.

Jacobs, Chapter 1. The Synthesis of Acetylenes. In: Organic Reactions. New York: Wiley & Sons, Inc., 1949. vol. 5, 1-78.

Jahnsen et al., Extensive recruitment of IL-3Rahigh dendritic-cell precursors to allergic nasal mucosa during allergen challenge. Immunology Lett. 1999;69(1):123. Abstract #32.2.

Jain et al., Chemical and pharmacological investigations of some omega-substituted alkylamino-3-aminopyridines. J Med Chem. Jan. 1968;11(1):87-92.

Jurk et al.. Human TLR7 and TLR8 independently confer responsiveness to the antiviral compound R-848. Nat Immunol. Jun. 2002;3(6):499.

Juweid, Radioimmunotherapy of B-Cell Non-Hodgkin's Lymphoma: From Clinical Trials to Clinical Practice. J Nuclear Med. 2002;43(11):1507-29.

Katritsky et al., Comprehensive Heterocyclic Chemistry: The Structure, Reactions, Synthesis and Uses of Heterocyclic Compounds. 1984;2:586-587.

Keating et al., Long-term follow-up of patients with chronic lymphocytic leukemia treated with fludarabine as a single agent. Blood. Jun. 1, 1993;81(11):2878-84.

Kerkmann et al., Activation with CpG-A and CpG-B oligonucleotides reveals two distinct regulatory pathways of type I IFN synthesis in human plasmacytoid dendritic cells. J Immunol. May 1, 2003;170(9):4465-74.

Klausen et al., Two complementary methods of assessing periodontal bone level in rats. Scand J Dent Res. Dec. 1989;97(6):494-9.

Klinman, Immunotherapeutic uses of CpG oligodeoxynucleotides. Nat Rev Immunol. Apr. 2004;4(4):249-58.

Kloek et al., An improved method for the synthesis of stabilized primary enamines and imines. J Org Chem. 1978;43:1460-62.

Kloetzel, Reactions of nitroparaffins. I. Synthesis and reduction of some ò-nitrokenes. J Am Chem Soc. 1947;69:2271-2275.

Kornman, Host modulation as a therapeutic strategy in the treatment of periodontal disease. Olin Infect Dis. Mar. 1999;28(3):520-6.

Kourafalos et al., Synthesis of 7-aminopyrazolo[3,4-c]pyridine as a probe for the preparation of compounds of pharmacological interest. Heterocycles. 2002;57(12):2335-2343.

Krause et al., Autoimmune aspects of cytokine and anticytokine therapies. Am J Med. Oct. 1, 2003;115(5):390-7.

Krenitsky et al., Imidazo[4,5-c]pyridines (3-deazapurines) and their nucleosides as immunosuppressive and anti-inflammatory agents. J Med Chem. Jan. 1986;29(1):138-43.

Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-8.

Lall et al., Serine and threonine beta-lactones: a new class of hepatitis A virus 3C cysteine proteinase inhibitors. J Org Chem. Mar. 8, 2002;67(5):1536-47.

Lee et al., p38 mitogen-activated protein kinase inhibitors—mechanisms and therapeutic potentials. Pharmacol Ther. 1999;82:389-97.

Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-9. Epub Feb. 13, 2004.

Lehner et al., The role of γδ cells and β-chemokines in mucosal protection against SIV infection. Immunology Lett. 1999;69:25-192. Abstract 2.1.

Levy et al., Unique efficacy of Toll-like receptor 8 agonists in activating human neonatal antigen-presenting cells. Blood. Aug. 15, 2006;108(4):1284-90. Epub Apr. 25, 2006.

Leynadier et al., Allergic reactions to North African scorpion venom evaluated by skin test and specific IgE. J Allergy Clin Immunol. Jun. 1997;99(6 Pt 9:851-3. 4 pages.

Li et al., An improved protocol for the preparation of 3-pyridyl- and some arylboronic acids. J Org Chem. Jul. 26, 2002;67(15):5394-7.

Li et al., Solubility behavior of imiquimod in alkanoic acids. 1997 American Association of Pharmaceutical Scientists Annual Meeting. Poster Presentation, Boston, MA, Nov. 2-6. Pharma Res. 1997;14(11):S475. Abstract 3029.

Li et al., Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-21.

Litt et al., Mucosal delivery of vaccine antigens displayed on the surface of *Lactococcus lactis*. Immunology Lett. 1999;69(1):61. Abstract #11.26.

Liu et al., Synthesis of halogen-substituted 3-deazaadenosine and 3-deazaguanosine analogues as potential antitumor/antiviral agents. Nucleosides Nucleotides Nucleic Acids. Dec. 2001;20(12):1975-2000.

Loesche et al., Treatment paradigms in periodontal disease. Compend Contin Educ Dent. Mar. 1997;18(3):221-6, 228-30, 232 passim; quiz 234. Review.

Luger et al., Evidence for an epidermal cytokine network. J Invest Dermatol. Dec. 1990;95(6 Suppl):100S-104S.

Luskin et al., Olefinic Derivatives of 2,4-Diamino-s-triazines. J Org Chem. 1958;23:1032-37.

Macchia et al., Synthesis and antiviral properties of 9-[(2-methyleneaminoxyethoxy)methyl]guanine derivatives as novel Acydovir analogues. Farmaco. Feb. 2000;55(2):104-8.

Majeski et al., Action of venom from the brown recluse spider (*Loxosceles recluse*) on human neutrophils. Toxicon. 1977;15(5):423-7.

Makarenkova et al., Identification of delta- and mu- type opioid receptors on human and murine dendritic cells. J Neuroimmunol. 2001;117:68-77.

Male et al., Introduction to the Immune System. In: Immunology. Elsevier. 2006:6-7.

Masihi, Progress on novel immunomodulatory agents for HIV-1 infection and other infectious diseases. Expert Opin Ther Patents. 2003;13(6):867-82.

Masiukiewicz et al., Scalable Syntheses of $N^\alpha$-Benzyloxy carbonyl-$_L$- Ornithine and of $N^\alpha$-(9-Fluorenylmethoxy)Carbonyl-$_L$- Ornithine. Org Prep Proced Int. 2002;34:531-37.

Mataka et al., Condensation reaction of 3,4-Dibenzoy1-1-methyl-2,5-diphenylpyrrole and -1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-5.

Mathur et al., Cell-mediated immune system regulation in periodontal diseases. Crit Rev Oral Biol Med. 1997;8(1):76-89.

Maynor et al., Brown recluse spider envenomation: a prospective trial of hyperbaric oxygen therapy. Acad Emerg Med. Mar. 1997;4(3):184-92.

Mbow et al., Small molecule and biologic modulators of the immune response to hepatitis C virus. Mini Rev Med Chem. May 2006;6(5):527-31.

McCarthy et al., Opioids, opioid receptors, and the immune response. Drug & Alcohol Dependence. 2001;62:111-23.

McKennon et al., A Convenient Reduction of Amino Acids and Their Derivatives. J Org Chem. 1993;58:3568-71.

McLaughlin et al., Opioid growth factor (OGF) inhibits the progression of human squamous cell carcinoma of the head and neck transplanted into nude mice. Cancer Lett. 2003;199:209-17.

Medzhitov, Toll-Like Receptors and Innate Immunity. Nature Rev Immunol. 2001;1:135-45.

Mee et al., Stille coupling made easier—the synergic effect of copper(I) salts and the fluoride ion. Angew Chem. 2004;116:1152-56.

Merigian et al., Envenomation From the Brown Recluse Spider: Review of Mechanism and Treatment Options. Am J Ther. Oct. 1996;3(10):724-734.

Miller et al., Imiquimod applied topically: a novel immune response modifier and new class of drug. Int J Immunopharmacol. Jan. 1999;21(1):1-14.

Minakawa et al., Nucleosides and Nucleotides. 184. Synthesis and Conformational Investigation of Anti-Fixed 3-Deaza-3-halopurine Ribonucleosides. J Org Chem. 1999;64:7158-72.

Moebius et al., The mysteries of sigma receptors: new family members reveal a role in cholesterol synthesis. Trends Pharmacol Sci. Mar. 1997;18(3):67-70.

Moldoveanu et al., Poly-L-lysine as a potential mucosal adjuvant. Immunology Lett. 1999;69(1):62. Abstract #11.28.

Mollick et al., MUC1-like tandem repeat proteins are broadly immunogenic in cancer patients. Cancer Immun. Mar. 17, 2003;3:3. 17 pages.

Moody et al., Lipoxygenase inhibitors prevent lung carcinogenesis and inhibit non-small cell lung cancer growth. Exp Lung Res. Jul.-Aug. 1998;24(4):617-28.

Moraczewski et al., Using Hydrogen Bonding to Control Carbamate C-N Rotamer Equilibria. Org. Chem. Oct. 16, 1998;63(21):7258-7262.

Mosbech et al., [Allergy to insect stings] Ugeskr Laeger. Oct. 28, 1991;153(44):3067-71. Danish.

Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 4, 2003. Abstract 0975.

Muller et al., An improved one-pot procedure for the synthesis of alkynes from aldehydes. Synlett. 1996;6:521-522.

Mutschler et al., 9.2 Anti-infectives. In: Drug Actions: Basic Principles and Therapeutic Aspects. 1995:515-80.

Muzio et al., Differential expression and regulation of toll-like receptors (TLR) in human leukocytes: selective expression of TLR3 in dendritic cells. J Immunol. Jun. 1, 2000;164(11):5998-6004.

Nagarajan et al., Condensed heterotricycles: synthesis of pyrazolo[3,4-c]quinoline derivatives. Indian Journal of Chemistry. 1992;31B:316-321.

Nagase et al., Expression and function of Toll-like receptors in eosinophils: activation by Toll-like receptor 7 ligand. J Immunol. Oct. 15, 2003;171(8):3977-82.

Nanjappan et al., An efficient synthesis of some 6-substituted 4,8-diaza-3,3,9,9-tetramethylundeca-2,10-dione dioximes (propylene amine oximes, PnAOs): Ligands for 99mTc complexes used in structure distribution relationship (SDR) studies. Tetrahedron. 1994;50(29):8617-32.

Ohana et al., Differential effect of adenosine on tumor and normal cell growth: focus on the A3 adenosine receptor. Journal of Cellular Physiology. Jan. 2001;186(1):19-23. Review.

O'Mahony et al., New patient-applied therapy for anogenital warts is rated favourably by patients. Intl J STD & AIDS. 2001;12:565-70.

Osol et al., Chapter 27: Structure-Activtiy Relationship and Drug Design. In: Remington's Pharmaceutical Sciences. 16th Ed. Mach Publishing. 1980:420-35.

Ottonello et al., Sulphonamides as anti-inflammatory agents: old drugs for new therapeutic strategies in neutrophilic inflammation? Clin Sci (Lond). Mar. 1995;88(3):331-6.

Ozinsky et al., The repertoire for pattern recognition of pathogens by the innate immune system is defined by cooperation between Toll-like receptors. Proc. Nat. Acad. Sci. 2000; 97(25):13766-71.

Page et al., Advances in the pathogenesis of periodontitis: summary of developments, clinical implications and future directions. Periodontol 2000. Jun. 1997;14:216-48.

Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.

Park et al., Sodium Dithionite Reduction of Nitroarenes Using Viologen as an Electron Phase-Transfer Catalyst. Tetrahedron Lett. 1993;34(46):7445-46.

Patel et al., The necrotic venom of the brown recluse spider induces dysregulated endothelial cell-dependent neutrophil activation. Differential induction of GM-CSF, IL-8, and E-selectin expression. J Clin Invest. Aug. 1994;94(2):631-42.

Pavletic et al., Outcome of allogeneic stem cell transplantation for B cell chronic lymphocytic leukemia. Bone Marrow Transplant, Apr. 2000;25(7):717-22.

Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-9.

Payvandi et al., Exogenous and Endogenous IL-10 Regulate IFN-α Production by Peripheral Blood Mononuclear Cells in Response to Viral Stimulation. J Immunol. 1998;160:5861-68.

Peschke et al., Synthesis and in vitro characterization of new growth hormone secretagogues derived from ipamorelin with dipeptidomimetic N-terminals. Eur J Med Chem. 1999;34:363-380.

Peterson et al., The opioid-cytokine connection. J Neuroimmunol. 1998;83:63-69.

Phillips et al., Therapy of brown spider envenomation: a controlled trial of hyperbaric oxygen, dapsons, and cyproheptadine. Ann Emerg Med. Mar. 1995; 25(3):363-8.

Pickersgill et al., Preparation of functionalized, conformationally constrained DTPA analogues from L- or D-serine and trans-4-hydroxy-L-proline. Hydroxymethyl substituents on the central acetic acid and on the backbone. J Org Chem. Jun. 30, 2000;65(13):4048-57.

Poljakovic et al., iNOS and COX-2 immunoreactivity in the mice bladder and kidney after bacterial instillation. Immunology Lett. 1999;69(1):122. Abstract #31.5.

Powell et al.; Compendium of excipients for parenteral formulations. PDA J Pharm Sci Technol. Sep.-Oct. 1998;52(5):238-311.

Prelog et al., Cycloalkeno-pyridine. Hely Chem Acta. 1945;28:1684-93. German.

Rees et al., Brown recluse spider bites. A comparison of early surgical excision versus dapsone and delayed surgical excision. Ann Surg. Nov. 1985;202(5):659-63.

Regan et al., Activation of p38 MAPK by feline infectious peritonitis virus regulates pro-inflammatory cytokine production in primary blood-derived feline mononuclear cells. Virology. Feb. 5, 2009;384(1):135-43. Epub Dec. 5, 2008.

Rhodes, Discovery of immunopotentiatory drugs: current and future strategies. Clin Exp Immunol. Dec. 2002;130(3):363-9.

Ribera et al., "Spontaneous" complete remissions in chronic lymphocytic leukemia: report of three cases and review of the literature. Blood Cells. 1987;12(2):471-79.

Ritter et al., A new reaction of nitriles; amides from alkenes and mononitriles. J Am Chem Soc. Dec. 1948;70(12):4045-8.

Rocca et al., Carbolines. Part VII. Ansidines, Convenient tools to synthesize fficien-β-carbolines. J Heterocyclic Chem. 1995;32:1171-1175.

Rocca et al., Connection between metalation and cross-coupling strategies. Anew convergent route to azacarbazoles. Tetrahedron. 1993;49(1):49-64.

Rollins, Chemokines. Blood. Aug. 1, 1997;90(3):909-28. Review.

Rosenberg et al., Treatment of 283 consecutive patients with metastatic melanoma or renal cell cancer using high-dose bolus interleukin 2. JAMA. Mar. 23-30, 1994;271(12):907-13.

Rothel et al., The use of recombinant ovine IL-1 beta and TNF-alpha as natural adjuvants and their physiological effects in vivo. Immunol Cell Biol. Apr. 1998;76(2):167-72.

Roy et al., QSAR of adenosine receptor antagonists II: exploring physicochemical requirements for selective binding of 2-arlypyrazolo[3,4-c] quinoline derivatives with adenosine Al and A3 receptor subtypes. QSAR & Comb Sci. 2003;22:614-621.

Royals et al., Studies in mixed ester condensations. IV. Acylations with methyl dimethoxyacetate. J Am Chem Soc. 1956;78:4161-4164.

Rozman et al., Chronic lymphocytic leukemia. N Engl J Med. Oct. 19, 1995;333(16):1052-7.

Sakthivel et al. Direct SnAr amination of fluorinated imizazo[4,5-c]pyridine nucleosides: efficient synthesis of 3-fluoro-3-3-deazaadenosine analogs. Tetrahedron Letters. May 2005;46(22):3883-3887.

Salaun et al., TLR3 Can Directly Trigger Apoptosis in Human Cancer Cells. J of Immunology. 2006;176:4894-901.

Salemink, Uber 2-Propyl-1- Und 2-Propyl-Desaza-Adenin. Recueil. 1961;80:545-55. German.

Sambhi et al., Local production of tumor necrosis factor encoded by recombinant vaccinia virus is effective in controlling viral replication in vivo. Proc Natl Acad Sci U S A. May 1, 1991;88(9):4025-9.

Sams et al., Necrotic arachnidism. J Am Acad Dermatol. Apr. 2001;44(4):561-73; quiz 573-6.

Sauder et al., Randomized, Single-Blind, Placebo-Controlled Study of Topical Application of the Immune Response Modulator Resiquimod in Healthy Adults. Antimicrobial Agents Chemo. 2003;47(12):3846-52.

Scheerlinck, Genetic adjuvants for DNA vaccines. Vaccine. Mar. 21, 2001;19(17-19):2647-56.

Scheuer et al., Application of the Ritter reaction to mesityl oxide and chalcone. J Am Chem Soc. 1957;22:674-676.

Schofield et al., Reply. Low-Dose Interferon-alpha in Chronic Myeloid Leukemia. Ann Internal Med. 1995;122(9):728-29. 1 page.

Schwandner et al., Peptidoglycan- and lipoteichoic acid-induced cell activation is mediated by toll-like receptor 2. J Biol Chem. Jun. 18, 1999;274(25):17406-9.

Seeman et al., Steric and Conformational Effects in Nicotine Chemistry. J Org Chem. 1981;46:3040-48.

Serrat et al., A highly efficient and straightforward stereoselective synthesis of novel chiral α-acetylenic ketones. Tetrahedron: Assymmetry. 1999;10:3417-30.

Severa et al., Sensitization to TLR7 agonist in IFN-beta-preactivated dendritic cells. J Immunol. May 15, 2007;178(10):6208-16.

Seymour et al., Cellular immunity and hypersensitivity as components of periodontal destruction. Oral Dis. Mar. 1996;2(1):96-101. Review.

Shelburne et al., Quantitation of Bacteroids forsythus in subgingival plaque comparison on immunoassay and quantitative polymerase chain reaction. J Microbiol Methods. 2000;39:97-107.

Sidky et al., Inhibition of murine tumor growth by an interferon-inducing imidazoquinolinamine. Cancer Res. Jul. 1, 1992;52(13):3528-33.

Siegal et al., The nature of the principal type 1 interferon-producing cells in human blood. Science. Jun. 11, 1999;284(5421):1835-7.

Sletzinger et al., The Synthesis of Isomethadone. J Am Chem Soc. 1952;74:5619-20.

Smith et al., The role of polymorphonuclear leukocytes in the lesion caused by the venom of the brown spider, *Loxosceles recluse*. Lab Invest. Jan. 1970;22(1):90-3.

Sofina et al., C: Possibility of Predicting the Spectrum of Antitumor Effect of Drugs on the Basis of Experimental Data. Experimental evaluation of antitumor drugs in the USA and USSR and clinical correlations. NCI Monograph 55. NIH Publication No. 80/1933. 1980:76-8.

Sommer et al., Recent Findings on How Proinflammatory Cytokines Cause Pain: Peripheral Mechanisms in Inflammatory and Neuropathic Hyperalgesia. Neurosci Letts. 2004;361:184-87.

Sonogashira et al., A convenient synthesis of acetylenes: catalytic substitutions of acetylenic hydrogen with bromoalkenes, Iodoarenes, and bromopyridines. Tetrahedron Letts. 1975;50:4467-4470.

Soria et al., Effect of food on the pharmacokinetics and bioavailability of oral imiquimod relative to a subcutaneous dose. Int J Clin Pharmacol Ther. Oct. 2000;38(10):476-81.

Spaner et al., A phase I/II trial of TLR-7 agonist immunotherapy in chronic lymphocytic leukemia. Leukemia. 2010; 24:222-26.

Spaner et at., Immunomodulatory effects of Toll-like receptor-7 activation on chronic lymphocytic leukemia cells. Leukemia. Feb. 2006;20(2):286-95.

Spaner et al., Toll-like receptor agonists in the treatment of chronic lymphocytic leukemia. Leukemia. Jan. 2007;21(1):53-60. Epub Oct. 26, 2006.

Spivey et al., Configurationally stable biaryl analogues of 4-(dimethylamino)pyridine: A novel class of chiral nucleophilic catalysts. J Org Chem. 1999;64:9430-9443.

Spruance et al., Application of a topical immune response modifier, resiquimod gel, to modify the recurrence rate of recurrent genital herpes: a pilot study. J Infect Dis. Jul. 15, 2001;184(2):196-200. Epub Jun. 8, 2001.

Stack, Images in clinical medicine. *Latrodectus mactans*. N Engl J Med. Jun. 5, 1997;336(23):1649.

Stashenko et at., Periapical inflammatory responses and their modulation. Crit Rev Oral Biol Med. 1998;9(4):498-521.

Steele et al., Lipoxygenase inhibitors as potential cancer chemopreventives. Cancer Epidemiol Biomarkers Prev. May 1999;8(5):467-83.

Steele et al., Potential use of lipoxygenase inhibitors for cancer chemoprevention. Expert Opin Investig Drugs. Sep. 2000;9(9):2121-38.

Steinmann et al., Topical imiquimod treatment of a cutaneous melanoma metastasis. J Am Acad Dermatol. Sep. 2000;43(3):555-6.

Stewart et al., Synthesis of a Carba-analog of S-Acetyl Coenzyme A, Acetonyl-dethio Coenzyme A; an Effective Inhibitor of Citrate Synthase. Liebigs Ann Chem. 1978:57-65.

Stillings et al., Substituted 1,3,4-thiadiazoles with anticonvulsant activity. 2. Aminoalkyl derivatives. J Med Chem. Nov. 1986;29(11):2280-4.

Strandtmann et al., Reaction of cyclic β-diketones with 3,4-dihydroisoquinolines and related compounds. Preparation and anticancer activity of 2-substituted 1,3-cyclohexanediones. J Med Chem. Nov. 1967;10(6):1063-5.

Stringfellow, Induction of interferon with low molecular weight compounds: fluorenone esters, ethers (tilorone), and pyrimidinones. Methods Enzymol. 1981;78(Pt A):262-84.

Ströher et al., Progress towards the treatment of Ebola haemorrhagic fever. Expert Opin Investig Drugs. Dec. 2006;15(12):1523-35.

Sugisaka et al., The Physicochemical properties of imiquimod, the first imidazoquinoline immune response modifier. 1997 American Association of Pharmaceutical Scientists Annual Meeting. Poster Presentation, Boston, MA, Nov. 2-6. Pharma Res. 1997;14(11):S475. Abstract 3030.

Surrey et al., The Synthesis of Some 3-Nitro- and 3-Amino-4-dialkylaminoalkylaminoquinoline Derivatives. J Am Chem Soc. 1951;73:2413-16.

Takeichi et al., Cytokine profiles of T-lymphocytes from gingival tissues with pathological pocketing. J Dent Res. Aug. 2000;79(8):1548-55.

Takeshita et al., Signal transduction pathways mediated by the interaction of CpG DNA with Toll-like receptor 9. Semin Immunol. Feb. 2004;16(1):17-22.

Takeuchi et al., Discrimination of bacterial lipoproteins by Toll-like receptor 6. Int Immunol. Jul. 2001;13(7):933-40.

Temple, Antimitotic agents: synthesis of imidazo[4,5-c]pyridin-6-ylcarbamates and imidazo[4,5-b]pyridin-5-ylcarbamates. J Med Chem. Feb. 1990;33(2):656-61.

Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3):697-700.

Testerman et al., Cytokine induction by the immunomodulators imiquimod and S-27609. J Leukoc Biol. Sep. 1995;58(3):365-72.

Thesing et al., [Darstellung und Eigenschaften des $\Delta^1$-Pyrrolin-$N$-oxyds.]. Chem Ber. 1959;92:1748-55. German.

Thiruvikraman et al., Synthesis and reactions of pyrazolo-[3,4-c]quinoline derivatives. Indian Journal of Chemistry. 1987;26B:695-696.

Tomai et al., Imiquimod: in vivo and in vitro characteristics and toxicology. In: Cutaneous Infection and Therapy. Aly et al., eds. Marcel Dekkar, Inc., New York. 1997:405-15.

Tomic et al., Sensitization of IL-2 Signaling through TLR-7 Enhances B Lymphoma Cell Immunogenicity. J Immunol. 2006;176:3830-39.

Tomioka et al., Asymmetric Alkylation of α-Alkyl β-Keto Esters. J Am Chem Soc. 1984;106:2718-19.

Totterman et al., Phorbol ester-induced differentiation of chronic lymphocytic leukaemia cells. Nature. Nov. 13, 1980;288(5787):176-8.

Tracy et al., Studies in the Pyridine Series. II. Synthesis of 2-Methyl-3-(β-Hydroxyethyl)pyridine and of the Pyridine Analog of Thiamine (Vitamin B2). J Org Chem. 1941;6:54-62.

Uno et al., TNF-related apoptosis-inducing ligand (TRAIL) frequently induces apoptosis in Philadelphia chromosome-positive leukemia cells. Blood. May 1, 2003;101(9):3658-67. Epub Dec. 27, 2002.

Urosevic et al., Imiquimod treatment induces expression of opioid growth factor receptor: a. novel tumor antigen induced by interferon-alpha? Clin Cancer Res. Aug. 1, 2004;10(15):4959-70.

Van de Kerhof, New Immunomodulatory Drugs. In: Skin and Environment: Perception and Protection. Ring et al., eds., 10th EADV Congress, Oct. 10-14, Munich, Germany. 2001:1:343-48.

Vasilakos et al., Adjuvant Activities of Immune Response Modifier R-848: Comparison with CoG ODN. Cell Immunol. 2000;204:64-74.

Vieweg et al., Tumor vaccines: from gene therapy to dendritic cells-the emerging frontier. Urol Clin North Am. Aug. 2003;30(3):633-43.

Vilcek, The cytokines: An overview. In: The Cytokine Handbook, Fourth Ed. M. Lotze and A.W. Thompson (eds.), 2003;1:3-14.

Vollhardt, 18-5. Amides: The Least-Reactive Carboxylic Acid Derivatives. Organic Chemistry. 1987:813.

Vollmer et al., Highly immunostimulatory CpG-free oligodeoxynucleotides for activation of human leukocytes. Antisense Nucleic Acid Drug Dev. Jun. 2002;12(3):165-75.

Wagner et al., Induction of cytokines in cynomolgus monkeys by the immune response modifiers, imiquimod, S-27609 and S-28463. Cytokine. Nov. 1997;9(11):837-45.

Wagner et al., Modulation of TH1 and TH2 Cytokine Production with the Immune Response Modifiers, R-848 and Imiguimod. Cellular Immunology. 1999;191:10-19.

Wang, Structure and Chemistry of 4-Hydroxy-6-methyl-2-pyridone. J Heterocyclic Chem. 1970;7:389-92.

Warren et al., Macrophage Growth Factor CSF-1 Stimulates Human Monocyte Production of Interferon, Tumor Necrosis Factor, and Colony Stimulating Activity. J Immunol. 1986;137(7):2281-85.

Wasserman et al., Loxoscelism and necrotic arachnidism. J Toxicol Clin Toxicol. 1983-1984;21(4-5):451-72.

Wedlock et al., Physiological effects and adjuvanticity of recombinant brushtail possum TNF-alpha. Immunol Cell Biol. Feb. 1999;77(1):28-33.

Wells, Additivity of Mutational Effects in Proteins. Biochemistry. 1990;29(37):8509-17.

Wermuth, Molecular Variations Based on Isosteric Replacements. Practice of Medicinal Chemistry.1996:203-37.

Wexler et al., Accurate identification of experimental pulmonary metastases. J Natl Cancer Inst. Apr. 1966; 36(4):641-5.

Wibaut et at., Syntheses of 3,4-Dimethylpyridine, 2,3-Dimethylpridine and 2-Methyl-3-Ethylpyridine. Rec Tray Chim. 1944;63:231-38.

Wierda et al., CD40-ligand (CD154) gene therapy for chronic lymphocytic leukemia. Blood. Nov. 1, 2000;96(9):2917-24.

Wieseler-Frank et al., Central proinflammatory cytokines and pain enhancement. Neurosignals. 2005;14(4):166-74.

Williams et al., Grignard Reactions to Chiral Oxazolidine Aldehydes. Tetrahedron. 1996;52:11673-94.

Wilson et al., Spiders and spider bites. Dermatol Clin. Apr. 1990;8(2):277-86.

Wozniak et al., The amination of 3-nitro-1, 5-naphthyridines by liquid ammonia/potassium permanganate1,2. A new and convenient animation method. J. Royal Netherlands Chem Soc. Dec. 12, 1983(102):511-3.

Wright et al., Clinical presentation and outcome of brown recluse spider bite. Ann Emerg Med. Jul. 1997;30(1):28-32.

Wu et al., Murine B16 melanoma vaccination-induced tumor immunity: identification of specific immune cells and functions involved. J Interferon Cytokine Res. Dec. 2001;21(12):1117-27.

Yamamoto et al., Essential role for TIRAP in activation of the signalling cascade shared by TLR2 and TLR4. Nature. Nov. 21, 2002;420(6913):324-9.

Yeung-Yue et al., The management of herpes simplex virus infections. Curr Opin Infect Dis. Apr. 2002; 15(2):115-22.

Yutilov et al., Synthesis and some reactions of 4-nitroimidazo[4-5-c]pyridin-2-ones. CAPLUS English Abstract DN 91:175261. VINITI.1978:1193-78. Abstract Only.

Zagon et al., Immunoelectron microscopic localization of the opioid growth factor receptor (OGFr) and OGF in the cornea. Brain Res. 2003;967:37-47.

Zagon et al., Opioids and the apoptotic pathway in human cancer cells. Neuropeptides. 2003;37:79-88.

Zagon et al., The biology of the opioid growth factor receptor (OGFr). Brain Res Rev. Feb. 2002;38(3):351-76. Review.

Zagon et al., The expression and function of the OGF-OGFr axis—a tonically active negative regulator of growth—in COS cells. Neuropeptides. Oct. 2003;37(5):290-7.

Zambon, Periodontal diseases: microbial factors. Ann Periodontol. Nov. 1996;1(1):879-925.

Zarubin et al., Theoretical Study of Antagonists and Inhibitors of Mammalian Adenosine Deaminase: I. Adenosine and Its Aza- and Deazaanalogues. Russ J Bioorg Chem. 2002;28(4):284-92.

Zhang et al., Structural features of azidopyridinyl neonicotinoid probes conferring high affinity and selectivity for mammalian alpha4beta2 and Drosophila nicotinic receptors. J Med Chem. Jun. 20, 2002;45(13):2832-40.

Zhu et al., Inhibition of murine dendritic cell activation by synthetic phosphorothioate oligodeoxynucleotides. J Leukoc Biol. Dec. 2002;72(6):1154-63.

Zhu et al., Inhibition of murine macrophage nitric oxide production by synthetic oligonucleotides. J Leukoc Biol. Apr. 2002;71(4):686-94.

Ziegler-Heitbrock et al., Favorable response of early stage B CLL patients to treatment with IFN-alpha 2. Blood. May 1, 1989;73(6):1426-30.

Zyryanov et al., Heterocyclization of 1-(2'-Carbethoxyphenyl)-5-Methyltetrazole. Chemistry of Heterocylic Compounds. English Edition. 1981;16(12):1286-88.

* cited by examiner

CHIRAL FUSED [1,2]IMIDAZO[4,5-C] RING COMPOUNDS

CROSS REFERENCE TO RELATED APPLICATIONS

This application is the National Stage of International Application No. PCT/US2005/047258, filed Dec. 29, 2005, which claims priority to U.S. Provisional Application Ser. No. 60/640,614, filed Dec. 30, 2004, and U.S. Provisional Application Ser. No. 60/697,257, filed Jul. 7, 2005, both of which are incorporated herein by reference.

BACKGROUND

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers, rendering them useful in the treatment of a variety of disorders.

There continues to be interest in and a need for compounds that have the ability to modulate the immune response, by induction of cytokine biosynthesis or other mechanisms.

SUMMARY

It has now been found that certain fused [1,2]imidazo[4,5-c]ring compounds modulate cytokine biosynthesis. Such compounds are of the following Formula I:

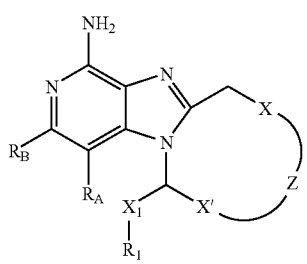

I and, more particularly, compounds of the following Formulas II, IIa, II-1, and II-1a:

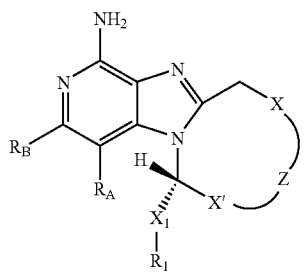

II

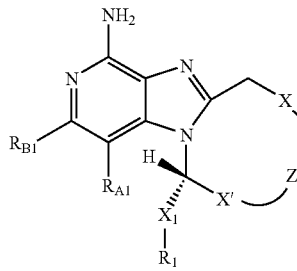

IIa

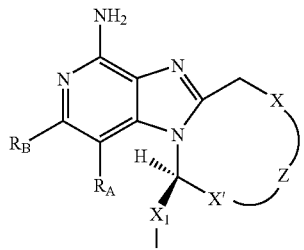

II-1

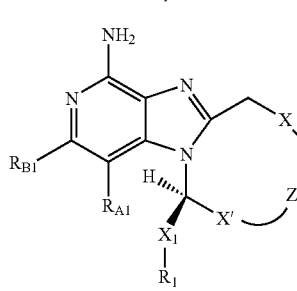

II-1a wherein: X, X', $X_1$, Z, $R_1$, $R_A$, $R_B$, $R_{A1}$, and $R_{B1}$ are as defined below.

The compounds of Formulas I, II, IIa, II-1, and II-1a are useful, for example, as immune response modifiers (IRMs) due to their ability to modulate cytokine biosynthesis (e.g., induce or inhibit the biosynthesis or production of one or more cytokines) and otherwise modulate the immune response when administered to animals. The ability to modulate cytokine biosynthesis, for example, induce the biosynthesis of one or more cytokines, makes the compounds useful in the treatment of a variety of conditions such as viral diseases and neoplastic diseases, that are responsive to such changes in the immune response.

The invention further provides pharmaceutical compositions containing an effective amount of a compound of Formulas I, II, IIa, II-1, or II-1a and methods of inducing cytokine biosynthesis in an animal, treating a viral infection and/or treating a neoplastic disease in an animal by administering an effective amount of a compound of Formula II or Formula IIa to the animal.

In addition, methods of synthesizing compounds of Formulas I, II, IIa, II-1, and II-1a and intermediates useful in the synthesis of these compounds are provided.

As used herein, "a", "an", "the", "at least one", and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I, II, IIa, II-1, II-1a, III, III-1, IV, IV-1, V, V-1, VI, VI-1, VII, and VII-1:

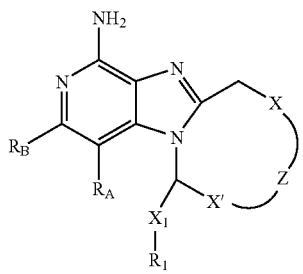

I

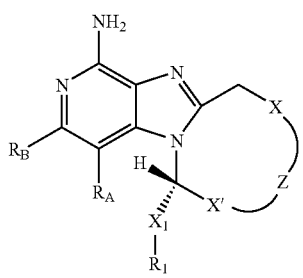

II

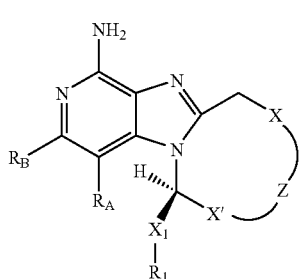

II-1

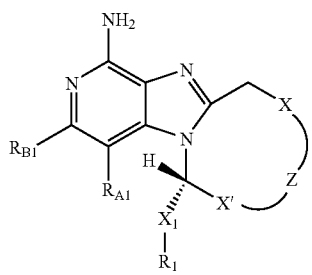

IIa

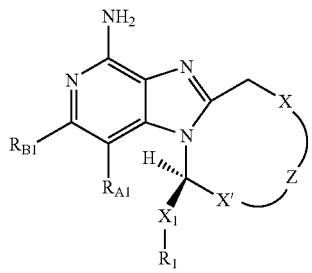

II-1a

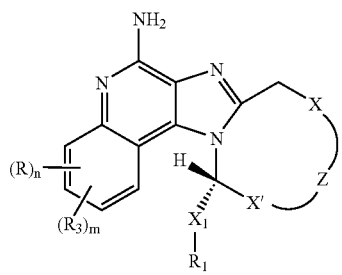

III

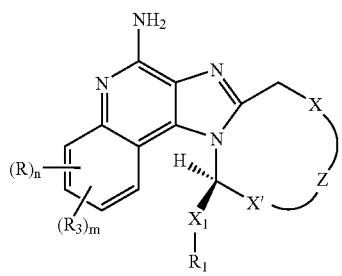

III-1

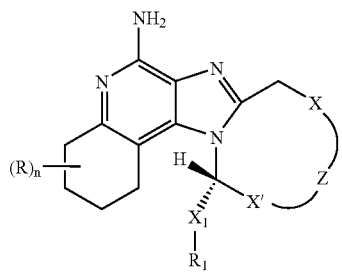

IV

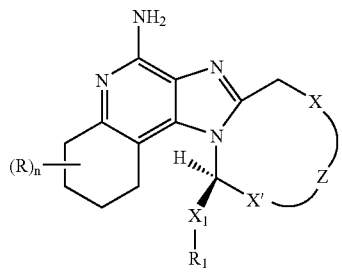

IV-1

-continued

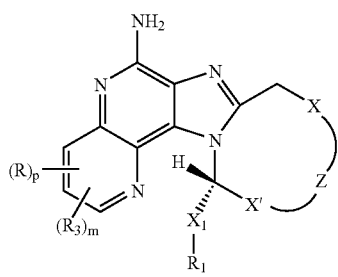

V

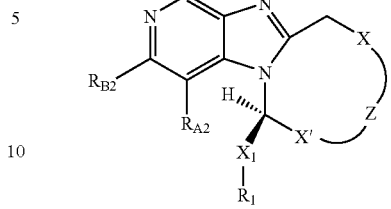

V-1

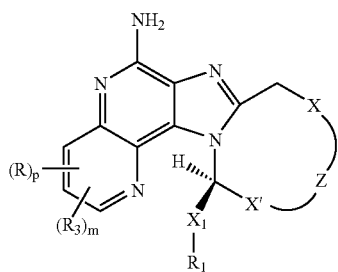

VI

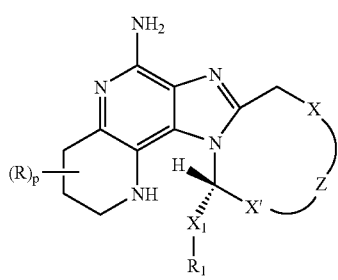

VI-1

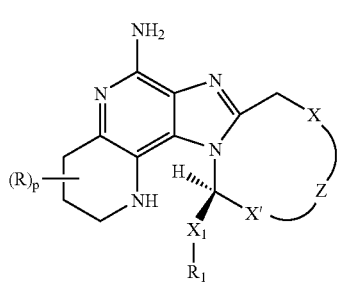

VII

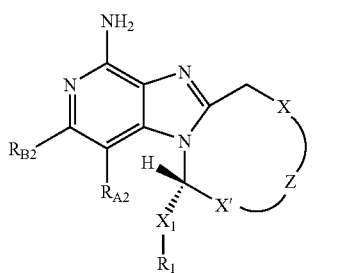

VII-1

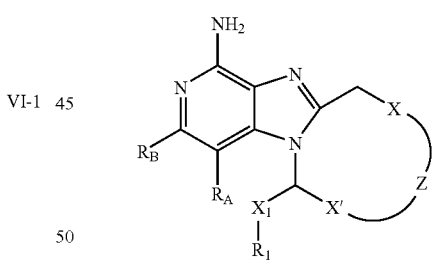

as well as intermediates of the following Formulas X and X-1:

X

X-1 wherein: X, X', $X_1$, Z, R, $R_1$, $R_3$, $R_4$, $R_B$, $R_{A1}$, $R_{B1}$, $R_{A2}$, $R_{B2}$, E, m, n, and p are as defined below.

In one embodiment, the present invention provides a compound of Formula I:

I wherein:

X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X' is a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X and X' are further characterized in that the sum of the ring carbon atoms contributed by X and X' is 1, 2, or 3;

Z is selected from the group consisting of —O— and —N(—Y—$R_2$)—;

$X_1$ is selected from the group consisting of a bond, alkylene, alkenylene, and alkynylene wherein the alkylene and alkenylene are optionally interrupted by one or more —O— groups, and are optionally substituted by a hydroxy or methoxy group;

$R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_1$ is heterocyclyl, then the one or more substituents may also be independently selected from the group consisting of arylalkylenyl, and aminocarbonyl;

$R_A$ and $R_B$ are each independently selected from the group consisting of:
hydrogen,
halogen,
alkyl,
alkenyl,
alkoxy,
alkylthio, and
—N($R_9$)$_2$;

or when taken together, $R_A$ and $R_B$ form a fused aryl ring or heteroaryl ring containing one heteroatom selected from the group consisting of N and S, wherein the fused aryl or heteroaryl ring is unsubstituted or substituted by one or more R' groups;

or when taken together, $R_A$ and $R_B$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—N($R_9$)$_2$;

R' is a non-interfering substituent;

$R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

Y is selected from the group consisting of:
a bond,
—S(O)$_2$—,
—S(O)$_2$—N($R_8$)—,
—C($R_6$)—,
—C($R_6$)—N($R_8$)—,
—C($R_6$)—N($R_8$)—C($R_6$)—,
—C($R_6$)—N($R_8$)—S(O)$_2$—, and
—C($R_6$)—O—;

$R_6$ is selected from the group consisting of =O and =S;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl; and $R_9$ is selected from the group consisting of hydrogen and alkyl;

or a pharmaceutically acceptable salt thereof.

In another embodiment of Formula I, $X_1$ is selected from the group consisting of a bond, alkylene, and alkenylene, wherein the alkylene and alkenylene are optionally interrupted by one or more —O— groups; and $R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino.

In one preferred embodiment, the present invention provides a compound of Formula II:

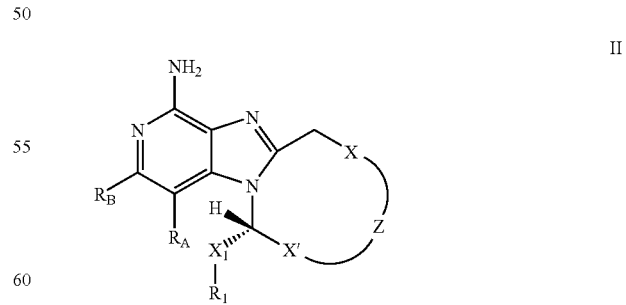

wherein:

X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X' is a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X and X' are further characterized in that the sum of the ring carbon atoms contributed by X and X' is 1, 2, or 3;

Z is selected from the group consisting of —O— and —N(—Y—$R_2$)—;

$X_1$ is selected from the group consisting of a bond, alkylene, alkenylene, and alkynylene wherein the alkylene and alkenylene are optionally interrupted by one or more —O— groups, and are optionally substituted by a hydroxy or methoxy group;

$R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_1$ is heterocyclyl, then the one or more substituents may also be independently selected from the group consisting of arylalkylenyl, and aminocarbonyl;

$R_A$ and $R_B$ are each independently selected from the group consisting of:
  hydrogen,
  halogen,
  alkyl,
  alkenyl,
  alkoxy,
  alkylthio, and
  —N($R_9$)$_2$;
or when taken together, $R_A$ and $R_B$ form a fused aryl ring or heteroaryl ring containing one heteroatom selected from the group consisting of N and S, wherein the fused aryl or heteroaryl ring is unsubstituted or substituted by one or more R' groups;

or when taken together, $R_A$ and $R_B$ form a fused 5 to 7 membered saturated ring, optionally containing one heteroatom selected from the group consisting of N and S, and unsubstituted or substituted by one or more R groups;

R is selected from the group consisting of:
  halogen,
  hydroxy,
  alkyl,
  alkenyl,
  haloalkyl,
  alkoxy,
  alkylthio, and
  —N($R_9$)$_2$;

R' is a non-interfering substituent;

$R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

Y is selected from the group consisting of:
  a bond,
  —S(O)$_2$—,
  —S(O)$_2$—N($R_8$)—,
  —C($R_6$)—,
  —C($R_6$)—N($R_8$)—,
  —C($R_6$)—N($R_8$)—C($R_6$)—,
  —C($R_6$)—N($R_8$)—S(O)$_2$—, and
  —C($R_6$)—O—;

$R_6$ is selected from the group consisting of =O and =S;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl; and $R_9$ is selected from the group consisting of hydrogen and alkyl;

or a pharmaceutically acceptable salt thereof.

In another embodiment of Formula II, $X_1$ is selected from the group consisting of a bond, alkylene, and alkenylene, wherein the alkylene and alkenylene are optionally interrupted by one or more —O— groups; and $R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino.

In other embodiments, the present invention provides a compound of Formula II-1:

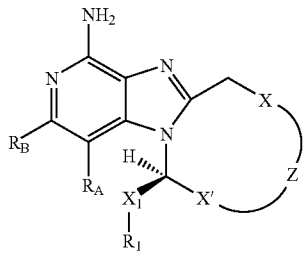

wherein X, X', Z, $R_1$, $X_1$, $R_A$, and $R_B$ are as defined in any one of the embodiments of Formula II above; or a pharmaceutically acceptable salt thereof.

In one preferred embodiment, there is provided a compound of Formula IIa:

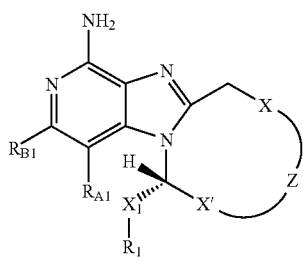

wherein:

X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X' is a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X and X' are further characterized in that the sum of the ring carbon atoms contributed by X and X' is 1, 2, or 3;

Z is selected from the group consisting of —O— and —N(—Y—$R_2$)—;

$X_1$ is selected from the group consisting of a bond, alkylene, alkenylene, and alkynylene wherein the alkylene and alkenylene are optionally interrupted by one or more —O— groups, and are optionally substituted by a hydroxy or methoxy group;

$R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_1$ is heterocyclyl, then the one or more substituents may also be independently selected from the group consisting of arylalkylenyl, and aminocarbonyl;

$R_{A1}$ and $R_{B1}$ are each independently selected from the group consisting of:
hydrogen,
halogen,
alkyl,
alkenyl,
alkoxy,
alkylthio, and
—N($R_9$)$_2$;

or when taken together, $R_{A1}$ and $R_{B1}$ form a fused aryl ring or heteroaryl ring containing one heteroatom selected from the group consisting of N and S, wherein the aryl or heteroaryl ring is unsubstituted or substituted by one or more R groups, or substituted by one $R_3$ group, or substituted by one $R_3$ group and one R group;

or when taken together, $R_{A1}$ and $R_{B1}$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—N($R_9$)$_2$;

$R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

Y is selected from the group consisting of:
a bond,
—S(O)$_2$—,
—S(O)$_2$—N($R_8$)—,
—C($R_6$)—,
—C($R_6$)—N($R_8$)—,
—C($R_6$)—N($R_8$)—C($R_6$)—,
—C($R_6$)—N($R_8$)—S(O)$_2$—, and
—C($R_6$)—O—;

$R_3$ is selected from the group consisting of:
—Y"—$R_4$,
—Z'—$R_4$,

—Z'—X"—Y—R$_4$,
—Z'—X"—Y'—X"—Y'—R$_4$, and
—Z'—X"—R$_5$;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y' is selected from the group consisting of:
—S(O)$_{0-2}$—,
—S(O)$_2$—N(R$_8$)—,
—C(R$_6$)—,
—C(R$_6$)—O—,
—O—C(R$_6$)—,
O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

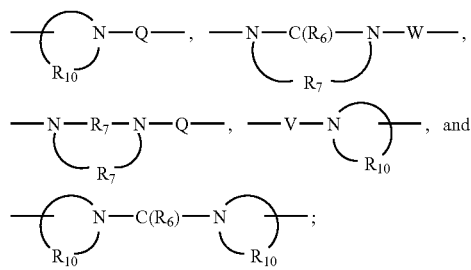

Y" is —O—C(R$_6$)—;
Z' is a bond or —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

R$_5$ is selected from the group consisting of

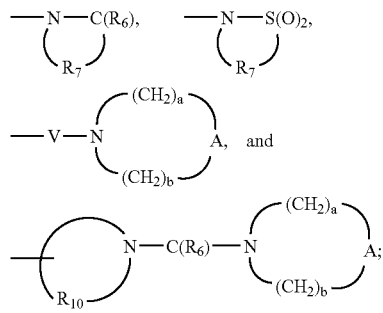

R$_6$ is selected from the group consisting of =O and =S;
R$_7$ is C$_{2-7}$ alkylene;
R$_8$ is selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;
R$_9$ is selected from the group consisting of hydrogen and alkyl;
R$_{10}$ is C$_{3-8}$ alkylene;

A is selected from the group consisting of —CH$_2$—, —O—, —C(O)—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$);

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

or a pharmaceutically acceptable salt thereof.

In another embodiment of Formula IIa, X$_1$ is selected from the group consisting of a bond, alkylene, and alkenylene, wherein the alkylene and alkenylene are optionally interrupted by one or more —O— groups;

R$_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when R$_1$ is aryl, arylalkylenyl, heteroaryl, or heteroarylalkylenyl, then the one or more substituents may also be independently selected from the group consisting of alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and R$_3$ is selected from the group consisting of:
—Z'—R$_4$,
—Z'—X"—Y'—X"—Y'—R$_4$, and
—Z'—X"—R$_5$.

In other embodiments, there is provided a compound of Formula II-1a:

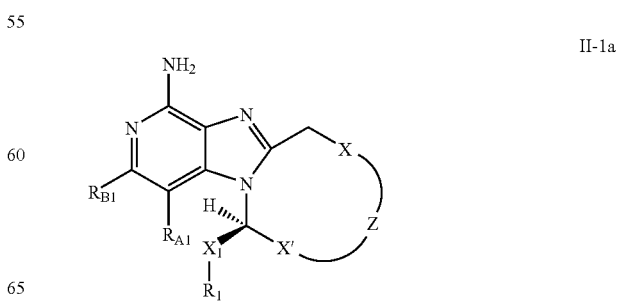

II-1a wherein X, X', Z, R$_1$, X$_1$, R$_{A1}$, and R$_{B1}$ are as defined in any one of the embodiments of Formula IIa above; or a pharmaceutically acceptable salt thereof.

In one preferred embodiment, there is provided a compound of Formula III:

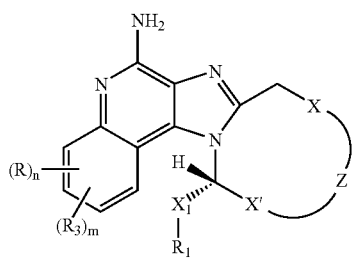

wherein:

X is a bond or a straight or branched chain C$_{1-8}$ alkylene optionally having a substituent at a carbon atom other than a carbon atom adjacent to a heteroatom, wherein the substituent is hydroxy, alkoxy, or one or more halogen atoms;

X' is a straight or branched chain C$_{1-8}$ alkylene optionally having a substituent at a carbon atom other than a carbon atom adjacent to a heteroatom, wherein the substituent is hydroxy, alkoxy, or one or more halogen atoms;

X and X' are further characterized in that the sum of the ring carbon atoms contributed by X and X' is 1, 2, or 3;

Z is selected from the group consisting of —O— and —N(—Y—R$_2$)—;

X$_1$ is selected from the group consisting of a bond, alkylene, alkenylene, and alkynylene wherein the alkylene and alkenylene are optionally interrupted by one or more —O— groups, and are optionally substituted by a hydroxy or methoxy group;

R$_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when R$_1$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when R$_1$ is heterocyclyl, then the one or more substituents may also be independently selected from the group consisting of arylalkylenyl, and aminocarbonyl;

R is selected from the group consisting of:
halogen,
hydroxy,
alkyl,
alkenyl,
haloalkyl,
alkoxy,
alkylthio, and
—N(R$_9$)$_2$;

n is an integer from 0 to 4;

R$_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

Y is selected from the group consisting of:
a bond,
—S(O)$_2$—,
—S(O)$_2$—N(R$_8$)—,
—C(R$_6$)—,
—C(R$_6$)—N(R$_8$)—,
—C(R$_6$)—N(R$_8$)—C(R$_6$)—,
—C(R$_6$)—N(R$_8$)—S(O)$_2$—, and
—C(R$_6$)—O—;

R$_3$ is selected from the group consisting of:
—Y"—R$_4$,
—Z'—R$_4$,
—Z'—X"—R$_4$,
—Z'—X"—Y'—X"—Y'—R$_4$, and
—Z'—X"—R$_5$;

m is 0 or 1; with the proviso that when m is 1, then n is 0 or 1;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y' is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

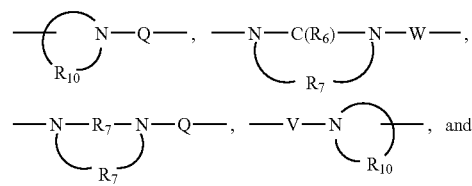

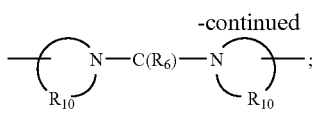

Y" is —O—C($R_6$)—;

Z' is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of

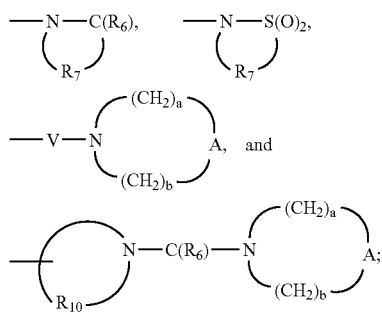

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

A is selected from the group consisting of —CH$_2$—, —O—, —C(O)—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$);

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7; or a pharmaceutically acceptable salt thereof.

In another embodiment of Formula III, $X_1$ is selected from the group consisting of a bond, alkylene, and alkenylene, wherein the alkylene and alkenylene are optionally interrupted by one or more —O— groups;

$R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and $R_3$ is selected from the group consisting of:
—Z'—R$_4$,
—Z'—X"—R$_4$,
—Z'—X"—Y'—R$_4$,
—Z'—X"—Y'—X"—Y'—R$_4$, and
—Z'—X"—R$_5$.

In other embodiments, there is provided a compound of Formula III-1:

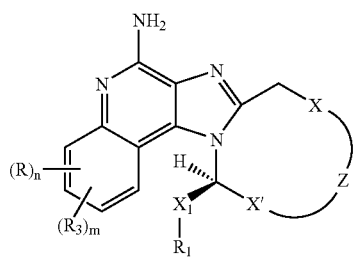

wherein X, X', Z, $R_1$, $X_1$, R, $R_3$, m, and n are as defined in any one of the embodiments Formula III above; or a pharmaceutically acceptable salt thereof.

In one preferred embodiment, there is provided a compound of Formula IV:

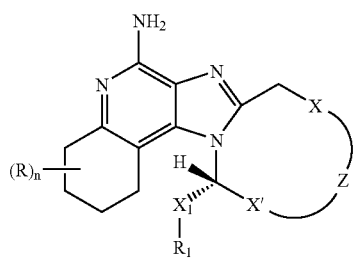

wherein:

X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X' is a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X and X' are further characterized in that the sum of the ring carbon atoms contributed by X and X' is 1, 2, or 3;

Z is selected from the group consisting of —O— and —N(—Y—$R_2$)—;

$X_1$ is selected from the group consisting of a bond, alkylene, alkenylene, and alkynylene wherein the alkylene and alkenylene are optionally interrupted by one or more —O— groups, and are optionally substituted by a hydroxy or methoxy group;

$R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_1$ is heterocyclyl, then the one or more substituents may also be independently selected from the group consisting of arylalkylenyl, and aminocarbonyl;

R is selected from the group consisting of:
halogen,
hydroxy,
alkyl,
alkenyl,
haloalkyl,
alkoxy,
alkylthio, and
—N($R_9$)$_2$;

n is an integer from 0 to 4;

$R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

Y is selected from the group consisting of:
a bond,
—S(O)$_2$—,
—S(O)$_2$—N($R_8$)—,
—C($R_6$)—,
—C($R_6$)—N($R_8$)—,
—C($R_6$)—N($R_8$)—C($R_6$)—,
—C($R_6$)—N($R_8$)—S(O)$_2$—, and
—C($R_6$)—O—;

$R_6$ is selected from the group consisting of =O and =S;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl; and $R_9$ is selected from the group consisting of hydrogen and alkyl; or a pharmaceutically acceptable salt thereof.

In another embodiment of Formula IV, $X_1$ is selected from the group consisting of a bond, alkylene, and alkenylene, wherein the alkylene and alkenylene are optionally interrupted by one or more —O— groups; and $R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino.

In other embodiments, there is provided a compound of Formula IV-1:

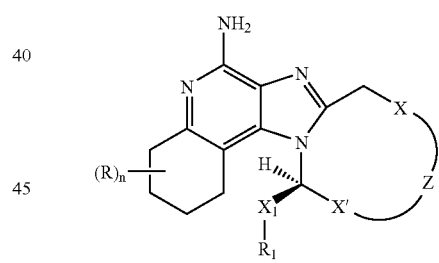

IV-1 wherein X, X', Z, $R_1$, $X_1$, R, and n are as defined in any one of the embodiments of Formula IV above; or a pharmaceutically acceptable salt thereof.

In one preferred embodiment, there is provided a compound of Formula V:

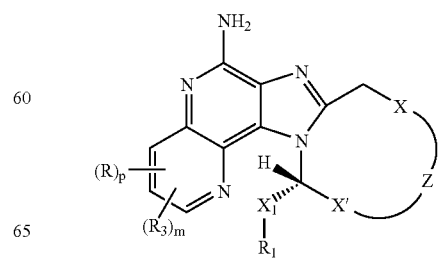

V wherein:

X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X' is a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X and X' are further characterized in that the sum of the ring carbon atoms contributed by X and X' is 1, 2, or 3;

Z is selected from the group consisting of —O— and —N(—Y—$R_2$)—;

$X_1$ is selected from the group consisting of a bond, alkylene, alkenylene, and alkynylene wherein the alkylene and alkenylene are optionally interrupted by one or more —O— groups, and are optionally substituted by a hydroxy or methoxy group;

$R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_1$ is heterocyclyl, then the one or more substituents may also be independently selected from the group consisting of arylalkylenyl, and aminocarbonyl;

R is selected from the group consisting of:
halogen,
hydroxy,
alkyl,
alkenyl,
haloalkyl,
alkoxy,
alkylthio, and
—N($R_9$)$_2$;

p is an integer from 0 to 3;

$R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

Y is selected from the group consisting of:
a bond,
—S(O)$_2$—,
—S(O)$_2$—N($R_8$)—,
—C($R_6$)—,
—C($R_6$)—N($R_8$)—,
—C($R_6$)—N($R_8$)—C($R_6$)—,
—C($R_6$)—N($R_8$)—S(O)$_2$—, and
—C($R_6$)—O—;

$R_3$ is selected from the group consisting of:
—Y"—$R_4$,
—Z'—$R_4$,
—Z'—X"—$R_4$,
—Z'—X"—Y'—X"—Y'—$R_4$, and
—Z'—X"—Y'—X"—Y—$R_4$, and
—Z'—X"—$R_5$;

m is 0 or 1; with the proviso that when m is 1, then p is 0 or 1;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y' is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

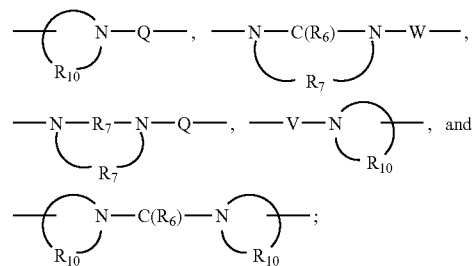

Y" is —O—C($R_6$)—;
Z' is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy;

heterocyclyl; amino; alkylamino; dialkylamino; (dialkylamino)alkyleneoxy; and, in the case of alkyl, alkenyl, alkynyl, and heterocyclyl, oxo;

R$_5$ is selected from the group consisting of

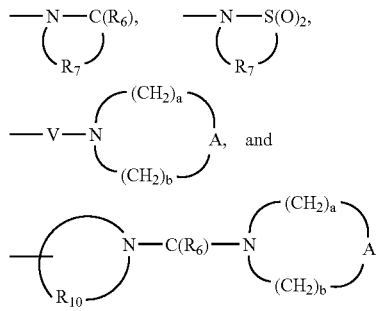

R$_6$ is selected from the group consisting of =O and =S;
R$_7$ is C$_{2-7}$ alkylene;
R$_8$ is selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;
R$_9$ is selected from the group consisting of hydrogen and alkyl;
R$_{10}$ is C$_{3-8}$ alkylene;
A is selected from the group consisting of —CH$_2$—, —O—, —C(O)—, —S(O)$_{0-2}$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$);
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7; or a pharmaceutically acceptable salt thereof.

In another embodiment of Formula V, X$_1$ is selected from the group consisting of a bond, alkylene, and alkenylene, wherein the alkylene and alkenylene are optionally interrupted by one or more —O— groups;

R$_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when R$_1$ is aryl, arylalkylenyl, heteroaryl, or heteroarylalkylenyl, then the one or more substituents may also be independently selected from the group consisting of alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and R$_3$ is selected from the group consisting of:
—Z'—R$_4$,
—Z'—X"—R$_4$,
—Z'—X"—Y'—R$_4$,
—Z'—X"—Y'—X"—Y—R$_4$, and
—Z'—X"—R$_5$.

In other embodiments, there is provided a compound of Formula V-1:

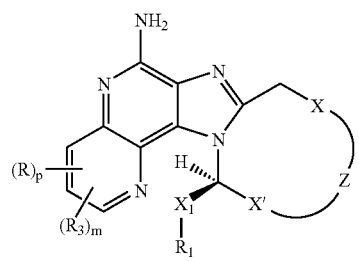

wherein X, X', Z, R$_1$, X$_1$, R, R$_3$, m, and p are as defined in any one of the embodiments of Formula V above; or a pharmaceutically acceptable salt thereof.

In one preferred embodiment, there is provided a compound of Formula VI:

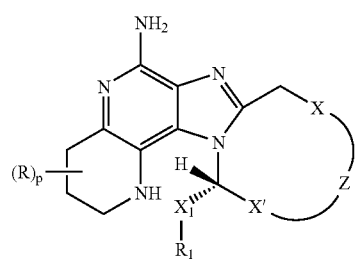

wherein:
X is a bond or a straight or branched chain C$_{1-8}$ alkylene optionally having a substituent at a carbon atom other than a carbon atom adjacent to a heteroatom, wherein the substituent is hydroxy, alkoxy, or one or more halogen atoms;
X' is a straight or branched chain C$_{1-8}$ alkylene optionally having a substituent at a carbon atom other than a carbon atom adjacent to a heteroatom, wherein the substituent is hydroxy, alkoxy, or one or more halogen atoms;
X and X' are further characterized in that the sum of the ring carbon atoms contributed by X and X' is 1, 2, or 3;
Z is selected from the group consisting of —O— and —N(—Y—R$_2$)—;
X$_1$ is selected from the group consisting of a bond, alkylene, alkenylene, and alkynylene wherein the alkylene and alkenylene are optionally interrupted by one or more —O— groups, and are optionally substituted by a hydroxy or methoxy group;
R$_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_1$ is heterocyclyl, then the one or more substituents may also be independently selected from the group consisting of arylalkylenyl, and aminocarbonyl;

R is selected from the group consisting of:
halogen,
hydroxy,
alkyl,
alkenyl,
haloalkyl,
alkoxy,
alkylthio, and
—N($R_9$)$_2$;

p is an integer from 0 to 3;

$R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

Y is selected from the group consisting of:
a bond,
—S(O)$_2$—,
—S(O)$_2$—N($R_8$)—,
—C($R_6$)—,
—C($R_6$)—N($R_8$)—,
—C($R_6$)—N($R_8$)—C($R_6$)—,
—C($R_6$)—N($R_8$)—S(O)$_2$—, and
—C($R_6$)—O—;

$R_6$ is selected from the group consisting of =O and =S;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl; and $R_9$ is selected from the group consisting of hydrogen and alkyl;

or a pharmaceutically acceptable salt thereof.

In another embodiment of Formula VI, $X_1$ is selected from the group consisting of a bond, alkylene, and alkenylene, wherein the alkylene and alkenylene are optionally interrupted by one or more —O— groups; and $R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino.

In other embodiments, there is provided a compound of Formula VI-1:

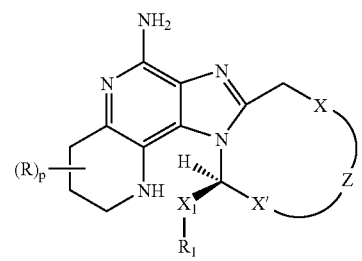

VI-1 wherein X, X', Z, $R_1$, $X_1$, R, and p are as defined in any one of the embodiments of Formula VI above; or a pharmaceutically acceptable salt thereof.

In one preferred embodiment, there is provided a compound of Formula VII:

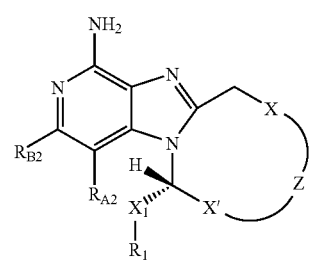

VII wherein:

X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X is a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X and X' are further characterized in that the sum of the ring carbon atoms contributed by X and X' is 1, 2, or 3;

Z is selected from the group consisting of —O— and —N(—Y—$R_2$)—;

$X_1$ is selected from the group consisting of a bond, alkylene, alkenylene, and alkynylene wherein the alkylene and alkenylene are optionally interrupted by one or more —O— groups, and are optionally substituted by a hydroxy or methoxy group;

$R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_1$ is heterocyclyl, then the one or more substituents may also be independently selected from the group consisting of arylalkylenyl, and aminocarbonyl;

$R_{A2}$ and $R_{B2}$ are each independently selected from the group consisting of:
hydrogen,
halogen,
alkyl,
alkenyl,
alkoxy,
alkylthio, and
—$N(R_9)_2$;

$R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

Y is selected from the group consisting of:
a bond,
—$S(O)_2$—,
—$S(O)_2$—$N(R_8)$—,
—$C(R_6)$—,
—$C(R_6)$—$N(R_8)$—,
—$C(R_6)$—$N(R_8)$—$C(R_6)$—,
—$C(R_6)$—$N(R_8)$—$S(O)_2$—, and
—$C(R_6)$—O—;

$R_6$ is selected from the group consisting of =O and =S;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl; and $R_9$ is selected from the group consisting of hydrogen and alkyl;

or a pharmaceutically acceptable salt thereof.

In another embodiment of Formula VII, $X_1$ is selected from the group consisting of a bond, alkylene, and alkenylene, wherein the alkylene and alkenylene are optionally interrupted by one or more —O— groups; and $R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino.

In other embodiments, there is provided a compound of Formula VII-1:

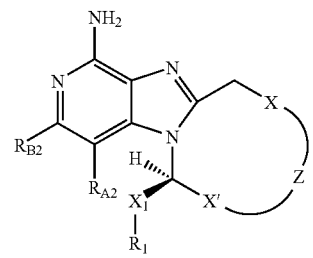

VII-1 wherein X, X', Z, $R_1$, $X_1$, $R_{A2}$, and $R_{B2}$ are as defined in any one of the embodiments of Formula VII above; or a pharmaceutically acceptable salt thereof.

For certain embodiments, the present invention provides a compound (which is a prodrug) of the Formula VIII:

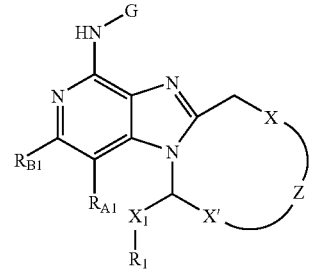

VIII wherein:

G is selected from the group consisting of:

—C(O)—R″,

α-aminoacyl,

α-aminoacyl-α-aminoacyl,

—C(O)—O—R″,

—C(O)—N(R‴)R″,

—C(=NY$_2$)—R″,

—CH(OH)—C(O)—OY$_2$,

—CH(OC$_{1-4}$ alkyl)Y$_0$,

—CH$_2$Y$_1$, and

—CH(CH$_3$)Y$_1$;

R′ and R‴ are independently selected from the group consisting of C$_{1-10}$ alkyl, C$_{3-7}$ cycloalkyl, and benzyl, each of which may be unsubstituted or substituted by one or more substitutents selected from the group consisting of halogen, hydroxy, nitro, cyano, carboxy, C$_{1-6}$ alkyl, C$_{1-4}$ alkoxy, aryl, heteroaryl, arylC$_{1-4}$ alkylenyl, heteroarylC$_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R‴ can also be hydrogen;

α-aminoacyl is an acyl group derived from an amino acid selected from the group consisting of racemic, D-, and L-amino acids;

Y$_2$ is selected from the group consisting of hydrogen, C$_{1-6}$ alkyl, and benzyl;

Y$_0$ is selected from the group consisting of C$_{1-6}$ alkyl, carboxyC$_{1-6}$ alkylenyl, aminoC$_{1-4}$ alkylenyl, mono-N—C$_{1-6}$ alkylaminoC$_{1-4}$ alkylenyl, and di-N,N—C$_{1-6}$ alkylaminoC$_{1-4}$ alkylenyl;

Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl; and X, X′, Z, R$_1$, X$_1$, R$_{A1}$, and R$_{B1}$ are as defined in any one of the embodiments of Formula IIa above;

or a pharmaceutically acceptable salt thereof.

For certain embodiments, there is provided a compound (which is a prodrug) of the Formula IX:

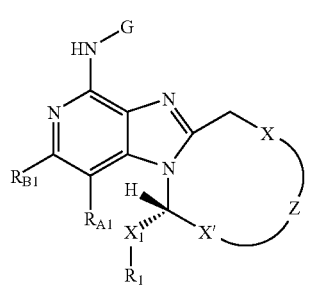

IX wherein G, X, X′, Z, R$_1$, X$_1$, R$_{A1}$, and R$_{B1}$ are as defined in any one of the embodiments Formula VIII above;

or a pharmaceutically acceptable salt thereof.

For certain embodiments, there is provided a compound (which is a prodrug) of the Formula IX-1:

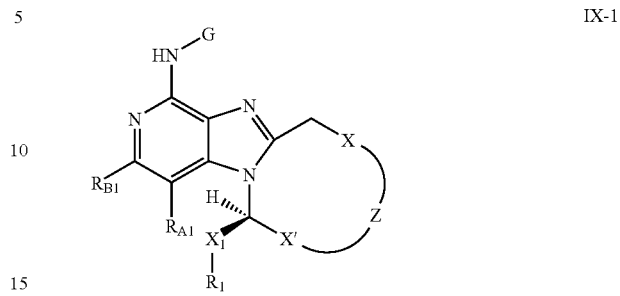

IX-1 wherein G, X, X′, Z, R$_1$, X$_1$, R$_{A1}$, and R$_{B1}$ are as defined in any one of the embodiments of Formula VIII above;

or a pharmaceutically acceptable salt thereof.

In one embodiment, there is provided an intermediate compound of the following Formula X:

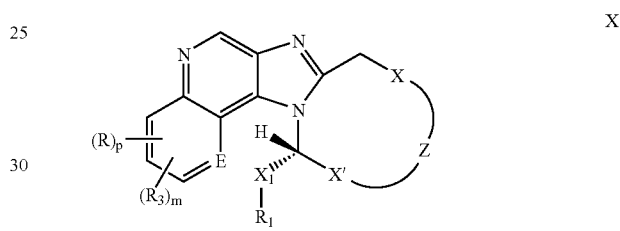

X wherein:

E is selected from the group consisting of CH, CR, CR$_3$, and N, with the proviso that when E is CR$_3$, m is 0, and p is 0 or 1, and with the further proviso that when E is CR and m is 1, p is 0;

X is a bond or a straight or branched chain C$_{1-8}$ alkylene optionally having a substituent at a carbon atom other than a carbon atom adjacent to a heteroatom, wherein the substituent is hydroxy, alkoxy, or one or more halogen atoms;

X′ is a straight or branched chain C$_{1-8}$ alkylene optionally having a substituent at a carbon atom other than a carbon atom adjacent to a heteroatom, wherein the substituent is hydroxy, alkoxy, or one or more halogen atoms;

X and X′ are further characterized in that the sum of the ring carbon atoms contributed by X and X′ is 1, 2, or 3;

Z is selected from the group consisting of —O— and —N(—Y—R$_2$)—;

X$_1$ is selected from the group consisting of a bond, alkylene, alkenylene, and alkynylene wherein the alkylene and alkenylene are optionally interrupted by one or more —O— groups, and are optionally substituted by a hydroxy or methoxy group;

R$_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl;

heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_1$ is heterocyclyl, then the one or more substituents may also be independently selected from the group consisting of arylalkylenyl, and aminocarbonyl;

R is selected from the group consisting of:
halogen,
hydroxy,
alkyl,
alkenyl,
haloalkyl,
alkoxy,
alkylthio, and
—N($R_9$)$_2$;

p is an integer from 0 to 3;

$R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

Y is selected from the group consisting of:
a bond,
—S(O)$_2$—,
—S(O)$_2$—N($R_8$)—,
—C($R_6$)—,
—C($R_6$)—N($R_8$)—,
—C($R_6$)—N($R_8$)—C($R_6$)—,
—C($R_6$)—N($R_8$)—S(O)$_2$—, and
—C($R_6$)—O—;

$R_3$ is selected from the group consisting of:
—Y"—$R_4$,
—Z'—$R_4$,
—Z'—X"—$R_4$,
—Z'—X"—Y'—$R_4$,
—Z'—X"—Y'—X"—Y'—$R_4$, and
—Z'—X"—$R_5$;

m is 0 or 1; with the proviso that when m is 1, then p is 0 or 1;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y' is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

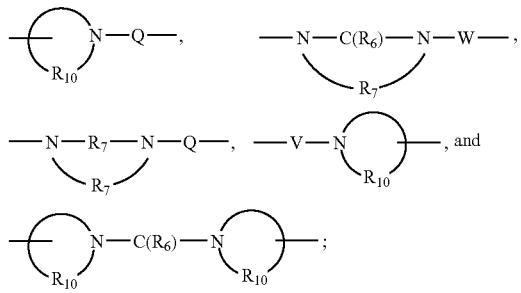

Y" is —O—C($R_6$)—;

Z' is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of

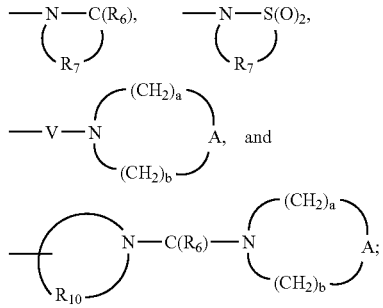

$R_6$ is selected from the group consisting of =O and =S;

$R_7$ is $C_{2-7}$ alkylene;

$R_8$ is selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

$R_9$ is selected from the group consisting of hydrogen and alkyl;

$R_{10}$ is $C_{3-8}$ alkylene;

A is selected from the group consisting of —CH$_2$—, —O—, —C(O)—, —S(O)$_{0-2}$—, and —N($R_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$);

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

or a pharmaceutically acceptable salt thereof.

In another embodiment of Formula X, X$_1$ is selected from the group consisting of a bond, alkylene, and alkenylene, wherein the alkylene and alkenylene are optionally interrupted by one or more —O— groups;

R$_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when R$_1$ is aryl, arylalkylenyl, heteroaryl, or heteroarylalkylenyl, then the one or more substituents may also be independently selected from the group consisting of alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and R$_3$ is selected from the group consisting of:
—Z'—R$_4$,
—Z'—X"—R$_4$,
—Z'—X"—Y'—R$_4$,
—Z'—X"—Y'—X"—Y'—R$_4$, and
—Z'—X"—R$_5$.

In other embodiments, intermediate compounds of Formula X-1:

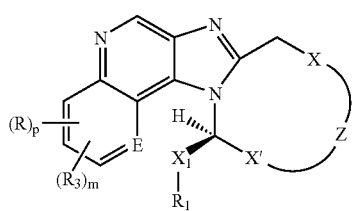

are provided wherein X, X', Z, R$_1$, X$_1$, E, R, R$_3$, m, and p are as defined in any one of the embodiments of Formula X above;

or a pharmaceutically acceptable salt thereof.

Herein, "non-interfering" means that the ability of the compound or salt, which includes a non-interfering substituent, to modulate the biosynthesis of one or more cytokines is not destroyed by the non-interfering substituent. For certain embodiments, R' is a non-interfering substituent. Illustrative non-interfering R' groups include those described above for R and R$_3$.

As used herein, the terms "alkyl," "alkenyl," "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. The terms, "alkylenyl," "alkenylenyl," and "alkynylenyl" are used when "alkylene," "alkenylene," and "alkynylene," respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. In some embodiments, the term "heteroaryl" includes one ring that contains 2-5 carbon atoms, 1-3 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. In some embodiments, the term "heterocyclyl" includes one or two rings that contain 2-9 carbon atoms, 1-3 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene," "heteroarylene," and "heterocyclylene" are the divalent forms of the "aryl," "heteroaryl," and "heterocyclyl" groups defined above. The terms, "arylenyl," "heteroarylenyl," and "heterocyclylenyl" are used when "arylene," "heteroarylene," and "heterocyclylene," respectively, are substituted. For example, an alkylarylenyl group comprises an arylene moiety to which an alkyl group is attached.

The term "fused aryl ring" includes fused carbocyclic aromatic rings or ring systems. Examples of fused aryl rings include benzo, naphtho, fluoreno, and indeno.

The term "fused heteroaryl ring" includes the fused forms of 5 or 6 membered aromatic rings that contain one heteroatom selected from S and N. Examples of fused heteroaryl rings include pyrido and thieno.

The term "fused 5 to 7 membered saturated ring" includes rings which are fully saturated except for the bond where the ring is fused. In one example, the ring is a cyclohexene ring. In other examples wherein one heteroatom (N or S) is present, the ring is tetrahydropyrido or dihydrothieno.

When a group (or substituent or variable) is present more than once in any Formula described herein, each group (or substituent or variable) is independently selected, whether explicitly stated or not. For example, for the formula $-N(R_9)_2$ each $R_9$ group is independently selected. In another example, when a Y and a Y' group are both present and both contain an $R_8$ group, each $R_8$ group is independently selected. In a further example, when more than one Y' group is present (i.e., $R_3$ contains two Y' groups) and each Y' group contains one or more $R_7$ groups, then each Y' group is independently selected, and each $R_7$ group is independently selected.

The invention is inclusive of the compounds described herein (including intermediates) in any of their pharmaceutically acceptable forms, including isomers (e.g., diastereomers and enantiomers), salts, solvates, polymorphs, prodrugs, and the like. In particular, the invention specifically includes mixtures of the compound with its enantiomer in any ratio as well as the racemic mixture. Ratios of the compound to its enantiomer include, for example, 50:50 or higher, 90:10 or higher, 95:5 or higher, 99:1 or higher, 99.9:0.1 or higher, or 100:0. It should be understood that the term "compound" includes any or all of such forms, whether explicitly stated or not (although at times, "salts" are explicitly stated).

The term "prodrug" means a compound that can be transformed in vivo to yield an immune response modifying compound in any of the salt, solvated, polymorphic, or isomeric forms described above. The prodrug, itself, may be an immune response modifying compound in any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For any of the compounds presented herein, each one of the following variables (e.g., X, X', $X_1$, Z, R, $R_1$, $R_3$, $R_4$, $R_B$, $R_{A1}$, $R_{B1}$, $R_{A2}$, $R_{B2}$, E, m, n, and p and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments, R is selected from the group consisting of halogen, hydroxy, alkyl, alkenyl, haloalkyl, alkoxy, alkylthio, and $-N(R_9)_2$.

For certain embodiments, R is halogen or hydroxy.

For certain embodiments, R is $-N(R_9)_2$.

For certain embodiments, R is (cyclopropylmethyl)amino.

For certain embodiments, $R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino. For certain of these embodiments, when $R_1$ is aryl, arylalkylenyl, heteroaryl, or heteroarylalkylenyl, then the one or more substituents may further be independently selected from the group consisting of arylalkylenyl, alkylarylenyl, alkoxyarylenyl, and haloarylenyl; and when $R_1$ is heterocyclyl, then the one or more substituents may further be independently selected from the group consisting of arylalkylenyl, and aminocarbonyl.

For certain embodiments, $R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo.

For certain embodiments, $R_1$ is selected from the group consisting of alkyl, aryl, arylalkylenyl, heteroaryl, and heteroarylalkylenyl, each of which is unsubstituted or substituted by one or more substituents selected from the group consisting of halogen, hydroxy, and alkoxy.

For certain embodiments, $R_1$ is selected from the group consisting of alkyl, aryl, arylalkylenyl, heteroaryl, and heteroarylalkylenyl, wherein alkyl is unsubstituted or substituted by one or more substituents selected from the group consisting of halogen and hydroxy.

For certain embodiments, $R_1$ is $C_{1-3}$ alkyl optionally substituted by hydroxy or one or more fluorine atoms.

For certain embodiments, $R_1$ is selected from the group consisting of alkyl, alkenyl, alkynyl, aryl, heteroaryl, and heterocyclyl, each of which is unsubstituted or substituted by one or more substituents independently selected from the group consisting of alkyl, alkoxy, hydroxyalkyl, haloalkyl, halogen, hydroxy, aryl, heteroaryl, and heterocyclyl; and wherein when $R_1$ is heteroaryl, then the one or more substituents may also be independently selected from the group consisting of haloarylenyl, alkoxyarylenyl, alkylarylenyl, and arylalkylenyl; and wherein when $R_1$ is heterocyclyl, then the one or more substituents may also be independently selected from the group consisting of arylalkylenyl and aminocarbonyl.

For certain embodiments, $R_1$ is heterocyclyl which is selected from the group consisting of morpholinyl, thiomorpholinyl, piperidinyl, pyrrolidinyl, thiazolidinyl, dihydroisoquinolin-(1H)-yl, octahydroisoquinolin-(1H)-yl, 1,3-dioxolanyl, oxetanyl, tetrahydrofuranyl, tetrahydropyranyl, each of which is unsubstituted or substituted by one or more substituents independently selected from the group consisting of $C_{1-4}$ alkyl, hydroxy$C_{1-4}$ alkyl, hydroxy, aminocarbonyl, aryl$C_{1-4}$ alkylenyl, and 5 to 7 membered heterocyclyl containing one or two heteroatoms.

For certain embodiments, $R_1$ is tetrahydro-2H-pyran-4-yl or 2,2,-dimethyl-1,3-dioxolanyl.

For certain embodiments, $R_1$ is heteroaryl which is selected from the group consisting of pyridyl, pyrazolyl, oxazolyl, and triazolyl, each of which is unsubstituted or substituted by one or more substituents independently selected from the group consisting of $C_{1-4}$ alkyl, hydroxy$C_{1-4}$ alkyl, halo$C_{1-4}$ alkyl, aryl, aryl substituted by fluoro, chloro, methyl, or methoxy, aryl$C_{1-4}$ alkylenyl, and heteroaryl.

For certain embodiments, $R_1$ is pyrazolyl, oxazolyl, or triazolyl; wherein triazolyl is unsubstituted or substituted by methyl, ethyl, propyl, butyl, hydroxymethyl, hydroxyethyl, phenyl, 2-methylphenyl, 3-methylphenyl, 4-methylphenyl, 2-fluorophenyl, 3-fluorophenyl, 4-fluorophenyl, 2-methoxyphenyl, 3-methoxyphenyl, 4-methoxyphenyl, 2-chlorophenyl, 3-chlorophenyl, 4-chlorophenyl, pyridin-2-yl, or pyridin-3-yl; and wherein pyrazolyl and oxazolyl are each unsubstituted or substituted by methyl, ethyl, n-butyl, 2-methylpropyl, trifluoromethyl, phenyl, or benzyl.

For certain embodiments, $R_1$ is selected from the group consisting of $C_{1-4}$ alkyl, $C_{1-4}$ alkenyl, and $C_{1-4}$ alkynyl, each of which is unsubstituted or substituted by one or more substituents independently selected from the group consisting of hydroxy, halogen, and aryl.

For certain embodiments, $R_1$ is methyl or isopropyl.

For certain embodiments, $R_1$ is 1-fluoro-1-methylethyl.

For certain embodiments, $R_1$ is 1-hydroxy-1-methylethyl.

For certain embodiments, $R_1$ is 1-hydroxyethyl.

For certain embodiments, $R_1$ is phenyl, benzyl, pyridinyl, or pyridinylmethyl, each of which is unsubstituted or substituted by one or more substituents selected from the group consisting of halogen, hydroxy, and alkoxy.

For certain embodiments, $R_1$ is phenyl, benzyl, pyridinyl, or pyridinylmethyl, each of which is unsubstituted or substituted by one or more substituents selected from the group consisting of fluoro, chloro, and hydroxy.

For certain embodiments, $R_1$ is phenyl, benzyl, pyridinyl, or pyridinylmethyl.

For certain embodiments, $R_1$ is benzyl.

For certain embodiments, $R_1$ is aryl which is unsubstituted or substituted by one or more substituents independently selected from the group consisting of halogen, hydroxy, $C_{1-4}$ alkoxy, $C_{1-4}$ alkyl, and hydroxy$C_{1-4}$ alkyl.

For certain embodiments, $R_1$ is phenyl.

For certain embodiments, $R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy.

For certain embodiments, $R_2$ is alkyl.

For certain embodiments, $R_2$ is methyl.

For certain embodiments, $R_3$ is selected from the group consisting of —Y"—$R_4$, —Z'—$R_4$, —Z'—X"—$R_4$, —Z'—X"—Y'—$R_4$, —Z'—X"—Y'—X"—Y'—$R_4$, and —Z'—X"—$R_5$.

For certain embodiments, $R_3$ is selected from the group consisting of —Z'—$R_4$, —Z'—X"—$R_4$, —Z'—X"—Y'—$R_4$, —Z'—X"—Y'—X"—Y'—$R_4$, and —Z'—X"—$R_5$.

For certain embodiments, $R_3$ is selected from the group consisting of benzyloxy which is unsubstituted or substituted by halogen or haloalkyl, 3-pyrrolylpropoxy, 2-(4-methoxyphenyl)-2-oxoethoxy, aryl, and heteroaryl, wherein aryl and heteroaryl are unsubstituted or substituted by one or more substituents independently selected from the group consisting of alkyl, hydroxy, hydroxyalkyl, alkoxy, halogen, dialkylamino, alkylcarbonylamino, alkylaminocarbonyl, dialkylaminocarbonyl, and heterocyclylcarbonyl. In certain of these embodiments, heterocyclylcarbonyl is pyrrolidinylcarbonyl or morpholinylcarbonyl.

For certain embodiments, $R_3$ is phenyl substituted by pyrrolidinylcarbonyl or morpholinylcarbonyl.

For certain embodiments, $R_3$ is benzyloxy.

For certain embodiments, $R_3$ is —Z'—$R_4$, and $R_4$ is selected from the group consisting of alkyl, alkenyl, alkynyl, aryl, heteroaryl, and heterocyclyl; wherein alkyl and alkenyl are unsubstituted or substituted by one or more substituents independently selected from the group consisting of hydroxy, alkoxy, cyano, and aryl; wherein aryl and heteroaryl are unsubstituted or substituted by one or more substituents independently selected from the group consisting of alkyl, alkoxy, hydroxyalkyl, halogen, cyano, and dialkylamino; and wherein heterocyclyl is unsubstituted or substituted by one or more substituents independently selected from alkyl and oxo.

For certain embodiments, $R_3$ is —Z'—$R_4$, Z' is —O—, and $R_4$ is alkynyl.

For certain embodiments, $R_3$ is —Z'—$R_4$, Z' is a bond, and $R_4$ is heterocyclyl which is selected from the group consisting of pyrrolidinyl, piperidinyl, oxazolidinyl, morpholinyl, and thiomorpholinyl, each of which is unsubstituted or substituted by one or more substituents independently selected from alkyl and oxo.

For certain embodiments, $R_3$ is 2-oxopyrrolidin-1-yl, morpholin-1-yl, or 2-oxo-1,3-oxazolidin-3-yl.

For certain embodiments, $R_3$ is —Z'—X"—$R_4$.

For certain embodiments, $R_3$ is —Z'—X"—$R_4$, wherein X" is $C_{1-3}$ alkylene or $C_{1-3}$ alkenylene, and $R_4$ is heterocyclyl or heteroaryl wherein heterocyclyl is unsubstituted or substituted by one or more substituents independently selected from alkyl and oxo, and wherein heteroaryl is unsubstituted or substituted by one or more substituents independently selected from the group consisting of alkyl, alkoxy, halogen, cyano, and dialkylamino.

For certain embodiments, $R_3$ is —Z'—X"—$R_4$; wherein X" is $C_{1-3}$ alkylene or $C_{1-3}$ alkenylene, and $R_4$ is heterocyclyl which is selected from the group consisting of pyrrolidinyl, piperidinyl, morpholinyl, and thiomorpholinyl, each of which is unsubstituted or substituted by one or more substituents independently selected from alkyl and oxo.

For certain embodiments, $R_3$ is —Z'—X"—$R_4$; wherein X" is $C_{1-3}$ alkylene or $C_{1-3}$ alkenylene, and $R_4$ is heteroaryl which is selected from the group consisting of thiazolyl, imidazolyl, isoxazolyl, and pyridinyl each of which is unsubstituted or substituted by one or more substituents independently selected from the group consisting of alkyl, alkoxy, halogen, cyano, and dialkylamino.

For certain embodiments, $R_3$ is —Z'—X"—$R_4$; wherein X" is $C_{1-3}$ alkylene, and $R_4$ is pyridin-3-yl, 1-methyl-1H-imidazol-2-yl, or 1,3-thiazol-4-yl.

For certain embodiments, $R_3$ is —Z'—X"—Y'—$R_4$.

For certain embodiments, $R_3$ is —Z'—X"—Y'—$R_4$; wherein X" is selected from the group consisting of $C_{1-3}$ alkylene, $C_{1-3}$ alkenylene, piperidin-1,4-diyl, and phenylene; Y' is selected from the group consisting of —C($R_6$)—, —C($R_6$)—O—, —C($R_6$)—N($R_8$)—, —N($R_8$)-Q-, and —S(O)$_2$— wherein Q is selected from the group consisting of a bond, —C(O)—, —S(O)$_2$—, and C($R_6$)—N($R_8$)—; $R_6$ is selected from the group consisting of =O and =S; and $R_8$ is selected from the group consisting of hydrogen, $C_{1-4}$ alkyl, and $C_{1-4}$ alkoxy$C_{1-4}$ alkylenyl; and $R_4$ is selected from the group consisting of hydrogen, alkyl, aryl, heteroaryl, and heterocyclyl; wherein alkyl is unsubstituted or substituted by one or more substituents independently selected from the group consisting of hydroxy, alkoxy, and aryl; wherein aryl is unsubstituted or substituted by one or more substituents independently selected from the group consisting of alkyl, halogen, cyano, dialkylamino, and alkoxy; and wherein heterocyclyl is unsubstituted or substituted by one or more substituents independently selected from the group consisting of alkyl and oxo.

For certain embodiments, $R_3$ is —Z'—X"—Y'—$R_4$; wherein X" is selected from the group consisting of $C_{1-3}$ alkylene, $C_{1-3}$ alkenylene, piperidin-1,4-diyl, and phenylene; Y' is —N($R_8$)-Q- wherein $R_8$ is hydrogen, and Q is —S(O)$_2$—, —C(O)—, or —C(O)—NH—; and $R_4$ is $C_{1-3}$ alkyl or pyridyl.

For certain embodiments, $R_3$ is —Z'—X"—Y'—$R_4$; wherein X" is selected from the group consisting of $C_{1-3}$ alkylene, $C_{1-3}$ alkenylene, piperidin-1,4-diyl, and phenylene, Y' is —NH—S(O)$_2$—, and $R_4$ is methyl; or Y' is —NH—C(O)—, and $R_4$ is 3-pyridyl; or Y' is —C(O)—NH—, and $R_4$ is hydrogen or $C_{1-3}$ alkyl.

For certain embodiments, $R_3$ is —Z'—X"—Y'—$R_4$; wherein Z' is a bond, X" is $C_{2-3}$ alkylene, Y' is —NH—S(O)$_2$—, —NH—C(O)—, or —NH—C(O)—NH—, and $R_4$ is $C_{1-3}$ alkyl.

For certain embodiments, $R_3$ is —Z'—X"—Y'—$R_4$; wherein Z' is —O—, X" is $C_{2-3}$ alkylene, Y' is —S(O)$_2$— or —NH—S(O)$_2$—, and $R_4$ is $C_{1-3}$ alkyl.

For certain embodiments, $R_3$ is —Z'—X"—Y'—$R_4$; wherein X" is selected from the group consisting of $C_{1-3}$ alkylene, $C_{1-3}$ alkenylene, piperidin-1,4-diyl, and phenylene, Y' is —C(O)—, and $R_4$ is heterocyclyl.

For certain embodiments, $R_3$ is —Z'—X"—Y'—$R_4$; wherein X" is selected from the group consisting of $C_{1-3}$ alkylene, $C_{1-3}$ alkenylene, piperidin-1,4-diyl, and phenylene, Y' is —C(O)—, and $R_4$ is selected from the group consisting of pyrrolidinyl, piperidinyl, thiazolidinyl, aziridinyl, azepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and piperazinyl, each of which is unsubstituted or substituted by one or more substituents selected from the group consisting of alkyl and oxo.

For certain embodiments, $R_3$ is —Z'—X"—Y'—$R_4$; wherein —Z'—X"— is

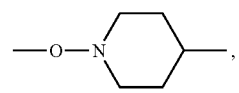

Y' is —C(O)—, —C(O)—NH—, or —S(O)$_2$—, and $R_4$ is methyl, ethyl, or 1-methylethyl.

For certain embodiments, $R_3$ is —Z'—X"—$R_5$.

For certain embodiments, $R_3$ is —Z'—X"—$R_5$; wherein X" is selected from the group consisting of $C_{1-3}$ alkylene and phenylene, and $R_5$ is selected from the group consisting of:

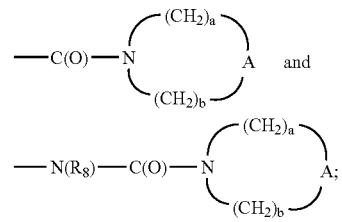

wherein A is —O—, —S—, or —SO$_2$—; $R_8$ is hydrogen or $C_{1-4}$ alkyl; and a and b are each independently an integer of 1 to 3.

For certain embodiments, $R_3$ is —Z'—X"—$R_5$; wherein X" is phenylene, and $R_5$ is

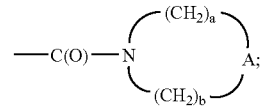

wherein A is —O—, and a and b are each 2.

For certain embodiments, $R_3$ is at the 3-position with the positions numbered as follows:

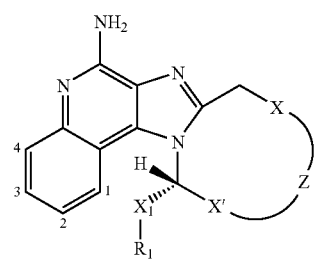

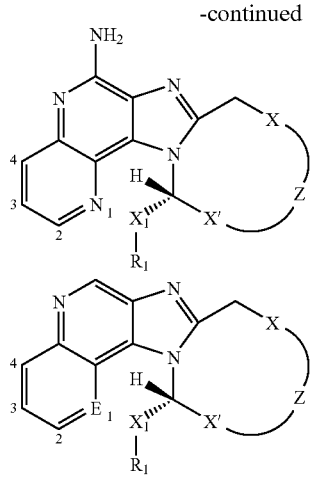

For certain embodiments, R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo.

For certain embodiments, R$_4$ is alkyl, arylalkylenyl, aryl, or heteroaryl.

For certain embodiments, R$_4$ is hydrogen or C$_{1-3}$ alkyl.

For certain embodiments, R$_4$ is C$_{1-3}$ alkyl or pyridyl.

For certain embodiments, R$_4$ is selected from the group consisting of hydrogen, alkyl, aryl, heteroaryl, and heterocyclyl; wherein alkyl is unsubstituted or substituted by one or more substituents independently selected from the group consisting of hydroxy, alkoxy, and aryl; wherein aryl is unsubstituted or substituted by one or more substituents independently selected from the group consisting of alkyl, halogen, cyano, dialkylamino, and alkoxy; and wherein heterocyclyl is unsubstituted or substituted by one or more substituents independently selected from the group consisting of alkyl and oxo.

For certain embodiments, R$_4$ is selected from the group consisting of alkyl, alkenyl, alkynyl, aryl, heteroaryl, and heterocyclyl; wherein alkyl and alkenyl are unsubstituted or substituted by one or more substituents independently selected from the group consisting of hydroxy, alkoxy, cyano, and aryl; wherein aryl and heteroaryl are unsubstituted or substituted by one or more substituents independently selected from the group consisting of alkyl, alkoxy, hydroxyalkyl, halogen, cyano, and dialkylamino; and wherein heterocyclyl is unsubstituted or substituted by one or more substituents independently selected from alkyl and oxo.

For certain embodiments, R$_4$ is heteroaryl which is selected from the group consisting of thiazolyl, imidazolyl, isoxazolyl, and pyridinyl each of which is unsubstituted or substituted by one or more substituents independently selected from the group consisting of alkyl, alkoxy, halogen, cyano, and dialkylamino.

For certain embodiments, R$_4$ is heterocyclyl.

For certain embodiments, R$_4$ is selected from the group consisting of pyrrolidinyl, piperidinyl, thiazolidinyl, aziridinyl, azepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and piperazinyl, each of which is unsubstituted or substituted by one or more substituents selected from the group consisting of alkyl and oxo.

For certain embodiments, R$_4$ is heterocyclyl which is selected from the group consisting of pyrrolidinyl, piperidinyl, morpholinyl, and thiomorpholinyl, each of which is unsubstituted or substituted by one or more substituents independently selected from alkyl and oxo.

For certain embodiments, R$_4$ heterocyclyl or heteroaryl wherein heterocyclyl is unsubstituted or substituted by one or more substituents independently selected from alkyl and oxo, and wherein heteroaryl is unsubstituted or substituted by one or more substituents independently selected from the group consisting of alkyl, alkoxy, halogen, cyano, and dialkylamino.

For certain embodiments, R$_4$ is heterocyclyl which is selected from the group consisting of pyrrolidinyl, piperidinyl, oxazolidinyl, morpholinyl, and thiomorpholinyl, each of which is unsubstituted or substituted by one or more substituents independently selected from alkyl and oxo.

For certain embodiments, R$_4$ is alkynyl.

For certain embodiments, R$_5$ is selected from the group consisting of:

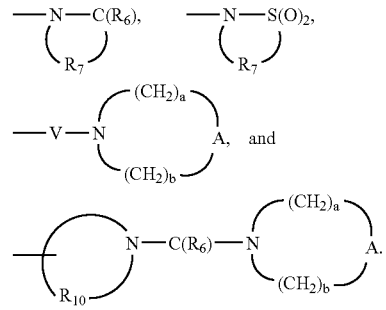

For certain embodiments, R$_5$ is selected from the group consisting of:

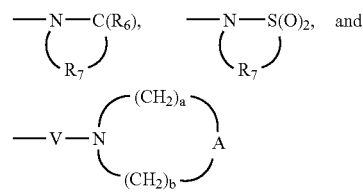

wherein V is —N(R$_8$)—C(O)—.

For certain embodiments, R$_5$ is selected from the group consisting of:

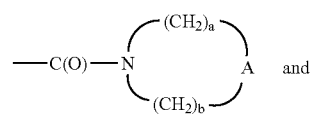

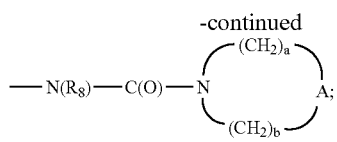

wherein A is —O—, —S—, or —SO$_2$—; R$_8$ is hydrogen or C$_{1-4}$ alkyl; and a and b are each independently an integer of 1 to 3.

For certain embodiments, R$_5$ is

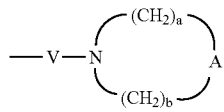

wherein V is —C(O)—.

For certain embodiments, R$_5$ is

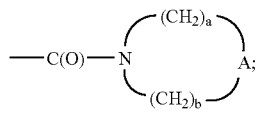

wherein A is —O—, and a and b are each 2.

For certain embodiments, R$_6$ is selected from the group consisting of =O and =S.

For certain embodiments, R$_6$ is =O.

For certain embodiments, R$_7$ is C$_{2-7}$ alkylene.

For certain embodiments, R$_7$ is propylene.

For certain embodiments, R$_8$ is selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl.

For certain embodiments, R$_8$ is selected from the group consisting of hydrogen, C$_{1-4}$ alkyl, and C$_{1-4}$ alkoxyC$_{1-4}$ alkylenyl For certain embodiments, R$_8$ is hydrogen or C$_{1-4}$ alkyl.

For certain embodiments, R$_8$ is hydrogen or methyl.

For certain embodiments, R$_8$ is hydrogen.

For certain embodiments, R$_9$ is selected from the group consisting of hydrogen and alkyl.

For certain embodiments, R$_9$ is alkyl.

For certain embodiments, R$_9$ is hydrogen.

For certain embodiments, R$_{10}$ is C$_{3-8}$ alkylene.

For certain embodiments, R$_{10}$ is pentylene.

For certain embodiments, R$_A$ and R$_B$ are each independently selected from the group consisting of hydrogen, halogen, alkyl, alkenyl, alkoxy, alkylthio, and —N(R$_9$)$_2$; or when taken together, R$_A$ and R$_B$ form a fused aryl ring or heteroaryl ring containing one heteroatom selected from the group consisting of N and S, wherein the fused aryl or heteroaryl ring is unsubstituted or substituted by one or more R' groups; or when taken together, R$_A$ and R$_B$ form a fused 5 to 7 membered saturated ring, optionally containing one heteroatom selected from the group consisting of N and S, and unsubstituted or substituted by one or more R groups.

For certain embodiments, R$_A$ and R$_B$ are each independently selected from the group consisting of hydrogen, halogen, alkyl, alkenyl, alkoxy, alkylthio, and —N(R$_9$)$_2$.

For certain embodiments, R$_A$ and R$_B$ form a fused aryl ring or heteroaryl ring.

For certain embodiments, R$_A$ and R$_B$ form a fused 5 to 7 membered saturated ring, optionally containing one heteroatom.

For certain embodiments, R$_{A1}$ and R$_{B1}$ are each independently selected from the group consisting of hydrogen, halogen, alkyl, alkenyl, alkoxy, alkylthio, and —N(R$_9$)$_2$; or when taken together, R$_{A1}$ and R$_{B1}$ form a fused aryl ring or heteroaryl ring containing one heteroatom selected from the group consisting of N and S, wherein the aryl or heteroaryl ring is unsubstituted or substituted by one or more R groups, or substituted by one R$_3$ group, or substituted by one R$_3$ group and one R group; or when taken together, R$_{A1}$ and R$_{B1}$ form a fused 5 to 7 membered saturated ring, optionally containing one heteroatom selected from the group consisting of N and S, and unsubstituted or substituted by one or more R groups.

For certain embodiments, R$_{A1}$ and R$_{B1}$ form a benzo ring which is unsubstituted or substituted by one or more R groups, or substituted by one R$_3$ group, or substituted by one R$_3$ group and one R group.

For certain embodiments, R$_{A1}$ and R$_{B1}$ form a benzo ring which is unsubstituted.

For certain embodiments, R$_{A1}$ and R$_{B1}$ form a pyrido ring which is unsubstituted or substituted by one or more R groups, or substituted by one R$_3$ group, or substituted by one R$_3$ group and one R group.

For certain embodiments, R$_{A1}$ and R$_{B1}$ form a pyrido ring which is unsubstituted.

For certain embodiments, the pyrido ring is

wherein the highlighted bond indicates the position where the ring is fused.

For certain embodiments, R$_{A1}$ and RBI form a fused 5 to 7 membered saturated ring, optionally containing one heteroatom selected from the group consisting of N and S, wherein the ring is unsubstituted.

For certain embodiments, R$_{A1}$ and R$_{B1}$ form a fused cyclohexene ring that is unsubstituted or substituted by one, two, three, or four R groups.

For certain embodiments, R$_{A1}$ and R$_{B1}$ form a fused cyclohexene ring that is unsubstituted.

For certain embodiments, R$_{A1}$ and RBI form a tetrahydropyrido ring that is unsubstituted or substituted on one or more ring carbon atoms by one, two, or three R groups.

For certain embodiments, R$_{A1}$ and R$_{B1}$ form a tetrahydropyrido ring that is unsubstituted.

For certain embodiments, the tetrahydropyrido ring is

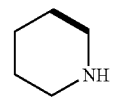

wherein the highlighted bond indicates the position where the ring is fused.

For certain embodiments, R$_{A2}$ and R$_{B2}$ are each independently selected from the group consisting of hydrogen, halogen, alkyl, alkenyl, alkoxy, alkylthio, and —N(R$_9$)$_2$.

For certain embodiments, R$_{A2}$ and R$_{B2}$ are each methyl.

For certain embodiments, A is selected from the group consisting of —CH$_2$—, —O—, —C(O)—, —S(O)$_{0-2}$—, and —N(R$_4$)—.

For certain embodiments, A is —O—, —S—, or —SO$_2$—.

For certain embodiments, A is —O—.

For certain embodiments, E is selected from the group consisting of CH, CR, $CR_3$, and N, with the proviso that when E is $CR_3$, m is 0, and p is 0 or 1, and with the further proviso that when E is CR and m is 1, p is 0. For certain embodiments, E is CH. For certain embodiments, E is N. For certain embodiments, E is CR. For certain embodiments, E is $CR_3$.

For certain embodiments, Q is selected from the group consisting of a bond, —$C(R_6)$—, —$C(R_6)$—$C(R_6)$—, —$S(O)_2$—, —$C(R_6)$—$N(R_8)$—W—, —$S(O)_2$—$N(R_8)$—, —$C(R_6)$—O—, and —$C(R_6)$—$N(OR_9)$.

For certain embodiments, Q is selected from the group consisting of a bond, —C(O)—, —$S(O)_2$—, - and $C(R_6)$—N($R_8$)—.

For certain embodiments, Q is —$S(O)_2$—, —C(O)—, or —C(O)—NH—.

For certain embodiments, Q is —$C(R_6)$—.

For certain embodiments, Q is —$S(O)_2$—.

For certain embodiments, Q is —$C(R_6)$—$N(R_8)$—W—.

For certain embodiments, V is selected from the group consisting of —$C(R_6)$—, —O—$C(R_6)$—, —$N(R_8)$—$C(R_6)$—, and —$S(O)_2$—.

For certain embodiments, V is —$N(R_8)$—C(O)—.

For certain embodiments, V is —C(O)—.

For certain embodiments, W is selected from the group consisting of a bond, —C(O)—, and —$S(O)_2$—.

For certain embodiments, W is a bond.

For certain embodiments, X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms.

For certain embodiments, X is a bond.

For certain embodiments, X' is a straight or branched chain $C_{1-8}$ alkylene optionally having a substituent at a carbon atom other than a carbon atom adjacent to a heteroatom, wherein the substituent is hydroxy, alkoxy, or one or more halogen atoms.

For certain embodiments, X' contributes one ring carbon atom.

For certain embodiments, X' is $C_{1-2}$ alkylene.

For certain embodiments, X' is methylene.

For certain embodiments, X' contributes two ring carbon atoms.

In each of the above embodiments of X and X', X and X' are further characterized in that the sum of the ring carbon atoms contributed by X and X' is 1, 2, or 3.

For certain embodiments, X, is selected from the group consisting of a bond, alkylene, alkenylene, and alkynylene wherein the alkylene and alkenylene are optionally interrupted by one or more —O— groups, and are optionally substituted by a hydroxy or methoxy group.

For certain embodiments, $X_1$ is selected from the group consisting of a bond, alkylene, and alkenylene, wherein the alkylene and alkenylene are optionally interrupted by one or more —O— groups.

For certain embodiments, $X_1$ is a bond or alkylene.

For certain embodiments, $X_1$ is $C_{1-4}$ alkylene.

For certain embodiments, $X_1$ is —$CH_2$—.

For certain embodiments, $X_1$ is a bond.

For certain embodiments, $X_1$ is $C_{1-4}$ alkylene substituted by a hydroxy or methoxy group.

For certain embodiments, $X_1$ is $C_{2-3}$ alkylene interrupted by one —O— group.

For certain embodiments, $X_1$ is $C_{2-3}$ alkenylene or $C_{2-3}$ alkynylene.

For certain embodiments, X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups.

For certain embodiments, X" is $C_{1-3}$ alkylene or $C_{1-3}$ alkenylene.

For certain embodiments, X" is alkylene.

For certain embodiments, X" is selected from the group consisting of $C_{1-3}$ alkylene, $C_{1-3}$ alkenylene, piperidin-1,4-diyl, and phenylene.

For certain embodiments, X" is selected from the group consisting of $C_{1-3}$ alkylene and phenylene.

For certain embodiments, Y is selected from the group consisting of a bond, —$S(O)_2$—, —$S(O)_2$—$N(R_8)$—, —$C(R_6)$—, —$C(R_6)$—$N(R_8)$—, —$C(R_6)$—$N(R_8)$—$C(R_6)$—, —$C(R_6)$—$N(R_8)$—$S(O)_2$—, and —$C(R_6)$—O—.

For certain embodiments, Y is selected from the group consisting of —C(O)—, —$S(O)_2$—, and —C(O)—NH—.

For certain embodiments, Y is —$S(O)_2$—.

For certain embodiments, Y' is selected from the group consisting of —$S(O)_{0-2}$—, —$S(O)_2$—$N(R_8)$—, —$C(R_6)$—, —$C(R_6)$—O—, —O—$C(R_6)$—, —O—C(O)—O—, —$N(R_8)$-Q-, —$C(R_6)$—$N(R_8)$—, —O—$C(R_6)$—$N(R_8)$—, —$C(R_6)$—$N(OR_9)$—,

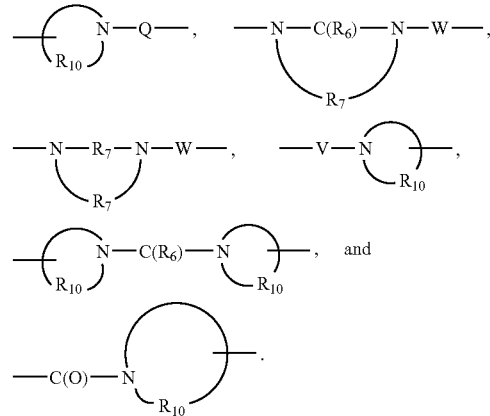

For certain embodiments, Y' is selected from the group consisting of —$S(O)_{0-2}$—, —$S(O)_2$—$N(R_8)$—, —$C(R_6)$—, —$C(R_6)$—O—, —O—$C(R_6)$—, —O—C(O)—O—, —$N(R_8)$-Q-, —$C(R_6)$—$N(R_8)$—, —O—$C(R_6)$—$N(R_8)$—, —$C(R_6)$—$N(OR_9)$—,

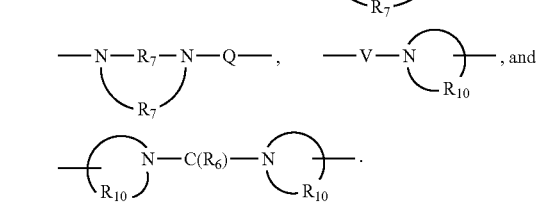

For certain embodiments, Z is selected from the group consisting of —O— and —N(—Y—$R_2$)—.

For certain preferred embodiments, Z is —O—.

For certain embodiments, Z is —N(—Y—$R_2$)—.

For certain embodiments, Z' is a bond or —O—.
For certain embodiments, Z' is a bond.
For certain embodiments, Z' is —O—.
For certain embodiments, a and b are independently integers from 1 to 6 with the proviso that a+b is ≦7.
For certain embodiments, a and b are each independently an integer of 1 to 3.
For certain embodiments, a and b are each 2.
For certain embodiments, m is 0 or 1.
For certain embodiments, m is 0.
For certain embodiments, m is 1.
For certain embodiments, n is an integer from 0 to 4.
For certain embodiments, n is 0 or 1.
For certain embodiments, n is 0.
For certain embodiments, n is 1.
For certain embodiments, n is 2.
For certain embodiments, n is 3 or 4.
For certain embodiments, p is an integer from 0 to 3.
For certain embodiments, p is 0 or 1.
For certain embodiments, p is 0.
For certain embodiments, p is 1.
For certain embodiments, m is 1 and n is 0.
For certain embodiments, m is 0 and n is 0.
For certain embodiments, m is 1 and p is 0.
For certain embodiments, m is 0 and p is 0.

In some embodiments, particularly embodiments of Formulas I, II, or II-1, the one or more R' groups are one or more R groups, or one $R_3$ group, or one $R_3$ group and one R group; wherein R and $R_3$ are as defined in Formula Ia or are any one of the embodiments of R and $R_3$ defined above.

In some embodiments, particularly embodiments of Formula I, $R_A$ and $R_B$ form a benzo ring which is unsubstituted or substituted by one or more R groups, or substituted by one $R_3$ group, or substituted by one $R_3$ group and one R group. For certain embodiments, $R_A$ and $R_B$ form a benzo ring which is unsubstituted.

In some embodiments, particularly embodiments of Formula I, $R_A$ and $R_B$ form a pyrido ring which is unsubstituted or substituted by one or more R groups, or substituted by one $R_3$ group, or substituted by one $R_3$ group and one R group. For certain embodiments, $R_A$ and $R_B$ form a pyrido ring which is unsubstituted. For certain embodiments, the pyrido ring is

wherein the highlighted bond indicates the position where the ring is fused.

In some embodiments, particularly embodiments of Formula I, $R_A$ and $R_B$ form a fused 5 to 7 membered saturated ring, optionally containing one heteroatom selected from the group consisting of N and S, wherein the ring is unsubstituted. For certain embodiments, $R_A$ and $R_B$ form a fused cyclohexene ring that is unsubstituted or substituted by one, two, three, or four R groups. For certain embodiments, $R_A$ and $R_B$ form a fused cyclohexene ring that is unsubstituted. For certain embodiments, $R_A$ and $R_B$ form a tetrahydropyrido ring that is unsubstituted or substituted on one or more ring carbon atoms by one, two, or three R groups. For certain embodiments, $R_A$ and $R_B$ form a tetrahydropyrido ring that is unsubstituted. For certain embodiments, the tetrahydropyrido ring is

wherein the highlighted bond indicates the position where the ring is fused.

In some embodiments, particularly embodiments of Formula I, $R_A$ and $R_B$ are each independently selected from the group consisting of hydrogen, halogen, alkyl, alkenyl, alkoxy, alkylthio, and —$N(R_9)_2$. For certain embodiments, $R_A$ and $R_B$ are each methyl.

In some embodiments, particularly embodiments of Formulas VII or VII-1, $R_{A2}$ and $R_{B2}$ are each independently selected from the group consisting of hydrogen, halogen, alkyl, alkenyl, alkoxy, alkylthio, and —$N(R_9)_2$. In certain of these embodiments, $R_{A2}$ and $R_{B2}$ are each methyl.

In some embodiments, particularly embodiments of Formulas III, III-1, IV, or IV-1, n is an integer from 0 to 4, with the proviso that in Formulas III and III-1 when m is 1, then n is 0 or 1. In certain of these embodiments, n is 0.

In some embodiments, particularly embodiments of Formulas V, V-1, VI or VI-1, p is an integer from 0 to 3, with the proviso that in Formulas V and V-1 when m is 1, then p is 0 or 1. In certain of these embodiments, p is 0.

In some embodiments, particularly embodiments of Formulas III or III-1, n is an integer from 0 to 4 and m is 0 or 1; with the proviso that when m is 1, then n is 0 or 1. In certain of these embodiments, n and m are 0.

In some embodiments, particularly embodiments of Formulas V or V-1, p is an integer from 0 to 3, and m is 0 or 1; with the proviso that when m is 1, then p is 0 or 1. In certain of these embodiments, p and m are 0.

In some embodiments, particularly embodiments of Formulas X, or X-1, E is CH or N, p is 0, and m is 0 or 1. In certain of these embodiments, p and m are 0.

In some embodiments, particularly embodiments of Formulas IIa, II-1a, III, III-1, V, V-1, VIII, IX, IX-1, X, or X-1, $R_3$ is selected from the group consisting of benzyloxy which is unsubstituted or substituted by halogen or haloalkyl, 3-pyrrolylpropoxy, 2-(4-methoxyphenyl)-2-oxoethoxy, aryl, and heteroaryl, wherein aryl and heteroaryl are unsubstituted or substituted by one or more substituents independently selected from the group consisting of alkyl, hydroxy, hydroxyalkyl, alkoxy, halogen, dialkylamino, alkylcarbonylamino, alkylaminocarbonyl, dialkylaminocarbonyl, and heterocyclylcarbonyl.

For certain embodiments, particularly embodiments of Formulas IIa, II-1a, III, III-1, V, V-1, VIII, IX, IX-1, X, or X-1, $R_3$ is phenyl substituted by pyrrolidinylcarbonyl or morpholinylcarbonyl.

In certain embodiments, particularly embodiments of Formulas IIa, II-1a, III, III-1, V, V-1, VIII, IX, IX-1, X, or X-1, $R_3$ is benzyloxy. For certain of these embodiments of Formulas III and III-1, n is 0. For certain of these embodiments of Formulas V, V-1, X, and X-1, p is 0

In some embodiments, particularly embodiments of Formulas I, II, II-1, IIa, II-1a, III, III-1, IV, IV-1, V, V-1, VI, VI-1, VIII, IX, IX-1, X, or X-1, R is halogen or hydroxy. For certain of these embodiments of Formulas III and III-1, m is 0, and n is 1. For certain of these embodiments of Formulas V, V-1, X, and X-1, m is 0 and p is 1.

In certain embodiments, particularly embodiments of Formulas I, II, II-1, IIa, II-1a, III, III-1, IV, IV-1, V, V-1, VI, VI-1, VIII, IX, IX-1, X, or X-1, R is —$N(R_9)_2$. For certain of these embodiments of Formulas III and III-1, m is 0, and n is 1. For certain of these embodiments of Formulas V and V-1, m is 0, and p is 1. For certain of these embodiments, R is (cyclopropylmethyl)amino.

In certain embodiments, particularly embodiments of Formulas Ia, II-1a, III, III-1, V, V-1, VIII, IX, IX-1, X, or X-1, wherein $R_3$ is benzyloxy, R is halogen or hydroxy. For certain of these embodiments of Formulas III and III-1, m is 1 and n is 1.

For certain embodiments, particularly embodiments of Formulas IIa, II-1a, III, III-1, V, V-1, VIII, IX, IX-1, X, or X-1, $R_3$ is —Z'—$R_4$. For certain of these embodiments, $R_4$ is selected from the group consisting of alkyl, alkenyl, alkynyl, aryl, heteroaryl, and heterocyclyl wherein alkyl and alkenyl are unsubstituted or substituted by one or more substituents independently selected from the group consisting of hydroxy, alkoxy, cyano, and aryl; wherein aryl and heteroaryl are unsubstituted or substituted by one or more substituents independently selected from the group consisting of alkyl, alkoxy, hydroxyalkyl, halogen, cyano, and dialkylamino; and wherein heterocyclyl is unsubstituted or substituted by one or more substituents independently selected from alkyl and oxo. For certain of these embodiments, Z' is —O—, and $R_4$ is alkynyl. For certain of these embodiments, $R_4$ is propynyl. Alternatively, for certain of these embodiments, Z' is a bond and $R_4$ is heterocyclyl which is selected from the group consisting of pyrrolidinyl, piperidinyl, oxazolidinyl, morpholinyl, and thiomorpholinyl, each of which is unsubstituted or substituted by one or more substituents independently selected from alkyl and oxo. For certain of these embodiments, —Z'—$R_4$ is 2-oxopyrrolidin-1-yl, morpholin-1-yl, or 2-oxo-1,3-oxazolidin-3-yl.

For certain embodiments, particularly embodiments of Formulas IIa, II-1a, III, III-1, V, V-1, VIII, IX, IX-1, X, X-1, embodiments of Formula III or III-1 wherein n is 0, or embodiments of Formula V or V-1 wherein p is 0, $R_3$ is —Z'—X"—$R_4$. For certain of these embodiments, X" is $C_{1-3}$ alkylene or $C_{1-3}$ alkenylene, and $R_4$ is heterocyclyl or heteroaryl wherein heterocyclyl is unsubstituted or substituted by one or more substituents independently selected from alkyl and oxo, and wherein heteroaryl is unsubstituted or substituted by one or more substituents independently selected from the group consisting of alkyl, alkoxy, halogen, cyano, and dialkylamino. For certain of these embodiments, $R_4$ is heterocyclyl which is selected from the group consisting of pyrrolidinyl, piperidinyl, morpholinyl, and thiomorpholinyl, each of which is unsubstituted or substituted by one or more substituents independently selected from alkyl and oxo. Alternatively, for certain of these embodiments, $R_4$ is heteroaryl which is selected from the group consisting of thiazolyl, imidazolyl, isoxazolyl, and pyridinyl each of which is unsubstituted or substituted by one or more substituents independently selected from the group consisting of alkyl, alkoxy, halogen, cyano, and dialkylamino. For certain of these embodiments, X" is $C_{1-3}$ alkylene, and $R_4$ is pyridin-3-yl, 1-methyl-1H-imidazol-2-yl, or 1,3-thiazol-4-yl.

For certain embodiments, particularly embodiments of Formulas IIa, II-1a, III, III-1, V, V-1, VIII, IX, IX-1, X, X-1, embodiments of Formula III or III-1 wherein n is 0, or embodiments of Formula V or V-1 wherein p is 0, $R_3$ is —Z'—X"—Y'—$R_4$. For certain of these embodiments, X" is selected from the group consisting of $C_{1-3}$ alkylene, $C_{1-3}$ alkenylene, piperidin-1,4-diyl, and phenylene, Y' is selected from the group consisting of —C($R_6$)—, —C($R_6$)—O—, —C($R_6$)—N($R_8$)—, —N($R_8$)-Q-, and —S(O)$_2$— wherein Q is selected from the group consisting of a bond, —C(O)—, —S(O)$_2$—, - and C($R_6$)—N($R_8$)—, $R_6$ is selected from the group consisting of =O and =S, and $R_8$ is selected from the group consisting of hydrogen, $C_{1-4}$ alkyl, and $C_{1-4}$ alkoxy$C_{1-4}$ alkylenyl; and $R_4$ is selected from the group consisting of hydrogen, alkyl, aryl, heteroaryl, and heterocyclyl; wherein alkyl is unsubstituted or substituted by one or more substituents independently selected from the group consisting of hydroxy, alkoxy, and aryl; wherein aryl is unsubstituted or substituted by one or more substituents independently selected from the group consisting of alkyl, halogen, cyano, dialkylamino, and alkoxy; and wherein heterocyclyl is unsubstituted or substituted by one or more substituents independently selected from the group consisting of alkyl and oxo. For certain of these embodiments, Y' is —N($R_8$)-Q- wherein $R_8$ is hydrogen, Q is —S(O)$_2$—, —C(O)—, or —C(O)—NH—, and $R_4$ is $C_{1-3}$ alkyl or pyridyl. For certain of these embodiments, Y' is —NH—S(O)$_2$— and $R_4$ is methyl, or Y' is —NH—C(O)— and $R_4$ is 3-pyridyl, or Y' is —C(O)—NH— and $R_4$ is hydrogen or $C_{1-3}$ alkyl. For certain of these embodiments, Z' is a bond, X" is $C_{2-3}$ alkylene, Y' is —NH—S(O)$_2$—, —NH—C(O)—, or —NH—C(O)—NH—, and $R_4$ is $C_{1-3}$ alkyl. Alternatively, for certain of these embodiments, Z' is —O—, X" is $C_{2-3}$ alkylene, Y' is —S(O)$_2$— or —NH—S(O)$_2$—, and $R_4$ is $C_{1-3}$ alkyl. Alternatively, for certain of these embodiments, Y' is —C(O)— and $R_4$ is heterocyclyl. For certain of these embodiments, heterocyclyl is selected from the group consisting of pyrrolidinyl, piperidinyl, thiazolidinyl, aziridinyl, azepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and piperazinyl, each of which is unsubstituted or substituted by one or more substituents selected from the group consisting of alkyl and oxo.

Alternatively, for certain of these embodiments, —Z'—X"— is

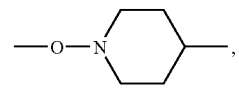

Y' is —C(O)—, —C(O)—NH—, or —S(O)$_2$—, and $R_4$ is methyl, ethyl, or 1-methylethyl.

For certain embodiments, particularly embodiments of Formulas IIa, II-1a, III, III-1, V, V-1, VIII, IX, IX-1, X, X-1, embodiments of Formula III or III-1 wherein n is 0, or embodiments of Formula V or V-1 wherein p is 0, $R_3$ is —Z'—X"—$R_5$. For certain of these embodiments, X" is selected from the group consisting of $C_{1-3}$ alkylene and phenylene, and $R_5$ is selected from the group consisting of:

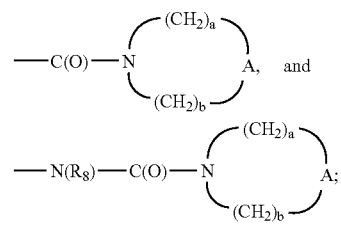

wherein A is —O—, —S—, or —SO$_2$—; $R_8$ is hydrogen or $C_{1-4}$ alkyl; and a and b are each independently an integer of 1 to 3. For certain of these embodiments, A is —O—, and a and b are each 2.

For certain embodiments, particularly embodiments of Formulas IIa, II-1a, III, III-1, V, V-1, VIII, IX, IX-1, X, X-1, embodiments of Formula III or III-1 wherein n is 0, or embodiments of Formula V or V-1 wherein p is 0, $R_3$ is —Y"—$R_4$. For certain of these embodiments, $R_4$ is heterocyclyl. For certain of these embodiments, $R_4$ is selected from the group consisting of pyrrolidinyl, piperidinyl, morpholinyl, and thiomorpholinyl, each of which is unsubstituted or substituted by one or more substituents independently selected from alkyl and oxo. For certain of these embodiments, $R_4$ is pyrrolidin-1-yl or morpholin-4-yl.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments, Z is —N(—Y—$R_2$)—.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments (except where Z is —N(—Y—$R_2$)—), Z is —O—.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments (except where Z is —O—), Y is selected from the group consisting of —C(O)—, —S(O)$_2$—, and —C(O)—NH—. In certain of these embodiments, Y is —S(O)$_2$— and $R_2$ is methyl.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments, $R_1$ is selected from the group consisting of alkyl, aryl, arylalkylenyl, heteroaryl, and heteroarylalkylenyl, each of which is unsubstituted or substituted by one or more substituents selected from the group consisting of halogen, hydroxy, and alkoxy. In certain of these embodiments, $R_1$ is selected from the group consisting of alkyl, aryl, arylalkylenyl, heteroaryl, and heteroarylalkylenyl, wherein alkyl is unsubstituted or substituted by one or more substituents selected from the group consisting of halogen and hydroxy. In certain of these embodiments, $R_1$ is $C_{1-3}$ alkyl optionally substituted by hydroxy or one or more fluorine atoms. In certain of these embodiments, $R_1$ is phenyl, benzyl, pyridinyl, or pyridinylmethyl, each of which is unsubstituted or substituted by one or more substituents selected from the group consisting of halogen, hydroxy, and alkoxy. In certain of these embodiments, $R_1$ is phenyl, benzyl, pyridinyl, or pyridinylmethyl.

For certain embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments which include the following definition of $R_1$, $R_1$ is selected from the group consisting of alkyl, alkenyl, alkynyl, aryl, heteroaryl, and heterocyclyl, each of which is unsubstituted or substituted by one or more substituents independently selected from the group consisting of alkyl, alkoxy, hydroxyalkyl, haloalkyl, halogen, hydroxy, aryl, heteroaryl, and heterocyclyl; and wherein when $R_1$ is heteroaryl, then the one or more substituents may also be independently selected from the group consisting of haloarylenyl, alkoxyarylenyl, alkylarylenyl, and arylalkylenyl; and wherein when $R_1$ is heterocyclyl, then the one or more substituents may also be independently selected from the group consisting of arylalkylenyl and aminocarbonyl. For certain of these embodiments, $R_1$ is heterocyclyl which is selected from the group consisting of morpholinyl, thiomorpholinyl, piperidinyl, pyrrolidinyl, thiazolidinyl, dihydroisoquinolin-(1H)-yl, octahydroisoquinolin-(1H)-yl, 1,3-dioxolanyl, oxetanyl, tetrahydrofuranyl, tetrahydropyranyl, each of which is unsubstituted or substituted by one or more substituents independently selected from the group consisting of $C_{1-4}$ alkyl, hydroxy$C_{1-4}$ alkyl, hydroxy, aminocarbonyl, aryl$C_{1-4}$ alkylenyl, and 5 to 7 membered heterocyclyl containing one or two heteroatoms. Alternatively, for certain of these embodiments, $R_1$ is heteroaryl which is selected from the group consisting of pyridyl, pyrazolyl, oxazolyl, and triazolyl, each of which is unsubstituted or substituted by one or more substituents independently selected from the group consisting of $C_{1-4}$ alkyl, hydroxy$C_{1-4}$ alkyl, halo$C_{1-4}$ alkyl, aryl, aryl substituted by fluoro, chloro, methyl, or methoxy, aryl$C_{1-4}$ alkylenyl, and heteroaryl.

For certain embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments which include the following definition of $R_1$, $R_1$ is selected from the group consisting of $C_{1-4}$ alkyl, $C_{1-4}$ alkenyl, and $C_{1-4}$ alkynyl, each of which is unsubstituted or substituted by one or more substituents independently selected from the group consisting of hydroxy, halogen, and aryl.

For certain embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments which include the following definition of $R_1$, $R_1$ is aryl which is unsubstituted or substituted by one or more substituents independently selected from the group consisting of halogen, hydroxy, $C_{1-4}$ alkoxy, $C_{1-4}$ alkyl, and hydroxy$C_{1-4}$ alkyl.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments, $X_1$ is a bond or alkylene. For certain of these embodiments, X is a bond. Alternatively, for certain of these embodiments, $X_1$ is —CH$_2$—.

For certain embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments which includes the following definition of $X_1$, $X_1$ is $C_{1-4}$ alkylene substituted by a hydroxy or methoxy group.

For certain embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments which includes the following definition of $X_1$, X is $C_{2-3}$ alkylene interrupted by one —O— group.

For certain embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments which includes the following definition of $X_1$, $X_1$ is $C_{2-3}$ alkenylene or $C_{2-3}$ alkynylene.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments, X is a bond.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments, X' contributes one ring carbon atom.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments, X' is $C_{1-2}$ alkylene. In certain of these embodiments, X' is methylene.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments (except where X' contributes one ring carbon atom or X' is methylene), X' contributes two ring carbon atoms.

For certain embodiments of the compounds of Formulas I, II, II-1, IIa, II-1a, III, III-1, IV, IV-1, V, V-1, VI, VI-1, VII, or VII-1, or any one of the above embodiments of these Formulas, the —$NH_2$ group can be replaced by an —NH-G group, as shown in the compounds of Formulas VIII, IX, and IX-1, to form prodrugs. In such embodiments, G is selected from the group consisting of: —C(O)—R", α-aminoacyl, α-aminoacyl-α-aminoacyl, —C(O)—O—R", —C(O)—N(R''')R", —C(=$NY_2$)—R", —CH(OH)—C(O)—$OY_2$, —CH($OC_{1-4}$ alkyl)$Y_0$, —$CH_2Y_1$, and —CH($CH_3$)$Y_1$. For certain embodiments, G is selected from the group consisting of —C(O)—R", α-aminoacyl, α-aminoacyl-α-aminoacyl, and —C(O)—O—R". Preferably, R" and R''' are independently selected from the group consisting of $C_{1-10}$ alkyl, $C_{3-7}$ cycloalkyl, and benzyl, each of which may be unsubstituted or substituted by one or more substitutents selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkylenyl, halo$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —S(O)$_2$—$NH_2$, with the proviso that R''' can also be hydrogen. Preferably, α-aminoacyl is an acyl group derived from an amino acid selected from the group consisting of racemic, D-, and L-amino acids. Preferably, $Y_2$ is selected from the group consisting of hydrogen, $C_{1-6}$ alkyl, and benzyl. Preferably, $Y_0$ is selected from the group consisting of $C_{1-6}$ alkyl, carboxy$C_{1-6}$ alkylenyl, amino$C_{1-4}$ alkylenyl, mono-N—$C_{1-6}$ alkylamino$C_{1-4}$ alkylenyl, and di-N,N—$C_{1-6}$ alkylamino$C_{1-4}$ alkylenyl. Preferably, $Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl.

In some embodiments, the present invention provides a pharmaceutical composition comprising a therapeutically effective amount of a compound or salt of any one of Formulas I, II, II-1, IIa, II-1a, III, III-1, IV, IV-1, V, V-1, VI, VI-1, VII, VII-1, VIII, IX, or IX-1 or any one of the above embodiments and a pharmaceutically acceptable carrier.

In some embodiments, the present invention provides a method of inducing cytokine biosynthesis in an animal comprising administering an effective amount of a compound or salt of any one of Formulas II, IIa, III, IV, V, VI, VII, IX, or any one of the above embodiments of these Formulas or administering any one of the above pharmaceutical compositions containing a compound or salt of any one of Formulas II, IIa, III, IV, V, VI, VII, IX, or any one of the above embodiments of these Formulas to the animal.

In some embodiments, the present invention provides a method of treating a viral disease in an animal in need thereof comprising administering a therapeutically effective amount of a compound or salt of any one of Formulas II, IIa, III, IV, V, VI, VII, IX, or any one of the above embodiments of these Formulas or administering any one of the above pharmaceutical compositions containing a compound or salt of any one of Formulas II, IIa, III, IV, V, VI, VII, IX, or any one of the above embodiments of these Formulas to the animal.

In some embodiments, the present invention provides a method of treating a neoplastic disease in an animal in need thereof comprising administering a therapeutically effective amount of a compound or salt of any one of Formulas II, IIa, III, IV, V, VI, VII, IX, or any one of the above embodiments of these Formulas or administering any one of the above pharmaceutical compositions containing a compound or salt of any one of Formulas II, IIa, III, IV, V, VI, VII, IX, or any one of the above embodiments of these Formulas to the animal.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

Compounds of the invention can be prepared according to Reaction Scheme I, wherein R, $R_1$, $X_1$, X, and X' are as defined above; Hal is chloro, bromo, or iodo; E is carbon (imidazoquinolines) or nitrogen (imidazonaphthyridines); n is an integer from 0 to 4 (imidazoquinoline ring) or 0 to 3 (imidazonaphthyridine ring); and P is a hydroxy protecting group. In step (1) of Reaction Scheme I, a 4-chloro-3-nitroquinoline or 4-chloro-3-nitro[1,5]naphthyridine of Formula XV is treated with an amino alcohol of Formula XVI to provide a compound of Formula XVII. Several amino alcohols of Formula XVI are commercially available, such as (S)-1-amino-2-propanol, L-valinol, (S)-2-phenylglycinol, and (S)-2-amino-3-phenyl-1-propanol. Others can be prepared by known synthetic methods; for example, see the methods described in Williams, L. et al., *Tetrahedron*, 52, pp. 11673-11694, (1996) and Genevois-Borella, A. et al., *Tetrahedron Lett.*, 31, pp. 4879-4882 (1990) for the preparation of amino alcohols wherein $R_1$ includes a hydroxy substituent. A hydroxy substituent on $R_1$ can readily be converted to a halogen substituent using a variety of known methods; for example, a hydroxy substituent can be converted to a fluoro substituent using (diethylaminosulfur) trifluoride in a suitable solvent such as dichloromethane at a sub-ambient temperature such as −78° C.

The reaction in step (1) is conveniently carried out by adding the amino alcohol of Formula XVI to a solution of 4-chloro-3-nitroquinoline or 4-chloro-3-nitro[1,5]naphthyridine of Formula XV in a suitable solvent such as dichloromethane in the presence of a tertiary amine such as triethylamine. The reaction can be carried out at ambient temperature or at an elevated temperature such as, for example, the reflux temperature of the solvent. Many compounds of Formula XV are known or can be prepared using known synthetic methods, see for example, U.S. Pat. Nos. 4,689,338; 5,175,296; 5,367,076; 5,389,640; 6,194,425; and U.S. Patent Publication Application No. US 2004/0147543 and the documents cited therein.

In step (2) of Reaction Scheme I, the hydroxy group of a 3-nitroquinolin-4-amine or 3-nitro[1,5]naphthyridin-4-amine of Formula XVII is protected using conventional techniques to provide a 3-nitroquinolin-4-amine or 3-nitro[1,5]naphthyridin-4-amine of Formula XVIII. A number of suitable protecting groups can be used; in particular, protecting groups that would survive the reduction in step (3) are preferred. Suitable protecting groups include but are not limited to silyl groups such as the tert-butyl dimethylsilyl group. The reaction is conveniently carried out by treating the hydroxy-substituted compound of Formula XVII with tert-butyldimethylsilyl chloride in the presence of a base such as triethylamine and catalytic 4-(dimethylamino)pyridine (DMAP). The reaction can be carried out in a suitable solvent such as dichloromethane or pyridine at an elevated temperature such as the reflux temperature of the solvent or a temperature in the range of 50° C. to 70° C.

Compounds of Formula XVIII may also be prepared in step (1) of Reaction Scheme I if the hydroxy group on a compound of Formula XVI is protected before the reaction. The protection of the hydroxy group on a compound of Formula XVI can be carried out as described above in step (2).

In step (3) of Reaction Scheme I, a 3-nitroquinolin-4-amine or 3-nitro[1,5]naphthyridin-4-amine of Formula XVIII is reduced to provide a quinoline-3,4-diamine or [1,5]naphthyridine-3,4-diamine of Formula XIX. The reaction can be carried out by hydrogenation using a heterogeneous hydrogenation catalyst such as platinum on carbon. The hydrogenation is conveniently carried out in a Parr apparatus in a suitable solvent such as toluene, methanol, isopropanol, ethyl acetate, or acetonitrile. The reaction can be carried out at ambient temperature.

In step (4) of Reaction Scheme I, a quinoline-3,4-diamine or [1,5]naphthyridine-3,4-diamine of Formula XIX is reacted with a carboxylic acid equivalent, which is selected such that it will provide the desired —X-Hal substituent in a 1H-imidazo[4,5-c]quinoline or 1H-imidazo[4,5-c][1,5]naphthyridine of Formula XX. Suitable carboxylic acid equivalents include ortho esters, acid halides, imidates, and imidate salts.

When the carboxylic acid equivalent is an imidate of formula Hal-CH$_2$—X—C(=NH)—O-alkyl or a salt thereof, the reaction is conveniently carried out by combining a quinoline-3,4-diamine or [1,5]naphthyridine-3,4-diamine of Formula XIX with the imidate in a suitable solvent such 1,2-dichloroethane, chloroform, or propyl acetate. The reaction can be carried out at an elevated temperature such as a temperature not lower than 55° C. and not higher than 85° C. or at the reflux temperature of the solvent. Some imidates of formula Hal-CH$_2$—X—C(=NH)—O-alkyl are known; others can be prepared by known methods. Ethyl chloroacetimidate hydrochloride, which can be used to provide a compound of Formula XX in which X is a bond, is a known compound that can be prepared according to the literature procedure: Stillings, M. R. et al., *J. Med. Chem.*, 29, pp. 2280-2284 (1986).

When the carboxylic acid equivalent is an acid halide of formula Hal-CH$_2$—X—C(O)Cl or Hal-CH$_2$—X—C(O)Br, the reaction is conveniently carried out by adding the acid halide to a solution of a quinoline-3,4-diamine or [1,5]naphthyridine-3,4-diamine of Formula XIX in a suitable solvent such as dichloromethane or 1,2-dichloroethane in the presence of a tertiary amine such as triethylamine. The reaction can be carried out at ambient temperature or at a sub-ambient temperature.

The reaction with an acid halide of formula Hal-CH$_2$—X—C(O)Cl or Hal-CH$_2$—X—C(O)Br may be carried out in two parts, which include (i) adding the acid halide to a solution of a quinoline-3,4-diamine or [1,5]naphthyridine-3,4-diamine of Formula XIX in a suitable solvent such as chloroform, dichloromethane, 1,2-dichloroethane optionally in the presence of a tertiary amine such as triethylamine to afford an amide intermediate and (ii) cyclizing to provide a 1H-imidazo[4,5-c]quinoline or 1H-imidazo[4,5-c][1,5]naphthyridine of Formula XX. The amide intermediate from part (i) can be optionally isolated using conventional techniques. The cyclization in part (ii) may be carried out by heating the amide intermediate from part (i) in a suitable solvent such as toluene. The cyclization in part (ii) can also be carried out in the presence of a base such as triethylamine or in the presence of an acid such as glacial acetic acid.

In step (5) of Reaction Scheme I, the hydroxy protecting group on a 1H-imidazo[4,5-c]quinoline or 1H-imidazo[4,5-c][1,5]naphthyridine of Formula XX is removed to reveal the hydroxy group in a product of Formula XXI. The deprotection reaction can be carried out using a variety of conventional methods, depending on the protecting group used. When P is a silyl group such as tert-butyldimethylsilyl, the deprotection can be carried out by adding tetrabutylammonium fluoride to a 1H-imidazo[4,5-c]quinoline or 1H-imidazo[4,5-c][1,5]naphthyridine of Formula XX in a suitable solvent such as tetrahydrofuran (THF). The reaction can be carried out at a sub-ambient temperature, such as −78° C., and then warmed to ambient temperature. When the reaction is carried out in dichloromethane, a product of Formula XXII is typically isolated, and the reaction shown in step (6) may be obviated.

In step (6) of Reaction Scheme I, a 1H-imidazo[4,5-c]quinoline or 1H-imidazo[4,5-c][1,5]naphthyridine of Formula XX is cyclized by an intramolecular displacement of the halogen under basic conditions to provide a compound of Formula XXII. The reaction is conveniently carried out by adding a base such as potassium tert-butoxide to a solution of a compound of Formula XXI in a suitable solvent such as THF. The reaction can be carried out at ambient temperature or at an elevated temperature.

In step (7) of Reaction Scheme I, a 1H-imidazo[4,5-c]quinoline or 1H-imidazo[4,5-c][1,5]naphthyridine of Formula XXII is oxidized to provide a 1H-imidazo[4,5-c]quinoline-5N-oxide or 1H-imidazo[4,5-c][1,5]naphthyridine-5N-oxide of Formula XXIII using a conventional oxidizing agent capable of forming N-oxides. The reaction is conveniently carried out by adding 3-chloroperoxybenzoic acid to a solution of a compound of Formula XXII in a solvent such as chloroform or dichloromethane. The reaction can be carried out at ambient temperature.

In step (8) of Reaction Scheme I, a 1H-imidazo[4,5-c]quinoline-5N-oxide or 1H-imidazo[4,5-c][1,5]naphthyridine-5N-oxide of Formula XXIII is aminated to provide a 1H-imidazo[4,5-c]quinolin-6-amine or 1H-imidazo[4,5-c][1,5]naphthyridin-6-amine of Formula XXIV, a subgenus of Formulas I, II, and IIa. Step (8) involves the activation of an N-oxide of Formula XXIII by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XXIII in a suitable solvent such as dichloromethane or chloroform and then adding p-toluenesulfonyl chloride. The reaction can be carried out at ambient temperature.

Alternatively, the oxidation and amination can be carried out as a one-pot procedure without isolating the N-oxide of Formula XXIII by adding 3-chloroperoxybenzoic acid to a solution of a compound of Formula XXII in a solvent such as dichloromethane or chloroform and then adding ammonium hydroxide and p-toluenesulfonyl chloride.

The amination reaction in step (8) of Reaction Scheme I can alternatively be carried out by treating a 5N-oxide of Formula XXIII with trichloroacetyl isocyanate followed by hydrolysis of the resulting intermediate to provide a compound of Formula XXIV. The reaction is conveniently carried out in two steps by (i) adding trichloroacetyl isocyanate to a solution of a 5N-oxide of Formula XXIII in a solvent such as dichloromethane and stirring at ambient temperature to provide an isolable amide intermediate. In step (ii), a solution of the intermediate in methanol is treated with a base such as sodium methoxide or ammonium hydroxide at ambient temperature.

A racemic mixture containing a compound of Formula XXIV may be obtained in this scheme if a racemic amino alcohol is used instead of a compound of Formula XVI. A racemic mixture thus prepared can be resolved by methods known to one skilled in the art, for example, by reacting the racemic mixture with an enantiomerically pure sulfonic acid or carboxylic acid and selectively crystallizing a salt of one of the enantiomers from the mixture. Alternatively, the enantiomer of a compound of Formula XXIV can be prepared using the enantiomer of the amino alcohol of Formula XVI in step (1) of Reaction Scheme I.

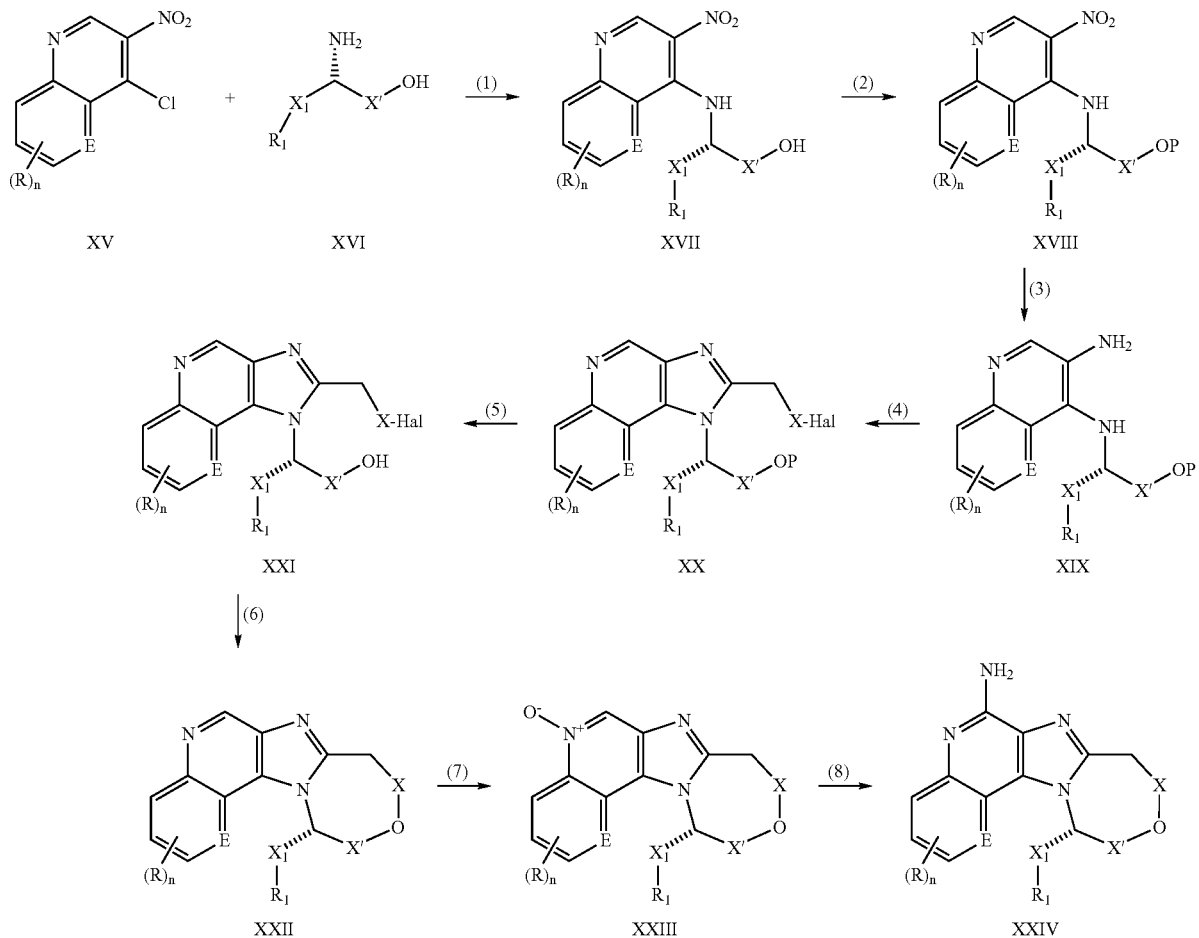

Reaction Scheme I

Compounds of the invention can also be prepared according to Reaction Scheme II, wherein R, $R_1$, $R_2$, X, X', $X_1$, Y, and Hal are as defined above; E and n are as defined in Reaction Scheme I; and Boc is tert-butoxycarbonyl.

In step (1) of Reaction Scheme II, a 4-chloro-3-nitroquinoline or 4-chloro-3-nitro[1,5]naphthyridine of Formula XV is treated with a Boc-protected diamine of Formula XXV to provide a compound of Formula XXVI. Boc-protected diamines of Formula XXV are available from the corresponding deprotected diamines, which are either commercially available or readily synthesized from amino alcohols of Formula XVI. The Boc protection can be carried out, for example, by treating a diamine such as 1,2-diaminopropane dihydrochloride with one equivalent of di-tert-butyl dicarbonate in the presence of a base such as 1,8-diazabicyclo[5.4.0]undec-7-ene (DBU). The protection reaction can be carried out at a sub-ambient temperature such as 0° C. and allowed to warm to ambient temperature. The reaction shown in step (1) of Reaction Scheme II is conveniently carried out under the conditions described in step (1) of Reaction Scheme I.

In steps (2) and (3) of Reaction Scheme II, a 3-nitroquinolin-4-amine or 3-nitro[1,5]naphthyridin-4-amine of Formula XXVI is first reduced to a quinoline-3,4-diamine or [1,5]naphthyridine-3,4-diamine of Formula XXVII, which is then treated with a halogen-substituted carboxylic acid equivalent to provide a 1H-imidazo[4,5-c]quinoline or 1H-imidazo[4,5-c][1,5]naphthyridine of Formula XXVIII. Steps (2) and (3) of Reaction Scheme II can be carried out according to the methods described in steps (3) and (4) of Reaction Scheme I.

In step (4) of Reaction Scheme II, a 1H-imidazo[4,5-c]quinoline or 1H-imidazo[4,5-c][1,5]naphthyridine of Formula XXVIII treated with acid to effect a removal of the Boc group and an intramolecular displacement of the halogen by the amino group to provide a compound of Formula XXIX. The reaction is conveniently carried out by treating the compound of Formula XXVIII with hydrogen chloride in a suitable solvent such as ethanol. The reaction can be carried out at ambient temperature or at an elevated temperature such as the reflux temperature of the solvent.

In step (5) of Reaction Scheme II, the secondary amine of a compound of Formula XXIX or a salt thereof is converted to an amide, sulfonamide, sulfamide, urea, or tertiary amine of Formula XXX using conventional methods. For example, a compound of Formula XXIX or a salt thereof can react with an acid chloride of Formula $R_2C(O)Cl$ to provide a compound of Formula XXX in which Y is —C(O)—. In addition, a compound of Formula XXIX can react with sulfonyl chloride of Formula $R_2S(O)_2Cl$ or a sulfonic anhydride of Formula $(R_2S(O)_2)_2O$ to provide a compound of Formula XXX in which Y is $S(O)_2$—. Numerous acid chlorides of Formula $R_2C(O)Cl$, sulfonyl chlorides of Formula $R_2S(O)_2Cl$, and sulfonic anhydrides of Formula $(R_2S(O)_2)_2O$ are commercially available; others can be readily prepared using known synthetic methods. The reaction is conveniently carried out by adding the acid chloride of Formula $R_2C(O)Cl$, sulfonyl chloride of Formula $R_2S(O)_2Cl$, or sulfonic anhydride of Formula $(R_2S(O)_2)_2O$ to a solution of the compound of Formula XXIX in a suitable solvent such as chloroform, dichloromethane, or N,N-dimethylformamide (DMF). Optionally a base such as triethylamine or N,N-diisopropylethylamine can be added. The reaction can be carried out at ambient temperature or a sub-ambient temperature such as 0° C.

Ureas of Formula XXX, where Y is —C(O)—NH— can be prepared by reacting a compound of Formula XXIX or a salt thereof with isocyanates of Formula $R_2N$=C=O. Numerous isocyanates of Formula $R_2N$=C=O are commercially available; others can be readily prepared using known synthetic methods. The reaction can be conveniently carried out by adding the isocyanate of Formula $R_2N$=C=O to a solution of the compound of Formula XXIX in a suitable solvent such as DMF or chloroform. Optionally a base such as triethylamine or N,N-diisopropylethylamine can be added. The reaction can be carried out at ambient temperature or a sub-ambient temperature such as 0° C. Alternatively, a compound of Formula XXIX can be treated with an isocyanate of Formula $R_2(CO)N$=C=O, a thioisocyanate of Formula $R_2N$=C=S, a sulfonyl isocyanate of Formula $R_2S(O)_2N$=C=O, or a carbamoyl chloride of Formula $R_2N$—$(R_8)$—C(O)Cl to provide a compound of Formula XXX, where Y is —C(O)—N($R_8$)—(CO)—, —C(S)—N($R_8$)—, —C(O)—N($R_8$)—S(O)$_2$—, or —C(O)—N($R_8$)—, respectively. Alternatively, a compound of Formula XXIX can be treated with a carbamoyl chloride of Formula Cl—C(O)-heterocyclyl, wherein heterocyclyl is attached at a nitrogen atom, to provide a compound of Formula XXX, wherein Y is —C(O)— and $R_2$ is heterocyclyl attached at a nitrogen atom.

Sulfamides of Formula XXX, where Y is —S(O)$_2$—N($R_8$)—, can be prepared by reacting a compound or salt of Formula XXIX with sulfuryl chloride to generate a sulfamoyl chloride in situ, and then reacting the sulfamoyl chloride with an amine of formula HN($R_8$)$R_2$. Alternatively, sulfamides of Formula XXX can be prepared by reacting a compound of Formula XXIX with a sulfamoyl chloride of formula $R_2(R_8)$N—S(O)$_2$Cl. Many sulfonyl chlorides of Formula $R_2S(O)_2Cl$ and amines of Formula HN($R_8$)$R_2$, and some sulfamoyl chlorides of formula $R_2(R_8)$N—S(O)$_2$Cl are commercially available; others can be prepared using known synthetic methods.

Compounds of Formula XXX where Y is a bond can be prepared by reductive alkylation of the secondary amine of compound of Formula XXIX. The alkylation is conveniently carried out in two parts by (i) adding an aldehyde or ketone to a solution of a compound of Formula XXIX or a salt thereof in a suitable solvent such as DMF or THF in the presence of a base such as N,N-diisopropylethylamine. In part (ii) the reduction is carried out by adding a suitable reducing agent such as the borane-pyridine complex. Both part (i) and part (ii) can be carried out at ambient temperature.

In steps (6) and (7) of Reaction Scheme II, a compound of Formula XXX is first oxidized to a 1H-imidazo[4,5-c]quinoline-5N-oxide or 1H-imidazo[4,5-c][1,5]naphthyridine-5N-oxide of Formula XXXI, which is then aminated to provide a 1H-imidazo[4,5-c]quinolin-6-amine or 1H-imidazo[4,5-c][1,5]naphthyridin-6-amine of Formula XXXII, a subgenus of Formulas I, II, and IIa. Steps (6) and (7) of Reaction Scheme II can be carried out as described in steps (7) and (8) of Reaction Scheme I.

The reactions described in Reaction Scheme II may also be carried out in a different order. For example, in step (4) of Reaction Scheme II, a compound of XXVIII may be cyclized under basic conditions to provide a fused piperazine, [1,4]diazepane, [1,4]diazocane, or [1,5]diazocane ring wherein the secondary amine is still protected by the Boc group. The reaction is conveniently carried out by adding a base such as potassium tert-butoxide to a solution of a compound of Formula XXVIII in a suitable solvent such as THF. The reaction can be carried out at ambient temperature or at a sub-ambient temperature such as 0° C. The resulting compound can then be oxidized and aminated according to the methods of steps (7) and (8) of Reaction Scheme I before the Boc group is removed under acidic conditions. The removal of the Boc group is conveniently carried out by adding a solution of hydrogen chloride in 1,4-dioxane or ethanol or a solution of trifluoroacetic acid in dichloromethane to the Boc-protected amine (i.e., a compound of Formula XXXII wherein Y is —C(O)—O— and $R_2$ is a tert-butyl group). The deprotection reaction may be run in a suitable solvent such as dichloromethane at ambient temperature or at an elevated temperature such as the reflux temperature of the solvent. The resulting secondary amine can then be treated according to one of the many methods described in step (5) of Reaction Scheme II to provide a compound of Formula XXXII wherein Y and $R_2$ are as defined above.

Alternatively, instead of a Boc-protected diamine of Formula XXV, the reaction sequence shown in Reaction Scheme II can be carried out starting with the reaction of a compound of Formula XV with a compound of Formula

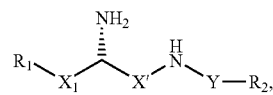

which can be synthesized from the corresponding diamine using one of the various methods described in step (5) of Reaction Scheme II. The product can then be treated according to the methods described in steps (2), (3), (4), (6), and (7) in Reaction Scheme II to provide a compound of Formula XXXII.

Reaction Scheme II

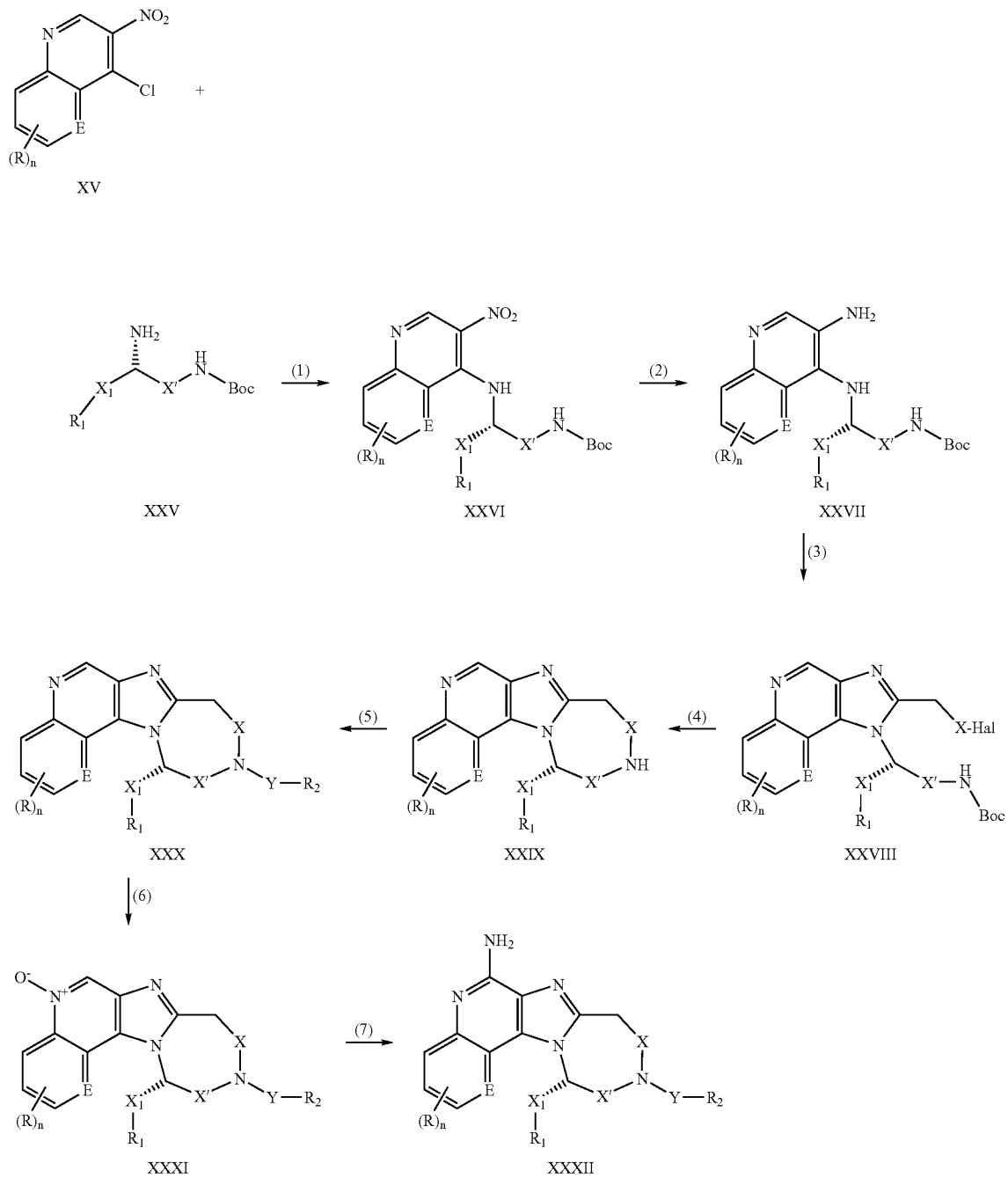

For some embodiments, compounds of the invention are prepared according to Reaction Scheme III, wherein R, $R_1$, X, X', $X_1$, and Z are as defined above; E is as defined in Reaction Scheme I; hal is bromo or iodo; n is 0 or 1; $R_{3a}$ is —Z'—$R_{4b}$, —Z'—$X''_a$—$R_4$, —Z'—$X''_b$—Y'—$R_4$, or —Z'—$X''_b$—$R_5$; where Z' is a bond; $X''_a$ is alkenylene; $X''_b$ is arylene, heteroarylene, and alkenylene interrupted or terminated by arylene or heteroarylene; $R_{4b}$ is aryl or heteroaryl where the aryl or heteroaryl groups can be unsubstituted or substituted as defined in $R_4$ above; and $R_4$, $R_5$, and Y' are as defined above. Compounds of Formula XXXIII can be prepared by the methods shown in Reaction Scheme I or Reaction Scheme II beginning with a compound of Formula XV wherein n is other than 0 and one of the R groups present is hal.

In Reaction Scheme III, a 1H-imidazo[4,5-c]quinolin-6-amine or 1H-imidazo[4,5-c][1,5]naphthyridin-6-amine of Formula XXXIII is coupled with a boronic acid of Formula $R_{3a}$—$B(OH)_2$, an anhydride thereof, or a boronic acid ester of Formula $R_{3a}$—$B(O\text{-alkyl})_2$ to provide a 1H-imidazo[4,5-c]quinolin-6-amine or 1H-imidazo[4,5-c][1,5]naphthyridin-6-amine of Formula XXXIV, which is a subgenus of Formulas I, II, and IIa. The Suzuki coupling is carried out by combining a compound of Formula XXXIII with a boronic acid or an ester or anhydride thereof in the presence of palladium (II) acetate, triphenylphosphine, and a base such as sodium carbonate in a suitable solvent such as n-propanol or solvent mixture such as n-propanol/water. The reaction can be carried out at an elevated temperature (e.g., 80° C.-100° C. or the reflux temperature). Many boronic acids of Formula $R_{3a}$—$B(OH)_2$, anhydrides thereof, and boronic acid esters of Formula $R_{3a}$—$B(O\text{-alkyl})_2$ are commercially available; others can be readily prepared using known synthetic methods. See, for example, Li, W. et al, *J. Org. Chem.*, 67, 5394-5397 (2002).

Other coupling reactions such as the Heck reaction, the Stille coupling, and the Sonogashira coupling can be used to prepare compounds of Formula XXXIV. Also, compounds of Formula XXXIV, wherein $R_{3a}$ is —Z—$X''_a$—$R_4$, —Z—$X''_b$—Y'—$R_4$, or —Z—$X''_b$—$R_5$ in which $X''_b$ is alkenylene interrupted or terminated by arylene or heteroarylene, can undergo reduction of the $X''_a$ or $X''_b$ alkenylene group. The reduction can be carried out by hydrogenation using a conventional heterogeneous hydrogenation catalyst such as palladium on carbon. The reaction can conveniently be carried out on a Parr apparatus in a suitable solvent such as ethanol, methanol, or mixtures thereof.

Reaction Scheme III

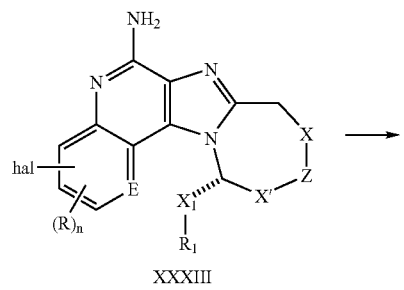

XXXIII

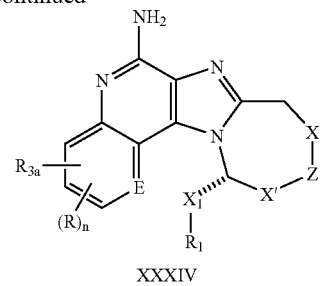

XXXIV

Compounds of the invention can be prepared according to Reaction Scheme IV where R, $R_1$, X, X', $X_1$, P, and Hal are as defined above; E is as defined in Reaction Scheme I; n is 0 or 1; $R_{3b}$ is —$R_4$, —X''—$R_4$, —X''—Y'—$R_4$, —X''—Y'—X''—Y'—$R_4$, or —X'—$R_5$, where $R_4$, X'', Y', and $R_5$ are as defined above. In step (1) of Reaction Scheme IV, a benzyloxyaniline or benzyloxyaminopyridine of Formula XXXV is treated with the condensation product generated from 2,2-dimethyl-1,3-dioxane-4,6-dione (Meldrum's acid) and triethyl orthoformate to provide an imine of Formula XXXVI. The reaction is conveniently carried out by adding a solution of a compound of Formula XXXV to a heated mixture of Meldrum's acid and triethyl orthoformate and heating the reaction at an elevated temperature such as 45° C. Many anilines and aminopyridines of Formula XXXV are commercially available; others can be prepared by known synthetic methods. For example, benzyloxypyridines of Formula XXXV can be prepared using the method of Holladay et al., *Biorg. Med. Chem. Lett.*, 8, pp. 2797-2802, (1998).

In step (2) of Reaction Scheme IV, an imine of Formula XXXVI undergoes thermolysis and cyclization to provide a compound of Formula XXXVII. The reaction is conveniently carried out in a medium such as DOWTHERM A heat transfer fluid at a temperature in the range of 200° C. and 250° C.

In step (3) of Reaction Scheme IV, a compound of Formula XXXVII is nitrated under conventional nitration conditions to provide a benzyloxy-3-nitroquinolin-4-ol of Formula XXXVIII. The reaction is conveniently carried out by adding nitric acid to the compound of Formula XXXVII in a suitable solvent such as propionic acid and heating the mixture at an elevated temperature such as 125° C.

In step (4) of Reaction Scheme IV, a benzyloxy-3-nitroquinolin-4-ol or benzyloxy-3-nitro[1,5]naphthyridin-4-ol of Formula XXXVIII is chlorinated using conventional chlorination chemistry to provide a benzyloxy-4-chloro-3-nitroquinoline or benzyloxy-4-chloro-3-nitro[1,5]naphthyridine of Formula XXXIX. The reaction is conveniently carried out by treating the compound of Formula XXXVIII with phosphorous oxychloride in a suitable solvent such as DMF. The reaction can be carried out at an elevated temperature such as 100° C., and the product can be isolated using conventional methods.

In step (5) of Reaction Scheme IV, a benzyloxy-4-chloro-3-nitroquinoline or benzyloxy-4-chloro-3-nitro[1,5]naphthyridine of Formula XXXIX is treated with an amino alcohol of Formula XVI to provide a benzyloxy-3-nitroquinolin-4-amine or benzyloxy-3-nitro[1,5]naphthyridin-4-amine of Formula XL. The reaction is conveniently carried out according to the methods described in step (1) of Reaction Scheme I.

In steps (6) and (7) of Reaction Scheme IV, the hydroxy group of a benzyloxy-3-nitroquinolin-4-amine or benzyloxy-3-nitro[1,5]naphthyridin-4-amine of Formula XL is protected to provide a compound of Formula XLI, which is reduced to provide a benzyloxyquinoline-3,4-diamine or benzyloxy[1,5]naphthyridine-3,4-diamine of Formula XLII. Steps (6) and (7) of Reaction Scheme IV can be carried out according to the methods described in steps (2) and (3) of Reaction Scheme I.

In steps (8) and (9) of Reaction Scheme IV, a benzyloxyquinoline-3,4-diamine or benzyloxy[1,5]naphthyridine-3,4-diamine of Formula XLII is treated with a halogen-substituted carboxylic acid equivalent to provide benzyloxy-1H-imidazo[4,5-c]quinoline or benzyloxy-1H-imidazo[4,5-c][1,5]naphthyridine of Formula XLIII, which can then undergo deprotection to provide a compound of Formula XLIV or XLV. Steps (8) and (9) of Reaction Scheme IV can be carried out according to the methods described in steps (4) and (5) of Reaction Scheme I.

If a benzyloxy-substituted a 1H-imidazo[4,5-c]quinoline or 1H-imidazo[4,5-c][1,5]naphthyridine of Formula XLIV is isolated from step (9), in step (10) of Reaction Scheme IV, the compound of Formula XLIV is cyclized by an intramolecular displacement of the halogen under basic conditions to provide a compound of Formula XLV. The reaction can be carried out under the conditions described in step (6) of Reaction Scheme I.

In step (11) of Reaction Scheme IV, the benzyl group of a benzyloxy-1H-imidazo[4,5-c]quinoline or benzyloxy-1H-imidazo[4,5-c][1,5]naphthyridine of Formula XLV is cleaved to provide a 1H-imidazo[4,5-c]quinolinol or 1H-imidazo[4,5-c][1,5]naphthyridinol of Formula XLVI. The cleavage is conveniently carried out on a Parr apparatus under hydrogenolysis conditions using a suitable heterogeneous catalyst such as palladium on carbon in a solvent such as ethanol. Alternatively, the reaction can be carried out by transfer hydrogenation in the presence of a suitable hydrogenation catalyst. The transfer hydrogenation is conveniently carried out by adding ammonium formate to a solution of a compound of Formula XLV in a suitable solvent such as ethanol in the presence of a catalyst such as palladium on carbon. The reaction is carried out at an elevated temperature, for example, the reflux temperature of the solvent.

In step (12) of Reaction Scheme IV a 1H-imidazo[4,5-c]quinolinol or 1H-imidazo[4,5-c][1,5]naphthyridinol of Formula XLVI is converted to an ether-substituted 1H-imidazo[4,5-c]quinoline or 1H-imidazo[4,5-c][1,5]naphthyridine of Formula XLVII using a Williamson-type ether synthesis. The reaction is effected by treating a compound of Formula XLVI with an alkyl halide of Formula Halide-$R_4$, Halide-$X''$—$Y'$—$R_4$, or Halide-$X''$—$R_5$ in the presence of a base. The reaction is conveniently carried out by combining the alkyl halide with a compound of Formula XLVI in a solvent such as DMF in the presence of a suitable base such as cesium carbonate. The reaction can be carried out at ambient temperature or at an elevated temperature, for example 65° C. or 85° C. Alternatively, the reaction can be carried out by treating a solution of a compound of Formula XLVI in a solvent such as DMF with sodium hydride and then adding a reagent of Formula Halide-$R_4$, Halide-$X''$—$Y'$—$R_4$, or Halide-$X''$—$R_5$.

Numerous reagents of Formulas Halide-$R_4$ and Halide-$X''$—$Y'$—$R_4$ are commercially available, for example, substituted benzyl bromides and chlorides, substituted or unsubstituted alkyl or arylalkylenyl bromides and chlorides, substituted fluorobenzenes, bromo-substituted ketones, esters, and heterocycles. Other reagents of Formulas Halide-$R_4$, Halide-$X''$—$Y'$—$R_4$, and Halide-$X''$—$R_5$ can be prepared using conventional synthetic methods; for example, a bromo-substituted acid halide of Formula ClC(O)—$X''$—Br can be treated with a secondary amine in a suitable solvent such as dichloromethane to provide a variety of bromo-substituted amides of Formula Br—$X''$—C(O)—N($R_8$)—$R_4$ or

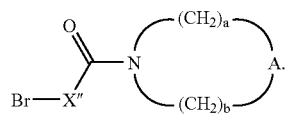

The reaction can be run at a sub-ambient temperature such as −25° C. Also, compounds of Formula I-$X''$—N($R_8$)—Boc are readily prepared in two steps from amino alcohols of Formula HO—$X''$—N($R_8$)H by first protecting the amine with a Boc group and then converting the hydroxy group to an iodo group. Both reactions can be carried out using conventional methods. The compound of Formula XLVII wherein $R_{3b}$ is —$X''$—$Y'$—$R_4$, wherein Y' is —N($R_8$)—C(O)—O— and $R_4$ is tert-butyl thus prepared can be converted into a compound wherein Y' is —N($R_8$)-Q- and Q and $R_4$ are as defined above using one of the methods described in step (5) of Reaction Scheme II.

Step (12) of Reaction Scheme IV can alternatively be carried out by treating a compound of Formula XLVI with an alcohol of Formula HO—$X''$—$Y'$—$R_4$, HO—$X''$—$R_5$, or HO—$R_4$ under Mitsunobu reaction conditions. Numerous alcohols of these formulas are commercially available; for example, 1-(3-hydroxypropyl)pyrrolidin-2-one, 1-(2-hydroxyethyl)pyrrolidin-2-one, and tert-butyl 4-hydroxypiperidine-1-carboxylate. Others can be prepared using conventional synthetic methods. The reaction is conveniently carried out by out by adding triphenylphosphine and an alcohol of Formula HO—$X''$—$Y'$—$R_4$, HO—$X''$—$R_5$, or HO—$R_4$ to a solution of a compound of Formula XLVI in a suitable solvent such as THF and then slowly adding diisopropyl azodicarboxylate or diethyl azodicarboxylate. The reaction can be carried out at ambient temperature or at a sub-ambient temperature, such as 0° C.

In steps (13) and (14) of Reaction Scheme IV, an ether-substituted compound of Formula XLVII is first oxidized to a 5N-oxide of Formula XLVIII, which is then aminated to provide a 1H-imidazo[4,5-c]quinolin-6-amine or 1H-imidazo[4,5-c][1,5]naphthyridin-6-amine of Formula XLIX, a subgenus of Formulas I, II, and IIa. Steps (13) and (14) of Reaction Scheme IV can be carried out as described in steps (7) and (8) of Reaction Scheme I.

Isomers of the compound of Formula XXXV or Formula XXXVII, wherein E is nitrogen, can also be synthesized and can be used to prepare compounds of the invention according to the methods of Reaction Scheme IV.

Reaction Scheme IV
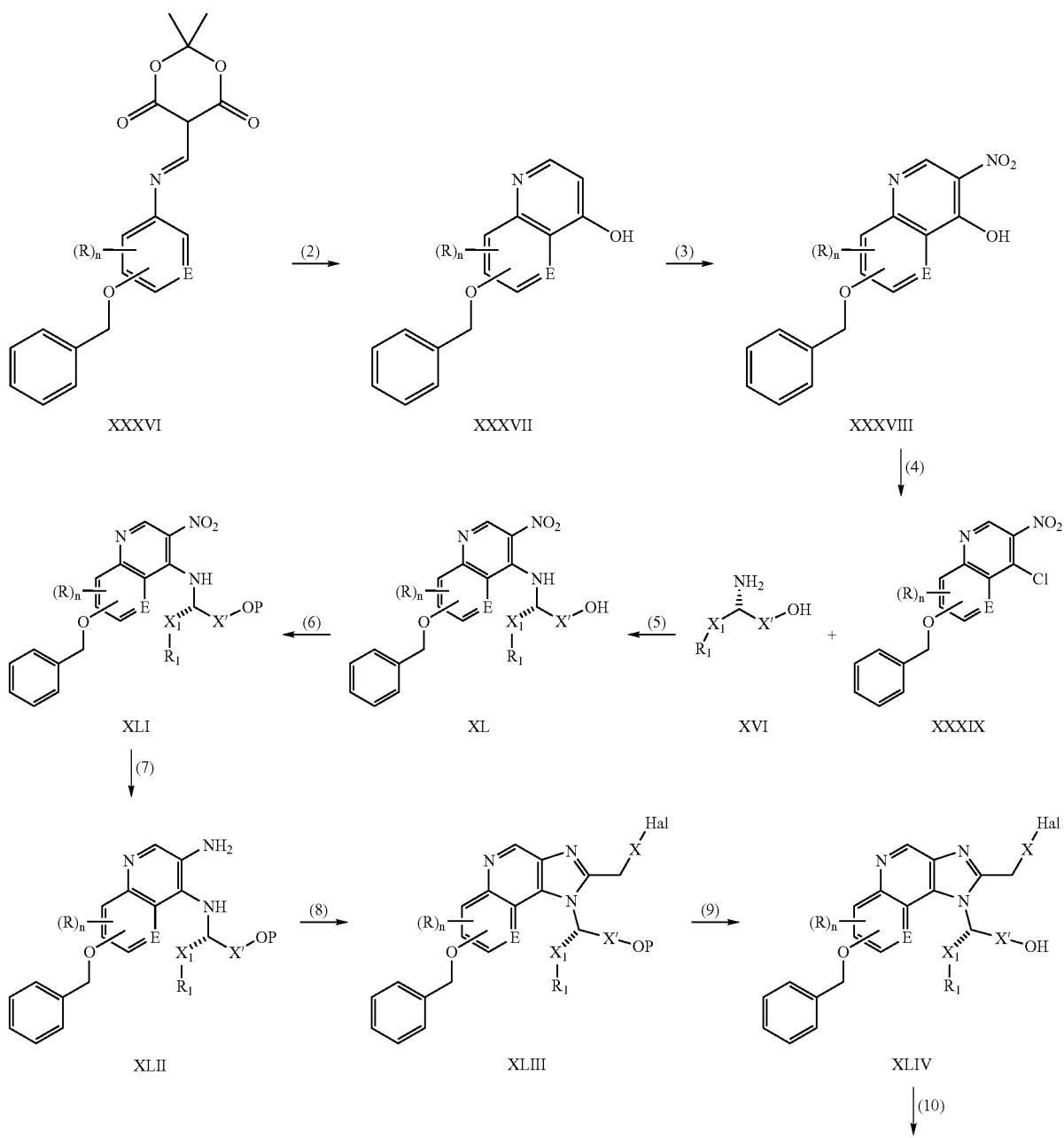

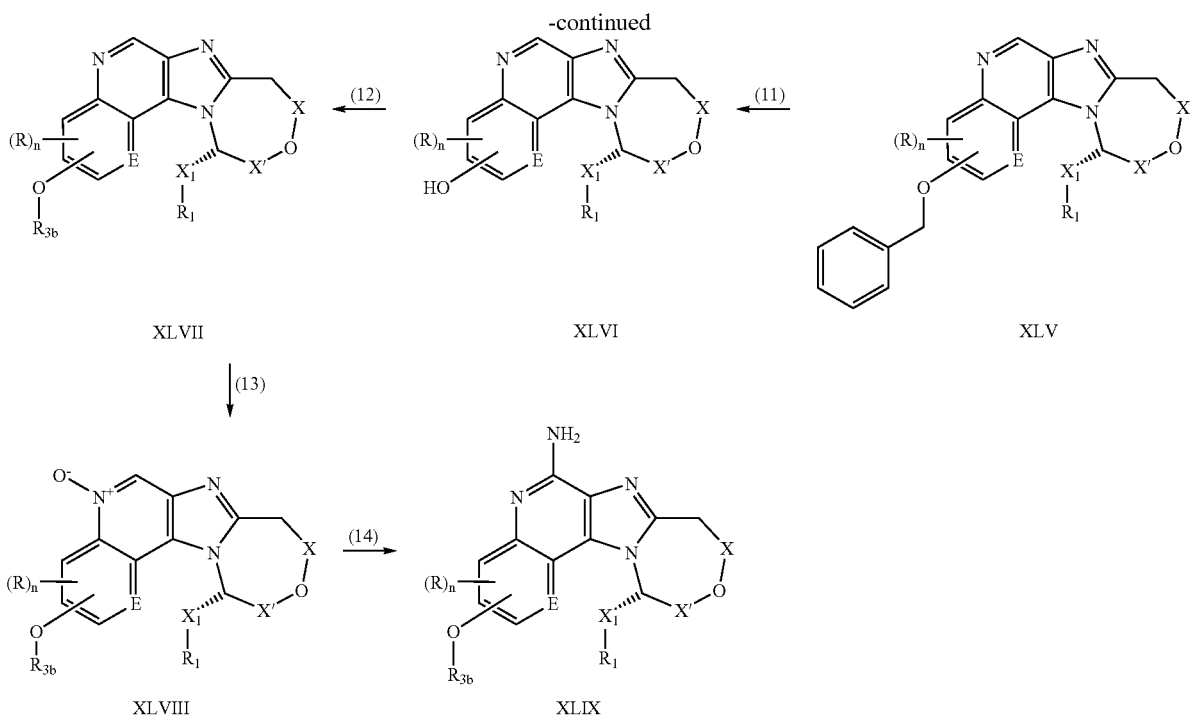

XLVII    XLVI    XLV

XLVIII    XLIX

Imidazopyridines of the invention can be prepared according to Reaction Scheme V, where Hal, P, $R_1$, $R_{A2}$, $R_{B2}$, X, X', and $X_1$ are as defined above. In steps (1) and (2) of Reaction Scheme V, a 2,4-dichloro-3-nitropyridine of Formula L is reacted with an amino alcohol of Formula XVI to form a 2-chloro-3-nitropyridine of Formula LI, which then undergoes protection of the hydroxy group to provide a compound of Formula LII. Steps (1) and (2) of Reaction Scheme V are conveniently carried out according to the methods described in steps (1) and (2) of Reaction Scheme I. Many 2,4-dichloro-3-nitropyridines of the Formula L are known and can be readily prepared using known synthetic methods (see, for example, Dellaria et al, U.S. Pat. No. 6,525,064 and the references cited therein).

In step (3) of Reaction Scheme V, a 2-chloro-3-nitropyridine of Formula LII is reacted with an alkali metal azide to provide an 8-nitrotetrazolo[1,5-a]pyridin-7-amine of Formula LIII. The reaction can be carried out by combining the compound of Formula LII with an alkali metal azide, for example, sodium azide, in a suitable solvent such as acetonitrile/water, preferably 90/10 acetonitrile/water, in the presence of cerium(III) chloride, preferably cerium(III) chloride heptahydrate. Optionally, the reaction can be carried out with heating, for example, at the reflux temperature. Alternatively, the reaction can be carried out by combining the compound of Formula LII with an alkali metal azide, for example, sodium azide, in a suitable solvent such as DMF and heating, for example to about 50° C. to 60° C., optionally in the presence of ammonium chloride.

Steps (4) through (7) of Reaction Scheme V can be carried out according to the methods described in steps (3) through (6) of Reaction Scheme I.

In step (8) of Reaction Scheme V, the tetrazolo ring is removed from a compound of Formula LVII by reaction with triphenylphosphine to form an N-triphenylphosphinyl intermediate, which is then hydrolyzed to provide a compound of Formula LVIII, a subgenus of Formulas I, II, IIa, and VII. The reaction with triphenylphosphine can be run in a suitable solvent such as toluene or 1,2-dichlorobenzene under an atmosphere of nitrogen with heating, for example at the reflux temperature. The hydrolysis step can be carried out by general methods well known to those skilled in the art, for example, by heating in a lower alkanol or an alkanol/water solution in the presence of an acid such as trifluoroacetic acid, acetic acid, or hydrochloric acid.

Reaction Scheme V

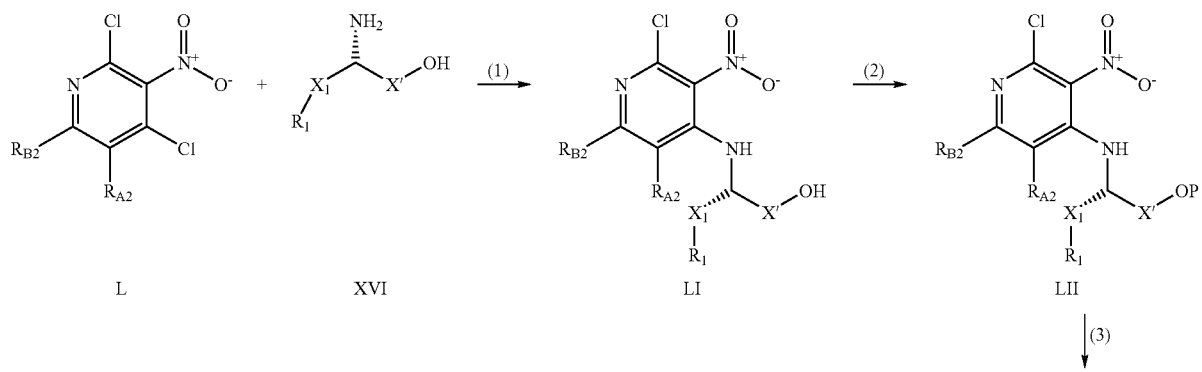

L    XVI    LI    LII (3)

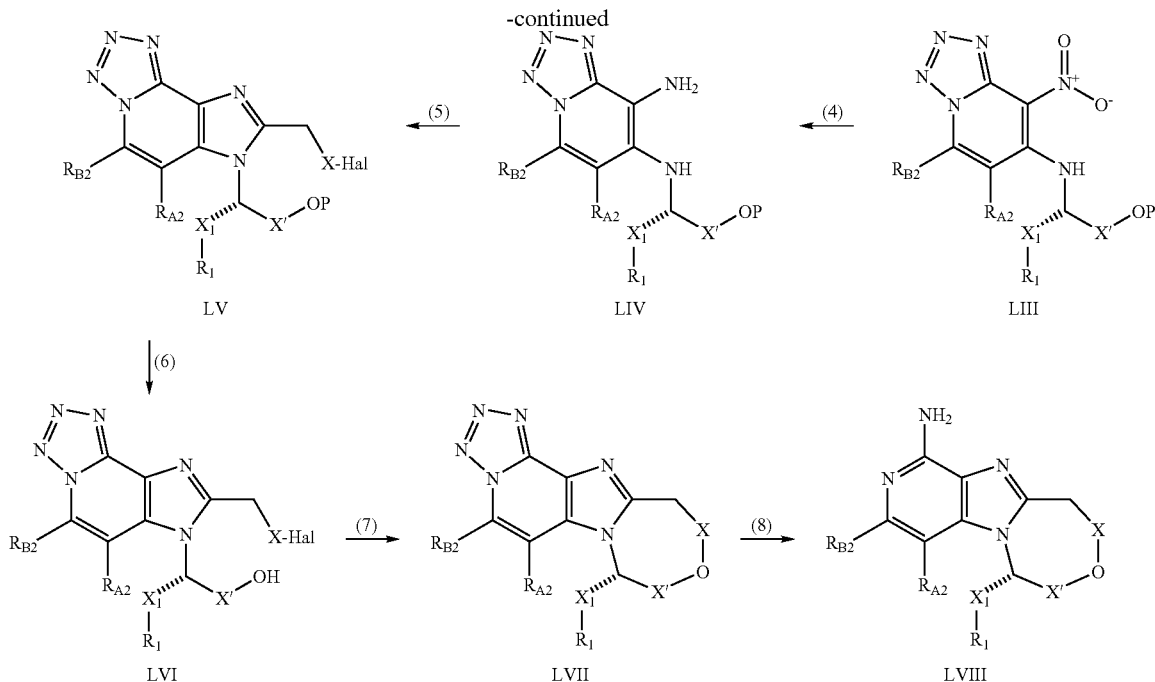

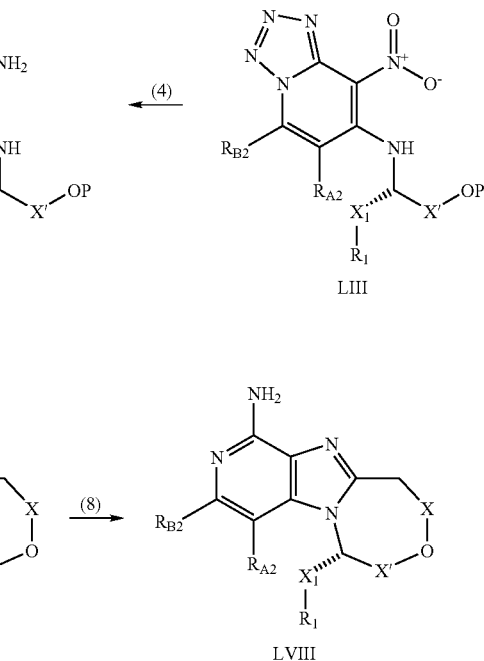

For some embodiments, naphthyridines of the invention can be prepared from tetrazolo compounds of Formulas LIX and LXIII according to Reaction Schemes VI and VII, wherein $R_1$, R, X, X', $X_1$, and p are as defined above, and —OTf is a trifluoromethanesulfonate group. Compounds of Formulas LIX and LXIII can be prepared by known synthetic routes; see, for example, U.S. Pat. No. 6,194,425 (Gerster et al.). The tetrazolo compounds of Formulas LIX and LXIII can each be treated with an amino alcohol of Formula XVI according to the method of step (1) of Reaction Scheme I to provide compounds of Formulas LX and LXIV, respectively. A hydroxy-substituted tetrazolonaphthyridine of Formula LX or LXIV is converted to a compound of Formula LXI or LXV according to the methods of steps (2) through (6) of Reaction Scheme I.

In step (7) of Reaction Scheme VI and VII, the tetrazolo group is removed from a compound of Formula LXI or LXV to provide a 1H-imidazo[4,5-c]naphthyridin-6-amine of Formula LXII or Formula LXVI. Removal of a tetrazolo group can be carried out in two steps by first treating the compound of Formula LXI or LXV with triphenylphosphine and then hydrolyzing the resulting intermediate. The reaction conditions described in U.S. Pat. No. 6,194,425 or the methods described in step (8) of Reaction Scheme V can be used.

Reaction Scheme VI

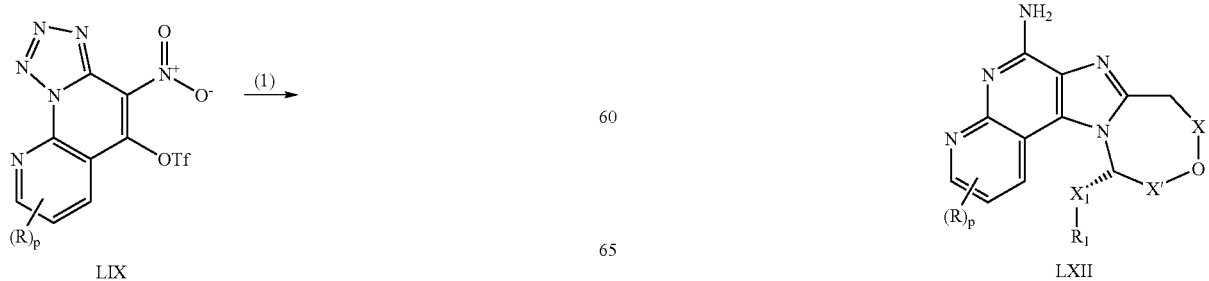

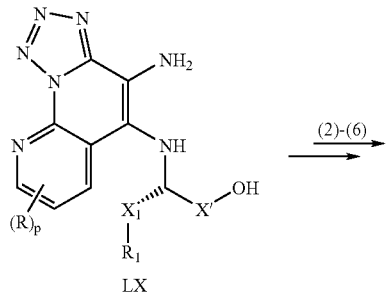

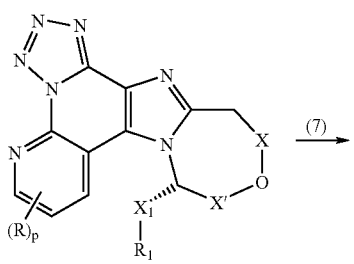

Reaction Scheme VII
-continued

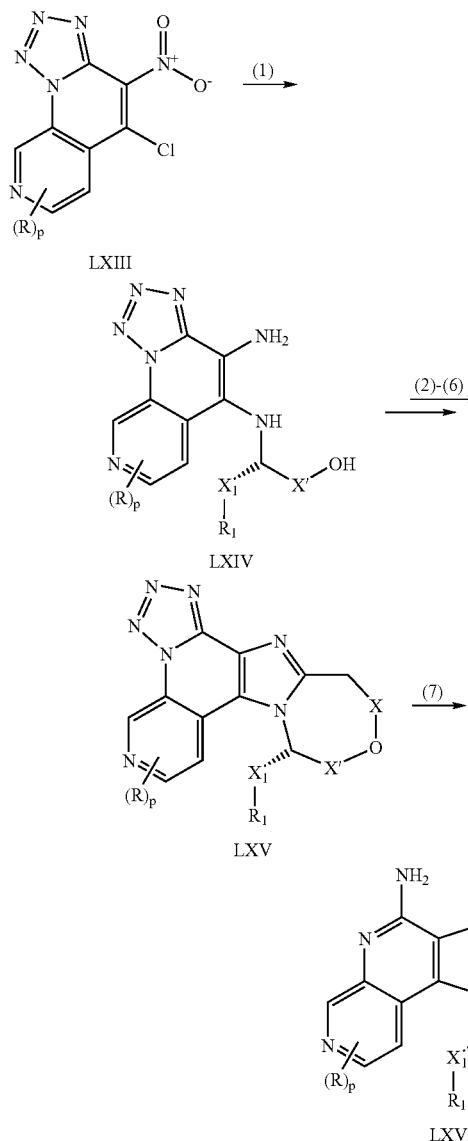

Reaction Scheme VIII

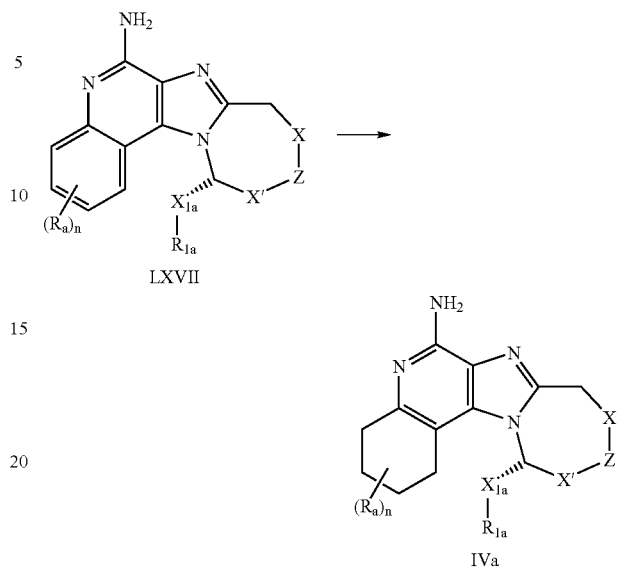

The reduction described in Reaction Scheme VIII can also be used to prepare a tetrahydro-1H-imidazo[4,5-c][1,5]naphthyridin-6-amine of Formula VIa, as shown in Reaction Scheme IX, wherein X, X', Z, p, $R_a$, $X_{1a}$, and $R_{1a}$ are as defined above. The product of Formula VIa is a subgenus of Formulas I, II, IIa, and VI.

Reaction Scheme IX

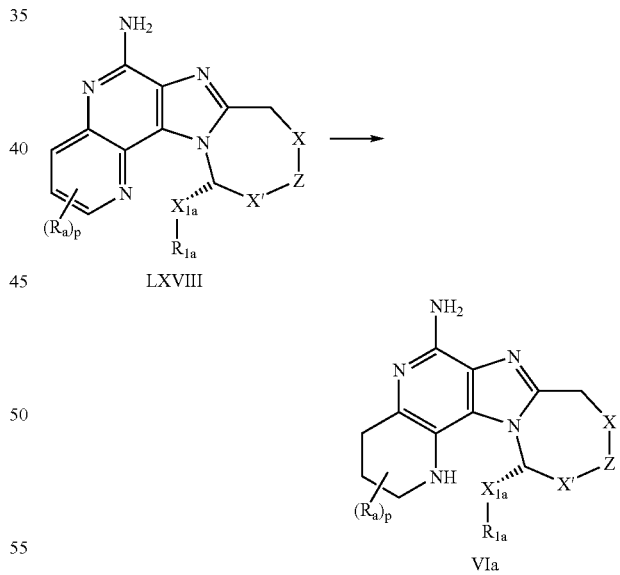

Compounds of the invention can also be prepared according to Reaction Scheme VIII, wherein X, X', and Z are as defined above; n is an integer from 0 to 4; $R_a$ is alkyl, alkoxy, hydroxy, or $-N(R_9)_2$; and $X_{1a}$ and $R_{1a}$ are subsets of $X_1$ and $R_1$ as defined above that do not include those substituents that one skilled in the art would recognize as being susceptible to reduction under the acidic hydrogenation conditions of the reaction. These susceptible groups include, for example, alkenyl, alkynyl, and aryl groups and groups bearing nitro substituents. Compounds of Formula LXVII can be prepared according to the methods of Reaction Scheme I or Reaction Scheme II.

In Reaction Scheme VIII, a 1H-imidazo[4,5-c]quinolin-6-amine of Formula LXVII is reduced to a tetrahydro-1H-imidazo[4,5-c]quinolin-6-amine of Formula IVa, a subgenus of Formulas I, II, IIa, and IV. The reaction is conveniently carried out under hetereogeneous hydrogenation conditions by adding platinum (IV) oxide to a solution of the compound of Formula LXVII in trifluoroacetic acid and placing the reaction under hydrogen pressure. The reaction can be carried out on a Parr apparatus at ambient temperature.

In some embodiments, compounds of the invention can be prepared according to Scheme X, wherein $R_1$, $R_{A2}$, $R_{B2}$, X, X', $X_1$, and P are as described above and Bn is benzyl. In step (1) of Reaction Scheme X, a 2-chloro-3-nitropyridine of Formula LII is treated with dibenzylamine to provide an $N^2$-dibenzyl-3-nitropyridin-2,4-diamine of Formula LXIX. The reaction can be carried out by combining the compound of Formula LII with dibenzylamine and a tertiary amine such as triethylamine in a suitable solvent such as toluene. The reaction can be carried out at an elevated temperature.

In steps (2), (3), (4), and (5) of Reaction Scheme X, an N²-dibenzyl-3-nitropyridin-2,4-diamine of Formula LXIX is converted to a compound of Formula LXX using the methods described in steps (4), (5), (6), and (7) respectively of Reaction Scheme V.

In step (6) of Reaction Scheme X, the benzyl groups of a compound of Formula LXX are cleaved using transfer hydrogenation to provide a compound of Formula LVIII. The reaction can be carried out by adding ammonium formate to a solution of the compound of Formula LXX in a suitable solvent such as ethanol or methanol in the presence of a catalyst such as palladium on carbon. The reaction can be carried out at an elevated temperature, for example, the reflux temperature of the solvent.

Reaction Scheme X

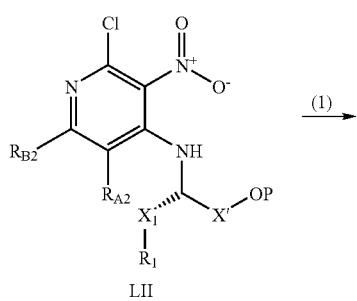

LII (1)

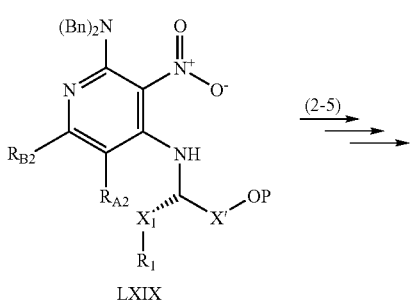

LXIX (2-5)

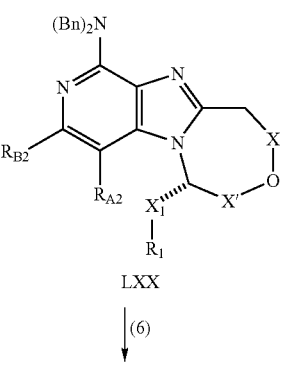

LXX (6)

-continued

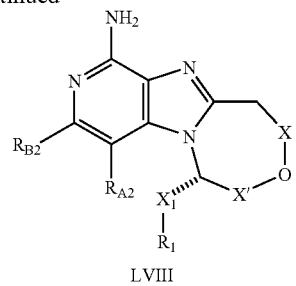

LVIII

In some embodiments, compounds of the invention can be prepared according to Reaction Scheme XI wherein R, X, Bn, E, and n are as defined above and

is a nitrogen containing heterocycle.

In step (1) of Reaction Scheme I, a 4-chloro-3-nitroquinoline or 4-chloro-3-nitro[1,5]naphthyridine of Formula XV is treated with an amino alcohol of Formula LXXI to provide a compound of Formula LXXII. The reaction can be carried out as described in step (1) of Reaction Scheme I.

In steps (2) through (8) of Reaction Scheme XI, a compound of Formula LXXII is converted to compound of Formula LXXIII using the methods described in steps (2) through (8) of Reaction Scheme I.

In step (9) of Reaction Scheme XI, the benzyl group of a compound of Formula LXXIII is cleaved to provide a hydroxy substituted compound of Formula LXXIV. The cleavage can be carried out on a Parr apparatus under hydrogenolysis conditions using a suitable heterogeneous catalyst such as palladium on carbon in a solvent such as methanol.

In step (10) of Reaction Scheme XI, a hydroxy substituted compound of Formula LXXIV is chlorinated to provide a chloro substituted compound of Formula LXXV. The reaction can be carried out by combining the compound of Formula LXXIV with thionyl chloride and heating the mixture at an elevated temperature, for example, 70° C.

In step (11) of Reaction Scheme XI, a chloro substituted compound of Formula LXXV is reacted with a nitrogen containing heterocycle of the Formula

to provide a compound of Formula LXXVI. The reaction can be carried out by heating a mixture of the compound of Formula LXXV and the heterocycle in a pressure vessel at an elevated temperature, such as, 150° C. Examples of suitable heterocycles include morpholine, thiomorpholine, 2,6-dimethylmorpholine, piperidine, 4-benzylpiperidine, 4-hydroxypiperidine, 4-(2-hydroxyethyl)piperidine, 4-(1-pyrrolidinyl)piperidine, (R)-3-pyrrolidinol, 4-piperidinecarboxamide, 1,2,3,4-tetrahydroisoquinoline, and thiazolidine.

Reaction Scheme XI

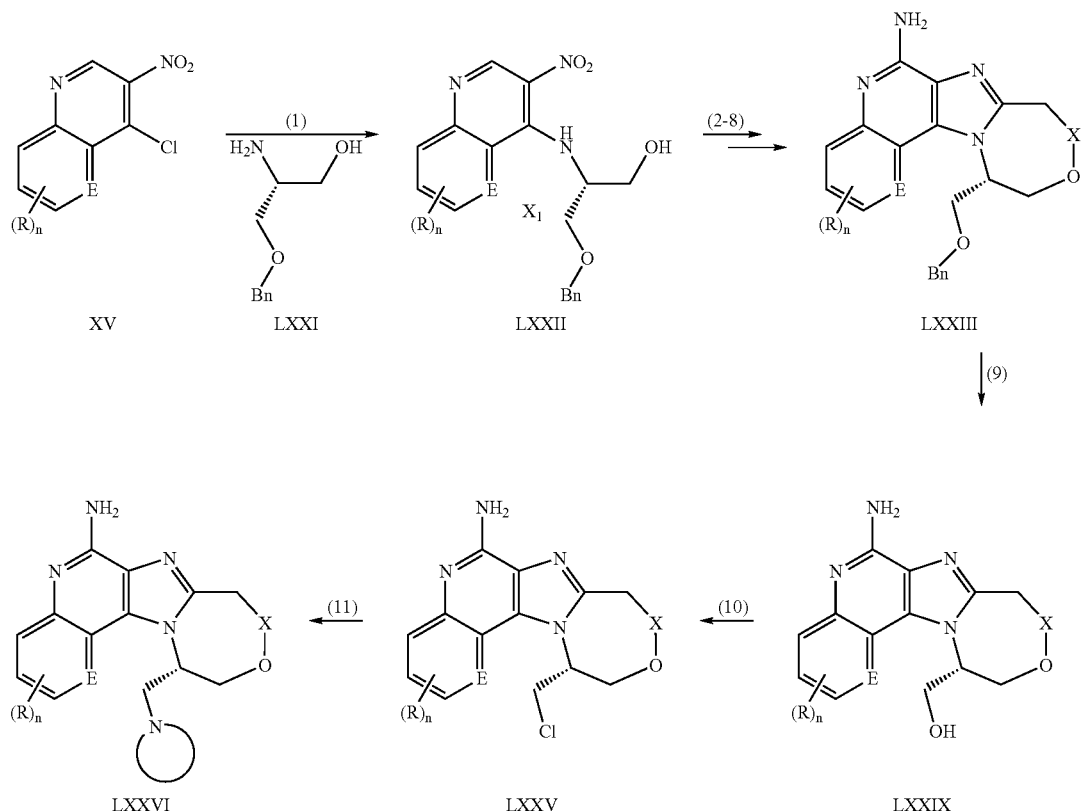

In some embodiments, compounds of the invention can be prepared according to Reaction Scheme XII, wherein R, Bn, E, X, and n are as defined above and $R_{1a}$ is phenyl which may be unsubstituted or substituted as described for $R_1$ above.

In steps (1) through (5) of Reaction Scheme XII, a compound of Formula LXXII is converted to a compound of Formula LXXVII using the methods describe in steps (2) through (6) of Reaction Scheme I.

In step (6) of Reaction Scheme XII, the benzyl group of a compound of Formula LXXVII is cleaved to provide a hydroxy substituted compound of Formula LXXVIII. The cleavage can be carried out using the method described in step (9) of Reaction Scheme XI.

In step (7) of Reaction Scheme XII, a hydroxy substituted compound of Formula LXXVIII is reacted with a benzyl bromide of the Formula $R_{1a}$—$CH_2$—Br to provide a benzyloxy substituted compound of Formula LXXIX. The reaction can be carried out by treating a solution of the compound of Formula LXXVIII in a suitable solvent, such as THF, with sodium hydride and then adding the benzyl bromide. The reaction can be carried out at ambient temperature or at a sub-ambient temperature, such as 0° C.

In steps (8) and (9) of Reaction Scheme XII, a compound of Formula LXXIX is converted to an amino substituted compound of Formula LXXX using the methods described in steps (7) and (8) respectively of Reaction Scheme I.

Reaction Scheme XII

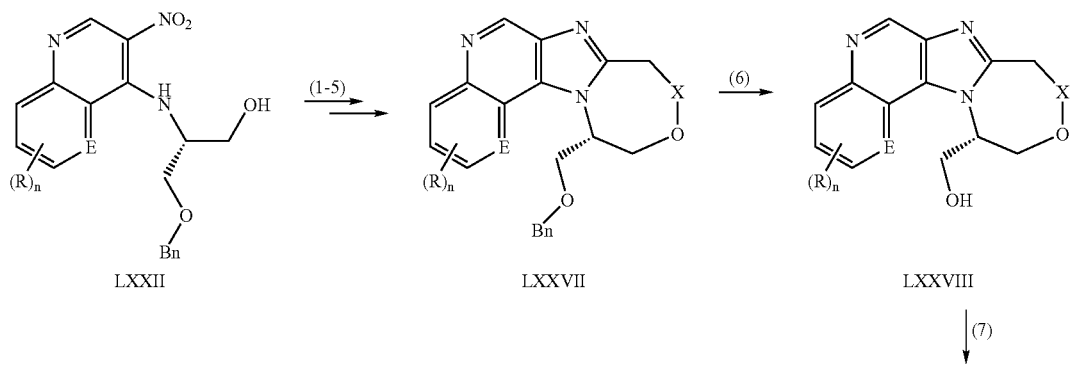

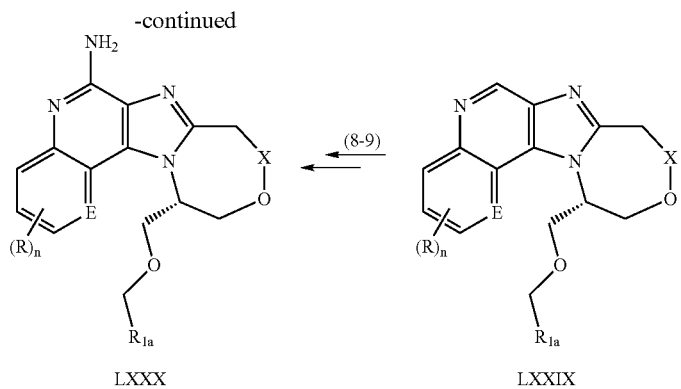

LXXX            LXXIX

In some embodiments, compounds of the invention can be prepared according to Reaction Scheme XIII, wherein R, $R_1$, X, X', $X_1$, Z, hal, and n are as defined above and wherein $R_{3d}$ is -heterocyclyl, -heterocyclylene-$R_4$, or -heterocyclylene-Y'—$R_4$, wherein $R_4$ and Y' are as defined above, and the heterocyclyl or heterocyclylene is attached to the quinoline or naphthyridine ring through a nitrogen atom. Compounds of Formula LXXXI can be prepared using a palladium-mediated coupling, which is carried out by combining a compound of the Formula XXXIII and the nitrogen-containing heterocyclyl compound in the presence of tris(dibenzylideneacetone)dipalladium, (±)-2,2'-bis(diphenylphosphino)-1,1'-binaphthyl, sodium tert-butoxide, and a suitable solvent such as toluene. The reaction can be carried out at an elevated temperature such as 80° C.

In step (1) of Reaction Scheme XIV, a compound of Formula LXXXII undergoes a Heck coupling reaction with an alkenyl-substituted phthalimide of the Formula

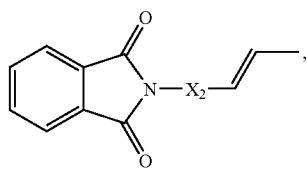

which is commercially available or can be prepared using known synthetic methods. The reaction can be carried out by combining a compound of Formula LXXXII and the alkenyl substituted phthalimide in the presence of palladium (II) acetate, triphenylphosphine or tri-ortho-tolylphosphine, and a base such as triethylamine or cesium carbonate in a suitable solvent such as acetonitrile, toluene, or DMF. The reaction can be carried out at an elevated temperature such as 85° C. to 125° C. under an inert atmosphere.

In step (2) of Reaction Scheme XIV, the alkenylene group is reduced to provide a compound of Formula LXXXIV. The reduction can be carried out as described in step (3) of Reaction Scheme I.

In steps (3) and (4) of Reaction Scheme XIV, a compound of Formula LXXXIV is oxidized and then aminated using the methods described in steps (7) and (8) respectively of Reaction Scheme I to provide a compound of Formula LXXXV.

In step (5) of Reaction Scheme XIV, the phthalimide group is removed from a compound of Formula LXXXV to provide an aminoalkyl substituted compound of Formula LXXXVI. The reaction can be carried out by adding hydrazine or hydrazine hydrate to a solution or suspension of a compound of Formula LXXXV in a suitable solvent such as ethanol. The reaction can be carried out at ambient temperature or at an elevated temperature, such as the reflux temperature of the solvent.

In step (6) of Reaction Scheme XIV, an aminoalkyl substituted compound of Formula LXXXVI is converted to a compound of Formula LXXXVII using the methods described in step (5) of Reaction Scheme II.

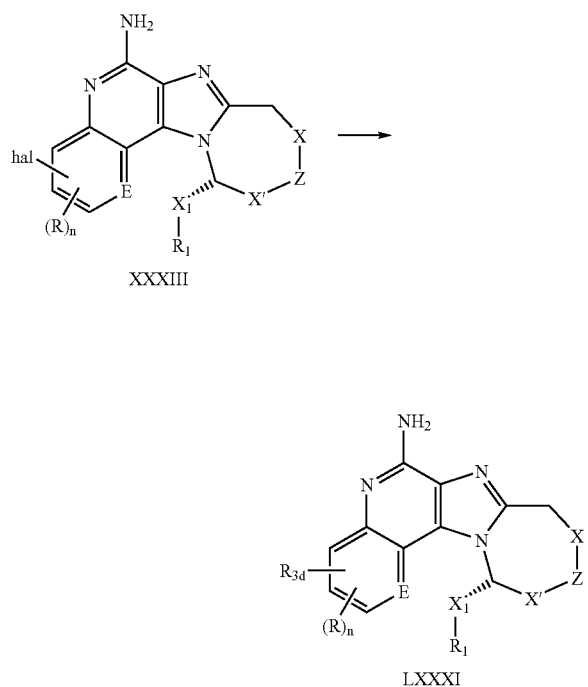

In some embodiments, compounds of the invention can be prepared according to Reaction Scheme XIV, wherein hal, $R_1$, $R_4$, X, X', $X_1$, Y, and Z are as defined above and $X_2$ is a bond or $C_{1-4}$ alkylene.

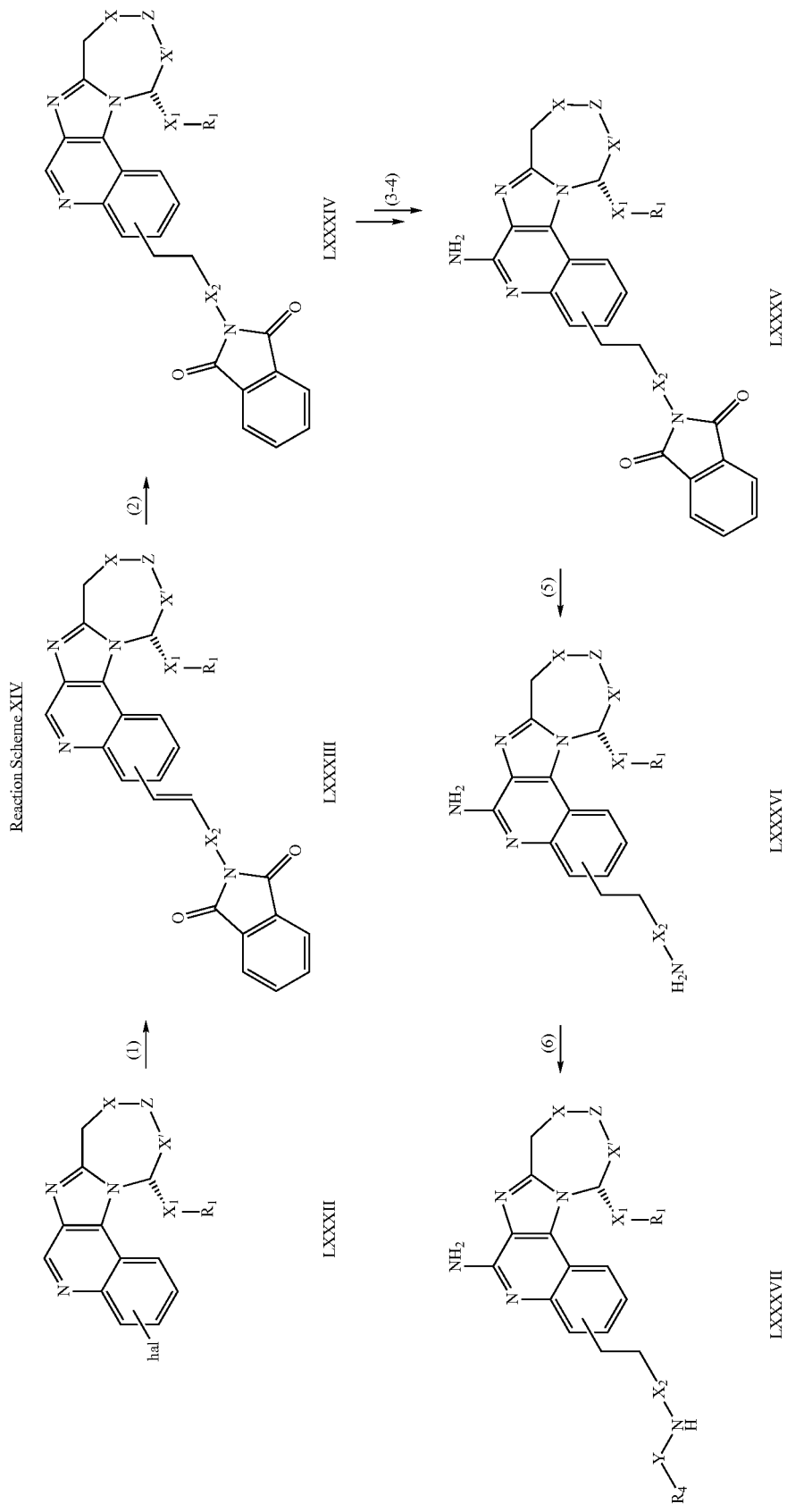

Compounds of the invention can also be prepared using variations of the synthetic routes shown in Reaction Schemes I through XIV that would be apparent to one of skill in the art. For example, the synthetic route shown in Reaction Scheme IV or Reaction Scheme V for the preparation of compounds wherein Z is —O— can be used to prepare compounds wherein Z is —N—Y—$R_2$— by using a Boc-protected diamine of Formula XXV in lieu of the amino alcohol of Formula XVI. In addition, the enantiomer of the products shown in Reaction Schemes I through IX or racemic mixtures can be prepared by using enantiomers of compounds of Formulas XVI or XXV or racemic reagents. Compounds of the invention can also be prepared using the synthetic routes described in the EXAMPLES below.

Prodrugs can be prepared in a variety of ways. For example, a compound with a hydroxy substituent may be converted to an ester, an ether, a carbonate, or a carbamate. For compounds containing an alcohol functional group, a prodrug can be formed by the replacement of the hydrogen atom of the alcohol group with a group such as $C_{1-6}$ alkanoyloxymethyl, 1-($C_{1-6}$ alkanoyloxy)ethyl, 1-methyl-1-($C_{1-6}$ alkanoyloxy)ethyl, $C_{1-6}$ alkoxycarbonyloxymethyl, N—($C_{1-6}$ alkoxycarbonyl)aminomethyl, succinoyl, $C_{1-6}$ alkanoyl, α-amino$C_{1-4}$ alkanoyl, arylacyl, —P(O)(OH)$_2$, —P(O)(O—$C_{1-6}$ alkyl)$_2$, $C_{1-6}$ alkoxycarbonyl, $C_{1-6}$ alkylcarbamoyl, and α-aminoacyl or α-aminoacyl-α-aminoacyl, where each α-aminoacyl group is independently selected from racemic, D, and L-amino acids. For compounds containing an alcohol functional group, particularly useful prodrugs are esters made from carboxylic acids containing one to six carbon atoms, unsubstituted or substituted benzoic acid esters, or esters made from naturally occurring L-amino acids.

Prodrugs can also be made from a compound containing an amino group by conversion of the amino group to a functional group such as an amide, carbamate, urea, amidine, or another hydroylizable group using conventional methods. A prodrug of this type can be made by the replacement of a hydrogen atom in an amino group, particularly the amino group at the 4-position, with a group such as —C(O)—R''', α-aminoacyl, α-aminoacyl-α-aminoacyl, —C(O)—O—R''', —C(O)—N(R''')—R''', —C(=N$Y_2$)—R''', —CH(OH)—C(O)—O$Y_2$, —CH(O$C_{1-4}$ alkyl)$Y_0$, —CH$_2Y_1$, or —CH(CH$_3$)$Y_1$; wherein R''' and R'''' are each independently $C_{1-10}$ alkyl, $C_{3-7}$ cycloalkyl, or benzyl, each of which may be unsubstituted or substituted by one or more substituents selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkylenyl, halo$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$; with the proviso that R'''' may also be hydrogen; each α-aminoacyl group is independently selected from racemic, D, or L-amino acids; $Y_2$ is hydrogen, $C_{1-6}$ alkyl, or benzyl; $Y_0$ is $C_{1-6}$ alkyl, carboxy$C_{1-6}$ alkylenyl, amino$C_{1-4}$ alkylenyl, mono-N—$C_{1-6}$ alkylamino$C_{1-4}$ alkylenyl, or di-N,N—$C_{1-6}$ alkylamino$C_{1-4}$ alkylenyl; and $Y_1$ is mono-N—$C_{1-6}$ alkylamino, di-N,N—$C_{1-6}$ alkylamino, morpholin-4-yl, piperidin-1-yl, pyrrolidin-1-yl, or 4-$C_{1-4}$ alkylpiperazin-1-yl. For compounds containing an amine functional group, particularly useful prodrugs are amides derived from carboxylic acids containing one to ten carbon atoms, amides derived from amino acids, and carbamates containing one to ten carbon atoms.

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In other embodiments, the compositions of the invention will contain sufficient active ingredient or prodrug to provide a dose of, for example, from about 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)× 0.007184, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A variety of dosage forms may be used, such as tablets, lozenges, capsules, parenteral formulations, syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce, and certain compounds or salts of the invention may inhibit, the production of certain cytokines in experiments performed according to the tests set forth below. These results indicate that the compounds or salts or compositions are useful for modulating the immune response in a number of different ways, rendering them useful in the treatment of a variety of disorders.

Cytokines whose production may be induced by the administration of compounds or salts of the invention, particularly compounds or salts of Formulas II, IIa, III, IV, V, VI, VII, and IX, generally include interferon-α (IFN-α) and tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts described herein can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Other cytokines whose production may be inhibited by the administration of compounds or salts of the invention, particularly compounds or salts of Formulas II-1, II-1a, III-1, IV-1, V-1, VI-1, VII-1, and IX-1, or compounds or salts of Formulas II, IIa, III, IV, V, VI, VII, and IX wherein Z is —N(—Y—$R_2$)—, include tumor necrosis factor-α (TNF-α). Among other effects, inhibition of TNF-α production can provide prophylaxis or therapeutic treatment of TNF-α mediated diseases in animals, making the compounds or salt useful in the treatment of, for example, autoimmune diseases. Accordingly, the invention provides a method of inhibiting TNF-α biosynthesis in an animal comprising administering an effective amount of a compound or salt or composition of the invention to the animal. The animal to which the compound or salt or composition is administered for inhibition of TNF-α biosynthesis may have a disease as described infra, for example an autoimmune disease, and administration of the compound or salt may provide therapeutic treatment. Alternatively, the compound or salt may be administered to the animal prior to the animal acquiring the disease so that administration of the compound or salt may provide a prophylactic treatment.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such as chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia greata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce or inhibit cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) or decreased (inhibited) over a background level of such cytokines. The precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments the induction or inhibition of cytokine biosynthesis may be performed by administering a compound or salt in a dose outside this range. In some of these embodiments, the method includes administering sufficient compound or salt or composition to provide a dose of from about 0.1 mg/m$^2$ to about 2.0 mg/m$^2$ to the subject, for example, a dose of from about 0.4 mg/m$^2$ to about 1.2 mg/m$^2$.

The invention also provides a method of treating a viral infection in an animal and a method of treating a neoplastic disease in an animal comprising administering an effective amount of a compound or salt of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m$^2$ to about 2.0 mg/m$^2$ to the subject, for example, a dose of from about 0.4 mg/m$^2$ to about 1.2 mg/m$^2$.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

For Examples 1, 5, 6, 9, 10, 11, 13, and 23 the enantiomer of the compound was prepared in a separate experiment; see Examples 25 through 32. A mixture of the two enantiomers was prepared and analyzed by chiral stationary phase high-performance liquid chromatography using a Chiralcel OD-RH column, 0.46 mm×15 cm, eluting with 30% methanol in pentane/methanol/triethylamine 90:10:0.2 (v/v/v) at a flow rate of 1.0 mL/min. Each of these examples was analyzed in comparison to the mixture of the two enantiomers, and the ratio favoring the enantiomer shown was greater than 99:1.

Example 1

(11S)-11-Isopropyl-10,11-dihydro-8H-[1,4]oxazino[4',3':1,2]imidazo[4,5-c]quinolin-6-amine

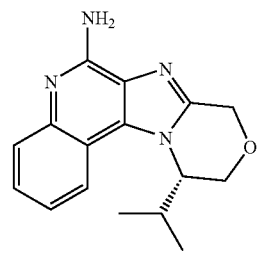

Part A

A suspension of 3-chloro-4-nitroquinoline (4.16 g, 20.0 mmol) in 200 mL of $CH_2Cl_2$ was treated with triethylamine (5.56 mL, 40.0 mmol) under an atmosphere of $N_2$. (2S)-2-Amino-3-methylbutan-1-ol (2.06 g, 20.0 mmol) was then added. The reaction mixture quickly turned yellow and the mixture was stirred overnight. The reaction mixture was then concentrated under reduced pressure to give a yellow solid. The resulting solid was partitioned between 100 mL of $H_2O$ and 100 mL $CH_2Cl_2$. The layers were separated and the organic portion was washed with $H_2O$ and brine. The organic layer was dried over $Na_2SO_4$, filtered, and concentrated to give (2S)-3-methyl-2-[(3-nitroquinolin-4-yl)amino]butan-1-ol (3.97 g) as a yellow solid.

Part B (2S)-3-Methyl-2-[(3-nitroquinolin-4-yl)amino]butan-1-ol (3.97 g, 14.4 mmol) was dissolved in 15 mL of dry pyridine and treated with tert-butyldimethylsilyl chloride (2.40 g, 15.9 mmol) and a catalytic amount of 4-(dimethylamino)pyridine (DMAP) (176 mg, 1.44 mmol). The reaction mixture was stirred under $N_2$ and heated to 56° C. After 2 days, the reaction mixture was concentrated under reduced pressure. The resulting solid was partitioned between 100 mL of $H_2O$ and 100 mL of ethyl acetate. The layers were separated and the organic portion was washed with $H_2O$ and brine. The organic portion was then dried over $Na_2SO_4$, filtered and concentrated under reduced pressure. Chromatography ($SiO_2$, 20% ethyl acetate/hexanes) gave N-[(1S)-1-({[tert-butyl(dimethyl)silyl]oxy}methyl)-2-methylpropyl]-3-nitroquinolin-4-amine (5.46 g) as a yellow syrup.

Part C

N-[(1S)-1-({[tert-Butyl(dimethyl)silyl]oxy}methyl)-2-methylpropyl]-3-nitroquinolin-4-amine (5.46 g, 14.0 mmol) was dissolved in 50 mL of toluene and the solution was placed in a pressure bottle. Platinum on carbon (5%, 1.0 g) was then added and the reaction mixture was shaken under $H_2$ at 48 PSI ($3.3 \times 10^5$ Pa). After 5 hours, the reaction mixture was filtered through a pad of CELITE filter agent. The pad was rinsed with toluene and the combined filtrates were concentrated under reduced pressure to give N'-[(1S)-1-({[tert-butyl(dimethyl) silyl]oxy}methyl)-2-methylpropyl]quinoline-3,4-diamine (5.05 g) as a brown foam.

Part D

N-[(1S)-1-({[tert-Butyl(dimethyl)silyl]oxy}methyl)-2-methylpropyl]quinoline-3,4-diamine (5.05 g, 14.0 mmol) was dissolved in 140 mL of dry 1,2-dichloroethane and the solution was stirred under $N_2$. Ethyl 2-chloroethanimidoate hydrochloride (3.33 g, 21.1 mmol) was then added and the reaction mixture was heated to 70° C. After stirring for 2 days, the reaction mixture was cooled and treated with 70 mL of $CHCl_3$ and 100 mL of saturated sodium bicarbonate ($NaHCO_3$) solution. The layers were separated and the organic portion was washed with $H_2O$ and brine. The organic portion was then dried over $Na_2SO_4$, filtered and concentrated under reduced pressure. Chromatography ($SiO_2$, 33%-50% ethyl acetate/hexanes) gave 1-[(1S)-1-({[tert-butyl(dimethyl)silyl]oxy}methyl)-2-methylpropyl]-2-(chloromethyl)-1H-imidazo[4,5-c]quinoline (4.85 g) as a dull yellow solid.

Part E

1-[(1S)-1-({[tert-Butyl(dimethyl)silyl]oxy}methyl)-2-methylpropyl]-2-(chloromethyl)-1H-imidazo[4,5-c]quinoline (4.85 g, 11.6 mmol) was dissolved in 110 mL of tetrahydrofuran (THF) and the solution was cooled to −78° C. under $N_2$. A 1.0 M solution of tetrabutylammonium fluoride in THF (12.8 mL) was added and the reaction mixture was allowed to warm to 0° C. overnight. The reaction mixture was then treated with 50 mL of saturated sodium bicarbonate solution and 100 mL of $CHCl_3$. The layers were separated and the organic portion was washed with $H_2O$ (50 mL) and brine (4×25 mL). The organic layer was dried over $Na_2SO_4$, filtered and concentrated under reduced pressure to give a yellow syrup. The syrup was concentrated from toluene (3×) to give a pale yellow foam. This material was dissolved in 100 mL of anhydrous THF and the solution was cooled 0° C. and stirred under $N_2$. Solid potassium tert-butoxide was then added and the reaction mixture was allowed to warm to ambient overnight. The THF was then removed under reduced pressure and the resulting material was partitioned between 100 mL of $CHCl_3$ and 100 mL of saturated sodium bicarbonate solution. The layers were separated and the organic portion was washed with $H_2O$ and brine. The organic portion was then dried over $Na_2SO_4$, filtered and concentrated under reduced to give brown foam. Chromatography ($SiO_2$, 0%-50% 80:18:2 $CHCl_3$/methanol/concentrated $NH_4OH$(CMA) in $CHCl_3$) gave (11S)-11-isopropyl-10,11-dihydro-8H-[1,4]oxazino[4',3':1,2]imidazo[4,5-c]quinoline (2.13 g) as a light yellow solid.

Part F (11S)-11-Isopropyl-10,11-dihydro-8H-[1,4]oxazino[4',3':1,2]imidazo[4,5-c]quinoline (1.13 g, 4.23 mmol) was dissolved in 40 mL of $CH_2Cl_2$ and treated with 3-chloroperoxybenzoic acid (MCPBA) (1.13 g, 77% max). After stirring for 75 minutes, the reaction was treated with 20 mL of 2% $Na_2CO_3$ solution and the layers were separated. The aqueous layer was then extracted with $CH_2Cl_2$ (3×10 mL). The combined organic layers were washed with 10 mL of brine. The organic portion was then dried over $Na_2SO_4$, filtered and concentrated under reduced pressure to give (11S)-1-isopropyl-10,11-dihydro-8H-[1,4]oxazino[4',3':1,2]imidazo[4,5-c]quinoline 5-oxide (1.20 g) as a crusty, off-white solid.

Part G (11S)-11-Isopropyl-10,11-dihydro-8H-[1,4]oxazino[4',3':1,2]imidazo[4,5-c]quinoline 5-oxide (1.20 g, 4.23 mmol) was dissolved in 50 mL of $CH_2Cl_2$ and treated with 5 mL of concentrated ammonium hydroxide solution. The mixture was stirred rapidly and then p-toluenesulfonyl chloride (849 mg, 4.45 mmol) was carefully added. Rapid stirring was continued for 2 hours. The reaction mixture was then diluted with 25 mL of $CH_2Cl_2$ and 25 mL of $H_2O$. The layers were separated and the organic portion was washed with 2% $Na_2CO_3$ solution (3×25 mL), $H_2O$ and brine. The organic portion was dried over $Na_2SO_4$, filtered and concentrated under reduced pressure. Chromatography ($SiO_2$, 5-25% CMA/$CHCl_3$) gave an off-white powder. Crystallization from ethyl acetate gave (11S)-11-isopropyl-10,11-dihydro-8H-[1,4]oxazino[4',3':1,2]imidazo[4,5-c]quinolin-6-amine (479 mg) as amber crystals, mp 249.0-250.0° C.

$^1$H NMR (300 MHz, $CDCl_3$) δ 7.82 (t, J=9.2 Hz, 2H), 7.52 (ddd, J=1.2, 7.1, 8.3 Hz, 1H), 7.32 (ddd, J=1.0, 7.2, 8.0 Hz, 1H), 5.38 (s, 2H), 5.17 (d, J=15.8 Hz, 1H), 4.96 (d, J=15.8 Hz, 1H), 4.61 (t, J=3.8 Hz, 1H), 4.48 (d, J=12.6 Hz, 1H), 4.05 (dd, J=3.3, 12.5 Hz, 1H), 2.66 (m, 1H), 1.22 (d, J=7.1 Hz, 3H), 0.89 (d, J=6.9 Hz, 3H); $^{13}$C NMR (75 MHz, $CDCl_3$) δ 151.3, 146.0, 144.8, 132.5, 127.3, 127.2, 122.3, 119.9, 115.6, 65.0, 63.8, 58.9, 31.4, 29.7, 19.4, 17.2; MS m/z 283 (M+H)$^+$. Anal. calcd for $C_{16}H_{18}N_4O$: C, 68.06; H, 6.43; N, 19.84. Found: C, 67.85; H, 6.65; N, 20.01.

Example 2

(11S)-11-Isopropyl-2,3,4,8,10,11-hexahydro-1H-[1,4]oxazino[4',3':1,2]imidazo[4,5-c]quinolin-6-amine

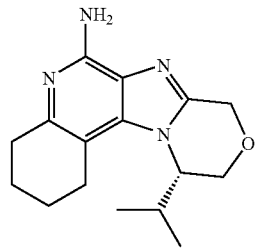

(11S)-11-Isopropyl-10,11-dihydro-8H-[1,4]oxazino[4',3':1,2]imidazo[4,5-c]quinolin-6-amine (320 mg, 1.13 mmol) was dissolved in 3 mL of trifluoroacetic acid and the solution was placed in a pressure bottle. Platinum oxide (250 mg) was then added and the reaction mixture was shaken under $H_2$ at 50 PSI ($3.4 \times 10^5$ Pa). After 20 hours, the reaction mixture was filtered through a pad of CELITE filter agent. The pad was rinsed with a mixture of iso-propanol and $CH_2Cl_2$ and the combined filtrates were concentrated under reduced pressure to give a syrup. The syrup was partitioned between $H_2O$ and $CHCl_3$. The aqueous portion was made basic by addition of 10% NaOH solution until pH >12. The layers were separated and the organic portion was washed successively with 10% NaOH (2×), $H_2O$ and brine. The organic portion was then dried over $Na_2SO_4$, filtered and concentrated under reduced pressure to give a tan foam. Crystallization from ethyl acetate gave the title compound (215 mg) as light amber crystals, mp 158.0-160.0° C.

¹H NMR (300 MHz, CDCl₃) δ 5.07 (d, J=15.8 Hz, 1H), 4.86 (d, J=15.7 Hz, 1H), 4.86 (s, 2H), 4.35 (d, J=12.5 Hz, 1H), 4.30 (t, J=4.0 Hz, 1H), 3.95 (dd, J=2.5, 12.5 Hz, 1H), 2.95-2.80 (m, 4H), 2.35 (m, 1H), 2.00-1.71 (m, 4H), 1.09 (d, J=7.1 Hz, 3H), 0.85 (d, J=7.0 Hz, 3H); ¹³C NMR (75 MHz, CDCl₃) δ 149.2, 147.8, 146.4, 138.3, 125.6, 107.6, 65.2, 64.4, 58.9, 33.9, 32.9, 24.4, 23.4, 23.3, 19.6, 17.8; MS m/z 287 (M+H)⁺. Anal. calcd for C₁₆H₂₂N₄O.0.28H₂O: C, 65.94; H, 7.80; N, 19.23. Found: C, 66.25; H, 7.92; N, 19.47.

Example 3

(11S)-3-(Benzyloxy)-11-isopropyl-10,11-dihydro-8H-[1,4]oxazino[4',3':1,2]imidazo[4,5-c]quinolin-6-amine

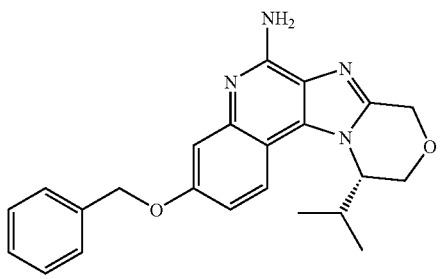

Part A

A mixture of triethyl orthoformate (92 mL, 0.55 mol) and 2,2-dimethyl-[1,3]-dioxane-4,6-dione (75.3 g, 0.522 mol) (Meldrum's acid) was heated at 55° C. for 90 minutes and then cooled to 45° C. A solution of 3-benzyloxyaniline (100.2 g, 0.5029 mol) in methanol (200 mL) was slowly added to the reaction over a period 45 minutes while maintaining the reaction temperature below 50° C. The reaction was then heated at 45° C. for one hour, allowed to cool to room temperature, and stirred overnight. The reaction mixture was cooled to 1° C., and the product was isolated by filtration and washed with cold ethanol (~400 mL) until the filtrate was colorless. 5-{[(3-Benzyloxy)phenylimino]methyl}-2,2-dimethyl-[1,3]-dioxane-4,6-dione (170.65 g) was isolated as a tan, powdery solid.

¹H NMR (300 MHz, DMSO-d₆): δ 11.21 (d, J=14.2 Hz, 1H), 8.61 (d, J=14.2 Hz, 1H), 7.49-7.30 (m, 7H), 7.12 (dd, J=8.1, 1.96 Hz, 1H), 6.91 (dd, J=8.4, 2.1 Hz, 1H), 5.16 (s, 2H), 1.68 (s, 6H).

Part B

A mixture of 5-{[(3-benzyloxy)phenylimino]methyl}-2,2-dimethyl-[1,3]-dioxane-4,6-dione (170.65 g, 0.483 mol) and DOWTHERM A heat transfer fluid (800 mL) was heated to 100° C. and then slowly added to a flask containing DOWTHERM A heat transfer fluid (1.3 L, heated at 210° C.) over a period of 40 minutes. During the addition, the reaction temperature was not allowed to fall below 207° C. Following the addition, the reaction was stirred at 210° C. for one hour, and then allowed to cool to ambient temperature. A precipitate formed, which was isolated by filtration, washed with diethyl ether (1.7 L) and acetone (0.5 L), and dried in an oven to provide 76.5 g of 7-benzyloxyquinolin-4-ol as a tan powder.

¹H NMR (300 MHz, DMSO-d₆): δ 11.53 (s, 1H), 7.99 (dd, J=2.4, 7.4 Hz, 1H), 7.79 (d, J=7.4 Hz, 1H), 7.50-7.32 (m, 5H), 7.00 (s, 1H), 6.98 (dd, J=2.5, 7.4 Hz, 1H), 5.93 (d, J=7.5 Hz, 1H), 5.20 (s, 2H).

Part C

A mixture of 7-benzyloxyquinolin-4-ol (71.47 g, 0.2844 mol) and propionic acid (700 mL) was heated to 125° C. with vigorous stirring. Nitric acid (23.11 mL of 16 M) was slowly added over a period of 30 minutes while maintaining the reaction temperature between 121° C. and 125° C. After the addition, the reaction was stirred at 125° C. for 1 hour then allowed to cool to ambient temperature. The resulting solid was isolated by filtration, washed with water, and dried in an oven for 1.5 days to provide 69.13 g of 7-benzyloxy-3-nitroquinolin-4-ol as a grayish powder.

¹H NMR (300 MHz, DMSO-d₆): δ 12.77 (s, 1H), 9.12 (s, 1H), 8.17 (dd, J=3.3, 6.3 Hz, 1H), 7.51-7.33 (m, 5H), 7.21-7.17 (m, 2H), 5.25 (s, 2H).

Part D

N,N-Dimethylformamide (DMF) (100 mL) was cooled to 0° C., and phosphorous oxychloride (27.5 mL, 0.295 mol) was added dropwise. The resulting solution was stirred for 25 minutes and then added dropwise to a mixture of 7-benzyloxy-3-nitroquinolin-4-ol (72.87 g, 0.2459 mol) in DMF (400 mL). Following the addition, the reaction was heated at 100° C. for 5 minutes, cooled to ambient temperature, and poured into ice water with stirring. A tan precipitate formed, which was isolated by filtration and dissolved in dichloromethane. The resulting solution was dried over magnesium sulfate, filtered, and concentrated under reduced pressure to yield 72.9 g of 7-benzyloxy-4-chloro-3-nitroquinoline as a light brown solid.

¹H NMR (300 MHz, DMSO-d₆): δ 9.34 (s, 1H), 8.36 (d, J=8.7 Hz, 1H), 7.71 (d, J=2.4 Hz, 1H), 7.66 (dd, J=2.4, 9.3 Hz, 1H), 7.56-7.51 (m, 2H), 7.46-7.34 (m, 3H), 5.40 (s, 2H).

Part E

The title compound was prepared from 7-benzyloxy-3-chloro-4-nitroquinoline and (2S)-2-amino-3-methylbutan-1-ol following Parts A through G listed for the preparation of Example 1 with the modification that Parts F and G were carried out in CHCl₃ as the solvent. Chromatography (SiO₂, 0-20% CMA/CHCl₃) gave an off-white powder. The white powder was slurried in 10 mL of CHCl₃ and filtered to give a white solid. The white solid was dissolved in a mixture of CH₂Cl₂ and methanol and then concentrated and the resulting solid was dried under vacuum at 65° C. to give (11S)-3-(benzyloxy)-11-isopropyl-10,11-dihydro-8H-[1,4]oxazino[4',3':1,2]imidazo[4,5-c]quinolin-6-amine as a white solid, mp 227-229° C.

¹H NMR (500 MHz, DMSO-d₆) δ 7.80 (d, J=9.0 Hz, 1H), 7.49 (d, J=7.3 Hz, 2H), 7.40 (m, 2H), 7.33 (t, J=7.3 Hz, 1H), 7.14 (d, J=2.6 Hz, 1H), 6.99 (dd, J=8.9, 2.6 Hz, 1H), 6.55 (s, 2H), 5.21 (s, 2H), 5.04 (d, J=15.5 Hz, 1H), 4.90 (d, J=15.5 Hz, 1H), 4.79 (m, 1H), 4.40 (d, J=12.6 Hz, 1H), 4.04 (dd, J=12.6, 3.3 Hz, 1H), 2.41 (m, 1H), 1.12 (d, J=7.0 Hz, 3H), 0.75 (d, J=7.0 Hz, 3H); ¹³C NMR (125 MHz, DMSO-d₆) δ 157.5, 152.6, 146.8, 145.6, 137.7, 132.3, 128.8, 128.1, 127.9, 125.5, 121.8, 112.3, 109.4, 109.0, 69.5, 64.5, 63.7, 57.8, 31.3, 19.2, 17.4; MS (ESI) m/z 389 (M+H)⁺. Anal. calcd for $C_{23}H_{24}N_4O_2$: C, 71.11; H, 6.23: N, 14.42. Found: C, 70.83; H, 5.88; N, 14.40.

Example 4

(11S)-6-Amino-11-isopropyl-10,11-dihydro-8H-[1,4]oxazino[4',3':1,2]imidazo[4,5-c]quinolin-3-ol

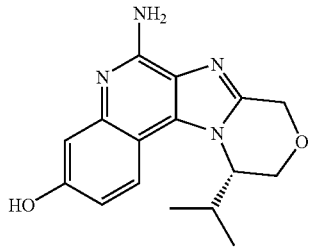

(11S)-3-(Benzyloxy)-11-isopropyl-10,11-dihydro-8H-[1,4]oxazino[4',3':1,2]imidazo[4,5-c]quinolin-6-amine (800 mg, 2.05 mmol) was dissolved in 260 mL of ethanol and the solution was placed in a pressure bottle. Palladium on carbon (10%, 460 mg) was then added and the reaction mixture was shaken under $H_2$ at 48 PSI ($3.3 \times 10^5$ Pa) overnight. The reaction mixture was filtered through a pad of CELITE filter agent. The pad was rinsed with 1:1 $CH_2Cl_2$/ethanol and the combined filtrates were concentrated under reduced pressure to give an off-white solid. Chromatography ($SiO_2$, 20-40% CMA/$CHCl_3$) gave the desired product (370 mg) as an off-white solid, mp 210-215° C.

¹H NMR (500 MHz, DMSO-$d_6$) δ 9.52 (br s, 1H), 7.71 (d, J=8.8 Hz, 1H), 6.97 (d, J=2.5 Hz, 1H), 6.81 (dd, J=8.8, 2.5 Hz, 1H), 6.48 (s, 2H), 5.03 (d, J=15.4 Hz, 1H), 4.89 (d, J=15.4 Hz, 1H), 4.75 (m, 1H), 4.40 (d, J=12.6 Hz, 1H), 4.03 (dd, J=12.6, 3.3 Hz, 1H), 2.42 (m, 1H), 1.12 (d, J=7.0 Hz, 3H), 0.75 (d, J=7.0 Hz, 3H); ¹³C NMR (125 MHz, DMSO-$d_6$) δ 156.6, 152.4, 147.0, 145.1, 132.5, 125.0, 121.7, 112.4, 110.0, 108.4, 64.5, 63.7, 57.8, 31.2, 19.2, 17.4; MS (ESI) m/z 299 (M+H)⁺. Anal. calcd for $C_{16}H_{18}N_4O_2 \cdot 0.61 H_2O$: C, 62.13; H, 6.26; N, 18.11. Found: C, 61.75; H, 6.10; N, 17.93.

Example 5

(11S)-11-Methyl-10,11-dihydro-8H-[1,4]oxazino[4',3':1,2]imidazo[4,5-c]quinolin-6-amine

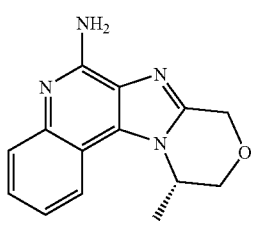

The title compound was prepared from 3-chloro-4-nitroquinoline and (S)-2-amino-1-propanol following Parts A through G listed for the preparation of Example 1 with the modification that Part F was carried out in $CHCl_3$ as the solvent. Crystallization from 1,2-dichloroethane gave (11S)-11-methyl-10,11-dihydro-8H-[1,4]oxazino[4',3':1,2]imidazo[4,5-c]quinolin-6-amine as an off-white solid, mp 280-282° C.

¹H NMR (300 MHz, DMSO-$d_6$) δ 8.00 (d, J=7.7 Hz, 1H), 7.64 (d, J=7.7 Hz, 1H), 7.44 (m, 1H), 7.28 (m, 1H), 6.60 (s, 2H), 5.08 (m, 2H), 4.95 (d, J=15.6 Hz, 1H), 4.12 (m, 2H), 1.56 (d, J=6.5 Hz, 3H); ¹³C NMR (75 MHz, DMSO-$d_6$) δ 152.2, 145.4, 145.0, 131.6, 126.9, 126.6, 121.6, 120.7, 114.8, 68.7, 65.1, 50.5, 19.3; MS m/z 255 (M+H)⁺. Anal. calcd for $C_{14}H_{14}N_4O$: C, 66.13; H, 5.55; N, 22.03. Found: C, 65.82; H, 5.58; N, 21.98.

Example 6

(11S)-11-Methyl-2,3,4,8,10,11-hexahydro-1H-[1,4]oxazino[4',3':1,2]imidazo[4,5-c]quinolin-6-amine

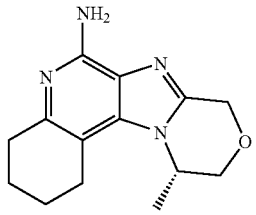

(11S)-11-Methyl-10,11-dihydro-8H-[1,4]oxazino[4',3':1,2]imidazo[4,5-c]quinolin-6-amine (1.13 g, 4.45 mmol) was dissolved in 20 mL of trifluoroacetic acid and the solution was placed in a pressure bottle. Platinum oxide (1.34 g) was then added and the reaction mixture was shaken under $H_2$ at 50 PSI ($3.4 \times 10^5$ Pa). After 2 days, the reaction mixture was filtered through a pad of CELITE filter agent. The pad was rinsed with 1,2-dichloroethane and the combined filtrates were concentrated under reduced pressure to give a peach colored oil. The oil was partitioned between dilute $NH_4OH$ solution and $CH_2Cl_2$. The layers were separated and the organic portion was washed successively with dilute $NH_4OH$ solution and brine. The organic portion was then dried over $Na_2SO_4$, filtered and concentrated under reduced pressure to give a white foam. Chromatography ($SiO_2$, 10-30% CMA/$CHCl_3$) gave (11S)-11-methyl-2,3,4,8,10,11-hexahydro-1H-[1,4]oxazino[4',3':1,2]imidazo[4,5-c]quinolin-6-amine (0.57 g) as a white solid, mp 209-211° C.

¹H NMR (300 MHz, DMSO-$d_6$) δ 5.75 (s, 2H), 4.97 (d, J=15.6 Hz, 1H), 4.84-4.75 (m, 2H), 3.99 (s, 2H), 2.99 (m, 1H), 2.91 (m, 1H), 2.67 (m, 2H), 1.78 (m, 4H), 1.43 (d, J=6.5 Hz, 3H); ¹³C NMR (75 MHz, DMSO-$d_6$) δ 148.3, 145.2, 143.5, 135.9, 123.6, 104.3, 67.5, 63.6, 48.7, 31.2, 21.9, 21.8, 21.7, 19.7; MS m/z 259 (M+H)⁺. Anal. calcd for $C_{14}H_{18}N_4O$: C, 65.09; H, 7.02; N, 21.69. Found: C, 64.87; H, 7.22; N, 21.59.

Example 7

(11S)-3-(Benzyloxy)-11-methyl-10,11-dihydro-8H-[1,4]oxazino[4',3':1,2]imidazo[4,5-c]quinolin-6-amine

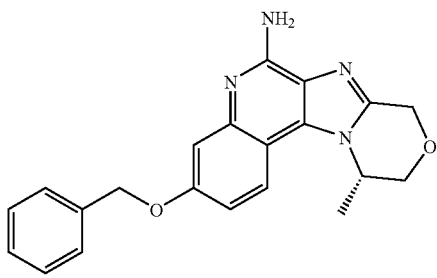

The title compound was prepared from 7-benzyloxy-3-chloro-4-nitroquinoline and (S)-2-amino-1-propanol following Parts A through G listed for the preparation of Example 1 with the modification that Parts F and G were carried out in $CHCl_3$ as the solvent. Chromatography ($SiO_2$, 0-20% CMA/$CHCl_3$) gave an off-white powder. The white powder was slurried in 10 mL of $CHCl_3$ and filtered to give a white solid. The white solid was dissolved in a mixture of $CH_2Cl_2$ and methanol and then concentrated to give (11S)-3-(benzyloxy)-11-methyl-10,11-dihydro-8H-[1,4]oxazino[4',3':1,2]imidazo[4,5-c]quinolin-6-amine as a white solid, mp 218-220° C.

¹H NMR (300 MHz, DMSO-$d_6$) δ 7.90 (d, J=8.9 Hz, 1H), 7.49 (m, 2H), 7.43-7.33 (m, 3H), 7.15 (d, J=2.5 Hz, 1H), 7.00 (dd, J=8.9, 2.5 Hz, 1H), 6.52 (s, 2H), 5.21 (s, 2H), 5.06 (m, 2H), 4.91 (d, J=15.5 Hz, 1H), 4.10 (m, 2H), 1.52 (d, J=6.4 Hz, 3H); ¹³C NMR (125 MHz, DMSO-$d_6$) δ 157.6, 152.5, 146.8, 144.6, 137.7, 132.0, 128.8, 128.1, 128.0, 125.4, 121.8, 112.4, 109.1, 108.9, 69.5, 68.7, 65.1, 50.3, 19.2; MS (ESI) m/z 361 (M+H)⁺. Anal. calcd for $C_{21}H_{20}N_4O_2$: C, 69.98; H, 5.59; N, 15.54. Found: C, 69.30; H, 5.48; N, 15.38.

Example 8

(11S)-6-Amino-11-methyl-10,11-dihydro-8H-[1,4]oxazino[4',3':1,2]imidazo[4,5-c]quinolin-3-ol

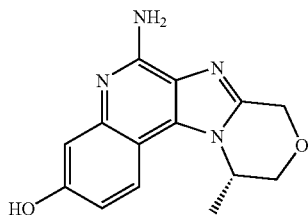

(11S)-3-(Benzyloxy)-11-methyl-10,11-dihydro-8H-[1,4]oxazino[4',3':1,2]imidazo[4,5-c]quinolin-6-amine (770 mg, 2.05 mmol) was dissolved in 200 mL of ethanol and the solution was placed in a pressure bottle. Palladium on carbon (10%, 430 mg) was then added and the reaction mixture was shaken under $H_2$ at 48 PSI (3.3×10⁵ Pa) for 3 days. The reaction mixture was filtered through a pad of CELITE filter agent. The pad was rinsed with 1:1 $CH_2Cl_2$/ethanol and the combined filtrates were concentrated under reduced pressure to give an off-white solid. Chromatography ($SiO_2$, 30-50% CMA/$CHCl_3$) gave an off-white solid. Recrystallization from acetonitrile and methanol gave (11S)-6-amino-11-methyl-10,11-dihydro-8H-[1,4]oxazino[4',3':1,2]imidazo[4,5-c]quinolin-3-ol (110 mg) as a white powder. mp>250° C.; ¹H NMR (500 MHz, DMSO-$d_6$) δ 9.49 (br s, 1H), 7.81 (d, J=8.9 Hz, 1H), 6.97 (d, J=2.5 Hz, 1H), 6.80 (dd, J=8.9, 2.5 Hz, 1H), 6.42 (s, 2H), 5.05 (d, J=15.4 Hz, 1H), 5.00 (m, 1H), 4.91 (d, J=15.4 Hz, 1H), 4.10 (m, 2H), 1.52 (d, J=6.5 Hz, 3H); ¹³C NMR (125 MHz, DMSO-$d_6$) δ 156.7, 152.3, 147.0, 144.2, 132.2, 125.0, 121.6, 112.4, 110.1, 108.2, 68.8, 65.1, 50.3, 19.2; MS (ESI) m/z 271 (M+H)⁺. Anal. calcd for $C_{14}H_{14}N_4O_2$: C, 62.21; H, 5.22; N, 20.73. Found: C, 61.99; H, 5.05; N, 20.62.

Example 9

(11S)-11-Phenyl-10,11-dihydro-8H-[1,4]oxazino[4',3':1,2]imidazo[4,5-c]quinolin-6-amine

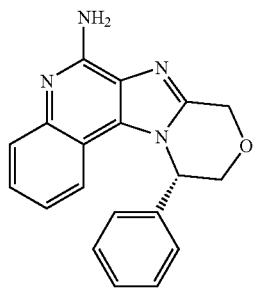

The title compound was prepared from 3-chloro-4-nitroquinoline and (2S)-2-amino-2-phenylethanol following Parts A through G listed for the preparation of Example 1 with the modification that Part C was carried out in acetonitrile as the solvent and Part F was carried out in $CHCl_3$ as the solvent. Chromatography ($SiO_2$, 0-20% CMA/$CHCl_3$) gave an off-white solid. A second chromatography ($SiO_2$, 50% methanol/$CHCl_3$) gave (11S)-11-phenyl-10,11-dihydro-8H-[1,4]oxazino[4',3':1,2]imidazo[4,5-c]quinolin-6-amine as a white solid. mp 284-286° C.; ¹H NMR (300 MHz, DMSO-$d_6$) δ 7.60 (m, 1H), 7.54 (m, 1H), 7.29 (m, 4H), 7.06 (m, 2H), 7.00 (m, 1H), 6.64 (s, 2H), 6.26 (m, 1H), 5.23 (d, J=15.6 Hz, 1H), 5.09 (d, J=15.6 Hz, 1H), 4.43 (dd, J=12.0, 3.3 Hz, 1H), 4.22 (d, J=11.7 Hz, 1H); ¹³C NMR (125 MHz, DMSO-$d_6$) δ 152.2, 146.3, 145.1, 139.8, 132.2, 129.1, 128.1, 126.9, 126.8, 126.5, 126.3, 121.1, 120.9, 114.7, 70.7, 65.3, 58.0; MS (ESI) m/z 317 (M+H)+. Anal. calcd for C19H16N4O: C, 72.14; H, 5.10; N, 17.71. Found: C, 71.81; H, 4.97; N, 17.44.

Example 10

(11S)-1-Benzyl-10,11-dihydro-8H-[1,4]oxazino[4',3':1,2]imidazo[4,5-c]quinolin-6-amine

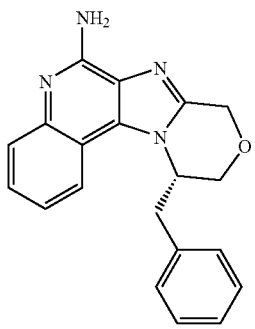

The title compound was prepared from 3-chloro-4-nitroquinoline and (2S)-2-amino-3-phenylpropan-1-ol following Parts A through G listed for the preparation of Example 1 with the modification that Part F was carried out in CHCl3 as the solvent. Crystallization from 2-propanol followed by chromatography (SiO2, 0-20% CMA/CHCl3) gave (11S)-11-benzyl-10,11-dihydro-8H-[1,4]oxazino[4',3':1,2]imidazo[4,5-c]quinolin-6-amine as an off-white solid, mp 170-177° C.

$^1$H NMR (500 MHz, DMSO-d6) δ 8.17 (d, J=8.1 Hz, 1H), 7.98 (dd, J=8.3, 1.0 Hz, 1H), 7.48 (m, 1H), 7.38 (m, 5H), 7.30 (m, 1H), 6.66 (s, 2H), 5.24 (d, J=10.9 Hz, 1H), 5.11 (d, J=15.5 Hz, 1H), 4.98 (d, J=15.5 Hz, 1H), 4.01 (m, 2H), 3.27 (m, 1H), 3.14 (m, 1H); $^{13}$C NMR (125 MHz, DMSO-d6) δ 152.3, 145.5, 145.1, 136.8, 131.7, 129.6, 129.1, 127.3, 127.0, 126.9, 126.7, 121.7, 120.6, 114.9, 65.1, 64.8, 55.2, 37.9; MS (ESI) m/z 331 (M+H)+. Anal calcd for C20H18N4O.0.10H2O: C, 72.31; H, 5.52; N, 16.87. Found: C, 72.04; H, 5.42; N, 16.65.

Example 11

(11R)-11-(1-Fluoro-1-methylethyl)-10,11-dihydro-8H-[1,4]oxazino[4',3':1,2]imidazo[4,5-c]quinolin-6-amine

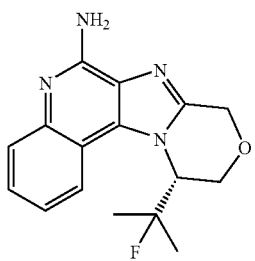

Part A tert-Butyl (4R)-4-(1-hydroxy-1-methylethyl)-2,2-dimethyl-1,3-oxazolidine-3-carboxylate (3.80 g, 14.7 mmol), prepared by the method of Joullie, Tetrahedron, 52, pp. 11673-11694, (1996) was dissolved in 90 mL of anhydrous CH2Cl2. The solution was cooled to −78° C. under an atmosphere of N2. (Diethylamino)sulfur trifluoride (DAST) (2.25 mL, 17.0 mmol) was added and the reaction was allowed to warm to ambient temperature overnight. The reaction was quenched with saturated NaHCO3 solution and the layers were separated. The organic portion was washed successively with H2O and brine, dried over Na2SO4 and concentrated under reduced pressure. Chromatography (SiO2, 7% EtOAc/hexanes) gave tert-butyl (4R)-4-(1-fluoro-1-methylethyl)-2,2-dimethyl-1,3-oxazolidine-3-carboxylate (1.98 g) as a nearly colorless liquid.

Part B tert-Butyl (4R)-4-(1-fluoro-1-methylethyl)-2,2-dimethyl-1,3-oxazolidine-3-carboxylate (1.98 g, 7.59 mmol) was dissolved in 20 mL of ethanol and treated with a 4.3 M solution of HCl in ethanol (7.5 mL). The solution was heated to 100° C. for 1 hour. The reaction mixture was cooled and concentrated under reduced pressure to give a white solid. The white solid was applied to a SiO2 column. Elution with 1:1 CHCl3/CMA gave (2R)-2-amino-3-fluoro-3-methylbutan-1-ol (678 mg) as a colorless oil.

Part C

The title compound was prepared from 3-chloro-4-nitroquinoline and (2R)-2-amino-3-fluoro-3-methylbutan-1-ol following Parts A through G listed for the preparation of Example 1 with the following modification. In Part E, a solution of 1-[(1S)-1-({[tert-butyl(dimethyl)silyl]oxy}methyl)-2-fluoro-2-methylpropyl]-2-(chloromethyl)-1H-imidazo[4,5-c]quinoline (1.63 g, 3.78 mmol) in CH2Cl2 (100 mL) was cooled to −78° C. A solution of tetrabutylammonium fluoride in THF (4.16 mL of 1.0 M) was added, and the reaction mixture was allowed to warm to room temperature overnight. The solution was cooled again to −78° C., and additional tetrabutylammonium fluoride in THF (0.4 mL) was added, and the reaction mixture was allowed to warm to room temperature and stirred for one day. The reaction mixture was washed with saturated aqueous NaHCO3 followed by brine (4×50 mL), dried over Na2SO4, filtered and concentrated under reduced pressure. Chromatography (SiO2, eluting with 3% methanol in CHCl3) provided (11R)-11-(1-fluoro-1-methylethyl)-10,11-dihydro-8H-[1,4]oxazino[4',3':1,2]imidazo[4,5-c]quinoline as a light yellow foam.

Crystallization of the final compound from ethyl acetate gave (11R)-11-(1-fluoro-1-methylethyl)-10,11-dihydro-8H-[1,4]oxazino[4',3':1,2]imidazo[4,5-c]quinolin-6-amine as peach colored crystals, mp 242-244° C.

$^1$H NMR (300 MHz, CDCl3) δ 8.11 (ddd, J=1.2, 3.7, 8.3 Hz, 1H), 7.79 (dd, J=1.0, 8.4 Hz, 1H), 7.49 (ddd, J=1.4, 7.0, 8.4 Hz, 1H), 7.27 (ddd, J=1.3, 7.0, 8.3 Hz, 1H), 5.37 (s, 2H), 5.22 (d, J=16.2 Hz, 1H), 5.04 (dd, J=2.5, 9.5 Hz, 1H), 5.04 (d, J=16.1 Hz, 1H), 4.39 (d, J=12.8 Hz, 1H), 4.10 (ddd, J=3.0, 4.6, 12.8 Hz, 1H), 1.71 (d, J=21.5 Hz, 3H), 1.27 (d, J=23.5 Hz, 3H); $^{13}$C NMR (75 MHz, CDCl3) δ 151.1, 145.4, 145.0, 134.1, 127.2, 126.9, 121.6, 121.4, 115.9, 97.9 (d, J=172.8 Hz), 65.1 (d, J=8.7 Hz), 65.0, 61.6 (d, J=21.4 Hz), 25.7 (d, J=23.6 Hz), 23.5 (d, J=24.2 Hz); MS m/z 301 (M+H)+. Anal. calcd for $C_{16}H_{17}FN_4O$: C, 63.99; H, 5.71; N, 18.65. Found: C, 63.62; H, 5.90; N, 18.40.

Example 12

(11R)-11-(1-Fluoro-1-methylethyl)-2,3,4,8,10,11-hexahydro-1H-[1,4]oxazino[4',3':1,2]imidazo[4,5-c]quinolin-6-amine

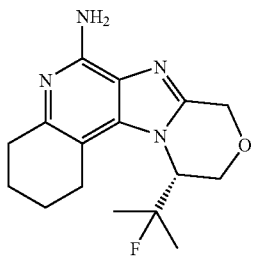

(11R)-11-(1-Fluoro-1-methylethyl)-10,11-dihydro-8H-[1,4]oxazino[4',3':1,2]imidazo[4,5-c]quinolin-6-amine (300 mg, 1.00 mmol) was dissolved in 10 mL of trifluoroacetic acid and the solution was placed in a pressure bottle. Platinum oxide (227 mg) was then added and the reaction mixture was shaken under H2 at 50 PSI (3.4×10⁵ Pa). After 20 hours, an additional 200 mg of catalyst was added and the mixture was shaken under $H_2$ at 50 PSI (3.4×10⁵ Pa) for an additional 24 h. The reaction mixture was filtered through a pad of CELITE filter agent. The pad was rinsed with a mixture of 2-propanol and $CH_2Cl_2$ and the combined filtrates were concentrated under reduced pressure to give a syrup. The syrup was partitioned between $H_2O$ and $CHCl_3$. The aqueous portion was made basic by addition of 10% NaOH solution until the pH was higher than 12. The layers were separated and the organic portion was washed successively with 10% NaOH (2×), $H_2O$ and brine. The organic portion was then dried over $Na_2SO_4$, filtered and concentrated under reduced pressure to give a tan foam. Chromatography ($SiO_2$, 25-33% CMA/$CHCl_3$) followed by crystallization from ethyl acetate gave (11R)-11-(1-fluoro-1-methylethyl)-2,3,4,8,10,11-hexahydro-1H-[1,4]oxazino[4',3':1,2]imidazo[4,5-c]quinolin-6-amine (159 mg) as off-white crystals, mp 195.5-197.0° C.

¹H NMR (300 MHz, $CDCl_3$) δ 5.12 (d, J=16.0 Hz, 1H), 4.93 (d, J=16.0 Hz, 1H), 4.86 (s, 2H), 4.69 (dd, J=1.9, 2.5 Hz, 1H), 4.27 (d, J=12.8 Hz, 1H), 4.05 (ddd, J=2.9, 4.7, 12.8 Hz, 1H), 3.20 (m, 1H), 2.93-2.77 (m, 2H), 2.65 (m, 1H), 1.95-1.64 (m, 4H), 1.61 (d, J=27.7 Hz, 3H), 1.17 (d, J=23.7 Hz, 3H); ¹³C NMR (75 MHz, $CDCl_3$) δ 149.0, 148.2, 145.9, 139.7, 125.6, 109.2, 97.7 (d, J=171.8 Hz), 65.7 (d, J=8.3 Hz), 65.3, 61.4 (d, J=21.1 Hz), 33.1, 25.8 (d, J=23.6 Hz), 24.7 (d, J=11.2 Hz), 23.7 (d, J=24.4 Hz), 23.5, 23.2; MS m/z 305 (M+H)+. Anal. calcd for $C_{16}H_{21}FN_4O$: C, 62.22; H, 7.02; N, 18.14. Found: C, 62.02; H, 7.18; N, 18.36.

Example 13

2-[(11R)-6-Amino-10,11-dihydro-8H-[1,4]oxazino[4',3':1,2]imidazo[4,5-c]quinolin-11-yl]propan-2-ol

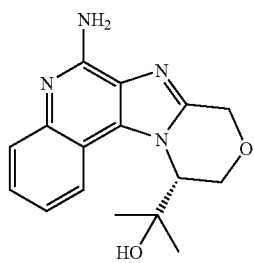

Part A tert-Butyl (4R)-4-(1-hydroxy-1-methylethyl)-2,2-dimethyl-1,3-oxazolidine-3-carboxylate (7.32 g, 27.8 mmol), prepared by the method of Joullie, *Tetrahedron*, 52, pp. 11673-11694, (1996), was dissolved in 20 mL of ethanol. A 4.3 M solution of hydrochloric acid in ethanol (15 mL) was then added and the reaction mixture was heated 85° C. After 2 hours, the solution was cooled and concentrated under reduced pressure. The resulting residue was concentrated with 2-propanol several times and then with $Et_2O$ to give crude (2R)-2-amino-3-methylbutane-1,3-diol hydrochloride (4.32 g) as a brown oil. This was used in the next reaction without further purification.

Part B (2R)-2-amino-3-methylbutane-1,3-diol hydrochloride (4.32 g, 27.8 mmol) was dissolved in 10 mL of pyridine and the solution was stirred under $N_2$. tert-Butyldimethylsilyl chloride (16.8 g, 111 mmol) and DMAP (339 mg, 2.8 mmol) were then added and the reaction mixture was heated to 65° C. After 3 days, the reaction was cooled and treated with in 3.5% $NaH_2PO_4$ solution. The solution was extracted with 200 mL $CH_2Cl_2$ and then with an additional 50 mL of $CH_2Cl_2$. The combined organic layers were washed with $H_2O$ and brine. The organic layer was then dried over $Na_2SO_4$, filtered and concentrate under reduced pressure. Chromatography ($SiO_2$, 3% MeOH/$CHCl_3$ with 0.1% $NH_4OH$) gave (1R)-2-{[tert-butyl(dimethyl)silyl]oxy}-1-({[tert-butyl(dimethyl)silyl]oxy}methyl)-2-methylpropylamine (5.85 g) as a light amber oil.

Part C (1R)-2-{[tert-butyl(dimethyl)silyl]oxy}-1-({[tert-butyl(dimethyl)silyl]oxy}methyl)-2-methylpropylamine (5.85 g, 16.9 mmol) was dissolved in 200 mL of anhydrous $CH_2Cl_2$ and the mixture was stirred under $N_2$. To this solution were added triethylamine (4.70 mL, 33.8 mmol) and 4-chloro-3-nitroquinoline (3.51 g, 16.9 mmol). The reaction mixture soon became bright yellow. After stirring for 3 days, the reaction mixture was concentrated under reduced pressure. The resulting yellow solid was partitioned between 200 mL $H_2O$ and 200 mL $CH_2Cl_2$. The layers were separated and the organic portion was washed with $H_2O$ and then brine. The organic portion was dried over $Na_2SO_4$, filtered and concentrated under reduced pressure. The resulting light brown oil was dissolved in about 200 mL of refluxing hexanes. A small amount of brown precipitate formed and was removed by filtration. The hexanes solution was concentrated to give a yellow solid. Chromatography (SiO$_2$, 10% ethyl acetate/CH$_2$Cl$_2$) gave N-[(1R)-2-{[tert-butyl(dimethyl)silyl]oxy}-1-({[tert-butyl(dimethyl)silyl]oxy}methyl)-2-methylpropyl]-3-nitroquinolin-4-amine (6.51 g) as a yellow solid.

Part D

N-[(1R)-2-{[tert-Butyl(dimethyl)silyl]oxy}-1-({[tert-butyl(dimethyl)silyl]oxy}methyl)-2-methylpropyl]-3-nitroquinolin-4-amine (6.51 g, 12.5 mmol) was dissolved in 75 mL toluene and the solution was placed in a pressure bottle. Platinum on carbon (5%, 2.0 g) was then added and the reaction mixture was shaken under H$_2$ at 48 PSI (3.3×10$^5$ Pa). After 6 hours, the reaction mixture was filtered through a pad of CELITE filter agent. The pad was rinsed with toluene and 2-propanol and the combined filtrates were concentrated under reduced pressure to give N$^4$-[(1R)-2-{[tert-butyl(dimethyl)silyl]oxy}-1-({[tert-butyl(dimethyl)silyl]oxy}methyl)-2-methylpropyl]quinoline-3,4-diamine (6.12 g) as a brown foam.

Part E

N$^4$-[(1R)-2-{[tert-Butyl(dimethyl)silyl]oxy}-1-({[tert-butyl(dimethyl)silyl]oxy}methyl)-2-methylpropyl]quinoline-3,4-diamine (6.12 g, 12.5 mmol) was dissolved in 100 mL of dry 1,2-dichloroethane and the solution was stirred under N$_2$. Ethyl 2-chloroethanimidoate hydrochloride (2.77 g, 17.5 mmol) was then added and the reaction mixture was heated to 70° C. After stirring for 3 days, the reaction mixture was treated with an additional 1.00 g of ethyl 2-chloroethanimidoate hydrochloride and the reaction temperature was increased to 85° C. After stirring for 2 days, the reaction was cooled and the 1,2-dichloroethane was removed under reduced pressure. The resulting material was partitioned between 200 mL of saturated NaHCO$_3$ solution and 200 mL of ethyl acetate. The layers were separated and the organic portion was washed with H$_2$O and brine. The organic portion was then dried over Na$_2$SO$_4$, filtered and concentrated under reduced pressure. Chromatography (SiO$_2$, 25%-50% ethyl acetate/hexanes) gave 1-[(1R)-2-{[tert-butyl(dimethyl)silyl]oxy}-1-({[tert-butyl(dimethyl)silyl]oxy}methyl)-2-methylpropyl]-2-(chloromethyl)-1H-imidazo[4,5-c]quinoline (1.74 g) as a golden syrup.

Part F

1-[(1R)-2-{[tert-Butyl(dimethyl)silyl]oxy}-1-({[tert-butyl(dimethyl)silyl]oxy}methyl)-2-methylpropyl]-2-(chloromethyl)-1H-imidazo[4,5-c]quinoline (1.74 g, 3.18 mmol) was dissolved in 80 mL of CH$_2$Cl$_2$ and the solution was cooled to −78° C. under N$_2$. Tetrabutylammonium fluoride (1.0 M solution in THF, 3.50 mL) was added slowly and the stirred reaction mixture was allowed to warm to ambient temperature overnight. The reaction mixture was then treated with an additional 0.3 mL of tetrabutylammonium fluoride solution and stirring was continued for 2 days. The reaction mixture was then treated with saturated NaHCO$_3$ solution, and the layers were separated. The organic portion was washed with brine (4×20 mL), dried over Na$_2$SO$_4$, filtered and concentrated under reduced pressure. Chromatography (SiO$_2$, 2-5% MeOH/CHCl$_3$) gave (11R)-11-(1-{[tert-butyl(dimethyl)silyl]oxy}-1-methylethyl)-10,11-dihydro-8H-[1,4]oxazino[4',3':1,2]imidazo[4,5-c]quinoline (1.14 g) as a yellow syrup.

Part G (11R)-11-(1-{[tert-Butyl(dimethyl)silyl]oxy}-1-methylethyl)-10,11-dihydro-8H-[1,4]oxazino[4',3':1,2]imidazo[4,5-c]quinoline (1.14 g, 2.91 mmol) was dissolved in 30 mL of THF and the stirred solution was cooled to −50° C. Tetrabutylammonium fluoride (1.0 M solution in THF, 4.37 mL) was added slowly and the stirred reaction mixture was allowed top warm to ambient temperature over 4 hours. The reaction mixture was concentrated under reduced pressure and the resulting material was partitioned between 50 mL of CH$_2$Cl$_2$ and saturated NaHCO$_3$ solution. The layers were separated and the organic portion was washed with brine (4×20 mL), dried over Na$_2$SO$_4$, filtered and concentrated under reduced pressure. Chromatography (SiO$_2$, 8% MeOH/CHCl$_3$) gave 2-[(11R)-10,11-dihydro-8H-[1,4]oxazino[4',3':1,2]imidazo[4,5-c]quinolin-11-yl]propan-2-ol (755 mg) as an off-white solid.

Part H

2-[(11R)-10,11-Dihydro-8H-[1,4]oxazino[4',3':1,2]imidazo[4,5-c]quinolin-11-yl]propan-2-ol (755 mg, 2.67 mmol) was dissolved in 30 mL of CH$_2$Cl$_2$ and treated with MCPBA (57-86%, 806 mg). After stirring for 75 minutes, the reaction was treated with 50 mL of 2% Na$_2$CO$_3$ solution and the layers were separated. The aqueous layer was then extracted with 10% methanol/CHCl$_3$ (10×10 mL). The combined organic layers were washed with 10 mL of brine. The organic portion was then dried over Na$_2$SO$_4$, filtered and concentrated under reduced to give 2-[(11R)-5-oxido-10,11-dihydro-8H-[1,4]oxazino[4',3':1,2]imidazo[4,5-c]quinolin-11-yl]propan-2-ol (798 mg) as a light yellow solid.

Part I

2-[(11R)-5-Oxido-10,11-dihydro-8H-[1,4]oxazino[4',3':1,2]imidazo[4,5-c]quinolin-11-yl]propan-2-ol (798 mg, 2.67 mmol) was dissolved in 25 mL of CH$_2$Cl$_2$ and treated with 5 mL of concentrated NH$_4$OH solution. The mixture was stirred rapidly and p-toluenesulfonyl chloride (534 mg, 2.80 mmol) was carefully added. Rapid stirring was continued for 2 hours. The reaction mixture was then treated with 25 mL of H$_2$O and the layers were separated. The aqueous portion was extracted with additional CH$_2$Cl$_2$ (3×20 mL). The combined organic layers were dried over Na$_2$SO$_4$, filtered and concentrated under reduced pressure. Chromatography (SiO$_2$, 10% methanol/CHCl$_3$) gave a light yellow foam. Crystallization from ethyl acetate gave 2-[(11R)-6-amino-10,11-dihydro-8H-[1,4]oxazino[4',3':1,2]imidazo[4,5-c]quinolin-11-yl]propan-2-ol (220 mg) as white crystals, mp 216-217° C.

$^1$H NMR (300 MHz, DMSO-d$_6$) δ 8.40 (dd, J=1.0, 8.4 Hz, 1H), 7.55 (dd, J=1.1, 8.3 Hz, 1H), 7.35 (ddd, J=1.3, 6.9, 8.4 Hz, 1H), 7.14 (ddd, J=1.3, 7.0, 8.3 Hz, 1H), 6.45 (s, 2H), 5.12 (d, J=16.0 Hz, 1H), 4.98 (d, J=15.8 Hz, 1H), 4.95 (d, J=1.7 Hz, 1H), 4.72 (s, 1H), 4.40 (d, J=12.4 Hz, 1H), 4.02 (dd, J=2.7, 12.6 Hz, 1H), 1.36 (s, 3H), 1.06 (s, 3H); $^{13}$C NMR (75 MHz, DMSO-d$_6$) δ 152.1, 146.5, 145.1, 134.1, 126.8, 126.4, 126.0, 123.6, 120.1, 116.3, 73.6, 65.3, 64.2, 62.3, 28.6, 27.0;

MS m/z 299 (M+H)+. Anal. calcd for $C_{16}H_{18}N_4O_2$: C, 64.41; H, 6.08; N, 18.78. Found: C, 64.18; H, 5.93; N, 18.67.

Example 14

(11S)-1-Isopropyl-10,11-dihydro-8H-[1,4]oxazino[4',3':1,2]imidazo[4,5-c][1,5]naphthyridin-6-amine

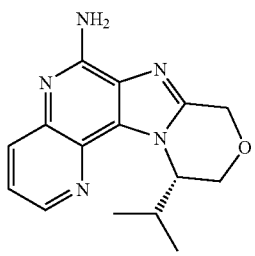

The title compound was prepared from 4-chloro-3-nitro[1,5]naphthyridine (see U.S. Pat. No. 6,194,425, Example 29) and (2S)-2-amino-3-methylbutan-1-ol following Parts A through G listed for the preparation of Example 1 with the modification that Part F was carried out in $CHCl_3$ as the solvent. Chromatography ($SiO_2$, 0-20% $CMA/CHCl_3$) gave a light yellow solid. Recrystallization from 1,2-dichloroethane gave (11S)-11-isopropyl-10,11-dihydro-8H-[1,4]oxazino[4',3':1,2]imidazo[4,5-c][1,5]naphthyridin-6-amine (0.72 g) as a white solid, mp 194-196° C.

$^1$H NMR (300 MHz, DMSO-$d_6$) δ 8.52 (dd, J=1.5, 4.3 Hz, 1H), 7.94 (dd, J=1.5, 8.4 Hz, 1H), 7.44 (m, 1H), 6.92 (s, 2H), 5.13 (d, J=15.9 Hz, 1H), 4.97 (m, 2H), 4.39 (d, J=12.6 Hz, 1H), 4.04 (dd, J=3.4, 12.6 Hz, 1H), 2.75 (m, 1H), 1.08 (d, J=7.0 Hz, 3H), 0.79 (d, J=7.0 Hz, 3H); $^{13}$C NMR (125 MHz, DMSO-$d_6$) δ 152.6, 147.2, 143.7, 140.3, 134.0, 132.9, 131.6, 129.5, 122.2, 64.4, 63.7, 58.5, 31.4, 19.4, 17.6; MS (ESI) m/z 284 (M+H)+; Anal. calcd for $C_{15}H_{17}N_5O$: C, 63.59; H, 6.05; N, 24.72. Found: C, 63.40; H, 5.94; N, 25.00.

Example 15

(11S)-11-Methyl-10,11-dihydro-8H-[1,4]oxazino[4',3':1,2]imidazo[4,5-c][1,5]naphthyridin-6-amine

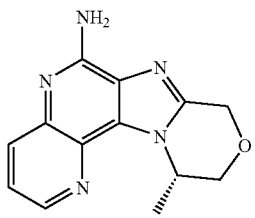

The title compound was prepared from 4-chloro-3-nitro[1,5]naphthyridine and (S)-(+)-2-amino-1-propanol following Parts A through G listed for the preparation of Example 1 with the modifications that in Part E the reaction with tetrabutylammonium fluoride was carried out in $CH_2Cl_2$ as the solvent, Part F was carried out in chloroform as the solvent, and Part G was carried out in 1,2-dichloroethane as the solvent. Chromatography ($SiO_2$, 10-30% $CMA/CHCl_3$) gave an off-white solid. Recrystallization from 1,2-dichloroethane gave (11S)-11-methyl-10,11-dihydro-8H-[1,4]oxazino[4',3':1,2]imidazo[4,5-c][1,5]naphthyridin-6-amine (0.68 g) as a white crystalline solid, mp 240-242° C.

$^1$H NMR (300 MHz, DMSO-$d_6$) δ 8.54 (dd, J=1.5, 4.4 Hz, 1H), 7.92 (dd, J=1.5, 8.4 Hz, 1H), 7.46 (m, 1H), 6.87 (s, 2H), 5.22 (m, 1H), 5.13 (d, J=15.8 Hz, 1H), 4.97 (d, J=15.8 Hz, 1H), 4.12 (m, 2H), 1.63 (d, J=6.4 Hz, 3H); $^{13}$C NMR (75 MHz, DMSO-$d_6$) δ 152.5, 146.5, 143.8, 140.2, 133.8, 132.8, 131.2, 129.4, 122.2, 68.7, 64.9, 51.2, 19.9; MS (ESI) m/z 296 (M+H)+; Anal. calcd for $C_{13}H_{13}N_5O$: C, 61.17; H, 5.13; N, 27.43. Found: C, 60.93; H, 5.14; N, 27.62.

Example 16

(11R)-11-(1-Fluoro-1-methylethyl)-10,11-dihydro-8H-[1,4]oxazino[4',3':1,2]imidazo[4,5-c][1,5]naphthyridin-6-amine

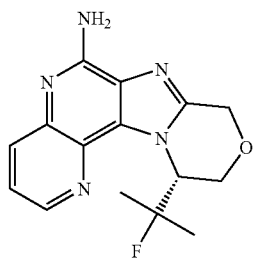

Part A

The title compound was prepared from 4-chloro-3-nitro[1,5]naphthyridine and (2R)-2-amino-3-fluoro-3-methylbutan-1-ol following Parts A through G listed for the preparation of Example 1 with the following modifications. Part D was carried out in propyl acetate as the solvent, and Part F was carried out in $CHCl_3$ as the solvent. Part E was carried out according to the modification described in Part C of Example 11. Chromatography on the final compound ($SiO_2$, 0-6% $MeOH/CH_2Cl_2$) afforded (11R)-11-(1-fluoro-1-methylethyl)-10,11-dihydro-8H-[1,4]oxazino[4',3':1,2]imidazo[4,5-c][1,5]naphthyridin-6-amine (0.72 g) as an off-white solid, mp 192-194° C.

$^1$H NMR (300 MHz, DMSO-$d_6$) δ 8.48 (dd, J=1.5, 4.3 Hz, 1H), 7.91 (dd, J=1.5, 8.4 Hz, 1H), 7.42 (m, 1H), 6.88 (s, 2H), 5.58 (dd, J=2.3, 12.9 Hz, 1H), 5.17 (d, J=16.1 Hz, 1H), 5.01 (d, J=16.1 Hz, 1H), 4.45 (d, J=12.6 Hz, 1H), 4.12 (dt, J=3.1, 12.7 Hz, 1H), 1.42 (m, 6H); $^{13}$C NMR (75 MHz, DMSO-$d_6$) δ 152.4, 147.4, 143.0, 140.3, 134.2, 132.4, 129.4, 122.3, 97.3 (d, J=174.6 Hz), 64.1, 63.8, 59.6 (d, J=21.5 Hz), 25.5 (d, J=23.5 Hz), 24.9 (d, J=23.9 Hz); MS (ESI) m/z 302 (M+H)+;

Anal. calcd for $C_{15}H_{16}FN_5O$: C, 59.79; H, 5.35; N, 23.24. Found: C, 59.69; H, 5.14; N, 23.21.

Example 17

(11R)-6-Amino-11-(1-fluoro-1-methylethyl)-10,11-dihydro-8H-[1,4]oxazino[4',3':1,2]imidazo[4,5-c]quinolin-3-ol

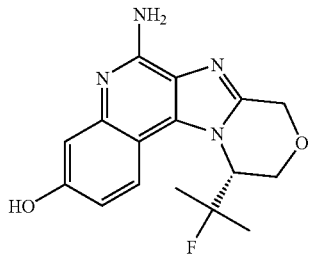

Part A (11R)-3-(Benzyloxy)-1-(1-fluoro-1-methylethyl)-10,11-dihydro-8H-[1,4]oxazino[4',3':1,2]imidazo[4,5-c]quinolin-6-amine was prepared from 7-(benzyloxy)-4-chloro-3-nitroquinoline and (2R)-2-amino-3-fluoro-3-methylbutan-1-ol following Parts A through G listed for the preparation of Example 1 with the modifications that Part C was carried out in acetonitrile as the solvent and Parts F and G were carried out in chloroform as the solvent. Chromatography ($SiO_2$, 0-20% $CMA/CHCl_3$) afforded (11R)-3-(benzyloxy)-1-(1-fluoro-1-methylethyl)-10,11-dihydro-8H-[1,4]oxazino[4',3':1,2]imidazo[4,5-c]quinolin-6-amine (310 mg) as an orange solid.

Part B (11R)-3-(Benzyloxy)-11-(1-fluoro-1-methylethyl)-10,11-dihydro-8H-[1,4]oxazino[4',3':1,2]imidazo[4,5-c]quinolin-6-amine (310 mg, 0.763 mmol) was dissolved in ethanol (50 mL) and the solution was placed in a pressure bottle. Palladium on carbon (10%, 140 mg) was added and the reaction mixture was shaken under H2 at 48 PSI ($3.3 \times 10^5$ Pa) overnight. The reaction mixture was filtered through a pad of CELITE filter agent. The pad was rinsed with 1:1 $CH_2Cl_2$/ethanol and the combined filtrates were concentrated under reduced pressure to give an off white solid. Chromatography ($SiO_2$, 30-50% $CMA/CHCl_3$) followed by recrystallization from 1,2-dichloroethane gave (11R)-6-amino-11-(1-fluoro-1-methylethyl)-10,11-dihydro-8H-[1,4]oxazino[4',3':1,2]imidazo[4,5-c]quinolin-3-ol (63 mg) as a white powder, mp 219-221° C.

$^1$H NMR (500 MHz, DMSO-$d_6$) δ 9.39 (s, 1H), 7.97 (dd, J=3.9, 9.0 Hz, 1H), 6.90 (d, J=2.5 Hz, 1H), 6.69 (dd, J=2.5, 9.0 Hz, 1H), 6.38 (s, 2H), 5.28 (m, 1H), 5.10 (d, J=15.8 Hz, 1H), 4.97 (d, J=15.8 Hz, 1H), 4.35 (d, J=13.0 Hz, 1H), 4.10 (m, 1H), 1.64 (d, J=22.1 Hz, 3H), 1.14 (d, J=23.6 Hz, 3H); $^{13}$C NMR (125 MHz, DMSO-$d_6$) δ 156.4, 152.2, 147.2, 144.9, 134.3, 125.0, 123.5 (d, J=8.7 Hz), 111.4, 109.5, 109.1, 98.7 (d, J=169.8 Hz), 64.9 (d, J=8.1 Hz), 64.4, 60.3 (d, J=20.3 Hz), 25.5 (d, J=22.9 Hz), 23.7 (d, J=23.9 Hz); MS (ESI) m/z 317 (M+H)$^+$; Anal. calcd for $C_{16}H_{17}FN_4O_2 \cdot 0.65H_2O \cdot 0.15 C_2H_4Cl_2$: C, 57.10; H, 5.56; N, 16.34. Found: C, 57.09; H, 5.20; N, 16.20.

Example 18

(11R)-2-(Benzyloxy)-11-methyl-10,11-dihydro-8H-[1,4]oxazino[4',3':1,2]imidazo[4,5-c]quinolin-6-amine

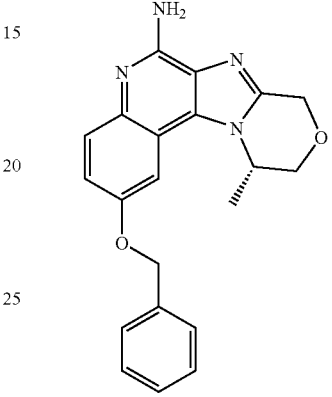

Part A 6-(Benzyloxy)-4-chloro-3-nitroquinoline (see International Publication No. WO2005/020999, Example 57, Parts A through D) and (S)-(+)-2-amino-1-propanol were combined following Parts A through F listed for the preparation of Example 1, with the modification that Part F was carried out in $CHCl_3$ as the solvent, to give (11S)-2-(benzyloxy)-11-methyl-10,11-dihydro-8H-[1,4]oxazino[4',3':1,2]imidazo[4,5-c]quinoline 5-oxide (2.02 g) as an orange foam.

Part B (11S)-2-(Benzyloxy)-11-methyl-10,11-dihydro-8H-[1,4]oxazino[4',3':1,2]imidazo[4,5-c]quinoline 5-oxide (2.02 g, 5.59 mmol) and trichloroacetyl isocyanate (0.87 mL, 7.27 mmol) were dissolved in dichloromethane (50 mL) under an atmosphere of $N_2$. After one hour, the reaction was quenched with a small amount of methanol, and the solvent was removed under reduced pressure. The resulting residue was suspended in methanol (50 mL) and treated with NaOMe (25% in MeOH, 8 mL) for 20 hours. The volatiles were removed under reduced pressure and the residue was partitioned between dichloromethane and water, adjusting to pH 11 with $NH_4OH$. The aqueous layer was extracted with dichloromethane (3×). The combined organic layers were then washed with brine and dried over $Na_2SO_4$, filtered, and concentrated to give a light-brown foam. Chromatography ($SiO_2$, 0-20% $CMA/CHCl_3$) gave (11R)-2-(benzyloxy)-11-methyl-10,11-dihydro-8H-[1,4]oxazino[4',3':1,2]imidazo[4,5-c]quinolin-6-amine (1.35 g) as an off white solid, mp 100-120° C.

$^1$H NMR (500 MHz, DMSO-$d_6$) δ 7.58 (d, J=9.1 Hz, 1H), 7.51 (m, 2H), 7.41 (m, 3H), 7.33 (m, 1H), 7.21 (dd, J=2.6, 9.1 Hz, 1H), 6.37 (s, 2H), 5.25 (q, J=12.2 Hz, 2H), 5.07 (m, 2H), 4.94 (d, J=15.5 Hz, 1H), 4.12 (m, 2H), 1.45 (d, J=6.5 Hz, 3H); $^{13}$C NMR (125 MHz, DMSO-d$_6$) δ 153.3, 150.8, 145.5, 140.0, 137.7, 131.3, 128.9, 128.1, 127.9, 127.9, 127.2, 117.4, 114.8, 103.4, 70.0, 68.7, 65.1, 50.3, 19.4; MS (APCI) m/z 361 (M+H)$^+$; Anal. calcd for C$_{21}$H$_{20}$N$_4$O$_2$: C, 69.98; H, 5.59; N, 15.54. Found: C, 69.86; H, 5.59; N, 15.64.

Example 19

(11S)-2-(Benzyloxy)-11-isopropyl-10,11-dihydro-8H-[1,4]oxazino[4',3':1,2]imidazo[4,5-c]quinolin-6-amine

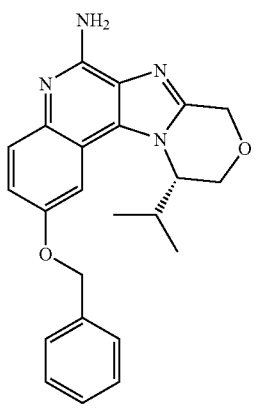

The title compound was prepared from 6-(benzyloxy)-4-chloro-3-nitroquinoline and (2S)-2-amino-3-methylbutan-1-ol following Parts A through F listed for the preparation of Example 1, with the modifications that Parts C and F were carried out in acetonitrile and CHCl$_3$, respectively, as the solvents, followed by Part B listed for the preparation of Example 18. Chromatography (SiO$_2$, 0-20% CMA/CHCl$_3$) followed by recrystallization from acetonitrile gave an off white solid. The material was dissolved in 1:1 dichloromethane/methanol and solvents were removed under reduced pressure (2×) to afforded (11S)-2-(benzyloxy)-11-isopropyl-10,11-dihydro-8H-[1,4]oxazino[4',3':1,2]imidazo[4,5-c]quinolin-6-amine (1.04 g) as a white solid, mp 139-141° C.

$^1$H NMR (500 MHz, DMSO-d$_6$) δ 7.57 (d, J=9.1 Hz, 1H), 7.47 (m, 2H), 7.40 (m, 3H), 7.34 (m, 1H), 7.19 (dd, J=2.6, 9.1 Hz, 1H), 6.37 (s, 2H), 5.29 (d, J=11.9 Hz, 1H), 5.15 (d, J=11.9 Hz, 1H), 5.07 (d, J=15.5 Hz, 1H), 4.92 (m, 2H), 4.42 (d, J=12.6 Hz, 1H), 4.06 (dd, J=3.3, 12.6 Hz, 1H), 2.45 (m, 1H), 1.11 (d, J=7.0 Hz, 3H), 0.75 (d, J=7.0 Hz, 3H); $^{13}$C NMR (125 MHz, DMSO-d$_6$) δ152.8, 150.4, 145.9, 139.7, 137.0, 131.2, 128.4, 127.7, 127.5, 126.8, 117.1, 114.6, 102.9, 69.6, 64.0, 63.1, 57.3, 31.2, 18.7, 16.9; MS (ESI) m/z 389 (M+H)$^+$; Anal. calcd for C$_{23}$H$_{24}$N$_4$O$_2$: C, 71.11; H, 6.23; N, 14.42. Found: C, 70.89; H, 6.08; N, 14.33.

Example 20

(11S)-6-Amino-11-isopropyl-10,11-dihydro-8H-[1,4]oxazino[4',3':1,2]imidazo[4,5-c]quinolin-2-ol

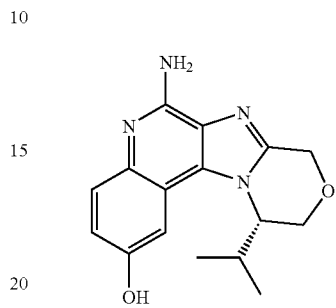

(11S)-2-(Benzyloxy)-11-isopropyl-10,11-dihydro-8H-[1,4]oxazino[4',3':1,2]imidazo[4,5-c]quinolin-6-amine (530 mg, 1.36 mmol) was dissolved in ethanol (50 mL) and the solution was placed in a pressure bottle. Palladium on carbon (10%, 220 mg) was added and the reaction mixture was shaken under H$_2$ at 48 PSI (3.3×10$^5$ Pa) for 20 hours. The reaction mixture was filtered through a pad of CELITE filter agent. The pad was rinsed with 1:1 CH$_2$Cl$_2$/ethanol (200 mL) and the combined filtrates were concentrated under reduced pressure to give a white solid. Chromatography (SiO$_2$, 30-50% CMA/CHCl$_3$) gave (11S)-6-amino-11-isopropyl-10,11-dihydro-8H-[1,4]oxazino[4',3':1,2]imidazo[4,5-c]quinolin-2-ol (240 mg) as a white powder, mp 208-210° C.

$^1$H NMR (500 MHz, DMSO-d$_6$) δ 9.43 (br s, 1H), 7.49 (d, J=8.9 Hz, 1H), 7.21 (d, J=2.5 Hz, 1H), 6.98 (dd, J=2.5, 8.9 Hz, 1H), 6.23 (s, 2H), 5.06 (d, J=15.5 Hz, 1H), 4.92 (d, J=15.5 Hz, 1H), 4.68 (t, J=3.6 Hz, 1H), 4.42 (d, J=12.6 Hz, 1H), 4.06 (dd, J=3.3, 12.6 Hz, 1H), 2.45 (m, 1H), 1.16 (d, J=6.9 Hz, 3H), 0.77 (d, J=6.9 Hz, 3H); $^{13}$C NMR (125 MHz, DMSO-d$_6$) δ 152.2, 150.2, 146.2, 138.9, 131.5, 127.8, 127.2, 117.4, 115.6, 104.0, 64.5, 63.6, 58.0, 31.6, 19.3, 17.4; MS (APCI) m/z 299 (M+H)$^+$; Anal. calcd for C$_{16}$H$_{18}$N$_4$O$_2$·0.35H$_2$O: C, 63.08; H, 6.19; N, 18.39. Found: C, 62.79; H, 6.23; N, 17.99.

Example 21

(11S)-6-Amino-11-methyl-10,11-dihydro-8H-[1,4]oxazino[4',3':1,2]imidazo[4,5-c]quinolin-2-ol

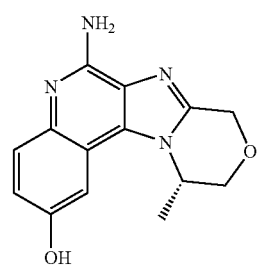

(11R)-2-(Benzyloxy)-11-methyl-10,11-dihydro-8H-[1,4]oxazino[4',3':1,2]imidazo[4,5-c]quinolin-6-amine (840 mg, 2.33 mmol) was dissolved in ethanol (50 mL) and the solution was placed in a pressure bottle. Palladium on carbon (10%, 620 mg) was added and the reaction mixture was shaken under $H_2$ at 48 PSI ($3.3 \times 10^5$ Pa) for 3 days. The reaction mixture was filtered through a pad of CELITE filter agent. The pad was rinsed with 1:1 $CH_2Cl_2$/acetonitrile and the combined filtrates were concentrated under reduced pressure to give a pink solid. Chromatography ($SiO_2$, 20-40% CMA/$CHCl_3$) gave a white solid, which was dissolved in methanol and concentrated under reduced pressure (2×) to give (11S)-6-amino-11-methyl-10,11-dihydro-8H-[1,4]oxazino[4',3':1,2]imidazo[4,5-c]quinolin-2-ol (265 mg) as an off white solid, mp 262-264° C.

$^1$H NMR (500 MHz, DMSO-$d_6$) δ 9.38 (br s, 1H), 7.49 (d, J=8.9 Hz, 1H), 7.33 (d, J=2.6 Hz, 1H), 6.99 (dd, J=2.6, 8.9 Hz, 1H), 6.20 (s, 2H), 5.08 (d, J=15.5 Hz, 1H), 4.96 (m, 2H), 4.12 (s, 2H), 1.57 (d, J=6.5 Hz, 3H); $^{13}$C NMR (125 MHz, DMSO-$d_6$) δ 152.3, 150.1, 145.2, 138.9, 131.2, 127.8, 127.2, 117.3, 115.3, 104.0, 68.7, 65.1, 50.4, 19.6; MS (ESI) m/z 271 (M+H)$^+$; Anal. calcd for $C_{14}H_{14}N_4O_2 \cdot 0.25 H_2O \cdot 0.50 CH_3OH$: C, 59.99; H, 5.56; N, 19.30. Found: C, 60.14; H, 5.86; N, 19.26.

Example 22

3-Bromo-12-methyl-11,12-dihydro-8H,10H-[1,4]oxazepino[4',3':1,2]imidazo[4,5-c]quinolin-6-amine

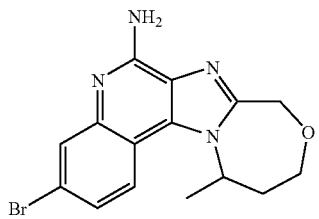

Part A

A suspension of lithium borohydride (26.57 g, 1.220 mol) in ethanol (800 mL) was cooled to approximately 0° C., and a solution of ethyl 3-aminobutyrate (40.0 g, 0.305 mol) was slowly added. The reaction mixture was heated at reflux for four hours and allowed to cool to room temperature. A solid was present and was removed by filtration and washed with diethyl ether. The filtrate was concentrated under reduced pressure, and the residue was dissolved in diethyl ether. The resulting solution was washed with 10% sodium carbonate, and the aqueous phase was extracted three times with diethyl ether. The combined organic fractions were concentrated under reduced pressure to provide 27.98 g of 3-aminobutan-1-ol containing some starting material.

Part B

Triethylamine (73.5 g, 726 mmol) and the material from Part A were added to a solution of 7-bromo-4-chloro-3-nitroquinoline (34.8 g, 121 mmol, U.S. patent application publication no. US 2004/0147543, Example 1, Parts A through D) in DMF (300 mL), and the reaction mixture was stirred overnight at room temperature. Additional triethylamine (48.97 g, 67.46) and tert-butyldimethylsilyl chloride (40.1 g, 266 mmol) were then added, and the reaction was stirred for two hours at room temperature and filtered. The filtrate was concentrated under reduced pressure, and the residue was dissolved in chloroform. The solution was washed twice with a 2:1 mixture of saturated aqueous sodium bicarbonate and water and three times with 10% aqueous sodium carbonate and then concentrated under reduced pressure. The resulting oil was passed through a plug of basic alumina to provide (7-bromo-3-nitroquinolin-4-yl)-[3-(tert-butyldimethylsilanyloxy)-1-methylpropyl]amine.

Part C

A mixture of the material from Part B, acetonitrile (1 L), and 5% platinum on carbon (15.45 g, 79.2 mmol) was placed in a hydrogenation vessel and placed under hydrogen pressure (30 PSI, $2.1 \times 10^5$ Pa) overnight. The reaction mixture was filtered, and the filtrate was concentrated under reduced pressure to provide 54.96 g of 7-bromo-$N^4$-[3-(tert-butyldimethylsilanyloxy)-1-methylpropyl]quinoline-3,4-diamine.

Part D

A solution of chloroacetyl chloride (16.1 g, 142 mmol) in chloroform (120 mL) was added dropwise to a solution of 7-bromo-$N^4$-[3-(tert-butyldimethylsilanyloxy)-1-methylpropyl]quinoline-3,4-diamine (54.96 g, 129.5 mmol) in chloroform (500 mL), and the reaction was stirred for three days at room temperature. The solvent was removed under reduced pressure, and the intermediate amide was heated at reflux for two hours in glacial acetic acid (600 mL). The acetic acid was removed under reduced pressure, and the residue was passed through a plug of silica gel (eluting with dichloromethane) to provide 9.53 g of 7-bromo-1-[3-(tert-butyldimethylsilanyloxy)-1-methylpropyl]-2-chloromethyl-1H-imidazo[4,5-c]quinoline and a mixture of three other products. The mixture of products was dissolved in glacial acetic acid and heated at reflux for two days. The acetic acid was removed under reduced pressure, and the residue was purified by column chromatography on silica gel (eluting with 0% to 5% 2 M methanolic ammonia in dichloromethane) to provide 9.14 g of 3-{2-[(acetyloxy)methyl]-7-bromo-1H-imidazo[4,5-c]quinolin-1-yl}butyl acetate.

Part E

Lithium hydroxide hydrate (5.3 g, 126 mmol) was added to a solution of 3-{2-[(acetyloxy)methyl]-7-bromo-1H-imidazo[4,5-c]quinolin-1-yl}butyl acetate (9.14 g, 21.0 mmol) in methanol (150 mL). The resulting mixture was stirred for two days at room temperature and filtered. The methanol was removed from the filtrate under reduced pressure. The crude product mixture was partitioned between dichloromethane and 10% aqueous sodium carbonate. The aqueous fraction was extracted with dichloromethane, and the combined organic fractions were concentrated under reduced pressure. The resulting solid was triturated with acetonitrile, isolated by filtration, and washed with cold acetonitrile to provide 2.13 g of 3-[7-bromo-2-(hydroxymethyl)-1H-imidazo[4,5-c]quinolin-1-yl]butan-1-ol. A portion of this material was mixed with material from a separate run.

Part F

A solution of 3-[7-bromo-2-(hydroxymethyl)-1H-imidazo[4,5-c]quinolin-1-yl]butan-1-ol (3.27 g, 9.34 mmol) in concentrated hydrochloric acid (35 mL) was stirred and heated at 120° C. for three hours and then poured into ice-cold deionized water (80 mL). Aqueous sodium hydroxide (50% w/w) was added to adjust the solution to pH 7, and a precipitate formed. The mixture was extracted with dichloromethane, and the dichloromethane was removed under reduced pressure. The solid residue was triturated with diethyl ether and isolated by filtration to provide 2.62 g of 3-bromo-12-methyl-11,12-dihydro-8H,10H-[1,4]oxazepino[4',3':1,2]imidazo[4,5-c]quinoline.

Part G

MCPBA (4.39 g of 77% purity, 25 mmol) was added to a solution of 3-bromo-12-methyl-11,12-dihydro-8H,10H-[1,4]oxazepino[4',3':1,2]imidazo[4,5-c]quinoline (2.6 g, 7.8 mmol) in chloroform (20 mL), and the reaction mixture was stirred overnight at room temperature. Aqueous ammonium hydroxide was added. The aqueous layer was separated and extracted twice with chloroform. The combined organic fractions were concentrated under reduced pressure and further dried under high vacuum to provide 3-bromo-12-methyl-5-oxido-11,12-dihydro-8H,10H-[1,4]oxazepino[4',3':1,2]imidazo[4,5-c]quinoline.

Part H

Phosphorous(III) oxychloride (1.43 g, 9.36 mmol) was slowly added to a solution of the material from Part G in DMF (20 mL), and the reaction was stirred for ten minutes at room temperature. Saturated aqueous sodium bicarbonate was then added, and the mixture was extracted with dichloromethane. The combined extracts were concentrated under reduced pressure and further dried under high vacuum to provide 3-bromo-6-chloro-12-methyl-11,12-dihydro-8H,10H-[1,4]oxazepino[4',3':1,2]imidazo[4,5-c]quinoline.

Part I

A solution of the material from Part H in 7 N ammonia in methanol (50 mL) was heated overnight in a pressure vessel at 150° C. and allowed to cool. The volatiles were removed under reduced pressure, and the residue was purified by column chromatography on silica gel (eluting with 4% methanol in dichloromethane) to provide two batches that were each recrystallized from isopropyl alcohol to provide 0.939 g of 3-bromo-12-methyl-11,12-dihydro-8H,10H-[1,4]oxazepino[4',3':1,2]imidazo[4,5-c]quinolin-6-amine as off-white needles, mp 247-248° C.

Anal. Calcd for $C_{15}H_{15}BrN_4O$: C, 51.89; H, 4.35; N, 16.14. Found: C, 51.94; H, 4.36; N, 16.08 (Batch 1). Found: C, 51.88; H, 4.38; N, 16.19 (Batch 2).

Example 23

(11S)-11-Methyl-9-(methylsulfonyl)-8,9,10,11-tetrahydropyrazino[1',2':1,2]imidazo[4,5-c]quinolin-6-amine

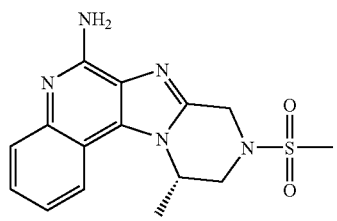

Part A (S)-(−)-1,2-Diaminopropane (2.00 g, 13.6 mmol) and 1,8-diazabicyclo[5.4.0]undec-7-ene (DBU) (4.46 mL, 28.8 mmol) were dissolved in dichloromethane (50 mL) and the solution was cooled to 0° C. under $N_2$. In another flask, di-tert-butyl dicarbonate (2.96 g, 13.6 mmol) was dissolved in dichloromethane (50 mL), and the solution was slowly added to the reaction mixture via cannula. After stirring for 2 hours, the reaction mixture was treated with $H_2O$ (50 mL) and the layers were separated. The organic portion was discarded and the aqueous portion was made basic by the addition of 3 mL of concentrated, aqueous $NH_4OH$ solution and then extracted with $CH_2Cl_2$ (5×250 mL). The combined organic layers were dried over $Na_2SO_4$, filtered, and concentrated under reduced pressure. Chromatography ($SiO_2$, 7% MeOH/$CHCl_3$ saturated with concentrated, aqueous NH4OH solution) afforded tert-butyl (2S)-2-aminopropylcarbamate (0.50 g) as a colorless liquid.

Part B

A suspension of 3-chloro-4-nitroquinoline (3.04 g, 14.5 mmol) in dichloromethane (150 mL) was treated with triethylamine (4.5 mL, 32.02 mmol) and the reaction mixture was cooled to 0° C. under an atmosphere of $N_2$. In a separate flask, tert-butyl (2S)-2-aminopropylcarbamate (2.79 g, 16.0 mmol) was dissolved in dichloromethane (50 mL) and the solution was added into the reaction via cannula. The reaction was allowed to slowly warm to ambient temperature overnight. The reaction mixture was then washed successively with water (2×150 mL) and brine (100 mL). The organic layer was dried over $Na_2SO_4$, filtered, and concentrated to yield tert-butyl (2S)-2-[(3-nitroquinolin-4-yl)amino]propylcarbamate (5.04 g) as a bright yellow solid.

Part C tert-Butyl (2S)-2-[(3-nitroquinolin-4-yl)amino]propylcarbamate (5.04 g, 14.5 mmol) was dissolved in acetonitrile (300 mL) and the solution was placed in a pressure bottle. Platinum on carbon (5%, 1.03 g) was then added and the reaction mixture was shaken under $H_2$ at 30 PSI ($2.1 \times 10^5$ Pa). After 20 hours, the reaction mixture was filtered through a pad of CELITE filter agent. The pad was rinsed with acetonitrile and the combined filtrates were concentrated under reduced pressure to give tert-butyl (2S)-2-[(3-aminoquinolin-4-yl)amino] propylcarbamate (4.60 g) as an orange foam.

Part D tert-Butyl (2S)-2-[(3-aminoquinolin-4-yl)amino]propylcarbamate (4.60 g, 14.55 mmol) was dissolved in 150 mL of anhydrous 1,2-dichloroethane and the solution was stirred under $N_2$. Ethyl 2-chloroethanimidoate hydrochloride (3.45 g, 21.8 mmol) was added and the reaction was heated to 60° C. for 24 hours. The reaction mixture was cooled and washed with saturated sodium bicarbonate solution (2×100 mL) followed by brine. The organic layer was dried over $Na_2SO_4$, filtered, and concentrated to give an orange solid. Chromatography ($SiO_2$, 60-80% EtOAc/hexanes) gave tert-butyl (2S)-2-[2-(chloromethyl)-1H-imidazo[4,5-c]quinolin-1-yl]propylcarbamate (2.54 g) as a tan solid.

Part E tert-Butyl (2S)-2-[2-(chloromethyl)-1H-imidazo[4,5-c]quinolin-1-yl]propylcarbamate (2.54 g, 6.77 mmol) was dissolved in 2.2 M HCl in EtOH (50 mL) and the solution was heated to reflux for 15 minutes. $N_2$ was bubbled through the reaction for 15 minutes, and the remaining volatiles were removed under reduced pressure. The resulting material was partitioned between dichloromethane and water. The organic layer was discarded and the aqueous layer was treated with concentrated $NH_4OH$ solution to adjust to pH 11. The aqueous layer was extracted with dichloromethane (3×100 mL), and the combined organic layers were washed with brine. Triethylamine (4 mL) was then added to the solution and it was stirred at ambient temperature overnight. The reaction was washed successively with water (2×100 mL) and brine. The organic layer was dried over $Na_2SO_4$, filtered, and concentrated to give an orange foam. Chromatography ($SiO_2$, 20-50% CMA/$CHCl_3$) gave (11S)-11-methyl-8,9,10,11-tetrahydropyrazino[1',2':1,2]imidazo[4,5-c]quinoline (1.06 g) as an orange foam.

Part F (11S)-11-Methyl-8,9,10,11-tetrahydropyrazino[1',2':1,2]imidazo[4,5-c]quinoline (1.06 g, 4.45 mmol) was dissolved in anhydrous dichloromethane (100 mL) under $N_2$. Triethylamine (1.25 mL, 8.9 mmol) and methanesulfonic anhydride (0.85 g, 4.89 mmol) were sequentially added to the reaction at 0° C. The reaction was allowed to slowly warm to room temperature overnight. The reaction mixture was then washed successively with water (2×100 mL) and brine. The organic layer was dried over Na$_2$SO$_4$, filtered, and concentrated to give a yellow foam. Chromatography (SiO$_2$, 10-30% CMA/CHCl$_3$) gave (11S)-11-methyl-9-(methylsulfonyl)-8,9,10,11-tetrahydropyrazino[1',2':1,2]imidazo[4,5-c]quinoline (1.01 g) as a yellow foam.

Part G (11S)-11-Methyl-9-(methylsulfonyl)-8,9,10,11-tetrahydropyrazino[1',2':1,2]imidazo[4,5-c]quinoline (1.01 g, 3.19 mmol) was dissolved in dichloromethane (40 mL) and treated with MCPBA (0.94 g, 77% max). After stirring overnight, the reaction was treated with 20 mL of 2% Na$_2$CO$_3$ solution and the layers were separated. The aqueous layer was then extracted with dichloromethane (10×10 mL). The combined organic layers were washed with brine, dried over Na$_2$SO$_4$, filtered and concentrated under reduced pressure to give (11S)-11-methyl-9-(methylsulfonyl)-8,9,10,11-tetrahydropyrazino[1',2':1,2]imidazo[4,5-c]quinoline 5-oxide (1.06 g) as a tan solid.

Part H (11S)-11-Methyl-9-(methylsulfonyl)-8,9,10,11-tetrahydropyrazino[1',2':1,2]imidazo[4,5-c]quinoline 5-oxide (1.06 g, 3.19 mmol) was dissolved in dichloromethane (100 mL) and treated with concentrated ammonium hydroxide solution (10 mL). The mixture was stirred rapidly and then p-toluenesulfonyl chloride (610 mg, 3.19 mmol) was carefully added. Rapid stirring was continued overnight. The reaction mixture was then diluted with 25 mL of CH$_2$Cl$_2$ and 25 mL of H$_2$O. The layers were separated and the organic portion was washed successively with aqueous saturated sodium bicarbonate solution (2×50 mL), H$_2$O and brine. The organic portion was dried over Na$_2$SO$_4$, filtered and concentrated under reduced pressure. Chromatography (SiO$_2$, 20-40% CMA/CHCl$_3$) gave (11S)-1-methyl-9-(methylsulfonyl)-8,9,10,11-tetrahydropyrazino[1',2':1,2]imidazo[4,5-c]quinolin-6-amine (520 mg) as a white solid, mp 258-261° C.

$^1$H NMR (300 MHz, DMSO-d$_6$) δ 8.03 (d, J=7.4 Hz, 1H), 7.64 (dd, J=1.1, 8.3 Hz, 1H), 7.45 (m, 1H), 7.29 (m, 1H), 6.62 (s, 2H), 5.32 (m, 1H), 4.78 (m, 1H), 4.59 (d, J=15.6 Hz, 1H), 3.87 (d, J=12.8 Hz, 1H), 3.64 (dd, J=12.8, 3.3 Hz, 1H), 3.16 (s, 3H), 1.55 (d, J=6.3 Hz, 3H); $^{13}$C NMR (125 MHz, DMSO-d$_6$) δ 152.1, 145.2, 143.9, 131.6, 127.1, 127.0, 126.7, 121.7, 120.7, 114.8, 50.6, 48.4, 45.2, 35.9, 19.5; MS (ESI) m/z 332 (M+H)$^+$; Anal. calcd for C$_{15}$H$_{17}$N$_5$O$_2$S: C, 54.37; H, 5.17; N, 21.13. Found: C, 54.13; H, 4.99; N, 21.20.

Example 24

12-Methyl-9-(methylsulfonyl)-9,10,11,12-tetrahydro-8H-[1,4]diazepino[1',2':1,2]imidazo[4,5-c]quinolin-6-amine formic acid salt

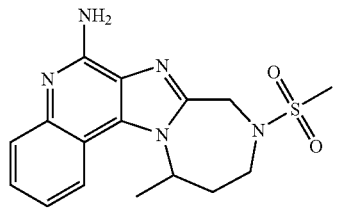

Part A

Triethylamine (12.8 mL, 91.8 mmol) was added to a solution of 4-chloro-3-nitroquinoline (8.0 g, 38 mmol) in DMF (100 mL). The resulting solution was stirred for five minutes at room temperature, and then ethyl 3-aminobutyrate (6.2 mL, 42 mmol) was added. The reaction was stirred overnight at room temperature and poured into deionized water (320 mL). The mixture was extracted with ethyl acetate (1×125 mL and 2×100 mL). The combined extracts were washed with brine (3×120 mL), dried over magnesium sulfate, filtered through a layer of CELITE filter agent, concentrated under reduced pressure, and further dried under high vacuum to provide 11.5 g of ethyl 3-[(3-nitroquinolin-4-yl)amino]butanoate as a yellow solid.

Part B

A Parr vessel was charged with a solution of ethyl 3-[(3-nitroquinolin-4-yl)amino]butanoate (11.5 g, 37.9 mmol) in acetonitrile (150 mL) followed by 5% platinum on carbon (1.2 g). The mixture was placed under hydrogen pressure overnight and then filtered through a layer of CELITE filter agent. The filtrate was concentrated under reduced pressure and further dried under high vacuum to provide 10.5 g of ethyl 3-[(3-aminoquinolin-4-yl)amino]butanoate as a sticky, yellow solid.

Part C

Ethyl 2-chloroethanimidoate hydrochloride (10.8 g, 68.4 mmol) was added to a solution of ethyl 3-[(3-aminoquinolin-4-yl)amino]butanoate (9.41 g, 34.4 mmol) in chloroform (130 mL), and the reaction was stirred at room temperature for three days and then heated at reflux for two hours. An analysis by liquid chromatography/mass spectrometry (LC/MS) indicated the presence of starting material, and additional ethyl 2-chloroethanimidoate hydrochloride (2.7 g) was added. The reaction was heated at reflux for an additional 1.5 hours, allowed to cool to room temperature, diluted with chloroform (100 mL), washed sequentially with brine (2×150 mL) and deionized water (100 mL), dried over magnesium sulfate, filtered through a layer of CELITE filter agent, concentrated under reduced pressure, and further dried overnight under high vacuum to provide 11.15 g of ethyl 3-[2-(chloromethyl)-1H-imidazo[4,5-c]quinolin-1-yl]butanoate as a dark yellow solid.

Part D

A solution of ethyl 3-[2-(chloromethyl)-1H-imidazo[4,5-c]quinolin-1-yl]butanoate (8.22 g, 24.8 mmol) in 7 N ammonia in methanol (140 mL) was stirred overnight at room temperature. The volatiles were removed under reduced pressure, and the residue was further dried under high vacuum and purified by automated flash chromatography (eluting with a gradient of dichloromethane/methanol/concentrated ammonium hydroxide in a gradient from 100:0:0 to 50:47.5:2.5) to provide 12-methyl-8,9,11,12-tetrahydro-10H-[1,4]diazepino[1',2':1,2]imidazo[4,5-c]quinolin-10-one as an orange solid. Automated flash chromatography was carried out using a combination of a COMBIFLASH system (an automated high-performance flash purification product available from Teledyne Isco, Inc., Lincoln, Nebr., USA) and a HORIZON HPFC system (an automated high-performance flash purification product available from Biotage, Inc, Charlottesville, Va., USA).

Part E

MCPBA (2.73 g of 77% purity, 16 mmol) was added to a solution of 12-methyl-8,9,11,12-tetrahydro-10H-[1,4]diazepino[1',2':1,2]imidazo[4,5-c]quinolin-10-one (1.3 g, 4.9 mmol) in chloroform (20 mL), and the reaction mixture was stirred for 15 minutes at room temperature. Concentrated ammonium hydroxide (30 mL) and p-toluenesulfonyl chloride (1.12 g, 5.86 mmol) were sequentially added, and the resulting mixture was stirred at room temperature for two hours. An analysis by LC/MS indicated the presence of the 5N-oxide, and additional p-toluenesulfonyl chloride (1 equivalent) was added. The mixture was stirred at room temperature overnight. The organic layer was separated and concentrated under reduced pressure. The residue was purified by column chromatography on silica gel (eluting with 0% to 15% 2 N methanolic ammonia in chloroform over a period of 42 minutes) followed by recrystallization from acetonitrile to provide 389 mg of 6-amino-12-methyl-8,9,11,12-tetrahydro-10H-[1,4]diazepino[1',2':1,2]imidazo[4,5-c]quinolin-10-one.

Part F

Borane THF complex (2.76 mL of a 1 M solution in THF) was added to a solution of 6-amino-12-methyl-8,9,11,12-tetrahydro-10H-[1,4]diazepino[1',2':1,2]imidazo[4,5-c]quinolin-10-one (0.389 g, 1.38 mmol) in THF (5 mL), and the mixture was stirred at room temperature overnight and then heated at reflux for six hours. An analysis by LC/MS indicated the reaction was incomplete, and additional borane tetrahydrofuran complex (2.76 mL) was added. The reaction mixture was heated at reflux overnight, allowed to cool, and concentrated under reduced pressure. The residue was treated with chloroform, and a solid was present that was isolated by filtration to provide 12-methyl-9,10,11,12-tetrahydro-8H-[1,4]diazepino[1',2':1,2]imidazo[4,5-c]quinolin-6-amine as a yellow solid.

Part G

Triethylamine (1.4 g, 14 mmol) and methanesulfonyl chloride (189.7 mg, 1.656 mmol) were sequentially added to the material from Part F in DMF (15 mL), and the reaction was stirred at room temperature for one hour. An analysis by LC/MS showed no reaction had taken place, and additional methanesulfonyl chloride (1 equivalent) was added. After the reaction was stirred for an additional hour, an analysis by LC/MS indicated the presence of starting material, and additional methanesulfonyl chloride (2 equivalents) was added. The reaction mixture was stirred for another hour and then filtered. The filtrate was concentrated under reduced pressure, and the residue was purified by column chromatography on silica gel (eluting with 0% to 25% 2 N methanolic ammonia in chloroform over a period of 42 minutes). The fractions containing product were combined and concentrated under reduced pressure, and the resulting product mixture was boiled in trifluoroacetic anhydride and then concentrated under reduced pressure. The residue was treated with aqueous sodium hydroxide and purified by reversed phase preparative HPLC (eluting with 5% to 30% solvent B in three minutes and 30% to 95% solvent B in seven minutes wherein solvent B is 0.5% formic acid in acetonitrile and solvent A is 0.5% formic acid in water) using a HPLC purification system obtained from Shimadzu corporation (based in Kyoto, Japan) to provide 48 mg of 12-methyl-9-(methylsulfonyl)-9,10,11,12-tetrahydro-8H-[1,4]diazepino[1',2':1,2]imidazo[4,5-c]quinolin-6-amine formic acid salt.

$^1$H NMR (300 MHz, DMSO-$d_6$) δ 8.17-8.15 (m, 1H), 7.64 (d, J=8.0 Hz, 1H), 7.46 (t, J=7.5 Hz, 1H), 7.28 (t, J=7.2 Hz, 1H), 6.80 (s, 2H), 5.56-5.52 (m, 1H), 4.80 (q, J=14.1 Hz, 2H), 3.81-3.57 (m, 4H), 2.65 (s, 3H), 1.64 (d, J=6.8 Hz, 3H); $^{13}$C NMR (75 MHz, DMSO-$d_6$) δ 165.9, 153.9, 152.2, 145.9, 129.6, 128.0, 127.6, 124.3, 123.0, 116.8, 54.0, 47.6, 46.1, 39.0, 33.1, 20.3; HRMS calcd. for $C_{16}H_{19}N_5O_2S$: 346.1338. Found: 346.1340.

Examples 25-31

The following examples are enantiomers of the compounds prepared in Examples 1, 5, 6, 9, 10, 11, and 13, and they were prepared according to the methods indicated in the table below using the amino alcohol listed in the table below instead of its enantiomer. In addition to the method and the amino alcohol used for the synthesis, the table provides the structure of the example obtained and its characterization data.

| Ex. | Method of | Amino alcohol | structure | mp (° C.) | Anal. |
|---|---|---|---|---|---|
| 25 | Ex. 1 | (2R)-2-Amino-3-methylbutan-1-ol | 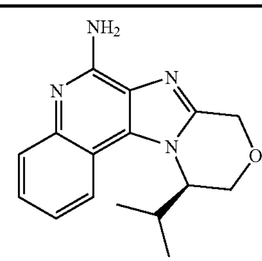 | 248-249 | Calcd for $C_{16}H_{18}N_4O$: C, 68.06; H, 6.43; N, 19.84. Found: C, 67.86; H, 6.50; N, 19.89. |
| 26 | Ex. 5 | (R)-2-amino-1-propanol | 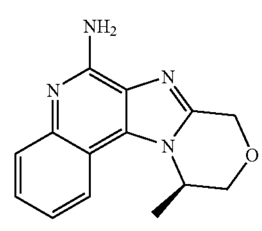 | 280-282 | Calcd for $C_{14}H_{14}N_4O$: C, 66.13; H, 5.55; N, 22.03. Found: C, 66.13; H, 5.53; N, 22.25. |

-continued

| Ex. | Method of | Amino alcohol | structure | mp (° C.) | Anal. |
|---|---|---|---|---|---|
| 27 | Ex. 6 | Not applicable[a] | 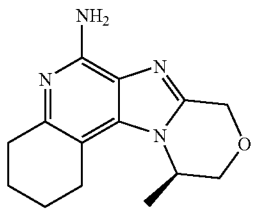 | 209-211 | Calcd for $C_{14}H_{18}N_4O$: C, 65.09; H, 7.02; N, 21.69. Found: C, 65.01; H, 7.01; N, 21.64. |
| 28 | Ex. 9 | (2R)-2-amino-2-phenylethanol | 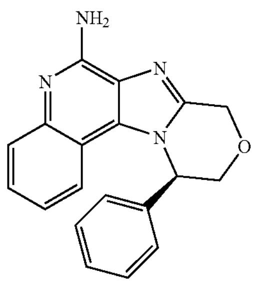 | 284-286 | Calcd for $C_{19}H_{16}N_4O$: C, 72.14; H, 5.10; N, 17.71. Found: C, 71.80; H, 4.96; N, 17.56. |
| 29 | Ex. 10 | (2R)-2-amino-3-phenylpropan-1-ol | 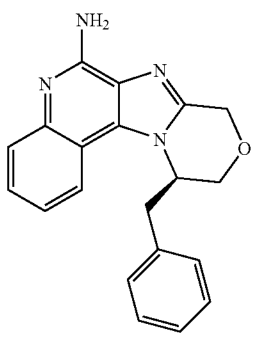 | 170-177 | Calcd for $C_{20}H_{18}N_4O \cdot 0.25 H_2O$: C, 71.73; H, 5.57; N, 16.73. Found: C, 71.92; H, 5.60; N, 16.79. |
| 30 | Ex. 11 | (2S)-2-amino-3-fluoro-3-methylbutan-1-ol | 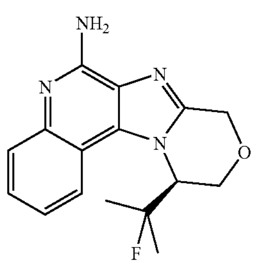 | 242-244 | Calcd for $C_{16}H_{17}FN_4O$: C, 63.99; H, 5.71; N, 18.65. Found: C, 63.78; H, 5.51; N, 18.52. |
| 31 | Ex. 13 | (2S)-2-amino-3-methylbutane-1,3-diol hydrochloride | 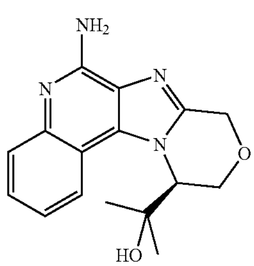 | 218-219 | Calcd for $C_{16}H_{18}N_4O_2$: C, 64.41; H, 6.08; N, 18.78. Found: C, 64.09; H, 6.26; N, 18.60. |

Example 32

(11R)-11-Methyl-9-(methylsulfonyl)-8,9,10,11-tetrahydropyrazino[1',2':1,2]imidazo[4,5-c]quinolin-6-amine

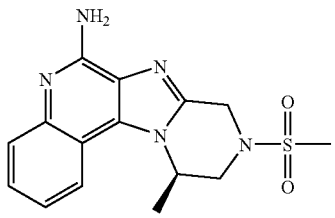

The methods described in Parts A through H of Example 23 were followed using (R)-(+)-1,2-diaminopropane instead of (S)-(−)-1,2-diaminopropane in Part A to provide the title compound as off-white needles, mp 258-261° C.

Anal. calcd for $C_{15}H_{17}N_5O_2S$: C, 54.37; H, 5.17; N, 21.13. Found: C, 53.99; H, 5.16; N, 21.15.

Example 33

2-[(11R)-6-Amino-10,11-dihydro-8H-[1,4]oxazino[4',3':1,2]imidazo[4,5-c]-1,5-naphthyridin-11-yl]propan-2-ol

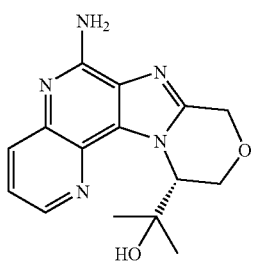

The title compound was prepared from (1R)-2-{[tert-butyl(dimethyl)silyl]oxy}-1-({[tert-butyl(dimethyl)silyl]oxy}methyl)-2-methylpropylamine and 4-chloro-3-nitro[1,5]naphthyridine following Parts C through I listed for the preparation of Example 13 with the modification that Part H was carried out in CHCl₃ as the solvent. Chromatography of the final compound (SiO₂, 0-20% CMA/CHCl₃) afforded 2-[(11R)-6-amino-10,11-dihydro-8H-[1,4]oxazino[4',3':1,2]imidazo[4,5-c]-1,5-naphthyridin-11-yl]propan-2-ol as an off white solid, mp 242-246° C.

$^1$H NMR (300 MHz, DMSO-$d_6$) δ 8.48 (dd, J=1.5, 4.4 Hz, 1H), 7.98 (dd, J=1.5, 8.4 Hz, 1H), 7.48 (m, 1H), 6.95 (s, 2H), 6.05 (s, 1H), 5.18 (m, 2H), 5.00 (d, J=16.3 Hz, 1H), 4.43 (d, J=12.6 Hz, 1H), 4.00 (dd, J=3.2, 12.6 Hz, 1H), 1.40 (s, 3H), 1.10 (s, 3H); $^{13}$C NMR (125 MHz, DMSO-$d_6$) δ 152.7, 147.9, 142.6, 140.4, 133.9, 132.7, 129.8, 122.5, 73.4, 64.9, 64.2, 62.0, 29.2, 26.5; MS (ESI) m/z 300 (M+H)⁺. Anal. calcd for $C_{15}H_{17}N_5O_2$: C, 60.19; H, 5.72; N, 23.40. Found: C, 59.93; H, 5.59; N, 23.35.

Example 34

(11S)-1-[(Benzyloxy)methyl]-10,11-dihydro-8H-[1,4]oxazino[4',3':1,2]imidazo[4,5-c]quinolin-6-amine

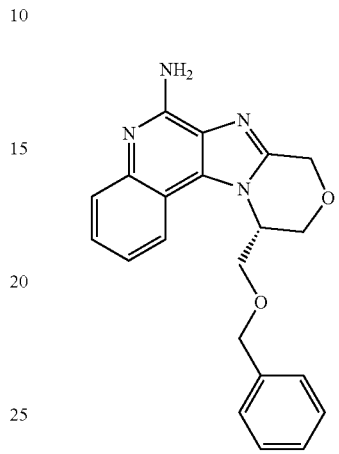

Part A

Methyl N-trityl-L-serinate (3.61 g, 10.0 mmol), prepared by the method of Baldwin, *Tetrahedron*, 49, pp. 6309-6330, (1993), was dissolved in 50 mL of CH₂Cl₂ followed by the addition of 25 mL of 50% aqueous NaOH solution. To the stirred mixture were added benzyltrimethylammonium chloride (186 mg, 1.00 mmol) and benzyl bromide (1.20 mL, 10.0 mmol). After stirring overnight, the mixture was treated with 100 mL of ice water. After all of the ice had melted, 100 mL of CH₂Cl₂ was added and the layers were separated. The aqueous portion was extracted with another 50 mL of CH₂Cl₂ and the combined organic layers were washed with H₂O (2×100 mL) and brine (3×50 mL). The organic portion was dried over Na₂SO₄, filtered and concentrated. Chromatography (SiO₂, 10-20% ethyl acetate/hexanes) gave 3.22 g of methyl O-benzyl-N-trityl-L-serinate as a colorless syrup.

Part B

Methyl O-benzyl-N-trityl-L-serinate (2.94 g, 6.52 mmol) was dissolved in 100 mL of anhydrous Et₂O and the solution was cooled to 0° C. under N₂. Lithium aluminum hydride (1.63 g, 42.9 mmol) was added and the mixture was stirred for 90 minutes. The reaction mixture was then sequentially treated with 1.63 mL of H₂O, 1.63 mL of 15% NaOH solution and 4.90 mL of H₂O. After stirring for 30 minutes, the reaction mixture was filtered to remove the white solid. The solid was washed with several portions of Et₂O and the combined filtrates were concentrated under reduced pressure. Chromatography (SiO₂, 15-20% ethyl acetate/hexanes) gave 2.78 g of (2R)-3-(benzyloxy)-2-(tritylamino)propan-1-ol as a colorless oil.

Part C

A solution of (2R)-3-(benzyloxy)-2-(tritylamino)propan-1-ol (2.68 g, 6.34 mmol) dissolved in 100 mL of CH₂Cl₂ was treated with triethylamine (1.00 mL, 7.19 mmol), tert-butyldimethylsilyl chloride (1.08 g, 7.15 mmol) and DMAP (79 mg, 0.65 mmol) and the reaction mixture was stirred under N₂ overnight. The reaction mixture was then concentrated and the resulting material was dissolved in 50 mL of CH₂Cl₂ and washed with H₂O and brine. The organic portion was then dried over Na$_2$SO$_4$, filtered and concentrated under reduced pressure. Chromatography (SiO$_2$, 10% ethyl acetate/hexanes) gave 3.03 g of (2S)-1-(benzyloxy)-3-{[tert-butyl(dimethyl)silyl]oxy}-N-tritylpropan-2-amine as a colorless syrup.

Part D (2S)-1-(Benzyloxy)-3-{[tert-butyl(dimethyl)silyl]oxy}-N-tritylpropan-2-amine (3.02 g, 5.62 mmol) was dissolved in 60 mL of anhydrous CH$_2$Cl$_2$ and 9.1 mL of glacial acetic acid. The reaction mixture was cooled to 0° C. under an atmosphere of N$_2$ and boron trifluoride diethyl etherate (0.75 mL, 5.92 mmol) was added dropwise over several minutes. After stirring for 5 hours, the reaction mixture was treated with 85 mL of cold, aqueous 10% NaOH solution. The layers were separated and the aqueous portion was extracted with CH$_2$Cl$_2$ (2×20 mL). The organic layers were combined and dried over Na$_2$SO$_4$, filtered and concentrated under reduced pressure. Chromatography (SiO$_2$, 0-5% methanol/CHCl$_3$) gave 1.57 g of (2S)-1-(benzyloxy)-3-{[tert-butyl(dimethyl)silyl]oxy}propan-2-amine as a white solid.

Part E (2S)-1-(Benzyloxy)-3-{[tert-butyl(dimethyl)silyl]oxy}propan-2-amine (1.55 g, 5.25 mmol) was dissolved in 60 mL of dry CH$_2$Cl$_2$. Triethylamine (1.46 mL, 10.5 mmol) and 4-chloro-3-nitroquinoline (1.09 g, 5.25 mmol) were then added and the reaction was stirred under N$_2$ for 2 days. The reaction mixture was then concentrated and the resulting material was partitioned between 50 mL of CH$_2$Cl$_2$ and 50 mL of saturated NaHCO$_3$ solution. The layers were separated and the organic portion was washed with H$_2$O and brine. The organic portion was dried over Na$_2$SO$_4$, filtered and concentrated under reduced pressure. Chromatography (SiO$_2$, 0-10% ethyl acetate/CH$_2$Cl$_2$) gave 1.81 g of N-[(1S)-2-(benzyloxy)-1-({[tert-butyl(dimethyl)silyl]oxy}methyl)ethyl]-3-nitroquinolin-4-amine as a yellow solid.

Part F

N-[(1S)-2-(Benzyloxy)-1-({[tert-butyl(dimethyl)silyl]oxy}methyl)ethyl]-3-nitroquinolin-4-amine (1.81 g, 3.88 mmol) was dissolved in 30 mL of acetonitrile and the solution was placed in a pressure bottle. Platinum on carbon (5%, 180 mg) was then added and the reaction mixture was shaken under H$_2$ at 50 PSI (3.4×10$^5$ Pa). After 5.5 hours, the reaction mixture was filtered through a pad of CELITE filter agent. The pad was rinsed with acetonitrile and the combined filtrates were concentrated under reduced pressure to give 1.66 g of N$^4$-[(1S)-2-(benzyloxy)-1-({[tert-butyl(dimethyl)silyl]oxy}methyl)ethyl]quinoline-3,4-diamine as an orange solid.

Part G

N$^4$-[(1S)-2-(Benzyloxy)-1-({[tert-butyl(dimethyl)silyl]oxy}methyl)ethyl]quinoline-3,4-diamine (1.66 g, 3.80 mmol) was dissolved in 40 mL of anhydrous 1,2-dichloroethane and the solution was stirred under N$_2$. Ethyl 2-chloroethanimidoate hydrochloride (1.80 g, 11.4 mmol) was then added and the reaction mixture was heated to 70° C. After stirring overnight, the reaction mixture was cooled and treated with 20 mL of saturated NaHCO$_3$ solution. The layers were separated and the organic portion was washed successively with H$_2$O and brine. The organic portion was dried over Na$_2$SO$_4$, filtered and concentrated under reduced pressure. Chromatography (SiO$_2$, 20-50% ethyl acetate/hexanes) gave 1.61 g of 1-[(1S)-2-(benzyloxy)-1-({[tert-butyl(dimethyl)silyl]oxy}methyl)ethyl]-2-(chloromethyl)-1H-imidazo[4,5-c]quinoline as a golden syrup.

Part H

1-[(1S)-2-(Benzyloxy)-1-({[tert-butyl(dimethyl)silyl]oxy}methyl)ethyl]-2-(chloromethyl)-1H-imidazo[4,5-c]quinoline (1.61 g, 3.13 mmol) was dissolved in 250 mL of anhydrous CH$_2$Cl$_2$ and the solution was cooled to −78° C. under N$_2$. A 1.0 M solution of tetrabutylammonium fluoride in THF (3.43 mL, 3.43 mmol) was added and the stirred solution was allowed to warm to ambient temperature overnight. The reaction mixture was then washed successively with 50 mL of saturated NaHCO$_3$ solution and brine (4×50 mL). The organic portion was dried over Na$_2$SO$_4$, filtered and concentrated under reduced pressure. Chromatography (SiO$_2$, 0-3% methanol/CHCl$_3$) gave 0.92 g of (11S)-11-[(benzyloxy)methyl]-10,11-dihydro-8H-[1,4]oxazino[4',3':1,2]imidazo[4,5-c]quinoline as a colorless syrup.

Part I (11S)-11-[(Benzyloxy)methyl]-10,11-dihydro-8H-[1,4]oxazino[4',3':1,2]imidazo[4,5-c]quinoline (0.92 g, 2.67 mmol) was dissolved in 25 mL of CH$_2$Cl$_2$ and treated with MCPBA (0.81 g, 57-86% purity). After stirring for 2 hours, the reaction mixture was treated with 25 mL of CH$_2$Cl$_2$ and 25 mL of 5% Na$_2$CO$_3$ solution and the layers were separated. The aqueous portion was extracted with an additional 10 mL of CH$_2$Cl$_2$. The combined organic layers were washed successively with H$_2$O (20 mL) and brine (20 mL). The organic portion was dried over Na$_2$SO$_4$, filtered and concentrated under reduced pressure to give 0.96 g of (11S)-11-[(benzyloxy)methyl]-10,11-dihydro-8H-[1,4]oxazino[4',3':1,2]imidazo[4,5-c]quinoline 5-oxide as a light-brown solid.

Part J (11S)-11-[(benzyloxy)methyl]-10,11-dihydro-8H-[1,4]oxazino[4',3':1,2]imidazo[4,5-c]quinoline 5-oxide (0.96 g, 2.67 mmol) was dissolved in 25 mL of CH$_2$Cl$_2$ and treated with 2.5 mL of concentrated aqueous NH$_4$OH solution. The mixture was stirred rapidly and then p-toluenesulfonyl chloride (0.51 g, 2.67 mmol) was carefully added. Rapid stirring was continued for 2.5 hours. The reaction mixture was then treated with 50 mL of CH$_2$Cl$_2$ and 25 mL of H$_2$O. The layers were separated and the organic portion was washed successively with 5% Na$_2$CO$_3$ solution (3×25 mL), H$_2$O and brine. The organic portion was dried over Na$_2$SO$_4$, filtered and concentrated under reduced pressure. Chromatography (SiO$_2$, 15-25% CMA/CHCl$_3$) gave a light-brown foam. Crystallization from ethyl acetate and a small amount of methanol gave (11S)-11-[(benzyloxy)methyl]-10,11-dihydro-8H-[1,4]oxazino[4',3':1,2]imidazo[4,5-c]quinolin-6-amine (420 mg) fine white needles, mp 184.6-186.2° C.

$^1$H NMR (300 MHz, DMSO-d$_6$) δ 7.89 (d, J=7.4 Hz, 1H), 7.61 (dd, J=1.0, 8.4 Hz, 1H), 7.42 (m, 1H), 7.34-7.28 (m, 5H), 7.23 (m, 1H), 6.59 (s, 2H), 5.09 (d, J=15.7 Hz, 1H), 5.09 (m, 1H), 4.97 (d, J=15.7 Hz, 1H), 4.61 (d, J=12.3 Hz, 1H), 4.55 (d, J=12.3 Hz, 1H), 4.38 (d, J=12.1 Hz, 1H), 4.10 (dd, J=2.4, 12.1 Hz, 1H), 3.86-3.76 (m, 2H); $^{13}$C NMR (125 MHz, DMSO-d$_6$) δ 151.7, 145.2, 144.6, 137.7, 131.5, 128.2, 127.5, 127.4, 126.5, 126.2, 126.1, 121.1, 120.0, 114.3, 72.3, 67.8, 64.5, 64.1, 53.3; MS (ESI) m/z 361 (M+H)⁺. Anal. calcd for $C_{21}H_{20}N_4O_2$: C, 69.98; H, 5.59; N, 15.55. Found: C, 69.65; H, 5.48; N, 15.52.

Example 35

[(11S)-6-Amino-10,11-dihydro-8H-[1,4]oxazino[4', 3':1,2]imidazo[4,5-c]quinolin-11-yl]methanol

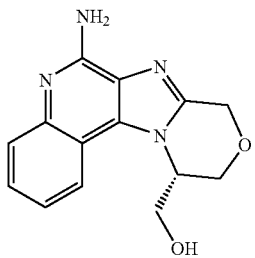

(11S)-11-[(Benzyloxy)methyl]-10,11-dihydro-8H-[1,4] oxazino[4',3':1,2]imidazo[4,5-c]quinolin-6-amine (297 mg, 0.825 mmol) was dissolved in 20 mL of methanol and the solution was placed in a pressure bottle. Palladium on carbon (10%, 230 mg) and 0.5 mL of 3 M HCl in ethanol were then added and the reaction mixture was shaken under H2 at 50 PSI ($3.4 \times 10^5$ Pa). After 18 hours, the reaction mixture was filtered through a pad of CELITE filter agent. The pad was rinsed with methanol and the combined filtrates were concentrated under reduced pressure. The residue was dissolved in H₂O and the solution was made basic by the addition of concentrated aqueous NH₄OH solution. The aqueous solution was extracted with 10% MeOH/CH₂Cl₂ several times and the combined organic layers were concentrated under reduced pressure. Chromatography (SiO₂, 25-75% CMA/ CHCl₃) gave a white powder. Crystallization from ethyl acetate gave 85 mg of the title compound as white, fluffy crystals, mp 238.6-239.8° C.

¹H NMR (300 MHz, DMSO-d₆) δ 8.04 (d, J=7.4 Hz, 1H), 7.63 (dd, J=1.0, 8.3 Hz, 1H), 7.45 (m, 1H), 7.27 (m, 1H), 6.57 (s, 2H), 5.50 (dd, J=5.0, 6.6 Hz, 1H), 5.08 (d, J=15.7 Hz, 1H), 4.96 (d, J=15.7 Hz, 1H), 4.83 (m, 1H), 4.43 (d, J=12.0 Hz, 1H), 4.05 (dd, J=2.0, 12.1 Hz, 1H), 3.86-3.69 (m, 2H); ¹³C NMR (125 MHz, DMSO-d₆) δ 151.7, 145.2, 144.6, 131.6, 126.5, 126.2, 126.1, 121.1, 120.2, 114.4, 64.6, 63.3, 59.5, 55.4; MS (ESI) m/z 271 (M+H)⁺. Anal. calcd for $C_{14}H_{14}N_4O_2$: C, 62.21; H, 5.22; N, 20.73. Found: C, 61.98; H, 5.01; N, 20.73.

Example 36

(11R)-11-(Chloromethyl)-10,11-dihydro-8H-[1,4] oxazino[4',3':1,2]imidazo[4,5-c]quinolin-6-amine

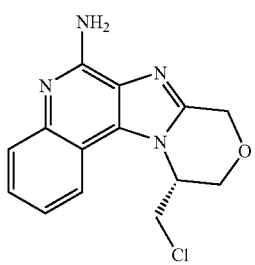

Thionyl chloride (1.5 mL, 20.7 mmol) was added neat to [(11S)-6-amino-10,11-dihydro-8H-[1,4]oxazino[4',3':1,2] imidazo[4,5-c]quinolin-11-yl]methanol (280 mg, 1.03 mmol). The nearly homogeneous yellow reaction mixture was heated to 70° C. for 2 hours and turned dark red. The reaction mixture was cooled to ambient temperature and poured over ice. While maintaining the temperature at 0° C., the pH of the mixture was brought to 14 by addition of 50% aqueous NaOH. The resulting white suspension was extracted with CHCl₃. The layers were separated and the organic layer was dried over Na₂SO₄ and concentrated under reduced pressure to provide a tan foam. The tan foam was slurried with acetonitrile and filtered to provide 185 mg of the desired product as a white solid, mp 230-232° C.

¹H NMR (300 MHz, DMSO-d₆) δ 7.89 (dd, J=1.1, 8.3 Hz, 1H), 7.64 (dd, J=1.0, 8.4 Hz, 1H), 7.46 (ddd, J=1.4, 7.0, 8.4 Hz, 1H), 7.31 (ddd, J=1.4, 7.0, 8.1 Hz, 1H), 6.63 (s, 2H), 5.27 (dt, J=2.9, 9.4 Hz, 1H), 5.12 (d, J=16 Hz, 1H), 5.00 (d, J=16 Hz, 1H), 4.42 (d, J=13 Hz, 1H), 4.16 (br d, J=12 Hz, 1H), 4.07-3.93 (m, 2H), ¹³C NMR (125 MHz, DMSO-d₆) δ 151.7, 145.0, 144.7, 131.3, 126.7, 126.31, 126.28, 121.3, 119.6, 114.2, 64.7, 63.7, 54.5, 42.1; MS (APCI) m/z 289 (M+H)⁺. Anal. calcd for $C_{14}H_{13}ClN_4O$: C, 58.24; H, 4.54; N, 19.40. Found: C, 58.06; H, 4.31; N, 19.57.

Example 37

(11S)-11-[(4-Methylpiperazin-1-yl)methyl]-10,11-dihydro-8H-[1,4]oxazino[4',3':1,2]imidazo[4,5-c] quinolin-6-amine

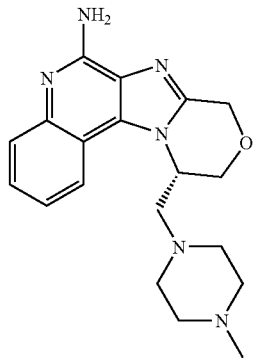

Methyl piperazine (0.3 mL, 2.5 mmol) was added to a vial containing (11R)-11-(chloromethyl)-10,11-dihydro-8H-[1, 4]oxazino[4',3':1,2]imidazo[4,5-c]quinolin-6-amine (90 mg, 0.31 mmol). The vial was placed in a stainless-steel, high-pressure vessel and heated to 150° C. for 18 hours. The reaction mixture was cooled to ambient temperature. The resulting light brown oil was purified by chromatography (SiO₂, 0-30% CMA/CHCl₃). The resulting oil was slurried in acetonitrile to produce a solid which was isolated by filtration to give 18 mg of the desired product as a tan solid, mp 187-190° C.

¹H NMR (300 MHz, DMSO-d₆) δ 8.01 (d, J=8.0 Hz, 1H), 7.63 (d, J=8.3 Hz, 1H), 7.46 (dd, J=7.2, 8.4 Hz, 1H), 7.31 (dd, J=7.0, 8.3 Hz, 1H), 6.66 (s, 2H), 5.16 (m, 1H), 5.10 (d, J=16 Hz, 1H), 5.00 (d, J=16 Hz, 1H), 4.46 (d, J=12 Hz, 1H), 4.02 (br d, J=12 Hz, 1H), 3.34-2.50 (m, 10H), 2.31 (s, 3H); ¹³C NMR (125 MHz, DMSO-d₆) δ 151.6, 145.4, 144.1, 131.4, 126.7, 126.2, 125.8, 121.1, 120.3, 114.2, 64.5, 64.1, 57.0, 54.1, 52.1, 51.8, 44.7; MS (APCI) m/z 353 (M+H)⁺. Anal. calcd for $C_{19}H_{24}N_6O \cdot 1.4H_2O$: C, 60.43; H, 7.15; N, 22.25. Found: C, 60.25; H, 7.09; N, 22.33.

Example 38

(11R)-11-[(1R)-1-(benzyloxy)ethyl]-10,11-dihydro-8H-[1,4]oxazino[4',3':1,2]imidazo[4,5-c]quinolin-6-amine

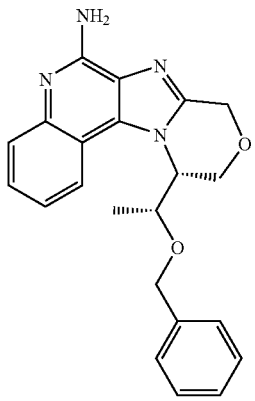

Part A

Methyl L-threoninate hydrochloride (16.9 g, 100 mmol), prepared by the method of Lall, *J. Org. Chem.*, 67, pp. 1536-1547, was dissolved in 200 mL of anhydrous $CH_2Cl_2$ and the solution was cooled to 0° C. under $N_2$. Triethylamine (27.8 mL, 200 mmol) was then added followed by triphenylmethylchloride (27.9 g, 100 mmol) and the reaction was stirred and allowed to warm to ambient temperature overnight. The reaction mixture was then filtered and the resulting solid was rinsed with several portions of $CH_2Cl_2$. The combined filtrates were concentrated under reduced pressure and the resulting syrup was dissolved in 150 mL of ethyl acetate and then washed successively with 100 mL of saturated aqueous $NaHCO_3$ solution, 100 mL of 10% aqueous citric acid solution, 50 mL of $H_2O$ and 50 mL of brine. The organic portion was then dried over $Na_2SO_4$, filtered and concentrated under reduced pressure to give a syrup. The syrup was treated with 200 mL of hexanes and the mixture was stirred rapidly overnight to give a white solid. The solvent was decanted and the solid was washed with an additional portion of hexanes. The mixture was filtered and the isolated white solid was dried under vacuum for several days to give methyl N-trityl-L-threoninate (32.4 g) as a sticky, white powder.

Part B

A 250-mL, round-bottomed flask, under an atmosphere of $N_2$, was charged with sodium hydride (60% oil dispersion, 772 mg, 19.3 mmol). The sodium hydride was washed with 3 portions of hexanes to remove the oil and then 8 mL of anhydrous DMF was added followed by benzyl bromide (3.38 mL, 28.4 mmol). The mixture was cooled to 0° C. and then a solution of methyl N-trityl-L-threoninate (4.83 g, 12.9 mmol) dissolved in 12 mL of DMF was added dropwise via cannula over 5 minutes. After stirring for 2 hours, the reaction mixture was treated with saturated aqueous $Na_2CO_3$ solution and 200 mL of $Et_2O$ and the layers were separated. The organic portion was washed successively with $H_2O$ (5×100 mL) and brine (100 mL), dried over $MgSO_4$, filtered and concentrated under reduced pressure. Chromatography ($SiO_2$, 5-10% ethyl acetate/hexanes) gave 4.61 g of methyl O-benzyl-N-trityl-L-threoninate as a colorless syrup.

Part C

Methyl O-benzyl-N-trityl-L-threoninate (4.61 g, 9.91 mmol) was dissolved in 100 mL of anhydrous $Et_2O$ and the solution was cooled to 0° C. under $N_2$. Lithium aluminum hydride (2.28 g, 60 mmol) was added and the mixture was stirred for 2 hours. The reaction mixture was then sequentially treated with 2.28 mL of $H_2O$, 2.28 mL of 15% NaOH solution and 6.84 mL of $H_2O$. After stirring for 30 minutes, the reaction mixture was filtered to remove the white solid. The solid was washed with several portions of $Et_2O$ and the combined filtrates were concentrated under reduced pressure. Chromatography ($SiO_2$, 10-20% ethyl acetate/hexanes) gave 4.34 g of (2R,3R)-3-(benzyloxy)-2-(tritylamino)butan-1-ol as a colorless syrup.

Part D

A solution of (2R,3R)-3-(benzyloxy)-2-(tritylamino)butan-1-ol (4.33 g, 9.91 mmol) dissolved in 150 mL of $CH_2Cl_2$ was treated with triethylamine (1.52 mL, 10.9 mmol), tert-butyldimethylsilyl chloride (1.65 g, 10.9 mmol) and DMAP (122 mg, 1.00 mmol) and the reaction mixture was stirred under $N_2$ overnight. The reaction mixture was then concentrated and the resulting material was dissolved in 50 mL of $CH_2Cl_2$ and washed successively with $H_2O$ and brine. The organic portion was then dried over $Na_2SO_4$, filtered and concentrated under reduced pressure. Chromatography ($SiO_2$, 5-10% ethyl acetate/hexanes) gave 3.26 g of (2R,3R)-3-(benzyloxy)-1-{[tert-butyl(dimethyl)silyl]oxy-}-N-tritylbutan-2-amine as a white solid.

Part E (2R,3R)-3-(benzyloxy)-1-{[tert-butyl(dimethyl)silyl]oxy}-N-tritylbutan-2-amine (3.26 g, 5.92 mmol) was dissolved in 75 mL of anhydrous $CH_2Cl_2$ and 9.6 mL of glacial acetic acid. The reaction mixture was cooled to 0° C. under an atmosphere of $N_2$ and boron trifluoride diethyl etherate (790 µL, 5.92 mmol) was added dropwise over several minutes. After stirring for 4 hours, the reaction mixture was treated with 90 mL of cold, aqueous 10% NaOH solution. The layers were separated and the aqueous portion was extracted with $CH_2Cl_2$ (3×20 mL). The combined organic layers were washed with brine (10 mL), dried over $Na_2SO_4$, filtered and concentrated under reduced pressure. Chromatography ($SiO_2$, 0-5% methanol/$CHCl_3$) gave 1.83 g of (2R,3R)-3-(benzyloxy)-1-{[tert-butyl(dimethyl)silyl]oxy}butan-2-amine as a white solid.

Part F

The title compound was prepared from 4-chloro-3-nitroquinoline and (2R,3R)-3-(benzyloxy)-1-{[tert-butyl(dimethyl)silyl]oxy}butan-2-amine following Parts E through J listed for the preparation of Example 34. Chromatography ($SiO_2$, 10-40% CMA/$CHCl_3$) gave a light-orange foam. Crystallization from ethyl acetate gave (11R)-11-[(1R)-1-(benzyloxy)ethyl]-10,11-dihydro-8H-[1,4]oxazino[4',3':1,2]imidazo[4,5-c]quinolin-6-amine as an off-white solid, mp 189.0-190.8° C.

¹H NMR (300 MHz, DMSO-$d_6$) δ 7.89 (d, J=7.5 Hz, 1H), 7.59 (dd, J=1.0, 8.4 Hz, 1H), 7.38 (m, 1H), 7.24-7.22 (m, 3H), 7.12-7.06 (m, 3H), 6.58 (s, 2H), 5.07 (d, J=15.7 Hz, 1H), 5.05

(m, 1H), 4.97 (d, J=15.7 Hz, 1H), 4.55 (d, J=12.4 Hz, 1H), 4.48 (d, J=12.5 Hz, 1H), 4.36 (d, J=12.4 Hz, 1H), 4.14-4.04 (m, 2H), 1.13 (d, J=6.3 Hz, 3H); $^{13}$C NMR (125 MHz, DMSO-$d_6$) δ 151.7, 145.2, 144.7, 138.0, 132.2, 128.0, 127.3, 127.2, 126.3, 125.9, 120.8, 120.7, 114.8, 73.5, 70.1, 64.0, 63.6, 56.5, 15.4; MS (ESI) m/z 375 (M+H)$^+$. Anal. calcd for $C_{22}H_{22}N_4O_2$: C, 70.57; H, 5.92; N, 14.96. Found: C, 70.55; H, 5.77; N, 15.15.

Example 39

(1R)-1-[(11R)-6-Amino-10,11-dihydro-8H-[1,4]oxazino[4',3':1,2]imidazo[4,5-c]quinolin-11-yl]ethanol

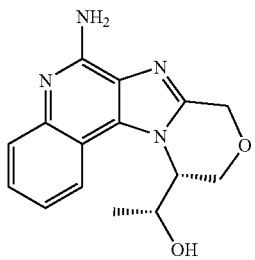

(11R)-11-[(1R)-1-(Benzyloxy)ethyl]-10,11-dihydro-8H-[1,4]oxazino[4',3':1,2]imidazo[4,5-c]quinolin-6-amine (512 mg, 1.37 mmol) was dissolved in 30 mL of methanol and the solution was placed in a pressure bottle. Palladium on carbon (10%, 200 mg) and 2.5 mL of 3 M HCl in ethanol were then added and the reaction mixture was shaken under $H_2$ at 50 PSI (3.4×10$^5$ Pa). After 24 hours, the reaction mixture was filtered through a pad of CELITE filter agent. The pad was rinsed with methanol and the combined filtrates were concentrated under reduced pressure. The residue was dissolved in $H_2O$ and the solution was made basic by the addition of concentrated aqueous $NH_4OH$ solution. The aqueous solution 10% MeOH/CHCl$_3$ several times and the combined organic layers were concentrated under reduced pressure. Chromatography (SiO$_2$, 25-50% CMA/CHCl$_3$) gave an off-white powder. Crystallization from ethyl acetate and methanol gave 353 mg of the title compound as white needles, mp 215.3-218.6° C.

$^1$H NMR (500 MHz, DMSO-$d_6$) δ 8.09 (d, J=7.4 Hz, 1H), 7.61 (dd, J=1.0, 8.3 Hz, 1H), 7.42 (ddd, J=1.3, 7.0, 8.3 Hz, 1H), 7.24 (ddd, J=1.2, 7.1, 8.1 Hz, 1H), 6.57 (s, 2H), 5.41 (d, J=4.4 Hz, 1H), 5.08 (d, J=15.6 Hz, 1H), 4.93 (d, J=15.6 Hz, 1H), 4.80 (m, 1H), 4.53 (d, J=12.4 Hz, 1H), 4.32 (m, 1H), 4.05 (dd, J=3.3, 12.4 Hz, 1H), 1.02 (d, J=6.5 Hz, 3H); $^{13}$C NMR (125 MHz, DMSO-$d_6$) δ 151.8, 145.3, 144.6, 132.1, 126.4, 126.3, 126.0, 120.8, 120.2, 114.8, 65.9, 64.0, 62.8, 57.9, 18.3; MS (ESI) m/z 285 (M+H)$^+$. Anal. calcd for $C_{15}H_{16}N_4O_2 \cdot 0.5H_2O$: C, 61.42; H, 5.84; N, 19.10. Found: C, 61.30; H, 5.58; N, 19.07.

Example 40

(11R)-11-[(1S)-1-(benzyloxy)ethyl]-10,11-dihydro-8H-[1,4]oxazino[4',3':1,2]imidazo[4,5-c]quinolin-6-amine

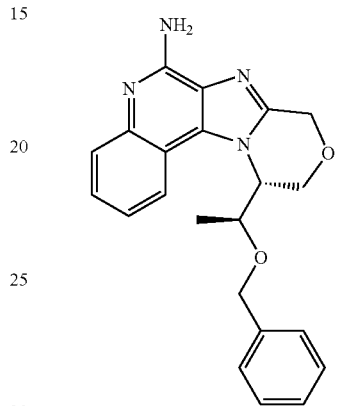

Part A

A 500-mL, round-bottomed flask was charged with methyl N-trityl-L-threoninate (3.75 g, 10.0 mmol), benzoic acid (2.44 g, 20.0 mmol) and triphenylphosphine (5.24 g, 20.0 mmol). Anhydrous THF (50 mL) was added and the solution was cooled to 0° C. under $N_2$ with stirring. A 40% solution of diethylazodicarboxylate in toluene (9.06 mL, 20.0 mmol) was added dropwise and the reaction mixture was allowed to warm to ambient temperature overnight. The reaction mixture was treated with 50 mL of ethyl acetate and 50 mL of saturated aqueous NaHCO$_3$ solution. The layers were separated and the organic portion was washed successively with $H_2O$ and brine, dried over Na$_2$SO$_4$, filtered and concentrated under reduced pressure to give a yellow syrup. The yellow syrup was dissolved in 25 mL of Et$_2$O and then treated with hexanes until a white precipitate formed. The solid was removed by filtration and the filtrate was concentrated to give a yellow oil. Chromatography (SiO$_2$, 33-100% CH$_2$Cl$_2$/hexanes) gave 1.24 g of methyl O-benzoyl-N-trityl-L-allothreoninate as a colorless solid.

Part B

A solution of the methyl O-benzoyl-N-trityl-L-allothreoninate (1.24 g, 2.59 mmol) dissolved in 15 mL of anhydrous methanol was treated with 0.1 mL of a 25% solution of sodium methoxide in methanol. The reaction mixture was stirred under $N_2$ for 2 days. The reaction was then treated with 10 mL of saturated aqueous NaHCO$_3$ solution and the methanol was removed under reduced pressure. The reaction mixture was then treated with 30 mL of ethyl acetate and washed successively with $H_2O$ and brine. The organic portion was dried over Na$_2$SO$_4$, filtered and concentrated under reduced pressure to give a colorless solid. Crystallization from ethyl acetate and hexanes gave methyl N-trityl-L-allothreoninate (0.60 g) as colorless crystals.

Part C (2R,3S)-3-(Benzyloxy)-1-{[tert-butyl(dimethyl)silyl]oxy}butan-2-amine was prepared from methyl N-trityl-L-allothreoninate following Parts B through E listed for the preparation of Example 38. The product was obtained as colorless syrup.

Part D

The title compound was prepared from (2R,3S)-3-(benzyloxy)-1-{[tert-butyl(dimethyl)silyl]oxy}butan-2-amine and 4-chloro-3-nitroquinoline and (2R,3S)-3-(benzyloxy)-1-{[tert-butyl(dimethyl)silyl]oxy}butan-2-amine following Parts E through J listed for the preparation of Example 34. Chromatography (SiO$_2$, 10-30% CMA/CHCl$_3$) gave a light-orange foam. Crystallization from acetonitrile gave (11R)-11-[(1S)-1-(benzyloxy)ethyl]-10,11-dihydro-8H-[1,4]oxazino[4',3':1,2]imidazo[4,5-c]quinolin-6-amine as white, fluffy crystals, mp 86.6-89.7° C.

$^1$H NMR (300 MHz, DMSO-d$_6$) δ 8.00 (d, J=7.5 Hz, 1H), 7.60 (dd, J=1.0, 8.3 Hz, 1H), 7.39 (m, 1H), 7.20-7.10 (m, 4H), 7.01-6.95 (m, 2H), 6.58 (s, 2H), 5.11 (d, J=1.9 Hz, 1H), 5.04 (d, J=15.6 Hz, 1H), 4.97 (d, J=15.6 Hz, 1H), 4.43 (dd, J=1.6, 12.2 Hz, 1H), 4.37 (d, J=12.0 Hz, 1H), 4.22-4.12 (m, 2H), 4.09 (d, J=12.0 Hz, 1H), 1.21 (d, J=6.5 Hz, 3H); $^{13}$C NMR (125 MHz, DMSO-d$_6$) δ 150.7, 145.3, 143.6, 136.9, 130.8, 126.8, 126.1, 126.0, 125.3, 125.0, 119.7, 119.6, 113.7, 73.6, 69.2, 63.0, 62.8, 56.2, 14.9; MS (ESI) m/z 375 (M+H)$^+$. Anal. calcd for C$_{22}$H$_{22}$N$_4$O$_2$: C, 70.57; H, 5.92; N, 14.96. Found: C, 70.40; H, 5.91; N, 15.01.

Example 41

(1S)-1-[(11R)-6-amino-10,11-dihydro-8H-[1,4]oxazino[4',3':1,2]imidazo[4,5-c]quinolin-11-yl]ethanol

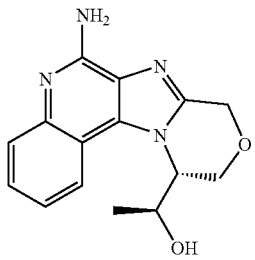

(11R)-11-[(1S)-1-(Benzyloxy)ethyl]-10,11-dihydro-8H-[1,4]oxazino[4',3':1,2]imidazo[4,5-c]quinolin-6-amine (512 mg, 1.37 mmol) was dissolved in 30 mL of methanol and the solution was placed in a pressure bottle. Palladium on carbon (10%, 200 mg) and 2.5 mL of 3 M HCl in ethanol were then added and the reaction mixture was shaken under H$_2$ at 50 PSI (3.4×10$^5$ Pa). After 24 hours, the reaction mixture was filtered through a pad of CELITE filter agent. The pad was rinsed with methanol and the combined filtrates were concentrated under reduced pressure. The residue was dissolved in H$_2$O and the solution was made basic by the addition of concentrated aqueous NH$_4$OH solution. The aqueous solution was extracted with 10% MeOH/CHCl$_3$ several times and the combined organic layers were concentrated under reduced pressure. Chromatography (SiO$_2$, 25-75% CMA/CHCl$_3$) gave an off-white powder. Crystallization from ethyl acetate and methanol gave 125 mg of the desired compound as a white, fluffy solid, mp 207.6-208.7° C.

$^1$H NMR (300 MHz, DMSO-d$_6$) δ 8.07 (d, J=7.6 Hz, 1H), 7.61 (dd, J=0.8, 8.3 Hz, 1H), 7.41 (ddd, J=1.1, 7.1, 8.2 Hz, 1H), 7.23 (ddd, J=1.2, 7.0, 8.1 Hz, 1H), 6.54 (s, 2H), 5.03 (d, J=5.9 Hz, 1H), 5.02 (d, J=15.6 Hz, 1H), 4.94 (d, J=15.5 Hz, 1H), 4.93 (m, 1H), 4.42 (dd, J=2.0, 12.0 Hz, 1H), 4.26 (m, 1H), 4.09 (dd, J=3.6, 12.0 Hz, 1H), 1.12 (d, J=6.6 Hz, 3H); $^{13}$C NMR (125 MHz, DMSO-d$_6$) δ 152.3, 146.8, 145.1, 132.5, 126.9, 126.7, 126.6, 121.4, 121.1, 115.5, 67.0, 64.5, 64.1, 58.7, 20.1; MS (ESI) m/z 285 (M+H)$^+$. Anal. calcd for C$_{15}$H$_{16}$N$_4$O$_2$: C, 63.37; H, 5.67; N, 19.71. Found: C, 63.16; H, 5.54; N, 19.49.

Example 42

(11S)-11-Tetrahydro-2H-pyran-4-yl-10,11-dihydro-8H-[1,4]oxazino[4',3':1,2]imidazo[4,5-c]quinoline

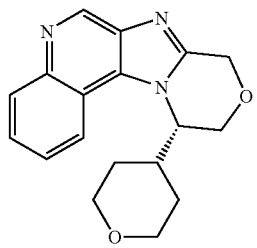

Part A

A solution of methyl tetrahydro-2H-pyran-4-carboxylate (13.3 mL, 100 mmol) in 400 mL of anhydrous Et$_2$O was cooled to −78° C. under N$_2$. A 1.23 M solution of diisobutylaluminum hydride in hexanes (90 mL, 111 mmol) was then added dropwise to the stirred solution over 40 minutes. The reaction mixture was stirred for an additional 60 minutes, and then treated with 100 mL of saturated aqueous potassium sodium tartrate solution and the mixture was allowed to warm to ambient temperature. The layers were separated and the aqueous portion was extracted with Et$_2$O (2×50 mL). The combined organic portions were washed with 50 mL of brine, dried over MgSO$_4$, filtered and concentrated under reduced pressure. Chromatography (SiO$_2$, 25-75% ethyl acetate/hexanes) gave 6.64 g of tetrahydro-2H-pyran-4-carbaldehyde as a colorless liquid.

Part B

A 500-mL, round-bottomed flask, under an atmosphere of N$_2$, was charged with sodium hydride (60% oil dispersion, 2.33 g, 58.3 mmol). The sodium hydride was washed with 3 portions of hexanes to remove the oil and then 200 mL of anhydrous THF was added. Methyltriphenylphosphonium bromide (20.8 g, 58.3 mmol) was then added and the mixture was heated to reflux, under N$_2$ for 120 minutes. The solution was cooled to ambient temperature and tetrahydro-2H-pyran-4-carbaldehyde (5.54 g, 48.6 mmol) was added to the bright yellow reaction mixture via syringe and stirring was continued overnight. Saturated aqueous NaHCO$_3$ solution (100 mL) and 200 mL of Et$_2$O were added to the reaction mixture and the layers were separated. The organic portion was washed successively with H$_2$O and brine, dried over MgSO$_4$, filtered and concentrated under reduced pressure to give a sticky solid. The solid was slurried in a mixture of Et$_2$O and pentane. The solids were removed by filtration and the filtrate was concentrated under reduced pressure at 0° C. to give a colorless liquid. Chromatography (SiO$_2$, 20% Et$_2$O/pentane) gave 1.70 g of 4-vinyltetrahydro-2H-pyran as a colorless liquid.

Part C

A 500-mL, round-bottomed flask was charged with potassium ferricyanide (III) (15.0 g, 45.6 mmol), 2,5-diphenyl-4,6-bis(9-O-dihydroquinidyl)pyrimidine ((DHQD)$_2$-PYR) (132 mg, 0.15 mmol) and K$_2$CO$_3$ (6.29 g, 45.6 mmol). A 1:1 mixture of tert-butyl alcohol/H$_2$O (150 mL) was added and the suspension was stirred under N$_2$. A 0.25 M solution of OsO$_4$ in toluene (0.60 mL, 0.15 mmol) was then added the mixture was cooled to 0° C. After stirring for 60 minutes, 4-vinyltetrahydro-2H-pyran (1.70 g, 15.2 mmol) was added and the mixture was stirred overnight. Solid Na$_2$S$_2$O$_5$ (22.5 g) was then added and the reaction mixture was allowed to warm to ambient temperature. CH$_2$Cl$_2$ (150 mL) was then added and the layers were separated. The aqueous layer was extracted with CH$_2$Cl$_2$ (3×30 mL) and the combined organic layers were dried over Na$_2$SO$_4$, filtered and concentrated under reduced pressure. Chromatography (SiO$_2$, 10% methanol/CHCl$_3$) gave 2.11 g of (1R)-1-tetrahydro-2H-pyran-4-ylethane-1,2-diol as a colorless oil.

Part D

A solution of (1R)-1-tetrahydro-2H-pyran-4-ylethane-1,2-diol (2.40 g, 16.2 mmol) in 60 mL of CH$_2$Cl$_2$ was cooled to 0° C. under N$_2$. 2,6-Lutidine (3.77 mL, 32.4 mmol) and tert-butyldimethylsilyl chloride (2.57 g, 17.0 mmol) were added and the reaction mixture was stirred and allowed to warm to ambient temperature overnight. The reaction mixture was treated with saturated aqueous NH$_4$Cl solution and the layers were separated. The organic portion was washed successively with aqueous 3.5% NaH$_2$PO$_4$ solution (2×), H$_2$O and brine, dried over Na$_2$SO$_4$, filtered and concentrated under reduced pressure. Chromatography (SiO$_2$, 20% ethyl acetate/hexanes) gave 3.29 g of (1R)-2-{[tert-butyl(dimethyl)silyl]oxy}-1-tetrahydro-2H-pyran-4-ylethanol as a colorless oil.

Part E

A solution of (1R)-2-{[tert-butyl(dimethyl)silyl]oxy}-1-tetrahydro-2H-pyran-4-ylethanol (3.29 g, 12.7 mmol) in 60 mL of CH$_2$Cl$_2$ was cooled to 0° C. under N$_2$. Triethylamine (3.58 mL, 25.7 mmol) was then added followed by methanesulfonyl chloride (2.57 g, 17.0 mmol) and DMAP (61 mg, 0.50 mmol) and the reaction mixture was stirred and allowed to warm to ambient temperature overnight. The reaction mixture was treated with saturated aqueous NaHCO$_3$ solution and the layers were separated. The organic portion was washed successively with aqueous 3.5% NaH$_2$PO$_4$ solution (2×), H$_2$O and brine, dried over Na$_2$SO4, filtered and concentrated under reduced pressure to give 4.29 g of (1R)-2-{[tert-butyl(dimethyl)silyl]oxy}-1-tetrahydro-2H-pyran-4-ylethyl methanesulfonate as a colorless oil.

Part F

A solution of (1R)-2-{[tert-butyl(dimethyl)silyl]oxy}-1-tetrahydro-2H-pyran-4-ylethyl methanesulfonate (4.29 g, 12.7 mmol) in 40 mL of DMF was treated with sodium azide (1.00 g, 15.2 mmol) and the mixture was heated to 60° C. for 12 hours and then to 80° C. for 8 hours. The reaction mixture was concentrated under reduced pressure and the resulting material was dissolved in 50 mL of ethyl acetate and washed successively with H$_2$O (3×25 mL) and brine (25 mL). The organic layer was dried over Na$_2$SO$_4$, filtered and concentrated under reduced pressure. Chromatography (SiO$_2$, 10-25% ethyl acetate/hexanes) gave 1.60 g of {[(2S)-2-azido-2-tetrahydro-2H-pyran-4-ylethyl]oxy}(tert-butyl)dimethylsilane as a colorless oil and 1.50 g of recovered (1R)-2-{[tert-butyl(dimethyl)silyl]oxy}-1-tetrahydro-2H-pyran-4-ylethyl methanesulfonate. The recovered starting material was again subjected to the reaction conditions to afford an additional 0.59 g of product.

Part G

{[(2S)-2-Azido-2-tetrahydro-2H-pyran-4-ylethyl]oxy}(tert-butyl)dimethylsilane (2.19 g, 7.68 mmol) was dissolved in 25 mL of methanol and the solution was placed in a pressure bottle. Palladium on carbon (10%, 250 mg) was then added and the reaction mixture was shaken under H$_2$ at 50 PSI (3.4×10$^5$ Pa). After 18 hours, the reaction mixture was filtered through a pad of CELITE filter agent. The pad was rinsed with methanol and the combined filtrates were concentrated under reduced pressure to give 1.94 g of (1S)-2-{[tert-butyl(dimethyl)silyl]oxy}-1-tetrahydro-2H-pyran-4-ylethanamine as a colorless syrup.

Part H

The title compound was prepared from 4-chloro-3-nitroquinoline and (1S)-2-{[tert-butyl(dimethyl)silyl]oxy}-1-tetrahydro-2H-pyran-4-ylethanamine following Parts E through H listed for the preparation of Example 34. Chromatography (SiO$_2$, 2-10% methanol/CHCl$_3$) gave a white powder. Crystallization from ethyl acetate gave (11S)-11-tetrahydro-2H-pyran-4-yl-10,11-dihydro-8H-[1,4]oxazino[4',3':1,2]imidazo[4,5-c]quinoline as colorless crystals, mp 234.0-237.0° C.

$^1$H NMR (300 MHz, DMSO-d$_6$) δ 8.30 (m, 1H), 8.18 (m, 1H), 7.77-7.69 (m, 2H), 7.23 (ddd, J=1.2, 7.0, 8.1 Hz, 1H), 5.18 (d, J=16.0 Hz, 1H), 5.07 (d, J=3.9 Hz, 1H), 5.02 (d, J=16.0 Hz, 1H), 4.49 (d, J=12.6 Hz, 1H), 4.12 (dd, J=3.1, 12.6 Hz, 1H), 3.86 (dd, J=3.2, 11.3 Hz, 1H), 3.76 (dd, J=3.5, 11.3 Hz, 1H), 3.19 (m, 1H), 2.97 (m, 1H), 2.35 (m, 1H), 1.80-1.55 (m, 3H), 1.10 (d, J=13.2 Hz, 1H); $^{13}$C NMR (125 MHz, DMSO-d$_6$) δ 148.6, 144.8, 144.3, 136.5, 132.6, 130.7, 127.2, 127.0, 121.4, 117.9, 67.6, 67.5, 64.5, 64.3, 57.7, 29.4, 28.5; MS (ESI) m/z 310 (M+H)$^+$. Anal. calcd for C$_{18}$H$_{19}$N$_3$O$_2$: C, 69.88; H, 6.19; N, 13.58. Found: C, 69.87; H, 6.23; N, 13.46.

Example 43

(11S)-11-Tetrahydro-2H-pyran-4-yl-10,11-dihydro-8H-[1,4]oxazino[4',3':1,2]imidazo[4,5-c]quinolin-6-amine

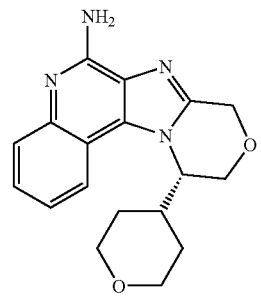

The title compound was prepared from 800 mg of (11S)-11-tetrahydro-2H-pyran-4-yl-10,11-dihydro-8H-[1,4]oxazino[4',3':1,2]imidazo[4,5-c]quinoline following Parts I and J listed for the preparation of Example 34. Chromatography (SiO$_2$, 25-50% CMA/CHCl$_3$) of the title compound gave a light-brown solid. The solid was dissolved in 20 mL of methanol and treated with about 200 mg of activated charcoal. After heating at reflux for 60 minutes, the reaction mixture was filtered through a CELITE pad. The pad was rinsed with methanol and the combined filtrates were concentrated under reduced pressure. Crystallization from methanol gave 305 mg of the title compound as a fluffy, white solid, mp 240.4-243.4° C.

$^1$H NMR (500 MHz, DMSO-$d_6$) δ 7.96 (d, J=7.9 Hz, 1H), 7.63 (dd, J=0.6, 8.3 Hz, 1H), 7.43 (ddd, J=0.9, 7.4, 8.0 Hz, 1H), 7.28 (ddd, J=1.0, 7.1, 8.0 Hz, 1H), 6.58 (s, 2H), 5.10 (d, J=15.6 Hz, 1H), 4.95 (d, J=15.8 Hz, 1H), 4.93 (m, 1H), 4.44 (d, J=12.5 Hz, 1H), 4.08 (dd, J=2.9, 12.6 Hz, 1H), 3.86 (dd, J=3.3, 11.1 Hz, 1H), 3.77 (dd, J=3.3, 11.3 Hz, 1H), 3.19 (m, 1H), 2.98 (m, 1H), 2.30 (m, 1H), 1.80-1.55 (m, 3H), 1.11 (d, J=13.3 Hz, 1H); $^{13}$C NMR (125 MHz, DMSO-$d_6$) δ 152.3, 146.2, 145.2, 132.0, 126.9, 126.8, 126.7, 121.5, 120.8, 115.2, 67.7, 67.5, 64.5, 64.3, 57.4, 29.5, 28.5; MS (ESI) m/z 325 (M+H)$^+$. Anal. calcd for $C_{18}H_{20}N_4O_2 \cdot 0.25H_2O$: C, 65.74; H, 6.28; N, 17.04. Found: C, 65.62; H, 6.25; N, 17.21.

Example 44

(4S)-4,6,7-Trimethyl-3,4-dihydro-1H-pyrido[3',4':4,5]imidazo[2,1-c][1,4]oxazin-9-amine

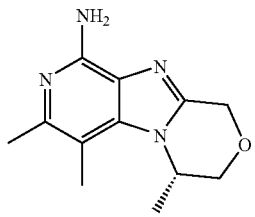

Part A

A solution of 2,4-dichloro-5,6-dimethyl-3-nitropyridine (5.0 g, 22.6 mmol) in 50 mL of dry DMF was cooled to 0° C. under an atmosphere of $N_2$. Triethylamine (6.3 mL, 45.2 mmol) and L-alaninol (2.1 mL, 27.1 mmol) were added sequentially. After approximately 15 minutes, the reaction was allowed to warm to ambient temperature, and then heated to 35° C. for 3 days. The reaction mixture was concentrated under reduced pressure to give an orange-brown solid. The resulting solid was partitioned between 50 mL of ethyl acetate and 50 mL of $H_2O$. The layers were separated and the organic portion was washed sequentially with $H_2O$ and brine, dried over $Na_2SO_4$, filtered, and concentrated under reduced pressure. Chromatography ($SiO_2$, 40-60% ethyl acetate/hexanes) afforded (2S)-2-[(2-chloro-5,6-dimethyl-3-nitropyridin-4-yl)amino]propan-1-ol (3.62 g) as an orange solid.

Part B (2S)-2-[(2-Chloro-5,6-dimethyl-3-nitropyridin-4-yl)amino]propan-1-ol (3.62 g, 13.9 mmol) was dissolved in 30 mL of dry pyridine under an atmosphere of $N_2$. tert-Butyldimethylsilyl chloride (2.52 g, 16.7 mmol) and DMAP (0.17 g, 1.39 mmol) were added sequentially, and the reaction was heated to 50° C. and stirred overnight. The reaction mixture was then concentrated under reduced pressure. The resulting residue was partitioned between 50 mL of ethyl acetate and 50 mL of $H_2O$. The layers were separated and the organic portion was washed with $H_2O$ and brine, dried over $Na_2SO_4$, filtered, and concentrated under reduced pressure. The resulting material was passed through a plug of $SiO_2$, eluting with a mixture of $CH_2Cl_2$, ethyl acetate and hexanes, to afford N-((1S)-2-{[tert-butyl(dimethyl)silyl]oxy}-1-methylethyl)-2-chloro-5,6-dimethyl-3-nitropyridin-4-amine (4.79 g) as an orange oil.

Part C

A pressure bottle was charged with platinum on carbon (5%, 1.16 g) followed by a solution of N-((1S)-2-{[tert-butyl(dimethyl)silyl]oxy}-1-methylethyl)-2-chloro-5,6-dimethyl-3-nitropyridin-4-amine (4.79 g, 12.8 mmol) dissolved in 125 mL of toluene. The reaction mixture was shaken under $H_2$ at 48 PSI (3.3×10$^5$ Pa). After 6 hours, the reaction mixture was filtered through a pad of CELITE filter agent. The pad was rinsed with toluene and $CH_2Cl_2$. The combined filtrates were concentrated under reduced pressure to give $N^4$-((1S)-2-{[tert-butyl(dimethyl)silyl]oxy}-1-methylethyl)-2-chloro-5,6-dimethylpyridine-3,4-diamine (4.39 g) as an orange oil.

Part D $N^4$-((1S)-2-{[tert-Butyl(dimethyl)silyl]oxy}-1-methylethyl)-2-chloro-5,6-dimethylpyridine-3,4-diamine (2.85 g, 8.29 mmol) was dissolved in 100 mL of dry 1,2-dichloroethane and the solution was cooled to 0° C. as it stirred under an atmosphere of $N_2$. Triethylamine (2.3 mL, 16.58 mmol) and chloroacetyl chloride (0.92 mL, 11.60 mmol) were added sequentially. After 30 minutes, the reaction mixture was allowed to warm to ambient temperature and stirred for 3 days followed by heating to 70° C. for 2 days. The reaction mixture was allowed to cool to ambient temperature and was washed with saturated $NaHCO_3$ solution (2×100 mL) and brine (100 mL). The organic layer was dried over $Na_2SO_4$, filtered and concentrated under reduced pressure to afford the crude product as a brown solid. Chromatography ($SiO_2$, 20-50% ethyl acetate/hexanes) gave 1-((1S)-2-{[tert-butyl(dimethyl)silyl]oxy}-1-methylethyl)-4-chloro-2-(chloromethyl)-6,7-dimethyl-1H-imidazo[4,5-c]pyridine (0.44 g) as a yellow oil.

Part E 1-((1S)-2-{[tert-Butyl(dimethyl)silyl]oxy}-1-methylethyl)-4-chloro-2-(chloromethyl)-6,7-dimethyl-1H-imidazo[4,5-c]pyridine (440 mg, 1.09 mmol) was dissolved in 10 mL of THF and the yellow solution was cooled to –78° C. under an atmosphere of $N_2$. A 1.0 M solution of tetrabutylammonium fluoride in THF (1.42 mL) was slowly added, and the reaction was allowed to warm to 0° C. overnight. The reaction was then treated with 20 mL of saturated $NaHCO_3$ and 20 mL of $CH_2Cl_2$. The layers were separated and the organic portion was washed with brine (4×20 mL), dried over $Na_2SO_4$, filtered and concentrated under reduced pressure to give (2S)-2-[4-chloro-2-(chloromethyl)-6,7-dimethyl-1H-imidazo[4,5-c]pyridin-1-yl]propan-1-ol (314 mg) as a tan solid. The tan solid was dissolved in 10 mL of anhydrous THF. The resulting yellow solution was cooled to 0° C. under an atmosphere of $N_2$. Solid potassium tert-butoxide (116 mg, 1.42 mmol) was then added and the reaction was stirred at 0° C. for 1 hour and was then allowed to warm to ambient temperature. After 2 hours, the reaction mixture was partitioned between 20 mL of $CH_2Cl_2$ and 20 mL of saturated $NaHCO_3$ solution. The layers were separated and the organic portion was washed sequentially with 20 mL of saturated $NaHCO_3$ solution and 20 mL of brine, dried over $Na_2SO_4$, filtered and concentrated under reduced pressure to give (4S)-9-chloro-4,6,7-trimethyl-3,4-dihydro-1H-pyrido[3',4':4,5]imidazo[2,1-c][1,4]oxazine (270 mg) as an orange solid.

Part F

A conical microwave vial was charged with a solution of (4S)-9-chloro-4,6,7-trimethyl-3,4-dihydro-1H-pyrido[3',4':4,5]imidazo[2,1-c][1,4]oxazine (270 mg, 1.07 mmol) dissolved in 3.5 mL of 2,2,2-trifluoroethanol. 4-Methoxybenzylamine (1.4 mL, 10.7 mmol) and pyridine hydrochloride (620 mg, 5.35 mmol) were added and the vial was sealed. The solution was heated in an Emrys Optimizer microwave (Personal Chemistry) at 160° C. for 120 minutes. The solvent was removed under reduced pressure, and the resulting residue was partitioned between 20 mL of $CH_2Cl_2$ and 20 mL of 10% aqueous $Na_2CO_3$. The layers were separated, and the organic portion was washed with 10% aqueous $Na_2CO_3$ solution and brine, dried over $Na_2SO_4$, filtered and concentrated under reduced pressures to give a crude oil. Chromatography (SiO$_2$, 0-20% CMA/CHCl$_3$) afforded (4S)—N-(4-methoxybenzyl)-4,6,7-trimethyl-3,4-dihydro-1H-pyrido[3',4':4,5]imidazo[2,1-c][1,4]oxazin-9-amine (350 mg) as an orange syrup.

Part G (4S)—N-(4-Methoxybenzyl)-4,6,7-trimethyl-3,4-dihydro-1H-pyrido[3',4':4,5]imidazo[2,1-c][1,4]oxazin-9-amine (350 mg, 0.99 mmol) was dissolved in 15 mL of trifluoroacetic acid and stirred at ambient temperature overnight. The solvent was removed under reduced pressure to give an orange residue which was then treated with 30 mL of aqueous 10% NaOH solution and the mixture was stirred for 2 hours. The solution was then extracted with CH$_2$Cl$_2$ (3×30 mL). The combined organic layers were washed with brine, dried over Na$_2$SO$_4$, filtered and concentrated under reduced pressure to give an orange solid. Chromatography (SiO$_2$, 10-30% CMA/CHCl$_3$) gave an off-white solid. Crystallization from acetonitrile gave (4S)-4,6,7-trimethyl-3,4-dihydro-1H-pyrido[3',4':4,5]imidazo[2,1-c][1,4]oxazin-9-amine (115 mg) as a white powder, mp 264-267° C.

$^1$H NMR (500 MHz, DMSO-d$_6$) δ 5.71 (s, 2H), 4.97 (d, J=15.6 Hz, 1H), 4.83 (d, J=15.6 Hz, 1H), 4.80 (s, 1H), 4.02 (s, 2H), 2.38 (s, 3H), 2.31 (s, 3H), 1.43 (d, J=6.5 Hz, 3H); $^{13}$C NMR (125 MHz, DMSO-d$_6$) δ 149.3, 146.2, 145.2, 137.8, 125.0, 103.3, 68.9, 65.0, 49.8, 22.0, 20.6, 12.7; MS (ESI) m/z 233 (M+H)$^+$. Anal. calcd for C$_{12}$H$_{16}$N$_4$O: C, 62.05; H, 6.94; N, 24.12. Found: C, 61.81; H, 6.93; N, 24.23.

Example 45

(11S)-11-{[(4-Fluorobenzyl)oxy]methyl}-10,11-dihydro-8H-[1,4]oxazino[4',3':1,2]imidazo[4,5-c]quinolin-6-amine

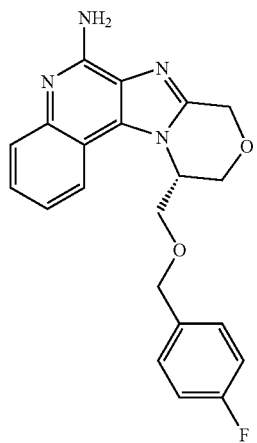

Part A (11S)-11-[(benzyloxy)methyl]-10,11-dihydro-8H-[1,4]oxazino[4',3':1,2]imidazo[4,5-c]quinoline (7.5 g, 22 mmol) was added to a mixture of methanol (270 mL) and acetyl chloride (3.0 mL, 43 mmol) in a pressure bottle. Palladium on carbon (10%, 1.5 g) was then added and the reaction mixture was shaken under H$_2$ at 48 PSI (3.3×10$^5$ Pa). After 11 days, the reaction mixture was filtered through a pad of CELITE filter agent. The pad was rinsed with methanol. The combined filtrates were treated with 2 mL of 50% aqueous NaOH solution and the mixture was concentrated under reduced pressure to afford an orange oil. Chromatography (SiO$_2$, 0-20% CMA/CHCl$_3$) gave an oil that was concentrated from acetonitrile under reduced pressure to give 2.0 g of (11S)-11-hydroxymethyl-10,11-dihydro-8H-[1,4]oxazino[4',3':1,2]imidazo[4,5-c]quinoline as a tan solid.

Part B

A 100-mL, round-bottomed flask, under an atmosphere of N$_2$, was charged with sodium hydride (60% oil dispersion, 72 mg, 1.78 mmol). The sodium hydride was washed with 3 portions of hexanes to remove the oil and then 20 mL of anhydrous THF was added. The reaction mixture was cooled to 0° C. and (11S)-11-hydroxymethyl-10,11-dihydro-8H-[1,4]oxazino[4',3':1,2]imidazo[4,5-c]quinoline (413 mg, 1.62 mmol) was added. After stirring for 75 minutes, 4-fluorobenzyl bromide (215 µL, 1.78 mmol) was added. The reaction was allowed to warm to ambient temperature overnight. After 20 hours the reaction mixture was treated with 20 mL of saturated NaHCO$_3$ solution and 20 mL of ethyl acetate and the layers were separated. The organic portion was washed with H$_2$O and brine, dried over Na$_2$SO$_4$, filtered, and concentrated under reduce pressure to give (11S)-11-{[(4-fluorobenzyl)oxy]methyl}-10,11-dihydro-8H-[1,4]oxazino[4',3':1,2]imidazo[4,5-c]quinoline (580 mg) as a light-yellow, glassy solid.

Part C (11S)-1-{[(4-Fluorobenzyl)oxy]methyl}-10,11-dihydro-8H-[1,4]oxazino[4',3':1,2]imidazo[4,5-c]quinoline (700 mg, 1.93 mmol) was dissolved in 25 mL of CHCl$_3$ and treated with MCPBA (570 mg, 77% max). The reaction was allowed to stir overnight and then 10 mL of aqueous 2% Na$_2$CO$_3$ solution was added and the layers were separated. The aqueous portion was extracted with CHCl$_3$ (3×20 mL). The combined organic layers were washed with brine, dried over Na$_2$SO$_4$, filtered, and concentrated under reduced pressure to afford (11S)-11-{[(4-fluorobenzyl)oxy]methyl}-10,11-dihydro-8H-[1,4]oxazino[4',3':1,2]imidazo[4,5-c]quinoline 5-oxide (732 mg) as an orange foam.

Part D (11S)-11-{[(4-Fluorobenzyl)oxy]methyl}-10,11-dihydro-8H-[1,4]oxazino[4',3':1,2]imidazo[4,5-c]quinoline 5-oxide (732 mg, 1.93 mmol) was dissolved in 50 mL of CH$_2$Cl$_2$ and treated with 5 mL of concentrated NH$_4$OH solution. The mixture was stirred rapidly and then p-toluenesulfonyl chloride (370 mg, 1.93 mmol) was carefully added. Rapid stirring continued overnight. The reaction mixture was treated with 5 mL of H$_2$O, and the layers were separated. The organic portion was washed with saturated NaHCO$_3$ (2×50 mL) followed by brine (50 mL). The organic layer was then dried over Na$_2$SO$_4$, filtered, and concentrated under reduced pressure to give a crude orange solid. Chromatography (SiO$_2$, 10-30% CMA/CHCl$_3$) gave 236 mg of (11S)-11-{[(4-fluorobenzyl)oxy]methyl}-10,11-dihydro-8H-[1,4]oxazino[4',3':1,2]imidazo[4,5-c]quinolin-6-amine as a tan solid, mp 134-137° C.

$^1$H NMR (500 MHz, DMSO-d$_6$) δ 7.85 (d, J=8.1 Hz, 1H), 7.64 (d, J=8.2 Hz, 1H), 7.43 (t, J=7.5 Hz, 1H), 7.35 (m, 2H), 7.20 (m, 1H), 7.14 (t, J=8.8 Hz, 2H), 6.68 (s, 2H), 5.10 (d, J=15.6 Hz, 1H), 5.07 (m, 1H), 4.97 (d, J=15.6 Hz, 1H), 4.87 (d, J=12.2 Hz, 1H), 4.52 (d, J=12.2 Hz, 1H), 4.37 (d, J=12.1 Hz, 1H), 4.10 (m, 1H), 3.81-3.78 (m, 2H); $^{13}$C NMR (125 MHz, DMSO-d$_6$) δ 162.0 (d, J=243.3 Hz), 152.2, 145.7, 145.0, 134.3, 132.0, 130.1 (d, J=8.1 Hz), 127.0, 126.7, 126.5, 121.5, 120.5, 115.4 (d, J=21.3 Hz), 114.7, 72.0, 68.1, 65.0, 64.6, 53.8; MS (APCI) m/z 379 (M+H)⁺. Anal. calcd for $C_{21}H_{19}FN_4O_2 \cdot 0.50\,H_2O$: C, 65.11; H, 5.20; N, 14.46. Found: C, 65.16; H, 5.04; N, 14.42.

Example 46

(11S)-11-(4-Fluorobenzyl)-10,11-dihydro-8H-[1,4]oxazino[4',3':1,2]imidazo[4,5-c]quinolin-6-amine

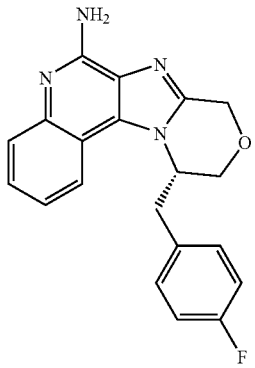

The title compound was prepared from (2S)-2-amino-3-(4-fluorophenyl)propan-1-ol, which was prepared from 4-fluoro-L-phenylalanine using the method described by McKennon and Meyers, *J. Org. Chem.*, 58, pp. 3568-3571, (1993), and 3-chloro-4-nitroquinoline following Parts A through G listed for the preparation of Example 1 with the following modifications. Part E was carried out according to the modification described in Part C of Example 11, and Part F was carried out in CHCl₃. Chromatography (SiO₂, 0-20% CMA/CHCl₃) gave an off-white solid. Crystallization from ethanol gave (11S)-11-(4-fluorobenzyl)-10,11-dihydro-8H-[1,4]oxazino[4',3':1,2]imidazo[4,5-c]quinolin-6-amine as a white solid, mp 170-172° C.

$^1$H NMR (500 MHz, DMSO-d₆) δ 8.13 (d, J=7.6 Hz, 1H), 7.67 (m, 1H), 7.47 (m, 1H), 7.34 (m, 3H), 7.19 (t, J=8.8 Hz, 2H), 6.66 (s, 2H), 5.27 (d, J=10.2 Hz, 1H), 5.08 (d, J=15.5 Hz, 1H), 4.98 (d, J=15.5 Hz, 1H), 4.02 (m, 2H), 3.26 (dd, J=3.7, 14.0 Hz, 1H), 2.51 (m, 1H); $^{13}$C NMR (125 MHz, DMSO-d₆) δ 161.6 (d, J=242.8 Hz), 152.3, 145.5, 145.1, 132.9, 131.7, 131.6 (d, J=7.9 Hz), 127.0, 126.9, 126.7, 121.6, 120.6, 115.8 (d, J=21.2 Hz), 114.9, 65.1, 65.0, 55.0, 37.2; MS (ESI) m/z 349 (M+H)⁺. Anal. calcd for $C_{20}H_{17}FN_4O$: C, 68.95; H, 4.92; N, 16.08. Found: C, 68.67; H, 4.86; N, 15.85.

Example 47

(11S)-11-Cyclohexyl-10,11-dihydro-8H-[1,4]oxazino[4',3':1,2]imidazo[4,5-c]quinolin-6-amine

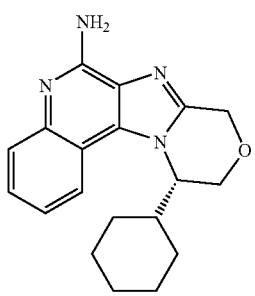

The title compound was prepared from (2S)-2-amino-2-cyclohexylethanol, which was prepared from (2S)-amino(cyclohexyl)ethanoic acid using the method described by McKennon and Meyers, *J. Org. Chem.*, 58, pp. 3568-3571, (1993), and 3-chloro-4-nitroquinoline following Parts A through G listed for the preparation of Example 1 with the following modifications. Part E was carried out according to the modification described in Part C of Example 11, and Part F was carried out in CHCl₃. Crystallization from 1,2-dichloroethane afforded the title compound as a white solid, mp 228-230° C.

$^1$H NMR (300 MHz, DMSO-d₆) δ 7.90 (d, J=7.4 Hz, 1H), 7.62 (dd, J=1.1, 8.3 Hz, 1H), 7.43 (m, 1H), 7.27 (m, 1H), 6.58 (s, 2H), 5.08 (d, J=15.6 Hz, 1H), 4.93 (d, J=15.6 Hz, 1H), 4.84 (m, 1H), 4.41 (d, J=12.6 Hz, 1H), 4.06 (dd, J=3.1, 12.6 Hz, 1H), 2.07 (m, 1H), 1.74 (m, 2H), 1.58 (m, 2H), 1.38 (m, 2H), 1.15 (m, 3H), 0.84 (m, 1H); MS (ESI) 323 m/z (M+H)⁺. Anal. calcd for $C_{19}H_{22}N_4O$: C, 70.78; H, 6.88; N, 17.38. Found: C, 70.58; H, 6.66; N, 17.34.

Example 48

4-{[(11S)-6-Amino-10,11-dihydro-8H-[1,4]oxazino[4',3':1,2]imidazo[4,5-c]quinolin-11-yl]methyl}phenol

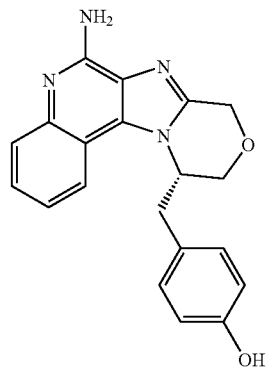

Part A

4-[(2S)-2-Amino-3-hydroxypropyl]phenol (26.8 g, 90.8 mmol), prepared by the method of McKennon and Meyers, *J. Org. Chem.*, 58, pp. 3568-3571, (1993), was suspended in 200 mL of dry CH₂Cl₂ under an atmosphere of N₂. The solution was cooled to 0° C. and sequentially treated with triethylamine (50 mL, 363 mmol) and 3-chloro-4-nitroquinoline (15.79 g, 75.7 mmol). After 30 minutes the reaction mixture was allowed to warm to ambient temperature and stirring was continued overnight. Additional 3-chloro-4-nitroquinoline (2.54 g, 12.2 mmol) was then added, and the reaction mixture was stirred for an additional 4 hours. The reaction mixture was then filtered to give the desired product as a yellow solid. Additional product was obtained by washing the filtrate with saturated NaHCO₃ solution (2×) and brine. The organic layer was dried over Na₂SO₄, filtered, and concentrated under reduced pressure until a yellow solid precipitated from the solution. The yellow solid was isolated by filtration and combined with the first crop to give 21.69 g of 4-{(2S)-3-hydroxy-2-[(3-nitroquinolin-4-yl)amino]propyl}phenol.

Part B

4-{(2S)-3-Hydroxy-2-[(3-nitroquinolin-4-yl)amino]propyl}phenol (21.69 g, 64.5 mmol) was dissolved in 100 mL of dry pyridine and treated with tert-butyldimethylsilyl chloride (22.4 g, 148 mmol) and a catalytic amount of DMAP (0.79 g, 6.45 mmol). The reaction mixture was stirred under $N_2$ and heated to 40° C. After 2.5 days, the reaction mixture was concentrated under reduced pressure. The resulting orange residue was partitioned between 200 mL of ethyl acetate and 200 mL of $H_2O$. The layers were separated and the organic portion was washed sequentially with $H_2O$ and brine. The organic layer was then dried over $Na_2SO_4$, filtered, and concentrated under reduced pressure to give N-[(1S)-2-{[tert-butyl(dimethyl)silyl]oxy}-1-(4-{[tert-butyl(dimethyl)silyl]oxy}benzyl)ethyl]-3-nitroquinolin-4-amine (25.24 g) as an orange solid.

Part C

N-[(1S)-2-{[tert-Butyl(dimethyl)silyl]oxy}-1-(4-{[tert-butyl(dimethyl)silyl]oxy}benzyl)ethyl]-3-nitroquinolin-4-amine (25.24 g, 44.45 mmol) was dissolved in 300 mL of toluene and the solution was placed in a pressure bottle. Platinum on carbon (5%, 1.47 g) was then added and the reaction mixture was shaken under $H_2$ at 35 PSI ($2.4\times10^5$ Pa). After 20 hours, the reaction mixture was filtered through a pad of CELITE filter agent. The pad was rinsed with toluene and acetonitrile and the combined filtrates were concentrated under reduced pressure to give $N^4$-[(1S)-2-{[tert-butyl(dimethyl)silyl]oxy}-1-(4-{[tert-butyl(dimethyl)silyl]oxy}benzyl)ethyl]quinoline-3,4-diamine (23.46 g) as an orange foam.

Part D $N^4$-[(1S)-2-{[tert-Butyl(dimethyl)silyl]oxy}-1-(4-{[tert-butyl(dimethyl)silyl]oxy}benzyl)ethyl]quinoline-3,4-diamine (23.46 g, 43.6 mmol) was dissolved in 400 mL of dry 1,2-dichloroethane and the yellow solution was stirred under $N_2$. Ethyl 2-chloroethanimidoate hydrochloride (13.8 g, 87.2 mmol) was then added and the reaction mixture was heated to 70° C. overnight. The reaction mixture was then cooled and treated with 300 mL of saturated $NaHCO_3$ solution. The layers were separated and the organic portion was washed sequentially with saturated $NaHCO_3$ solution and brine, dried over $Na_2SO_4$, filtered, and concentrated under reduced pressure. Chromatography ($SiO_2$, 10-60% ethyl acetate/hexanes) gave 1-[(1S)-2-{[tert-butyl(dimethyl)silyl]oxy}-1-(4-{[tert-butyl(dimethyl)silyl]oxy}benzyl)ethyl]-2-(chloromethyl)-1H-imidazo[4,5-c]quinoline (21.11 g) as a brown foam.

Part E

1-[(1S)-2-{[tert-Butyl(dimethyl)silyl]oxy}-1-(4-{[tert-butyl(dimethyl)silyl]oxy}benzyl)ethyl]-2-(chloromethyl)-1H-imidazo[4,5-c]quinoline (21.1 g, 35.4 mmol) was dissolved in 1.5 L of dry $CH_2Cl_2$ under $N_2$. The orange solution was cooled to −78° C. and a 1.0 M solution of tetrabutylammonium fluoride in THF (106 mL) was added over 30 minutes. The reaction mixture was allowed to slowly warm to ambient temperature overnight. The reaction mixture was then washed sequentially with saturated $NaHCO_3$ solution and brine (4×). The organic layer was dried over $Na_2SO_4$, filtered, and concentrated under reduced pressure to give a red oil. Chromatography ($SiO_2$, 20-40% CMA/$CHCl_3$) gave 14 g of a viscous brown oil which was then dissolved in $CH_2Cl_2$ and the solution was washed repeatedly with brine (7×). The organic layer was dried over $Na_2SO_4$, filtered, and concentrated under reduced pressure to give a tan foam. Additional purification by column chromatography ($SiO_2$, 3-6% methanol/$CH_2Cl_2$) gave 5 g of an off-white solid. The solid was stirred in 150 mL of refluxing 1,2-dichloroethane and then cooled to produce a precipitate. The solid was isolated by filtration to give 2.1 g of 4-[(11S)-10,11-dihydro-8H-[1,4]oxazino[4',3':1,2]imidazo[4,5-c]quinolin-11-ylmethyl]phenol as a white solid.

Part F

4-[(11S)-10,11-Dihydro-8H-[1,4]oxazino[4',3':1,2]imidazo[4,5-c]quinolin-11-ylmethyl]phenol (2.62 g, 7.91 mmol) was suspended in 50 mL of dry $CH_2Cl_2$ and stirred under $N_2$. The solution was treated with triethylamine (2.2 mL, 15.8 mmol) and acetic anhydride (0.89 mL, 9.45 mmol). After 18 hours, the reaction mixture was treated with 50 mL of $H_2O$. The layers were separated, and the organic portion was washed with $H_2O$ and brine. The organic layer was then dried over $Na_2SO_4$, filtered, and concentrated under reduced pressure to give 4-[(11S)-10,11-dihydro-8H-[1,4]oxazino[4',3':1,2]imidazo[4,5-c]quinolin-11-ylmethyl]phenyl acetate (2.95 g) as a white solid.

Part G

4-[(11S)-10,11-Dihydro-8H-[1,4]oxazino[4',3':1,2]imidazo[4,5-c]quinolin-11-ylmethyl]phenyl acetate (2.95 g, 7.91 mmol) was dissolved in 80 mL of $CHCl_3$ and treated with MCPBA (2.33 g, 77% max). After stirring for 18 hours, the reaction was treated with 25 mL of a 2% $Na_2CO_3$ solution and the layers were separated. The aqueous layer was then extracted with $CHCl_3$ (4×20 mL). The combined organic layers were washed with 20 mL of brine, dried over $Na_2SO_4$, filtered, and concentrated under reduced pressure to give 4-{[(11S)-5-oxido-10,11-dihydro-8H-[1,4]oxazino[4',3':1,2]imidazo[4,5-c]quinolin-11-yl]methyl}phenyl acetate (3.08 g) as a tan solid.

Part H

4-{[(11S)-5-Oxido-10,11-dihydro-8H-[1,4]oxazino[4',3':1,2]imidazo[4,5-c]quinolin-11-yl]methyl}phenyl acetate (3.08 g, 7.91 mmol) was dissolved in 100 mL of $CH_2Cl_2$ and treated with 10 mL of concentrated ammonium hydroxide solution. The mixture was stirred rapidly and then p-toluenesulfonyl chloride (1.51 g, 7.91 mmol) was carefully added. Rapid stirring continued for 1 hour. The reaction mixture was then treated with 20 mL of $H_2O$ and the layers were separated. The aqueous portion was extracted with $CH_2Cl_2$ (5×25 mL). The combined organic layers were washed with saturated $NaHCO_3$ solution. Methanol was added to the organic layer to aid in solubility. The organic layer was dried over $Na_2SO_4$, filtered, and concentrated under reduced pressure to give a brown solid. Chromatography ($SiO_2$, 20-40% CMA/$CHCl_3$) gave a yellow solid. This material was dissolved in 100 mL 6 N aqueous HCl, and the solution was heated at 50° C. overnight. The reaction mixture was cooled and treated with concentrated ammonium hydroxide until pH=11 and then diluted with 200 mL $H_2O$. The solution was extracted with 9:1 mixture of $CH_2Cl_2$/methanol (3×150 mL). The combined organic layers were washed sequentially with $H_2O$ and brine, dried over $Na_2SO_4$, filtered, and concentrated under reduced pressure to give a white solid. Crystallization from ethanol containing HCl gave 4-{[(11S)-6-amino-10,11-dihydro-8H-[1,4]oxazino[4',3':1,2]imidazo[4,5-c]quinolin-11-yl]methyl}phenol hydrochloride (0.47 g) as an off white solid, mp>240° C. (dec).

$^1$H NMR (500 MHz, DMSO-$d_6$) δ 9.43 (s, 1H), 8.80 (br s, 2H), 8.27 (d, J=8.2 Hz, 1H), 7.85 (d, J=8.2 Hz, 1H), 7.73 (m,

1H), 7.67 (m, 1H), 7.10 (d, J=8.4 Hz, 2H), 6.75 (d, J=8.4 Hz, 2H), 5.32 (m, 1H), 5.19 (d, J=15.9 Hz, 1H), 5.06 (d, J=15.9 Hz, 1H), 4.06 (s, 2H), 3.14 (m, 1H), 3.07 (m, 1H); $^{13}$C NMR (125 MHz, DMSO-$d_6$) δ 156.4, 149.1, 148.3, 133.8, 133.4, 130.3, 129.5, 125.6, 125.0, 124.5, 121.6, 118.5, 115.4, 112.3, 64.3, 55.6, 48.5, 36.7; MS (ESI) m/z 347 (M+H)$^+$. Anal. calcd for $C_{20}H_{18}N_4O_2$·HCl ~0.75 EtOH: C, 61.87; H, 5.67; N, 13.42; Cl, 8.49. Found: C, 61.46; H, 5.69; N, 13.06; Cl, 8.25.

Example 49

(11S)-11-(4-Methoxybenzyl)-10,11-dihydro-8H-[1,4]oxazino[4',3':1,2]imidazo[4,5-c]quinolin-6-amine

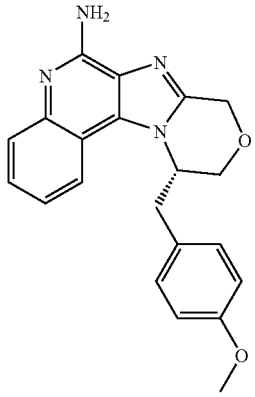

4-{[(11S)-6-Amino-10,11-dihydro-8H-[1,4]oxazino[4',3':1,2]imidazo[4,5-c]quinolin-11-yl]methyl}phenol (80 mg, 0.231 mmol) was dissolved in 3 mL of dry DMF and treated with cesium carbonate (150 mg, 0.462 mmol) under $N_2$. The reaction mixture was heated to 85° C. for 25 minutes. The reaction mixture was then removed from the heat source and iodomethane (14 µL, 0.231 mmol) was added. The reaction mixture was again heated to 85° C. After 18 hours, the reaction mixture was cooled and treated with 3 mL of methanol. The solvents were removed under reduced pressure, and the resulting orange-brown residue was partitioned between 10 mL of $CH_2Cl_2$ and 10 mL of $H_2O$. The organic layer was washed with $H_2O$ and brine, dried over $Na_2SO_4$, filtered, and concentrated under reduced pressure to give an orange solid (80 mg). Chromatography (SiO$_2$, 5-25% CMA/CHCl$_3$) gave the title compound (50 mg) as a yellow solid, mp 115-130° C. $^1$H NMR (500 MHz, DMSO-$d_6$) δ 8.17 (d, J=7.6 Hz, 1H), 7.66 (dd, J=0.8, 8.3 Hz, 1H), 7.47 (m, 1H), 7.36 (m, 1H), 7.26 (d, J=8.6 Hz, 2H), 6.95 (d, J=8.6 Hz, 2H), 6.60 (s, 2H), 5.21 (m, 1H), 5.10 (d, J=15.5 Hz, 1H), 4.99 (d, J=15.5 Hz, 1H), 4.01 (s, 2H), 3.37 (s, 3H), 3.19 (m, 1H), 3.07 (m, 1H); MS (ESI) m/z 361 (M+H)$^+$.

Example 50

(11R)-11-[3-(4-Fluorophenyl)isoxazol-5-yl]-10,11-dihydro-8H-[1,4]oxazino[4',3':1,2]imidazo[4,5-c]quinolin-6-amine

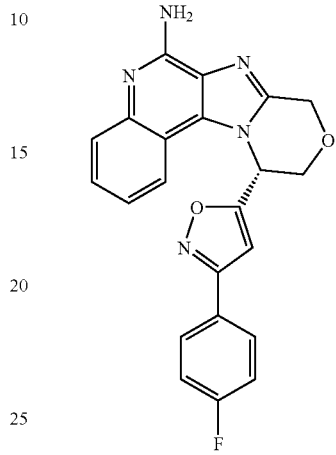

Part A tert-Butyl (4S)-4-ethynyl-2,2-dimethyl-1,3-oxazolidine-3-carboxylate (2.15 g, 9.55 mmol), prepared by the method of Serrat et al., *Tetrahdron: Asymmetry*, 10, pp. 3417-3430, (1999), was dissolved in 10 mL of ethanol and treated with 10 mL of 3 M HCl in ethanol. The solution was heated to 85° C. for 3 hours and then concentrated to give 1.16 g of (2S)-2-aminobut-3-yn-1-ol hydrochloride as a white solid.

Part B (11S)-11-ethynyl-10,11-dihydro-8H-[1,4]oxazino[4',3':1,2]imidazo[4,5-c]quinoline was prepared from (2S)-2-aminobut-3-yn-1-ol hydrochloride and 3-chloro-4-nitroquinoline following Parts A through E listed for the preparation of Example 1 with the following modification. Part E was carried out according to the modification described in Part C of Example 11. Chromatography (5% methanol/CHCl$_3$) gave the desired product as an off-white solid.

Part C

A solution of 4-fluorobenzaldehyde oxime (222 mg, 1.60 mmol) dissolved in 3 mL of DMF was treated with N-chlorosuccinimide (212 mg, 1.60 mmol) and the reaction mixture was heated at 50° C. for 3 hours. The reaction mixture was diluted with 25 mL of ethyl acetate and then washed with $H_2O$ (4×20 mL). The organic portion was washed with brine, dried over $Na_2SO_4$, filtered and concentrated to give 4-fluoro-N-hydroxybenzenecarboximidoyl chloride as a white solid. The material was dissolved in 10 mL of $CH_2Cl_2$ and the solution was cooled to 0° C. A solution of (11S)-11-ethynyl-10,11-dihydro-8H-[1,4]oxazino[4',3':1,2]imidazo[4,5-c]quinoline (190 mg, 0.76 mmol) dissolved in 3 mL of $CH_2Cl_2$ was then added followed by triethylamine (318 µL, 2.29 mmol). The reaction was allowed to warm to ambient temperature overnight. The reaction mixture was concentrated and chromatography (0-2% methanol/CHCl$_3$) gave (11R)-11-[3-(4-fluorophenyl)isoxazol-5-yl]-10,11-dihydro-8H-[1,4]oxazino[4',3':1,2]imidazo[4,5-c]quinoline as a light-brown solid.

Part D

The title compound was prepared from (11R)-11-[3-(4-fluorophenyl)isoxazol-5-yl]-10,11-dihydro-8H-[1,4]oxazino[4',3':1,2]imidazo[4,5-c]quinoline following Parts F and G listed for the preparation of Example 1. Chromatography (SiO$_2$, 10-35% CMA/CHCl$_3$) gave an off-white powder. Crystallization from ethyl acetate with a small amount of methanol gave the title compound as amber crystals, mp 261.0-262.0° C.

$^1$H NMR (300 MHz, DMSO-d$_6$) δ 7.85 (m, 2H), 7.71 (d, J=7.3 Hz, 1H), 7.59 (dd, J=0.9, 8.4 Hz, 1H), 7.37 (m, 1H), 7.27 (m, 2H), 7.13 (ddd, J=1.2, 7.0, 8.2 Hz, 1H), 6.87 (s, 1H), 6.68 (s, 2H), 6.65 (m, 1H), 5.23 (d, J=15.7 Hz, 1H), 5.13 (d, J=15.8 Hz, 1H), 4.55 (d, J=12.2 Hz, 1H), 4.44 (dd, J=3.1, 12.4 Hz, 1H); $^{13}$C NMR (125 MHz, DMSO-d$_6$) δ 170.1, 163.2 (d, J=248 Hz), 161.1, 151.7, 144.83, 144.75, 131.8, 129.0 (d, J=8.6 Hz), 126.6, 126.4, 126.1, 124.4, 120.9, 120.0, 116.0 (d, J=21.9 Hz), 114.1, 101.4, 67.2, 64.9, 52.0; MS (ESI) m/z 402 (M+H)$^+$. Anal. calcd for C$_{22}$H$_{16}$FN$_5$O$_2$.0.50 C$_4$H$_8$O$_2$: C, 64.71; H, 4.53; N, 15.72. Found: C, 64.49; H, 4.65; N, 15.83.

Example 51

(11S)-11-Methyl-2-(prop-2-ynyloxy)-10,11-dihydro-8H-[1,4]oxazino[4',3':1,2]imidazo[4,5-c]quinolin-6-amine

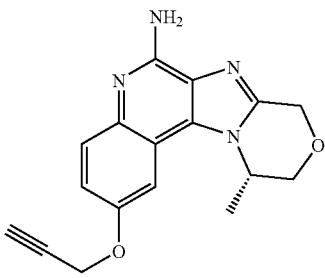

A solution of (11S)-6-amino-11-methyl-10,11-dihydro-8H-[1,4]oxazino[4',3':1,2]imidazo[4,5-c]quinolin-2-ol (100 mg, 0.370 mmol) dissolved in 15 mL of DMF was treated with cesium carbonate (241 mg, 0.740 mmol) and propargyl bromide (49 mg, 0.410 mmol) and stirred overnight at ambient temperature. The dark brown mixture was then poured into 150 mL of H$_2$O and stirred for 30 minutes. The mixture was filtered to give a dark brown solid. Chromatography (SiO$_2$, 0-30% CMA/CHCl$_3$) followed by crystallization from ethyl acetate gave 51 mg of the title compound as an off-white solid, mp 184-186° C.

$^1$H NMR (500 MHz, DMSO-d$_6$) δ 7.58 (d, J=9.0 Hz, 1H), 7.51 (d, J=2.5 Hz, 1H), 7.15 (dd, J=2.5, 9.0 Hz, 1H), 6.37 (br s, 2H), 5.15 (m, 1H), 5.10 (d, J=15.6 Hz, 1H), 4.96 (d, J=15.6 Hz, 1H), 4.93 (d, J=1.9 Hz, 2H), 4.14 (m, 2H), 3.60 (t, J=1.9 Hz, 1H), 1.60 (d, J=6.4 Hz, 3H); $^{13}$C NMR (125 MHz, DMSO-d$_6$) δ 151.6, 150.4, 145.0, 139.8, 130.9, 127.3, 126.7, 116.8, 114.0, 103.1, 79.3, 78.1, 68.2, 64.6, 55.7, 49.8, 19.1; MS (APCI) m/z 309 (M+H)$^+$. Anal. calcd for C$_{17}$H$_{16}$N$_4$O$_2$.0.5 C$_4$H$_8$O$_2$: C, 64.76; H, 5.72; N, 15.90. Found: C, 64.94; H, 5.47; N, 16.10.

Example 52

(11S)-11-Methyl-2-[(2-methyl-1,3-thiazol-4-yl)methoxy]-10,11-dihydro-8H-[1,4]oxazino[4',3':1,2]imidazo[4,5-c]quinolin-6-amine

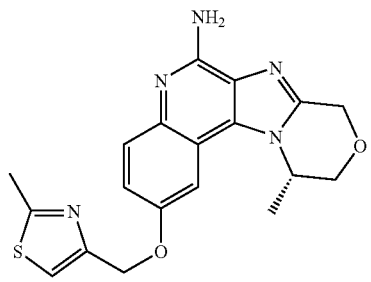

A solution of (11S)-6-amino-11-methyl-10,11-dihydro-8H-[1,4]oxazino[4',3':1,2]imidazo[4,5-c]quinolin-2-ol (500 mg, 1.85 mmol) dissolved in 15 mL of DMF was treated with cesium carbonate (1.80 g, 5.55 mmol), 4-chloromethyl-2-methylthiazole hydrochloride (375 mg, 2.03 mmol) and tetrabutylammonium bromide (715 mg, 2.22 mmol). After stirring overnight at 50° C., the dark brown mixture was poured into 150 mL of H$_2$O and stirred for 30 minutes. The reaction mixture was extracted with CHCl$_3$ (3×75 mL) and the combined extracts were dried over MgSO$_4$, filtered and concentrated under reduced pressure to give a brown solid. Chromatography (SiO$_2$, 0-20% CMA/CHCl$_3$) gave an off-white solid which was crystallized from acetonitrile to give 237 mg of the title compound as an off-white solid, mp 105-107° C. $^1$H NMR (500 MHz, DMSO-d$_6$) δ 7.59 (s, 1H), 7.57 (s, 1H), 7.51 (d, J=2.7 Hz, 1H), 7.19 (dd, J=2.7, 9.1 Hz, 1H), 6.35 (br s, 2H), 5.25 (m, 2H), 5.14 (m, 1H), 5.09 (d, J=15.5 Hz, 1H), 4.95 (d, J=15.5 Hz, 1H), 4.14 (m, 2H), 2.67 (s, 3H), 1.54 (d, J=6.5 Hz, 3H); $^{13}$C NMR (125 MHz, DMSO-d$_6$) δ 165.6, 152.7, 151.5, 150.3, 145.0, 139.6, 130.9, 127.4, 126.7, 117.6, 116.9, 114.3, 102.8, 68.2, 65.6, 64.6, 49.8, 19.0, 18.6; MS (APCI) m/z 382 (M+H)$^+$. Anal. calcd for C$_{19}$H$_{19}$N$_5$O$_2$.0.75 C$_4$H$_8$O$_2$.0.33H$_2$O: C, 58.88; H, 5.28; N, 19.26. Found: C, 58.62; H, 4.96; N, 19.10.

Example 53

(11S)-6-Amino-11-methyl-10,11-dihydro-8H-[1,4]oxazino[4',3':1,2]imidazo[4,5-c]quinolin-2-yl pyrrolidine-1-carboxylate

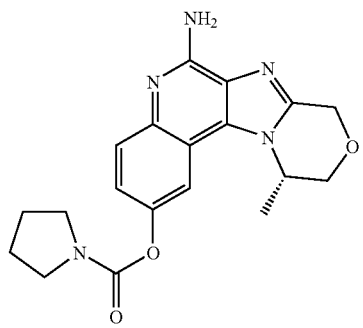

A solution of (11S)-6-amino-11-methyl-10,11-dihydro-8H-[1,4]oxazino[4',3':1,2]imidazo[4,5-c]quinolin-2-ol (500 mg, 1.85 mmol) dissolved in 15 mL of DMF was treated with cesium carbonate (1.80 g, 5.55 mmol) and pyrrolidinecarbonyl chloride (275 mg, 2.03 mmol). After stirring overnight at ambient temperature, the light brown mixture was poured into 150 mL of H$_2$O and stirred for 30 minutes. The reaction mixture was extracted with CHCl$_3$ (3×75 mL) and the combined extracts were dried over MgSO$_4$, filtered and concentrated under reduced pressure to give a brown solid. Chromatography (SiO$_2$, 0-20% CMA/CHCl$_3$) gave an off-white solid which was crystallized from acetonitrile to give 122 mg of the title compound as an off-white solid, mp 218-219° C.

$^1$H NMR (500 MHz, DMSO-d$_6$) δ 7.71 (d, J=2.5 Hz, 1H), 7.61 (d, J=9.0 Hz, 1H), 7.22 (dd, J=2.5, 9.0 Hz, 1H), 6.57 (br s, 2H), 5.09 (d, J=15.5 Hz, 1H), 5.06 (m, 1H), 4.95 (d, J=15.5 Hz, 1H), 4.11 (m, 2H), 3.56 (m, 2H), 3.37 (m, 2H), 1.96-1.85 (m, 4H), 1.54 (d, J=6.5 Hz, 3H); $^{13}$C NMR (125 MHz, DMSO-d$_6$) δ 152.5, 151.4, 145.2, 145.1, 142.0, 130.9, 126.6, 126.6, 121.4, 113.9, 112.1, 68.2, 64.5, 49.8, 46.1, 45.9, 25.2, 24.3, 18.8; MS (APCI) m/z 368 (M+H)$^+$. Anal. calcd for C$_{19}$H$_{21}$N$_5$O$_3$: C, 62.11; H, 5.76; N, 19.06. Found: C, 61.82; H, 5.63; N, 18.97.

Example 54

(11S)-11-Methyl-2-(1,3-thiazol-4-ylmethoxy)-10,11-dihydro-8H-[1,4]oxazino[4',3':1,2]imidazo[4,5-c]quinolin-6-amine

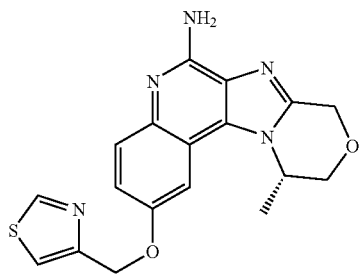

A solution of (11S)-6-amino-11-methyl-10,11-dihydro-8H-[1,4]oxazino[4',3':1,2]imidazo[4,5-c]quinolin-2-ol (500 mg, 1.85 mmol) dissolved in 15 mL of DMF was treated with cesium carbonate (1.80 g, 5.55 mmol), 4-chloromethyl thiazole hydrochloride (345 mg, 2.03 mmol), and tetrabutylammonium bromide (715 mg, 2.22 mmol). After stirring overnight at ambient temperature, the brown mixture was poured into 150 mL of H$_2$O and stirred for 30 minutes. The reaction mixture was extracted with CHCl$_3$ (3×75 mL) and the combined extracts were dried over MgSO$_4$, filtered and concentrated under reduced pressure to give a brown solid. Chromatography (SiO$_2$, 0-20% CMA/CHCl$_3$) gave an off-white solid which was crystallized from acetonitrile to give 179 mg of the title compound as an off-white solid, mp 240-242° C. $^1$H NMR (500 MHz, DMSO-d$_6$) δ 9.16 (d, J=2.0 Hz, 1H), 7.82 (d, J=1.9 Hz, 1H), 7.58 (d, J=9.1 Hz, 1H), 7.51 (d, J=2.7 Hz, 1H), 7.21 (dd, J=2.6, 9.1 Hz, 1H), 6.35 (br s, 2H), 5.36 (m, 2H), 5.14 (m, 1H), 5.09 (d, J=15.5 Hz, 1H), 4.95 (d, J=15.5 Hz, 1H), 4.13 (m, 2H), 1.52 (d, J=6.5 Hz, 3H); $^{13}$C NMR (125 MHz, DMSO-d$_6$) δ 154.4, 152.8, 152.7, 150.3, 145.0, 139.6, 130.9, 127.3, 126.7, 118.0, 116.9, 114.3, 102.8, 68.2, 65.6, 64.5, 49.8, 18.9; MS (APCI) m/z 368 (M+H)$^+$. Anal. calcd for C$_{18}$H$_{17}$N$_5$O$_2$S: C, 58.84; H, 4.66; N, 19.06. Found: C, 58.88; H, 4.63; N, 19.29.

Example 55

(11S)-11-Methyl-2-(2-morpholin-4-yl-2-oxoethoxy)-10,11-dihydro-8H-[1,4]oxazino[4',3':1,2]imidazo[4,5-c]quinolin-6-amine

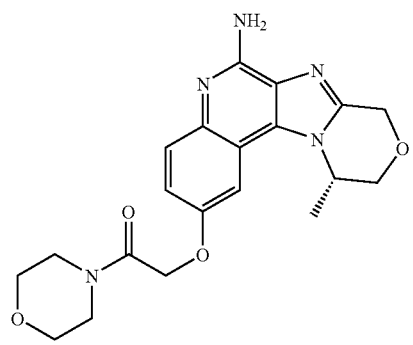

A solution of (11S)-6-amino-11-methyl-10,11-dihydro-8H-[1,4]oxazino[4',3':1,2]imidazo[4,5-c]quinolin-2-ol (500 mg, 1.85 mmol) dissolved in 15 mL of DMF was treated with cesium carbonate (1.80 g, 5.55 mmol) and 2-bromo-1-morpholin-4-yl-ethanone (462 mg, 2.03 mmol). After stirring overnight at 75° C., the brown mixture was poured into 150 mL of H$_2$O and stirred for 30 minutes. The reaction mixture was extracted with CHCl$_3$ (3×75 mL) and the combined extracts were dried over MgSO$_4$, filtered and concentrated under reduced pressure to give an off-white solid. Chromatography (SiO$_2$, 0-20% CMA/CHCl$_3$) gave an off-white solid which was crystallized from acetonitrile to give 272 mg of the title compound as an off-white solid, mp 226-228° C.

$^1$H NMR (500 MHz, DMSO-d$_6$) δ 7.57 (d, J=9.1 Hz, 1H), 7.37 (d, J=2.6 Hz, 1H), 7.14 (dd, J=2.7, 9.1 Hz, 1H), 6.37 (br s, 2H), 5.09 (m, 2H), 4.95 (m, 3H), 4.14 (s, 2H), 3.46-3.63 (m, 8H), 1.55 (d, J=6.5 Hz, 3H); $^{13}$C NMR (125 MHz, DMSO-d$_6$) δ 166.2, 152.4, 150.3, 145.0, 139.6, 130.8, 127.2, 126.7, 116.6, 114.2, 102.7, 68.2, 66.6, 66.0, 64.6, 49.8, 44.8, 41.5, 19.0; MS (APCI) m/z 398 (M+H)$^+$. Anal. calcd for C$_{20}$H$_{23}$N$_5$O$_4$: C, 60.44; H, 5.83; N, 17.62. Found: C, 60.58; H, 5.64; N, 17.67.

Example 56

(11S)-11-Methyl-2-(2-morpholin-4-ylethoxy)-10,11-dihydro-8H-[1,4]oxazino[4',3':1,2]imidazo[4,5-c]quinolin-6-amine

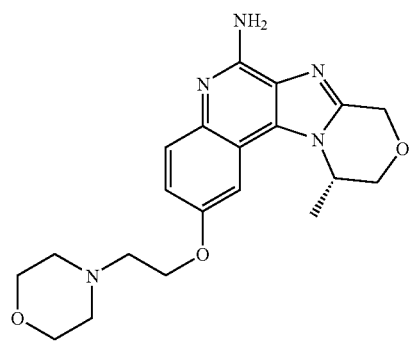

A solution of (11S)-6-amino-11-methyl-10,11-dihydro-8H-[1,4]oxazino[4',3':1,2]imidazo[4,5-c]quinolin-2-ol (500 mg, 1.85 mmol) dissolved in 15 mL of DMF was treated with cesium carbonate (1.80 g, 5.55 mmol), 4-(2-chloroethyl)morpholine hydrochloride (378 mg, 2.03 mmol), and tetrabutylammonium bromide (715 mg, 2.22 mmol). After stirring overnight at ambient temperature, the light brown mixture was poured into 150 mL of $H_2O$ and stirred for 30 minutes. The reaction mixture was extracted with $CHCl_3$ (3×75 mL) and the combined extracts were dried over $MgSO_4$, filtered and concentrated under reduced pressure to give an off-white solid. Chromatography ($SiO_2$, 0-20% CMA/$CHCl_3$) gave an off-white solid which was crystallized from acetonitrile to give 262 mg of the title compound as an off-white solid, mp 186-188° C.

$^1$H NMR (500 MHz, DMSO-$d_6$) δ 7.56 (d, J=9.1 Hz, 1H), 7.37 (d, J=2.7 Hz, 1H), 7.13 (dd, J=2.7, 9.1 Hz, 1H), 6.33 (br s, 2H), 5.16 (m, 1H), 5.09 (d, J=15.5 Hz, 1H), 4.96 (d, J=15.5 Hz, 1H), 4.26 (m, 1H), 4.17 (m, 1H), 4.12 (m, 2H), 3.61-3.59 (m, 4H), 2.75 (t, J=5.7 Hz, 2H), 2.52-5.49 (m, 4H), 1.57 (d, J=6.5 Hz, 3H); $^{13}$C NMR (125 MHz, DMSO-$d_6$) δ 152.9, 150.2, 145.0, 139.4, 130.8, 127.4, 126.7, 116.7, 114.3, 102.2, 68.2, 66.0, 65.5, 64.6, 57.0, 53.5, 49.7, 18.9; MS (ESI) m/z 384 (M+H)$^+$; Anal. calcd for $C_{20}H_{25}N_5O_3$: C, 62.65; H, 6.57; N, 18.26. Found: C, 62.82; H, 6.39; N, 18.49.

Example 57

(11S)-2-Ethoxy-11-methyl-10,11-dihydro-8H-[1,4]oxazino[4',3':1,2]imidazo[4,5-c]quinolin-6-amine

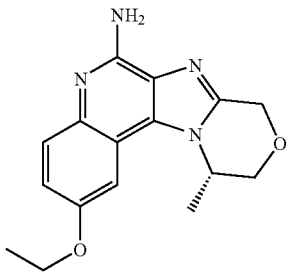

A solution of (11S)-6-amino-11-methyl-10,11-dihydro-8H-[1,4]oxazino[4',3':1,2]imidazo[4,5-c]quinolin-2-ol (500 mg, 1.85 mmol) dissolved in 15 mL of DMF was treated with cesium carbonate (1.80 g, 5.55 mmol) and ethyl iodide (346 mg, 2.03 mmol). After stirring overnight at 75° C., the light brown mixture was poured into 150 mL of $H_2O$ and stirred for 30 minutes. The reaction mixture was extracted with $CHCl_3$ (3×75 mL) and the combined extracts were dried over $MgSO_4$, filtered and concentrated under reduced pressure to give a brown solid. Chromatography ($SiO_2$, 0-20% CMA/$CHCl_3$) gave an off-white solid which was crystallized from acetonitrile to give 101 mg of the title compound as an off-white solid, mp 187-188° C.

$^1$H NMR (500 MHz, DMSO-$d_6$) δ 7.56 (d, J=9.0 Hz, 1H), 7.36 (d, J=2.7 Hz, 1H), 7.11 (dd, J=2.7, 9.0 Hz, 1H), 6.30 (br s, 2H), 5.14 (m, 1H), 5.09 (d, J=15.5 Hz, 1H), 4.95 (d, J=15.5 Hz, 1H), 4.21-4.07 (m, 4H), 1.57 (d, J=6.5 Hz, 3H), 1.39 (t, J=7.0 Hz, 3H); $^{13}$C NMR (125 MHz, DMSO-$d_6$) δ 153.0, 150.2, 144.9, 139.3, 130.8, 127.3, 126.7, 116.5, 114.4, 102.1, 68.2, 64.6, 63.1, 49.8, 18.9, 14.6; MS (ESI) m/z 299 (M+H)$^+$.

Anal. calcd for $C_{16}H_{18}N_4O_2$: C, 64.41; H, 6.08; N, 18.78. Found: C, 64.18; H, 5.89; N, 18.60.

Example 58

(11S)-11-Isopropyl-3-(2-morpholin-4-yl-2-oxoethoxy)-10,11-dihydro-8H-[1,4]oxazino[4',3':1,2]imidazo[4,5-c]quinolin-6-amine

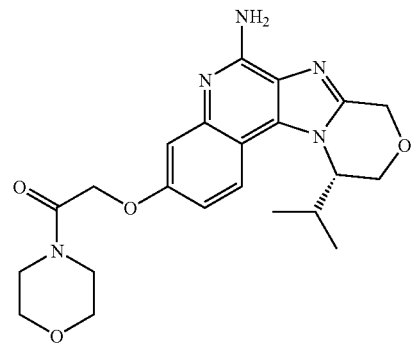

A solution of (11S)-6-amino-11-isopropyl-10,11-dihydro-8H-[1,4]oxazino[4',3':1,2]imidazo[4,5-c]quinolin-3-ol (0.30 g, 1.0 mmol) dissolved in 5 mL of DMF was treated with cesium carbonate (1.0 g, 3.0 mmol) and 4-(bromoacetyl)morpholine (0.23 g, 1.1 mmol). After stirring for 18 hours at 65° C., the reaction mixture was concentrated under reduced pressure to give a solid. The solid was dissolved in $CH_2Cl_2$ (100 mL) and washed with $H_2O$ (100 mL). The organic layer was concentrated under reduced pressure to give a solid. Chromatography ($SiO_2$, 0-15% CMA/$CHCl_3$) gave a white solid which was crystallized from acetonitrile to give 0.18 g of the title compound as white crystals, mp 137-139° C.

MS (APCI) m/z 426 (M+H)$^+$. Anal. calcd for $C_{22}H_{27}N_5O_4 \cdot 1.5H_2O$: C, 58.39; H, 6.68; N, 15.48. Found: C, 58.77; H, 7.36; N, 15.76.

Example 59

(11S)-11-Isopropyl-3-(2-morpholin-4-ylethoxy)-10,11-dihydro-8H-[1,4]oxazino[4',3':1,2]imidazo[4,5-c]quinolin-6-amine

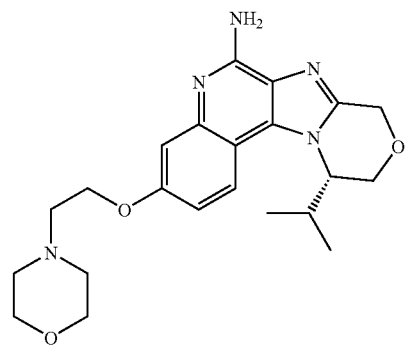

A solution of (11S)-6-amino-11-isopropyl-10,11-dihydro-8H-[1,4]oxazino[4',3':1,2]imidazo[4,5-c]quinolin-3-ol (0.30 g, 1.0 mmol) dissolved in 5 mL of DMF was treated with cesium carbonate (1.0 g, 3.0 mmol) and tetrabutylammonium bromide (0.30 g, 1.0 mmol) and a solution of 4-(2-chloroethyl)morpholine hydrochloride (0.21 g, 1.1 mmol). After stirring for 18 hours at 65° C., the reaction mixture was concentrated under reduced pressure to give a solid. The solid was dissolved in $CH_2Cl_2$ (100 mL) and washed with $H_2O$ (100 mL). The organic layer was concentrated under reduced pressure to give a solid. Chromatography ($SiO_2$, 0-15% CMA/$CHCl_3$) gave a white solid which was crystallized from acetonitrile to give 110 mg of the title compound as white, mp 194-195° C.

MS (APCI) m/z 412 (M+H)$^+$. Anal. calcd for $C_{22}H_{29}N_5O_3 \cdot 0.25H_2O$: C, 63.52; H, 7.15; N, 16.83. Found: C, 63.53; H, 6.96; N, 16.69.

Example 60

(11S)-3-Bromo-11-methyl-10,11-dihydro-8H-[1,4] oxazino[4',3':1,2]imidazo[4,5-c]quinolin-6-amine

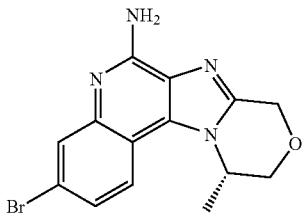

Part A

A 2-L, three-necked, Morton flask, equipped with overhead stirrer, was charged with 7-bromo-4-chloro-3-nitroquinoline (28.75 g, 100 mmol), anhydrous DMF (200 mL) and triethylamine (28 mL, 200 mmol). The reaction mixture was stirred at ambient temperature and a solution of L-alaninol (7.51 g, 0.1 mol) in 100 mL of DMF was slowly added. After stirring overnight, the reaction mixture was treated with saturated aqueous $K_2CO_3$ solution (100 ml) and $H_2O$ (800 mL). The mixture was stirred vigorously for 2 hours to produce a yellow precipitate. The yellow solid was collected by vacuum filtration and dried with suction to give 30.9 g of (2S)-2-[7-bromo-3-nitroquinolin-4-yl)amino]propan-1-ol as bright-yellow crystals.

Part B

A solution of (2S)-2-[(7-bromo-3-nitroquinolin-4-yl) amino]propan-1-ol (30.0 g, 92.0 mmol) dissolved in 100 mL of anhydrous pyridine was treated with tert-butyldimethylsilyl chloride (15.2 g, 101.2 mmol) and a catalytic amount of DMAP (112 mg, 0.92 mmol). After stirring overnight at ambient temperature under an atmosphere of $N_2$, the reaction mixture was concentrated under reduced pressure. The resulting solid was partitioned between $CH_2Cl_2$ (500 mL) and $H_2O$ (500 mL). The layers were separated and the organic portion was concentrated under reduced pressure to give 40.5 g of 7-bromo-N-((1S)-2-{[tert-butyl(dimethyl)silyl]oxy}-1-methylethyl)-3-nitroquinolin-4-amine as a yellow, crystalline solid.

Part C

A 2-L, stainless-steel, Parr vessel was charged with platinum on carbon (5%, 4.0 g) and 10 mL of acetonitrile. A solution of 7-bromo-N-((1S)-2-{[tert-butyl(dimethyl)silyl] oxy}-1-methylethyl)-3-nitroquinolin-4-amine (40.5 g, 92.0 mmol) dissolved in 1 L of acetonitrile was then added. The reaction mixture was placed on Parr apparatus and shaken under $H_2$ at 45 PSI (3.1×10$^5$ Pa) for 6 hours at ambient temperature. The reaction mixture was then filtered through a pad of CELITE filter agent. The pad rinsed with an additional 200 mL of acetonitrile and the combined filtrates were concentrated under reduced pressure to give 33.4 g 7-bromo-N$^4$-((1S)-2-{[tert-butyl(dimethyl)silyl]oxy}-1-methylethyl) quinoline-3,4-diamine as a yellow solid.

Part D

A 1-L, three-necked, Morton flask, equipped with overhead stirrer, was charged with 7-bromo-N$^4$-((1S)-2-{[tert-butyl(dimethyl)silyl]oxy}-1-methylethyl)quinoline-3,4-diamine (33.4 g, 81.0 mmol) and 1,2-dichloroethane (400 mL) and the mixture was stirred under $N_2$. Ethyl 2-chloroethanimidoate hydrochloride (29.1 g, 184.0 mmol) was then added in portions and the reaction mixture was heated to 70° C. for 3 days. The reaction mixture was then cooled to ambient temperature and treated with $CHCl_3$ (500 mL) and saturated aqueous $NaHCO_3$ solution (700 mL). The layers were separated and the organic portion was concentrated under reduced pressure to give 38 g of 7-bromo-1-((1S)-2-{[tert-butyl(dimethyl)silyl]oxy}-1-methylethyl)-2-(chloromethyl)-1H-imidazo[4,5-c]quinoline as a golden solid.

Part E

A 2-L, three-necked, Morton flask, equipped with mechanical stirrer, was charged with 7-bromo-1-((1S)-2-{[tert-butyl(dimethyl)silyl]oxy}-1-methylethyl)-2-(chloromethyl)-1H-imidazo[4,5-c]quinoline (38.0 g, 81.0 mmol) and 1,2-dichloroethane (900 mL) and the mixture was cooled to 1° C. A 1.0 M solution of tetrabutylammonium fluoride in THF (90 mL, 90 mmol) was slowly added over 1.5 hours. The reaction temperature was maintained at 1-2° C. during addition. The reaction was allowed to slowly warm to ambient temperature and stirring was continued for 2 days. The reaction was treated with saturated aqueous $K_2CO_3$ solution (500 mL) and $H_2O$ (400 mL). The layers were separated and the aqueous portion was extracted with $CH_2Cl_2$ (3×100 mL). The organic layers were combined and concentrated under reduced pressure to give a tan solid. Chromatography ($SiO_2$, 0-6% methanol/$CH_2Cl_2$) gave 12.5 g of (11S)-3-bromo-11-methyl-10,11-dihydro-8H-[1,4]oxazino[4',3':1,2]imidazo[4,5-c]quinoline as an off-white solid which was used without further purification. A small sample was crystallized from acetonitrile to give white crystals, mp 207-209° C.

MS (APCI) m/z 318 (M+H)$^+$. Anal. calcd for $C_{14}H_{12}BrN_3O \cdot 1.0H_2O$: C, 50.02; H, 4.20; N, 12.50. Found: C, 50.19; H, 3.86; N, 12.16.

Part F

A 2-L, three-necked, Morton flask, equipped with mechanical stirrer, was charged with (11S)-3-bromo-11-methyl-10,11-dihydro-8H-[1,4]oxazino[4',3':1,2]imidazo[4,5-c]quinoline (9.12 g, 28.7 mmol) and $CH_2Cl_2$ (500 mL). The mixture was stirred at ambient temperature and MCPBA (10.35 g, 50% purity) was then added slowly in portions. The reaction was stirred at ambient temperature for 2 hours. Concentrated aqueous $NH_4OH$ solution (200 mL) was then slowly added to the reaction mixture followed by careful addition of p-toluenesulfonyl chloride (6.29 g, 33.0 mmol) in small portions. The reaction was stirred rapidly at ambient temperature overnight. The reaction was then treated with $H_2O$ (500 mL) and vigorous stirring was maintained for 2 hours. The layers were allowed to separate and a tan precipitate formed. The aqueous layer was removed and the organic layer, containing the precipitate, was filtered to give 6.0 g of (11S)-3-bromo-11-methyl-10,11-dihydro-8H-[1,4]oxazino [4',3':1,2]imidazo[4,5-c]quinolin-6-amine as a tan solid. The product was used in subsequent reactions without further purification.

MS (APCI) m/z 333 (M+H)$^+$.

Example 61

(11S)-1-Methyl-3-[2-(methylsulfonyl)ethyl]-10,11-dihydro-8H-[1,4]oxazino[4',3':1,2]imidazo[4,5-c]quinolin-6-amine

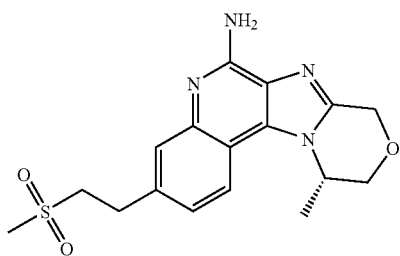

Part A

A scintillation vial was charged with palladium acetate (35.2 mg, 0.165 mmol), tri-o-tolylphosphine (96 mg, 0.32 mmol), anhydrous DMF (1.0 mL) and triethylamine (1.31 mL, 9.4 mmol). The orange homogeneous solution was then added to a solution of (11S)-3-bromo-11-methyl-10,11-dihydro-8H-[1,4]oxazino[4',3':1,2]imidazo[4,5-c]quinoline (1.00 g, 3.14 mmol) dissolved in 20 mL of anhydrous DMF followed by the addition of a solution of methyl vinyl sulfone (400 mg, 3.77 mmol) dissolved in 1.0 mL of anhydrous DMF. The mixture was transferred to a glass vessel and the vessel was purged with $N_2$, sealed and heated to 120° C. for 18 hours. The reaction mixture was cooled and concentrated to dryness under reduced pressure to give a golden solid. The solid was treated with $CH_2Cl_2$ and saturated aqueous $K_2CO_3$ solution and the layers were separated. The organic layer was concentrated to dryness to give a solid. Chromatography ($SiO_2$, 0-15% CMA/CHCl$_3$) gave a white solid that was crystallized from acetonitrile to give 0.5 g of (11S)-11-methyl-3-[(E)-2-(methylsulfonyl)ethenyl]-10,11-dihydro-8H-[1,4]oxazino[4',3':1,2]imidazo[4,5-c]quinoline as white crystals, mp 249-250° C.

MS (APCI) m/z 344 (M+H)$^+$. Anal. calcd for $C_{17}H_{17}N_3O_3S$: C, 59.46; H, 4.99; N, 12.24. Found: C, 59.54; H, 4.75; N, 12.06.

Part B

A 250-mL, glass Parr bottle was charged with palladium on carbon (10%, 0.04 g) and 2 mL of ethanol. A solution of (11S)-11-methyl-3-[(E)-2-(methylsulfonyl)ethenyl]-10,11-dihydro-8H-[1,4]oxazino[4',3':1,2]imidazo[4,5-c]quinoline (0.45 g, 1.31 mmol) dissolved in 125 mL of ethanol was then added. The reaction mixture was placed on Parr apparatus and shaken under $H_2$ at 50 PSI ($3.4 \times 10^5$ Pa) overnight at ambient temperature. The reaction mixture was then filtered through a pad of CELITE filter agent. The pad rinsed with ethanol and the combined filtrates were concentrated under reduced pressure to give 0.45 g of (11S)-11-methyl-3-[2-(methylsulfonyl)ethyl]-10,11-dihydro-8H-[1,4]oxazino[4',3':1,2]imidazo[4,5-c]quinoline as a white solid.

Part C

A 200-mL, round-bottomed flask was charged with (11S)-11-methyl-3-[2-(methylsulfonyl)ethyl]-10,11-dihydro-8H-[1,4]oxazino[4',3':1,2]imidazo[4,5-c]quinoline (0.45 g, 1.31 mmol) and $CH_2Cl_2$ (75 mL). The mixture was stirred at ambient temperature and MCPBA (0.45 g, 50% purity) was then added slowly in portions. The reaction was stirred at ambient temperature for 2 hours. Concentrated aqueous NH$_4$OH solution (25 mL) was then slowly added to the reaction mixture followed by careful addition of p-toluenesulfonyl chloride (0.27 g, 1.44 mmol). The reaction was stirred rapidly at ambient temperature overnight. The reaction was then treated with $H_2O$ (100 mL) and vigorous stirring was maintained for 2 hours. The layers were then separated and the aqueous layer was extracted with $CH_2Cl_2$ (3×50 mL). The combined organic layers were concentrated under reduced pressure. Chromatography ($SiO_2$, 0-15% CMA/CHCl$_3$) gave a white solid that was crystallized from acetonitrile to give 0.12 g of (11S)-11-methyl-3-[2-(methylsulfonyl)ethyl]-10,11-dihydro-8H-[1,4]oxazino[4',3':1,2]imidazo[4,5-c]quinolin-6-amine as a white, crystalline solid, mp 205-206° C.

MS (APCI) m/z 361 (M+H)$^+$. Anal. calcd for $C_{17}H_{20}N_4O_3S \cdot 0.66H_2O$: C, 54.84; H, 5.77; N, 15.05. Found: C, 54.78; H, 5.68; N, 15.04.

Example 62

(11S)-11-Methyl-3-[(1E)-3-morpholin-4-yl-3-oxo-prop-1-enyl]-10,11-dihydro-8H-[1,4]oxazino[4',3':1,2]imidazo[4,5-c]quinolin-6-amine

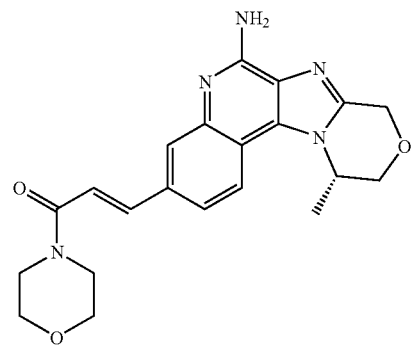

A scintillation vial was charged with palladium acetate (22 mg, 0.10 mmol), tri-o-tolylphosphine (61 mg, 0.20 mmol), anhydrous DMF (1.0 mL) and triethylamine (0.4 mL, 3.0 mmol). The orange homogeneous solution was then added to a solution of (11S)-3-bromo-11-methyl-10,11-dihydro-8H-[1,4]oxazino[4',3':1,2]imidazo[4,5-c]quinolin-6-amine (333 mg, 1.00 mmol) dissolved in 10 mL of anhydrous DMF followed by the addition of a solution of 4-acryloylmorpholine (169 mg, 1.20 mmol) dissolved in 1.0 mL of anhydrous DMF. The mixture was transferred to a glass vessel and the vessel was purged with $N_2$, sealed and heated to 120° C. for 18 hours. The reaction mixture was cooled and concentrated to dryness under reduced pressure to give a golden solid. The solid was treated with $CH_2Cl_2$ and saturated aqueous $K_2CO_3$ solution and the layers were separated. The organic layer was concentrated to dryness to give a light-brown solid. Chromatography ($SiO_2$, 0-15% CMA/CHCl$_3$) gave a tan solid that was crystallized from acetonitrile to give 250 mg of the title compound as beige crystals, mp>250° C.

MS (APCI) m/z 394 (M+H)+. Anal. calcd for $C_{21}H_{23}N_5O_3 \cdot 0.3$ $CH_3OH$: C, 63.47; H, 6.05; N, 17.38. Found: C, 63.62; H, 5.89; N, 17.15.

Example 63

(11S)-11-Methyl-3-(3-morpholin-4-yl-3-oxopropyl)-10,11-dihydro-8H-[1,4]oxazino[4',3':1,2]imidazo[4,5-c]quinolin-6-amine

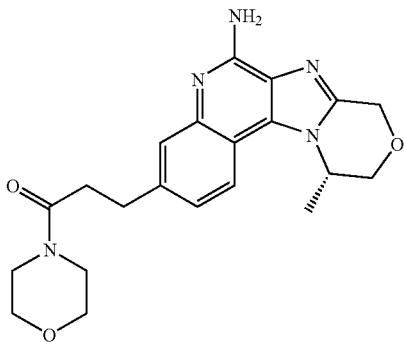

A 250-mL, glass Parr bottle was charged with palladium on carbon (10%, 0.05 g) and 2 mL of ethanol. A solution of (11S)-11-methyl-3-[(1E)-3-morpholin-4-yl-3-oxoprop-1-enyl]-10,11-dihydro-8H-[1,4]oxazino[4',3':1,2]imidazo[4,5-c]quinolin-6-amine (0.25 g, 0.63 mmol) dissolved in 125 mL of a 1:1 mixture of methanol/ethanol was then added. The reaction mixture was placed on Parr apparatus and shaken under $H_2$ at 50 PSI ($3.4 \times 10^5$ Pa) overnight at ambient temperature. The reaction mixture was treated with additional palladium on carbon (10%, 0.05 g) and shaken under $H_2$ at 50 PSI ($3.4 \times 10^5$ Pa) for 3 days. The reaction mixture was then filtered through a pad of CELITE filter agent. The pad rinsed with methanol and the combined filtrates were concentrated under reduced pressure to give a white solid. Chromatography ($SiO_2$, 0-15% CMA/$CHCl_3$) gave a white solid that was crystallized from acetonitrile to give 111 mg of the title compound as white crystals, mp 245-247° C.

MS (APCI) m/z 396 (M+H)+. Anal. calcd for $C_{21}H_{25}N_5O_3$: C, 63.78; H, 6.37; N, 17.71. Found: C, 63.81; H, 6.31; N, 17.73.

Example 64

3-[(11S)-6-Amino-1-methyl-10,11-dihydro-8H-[1,4]oxazino[4',3':1,2]imidazo[4,5-c]quinolin-3-yl]-N,N-dimethylpropanamide

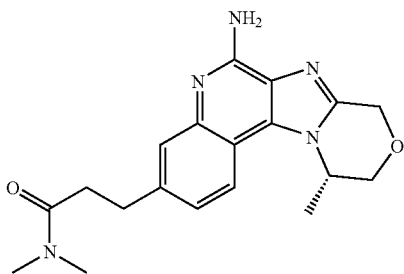

Part A

A scintillation vial was charged with palladium acetate (22 mg, 0.10 mmol), tri-o-tolylphosphine (61 mg, 0.20 mmol), anhydrous DMF (1.0 mL) and triethylamine (0.4 mL, 3.0 mmol). The orange homogeneous solution was then added to a solution of (11S)-3-bromo-11-methyl-10,11-dihydro-8H-[1,4]oxazino[4',3':1,2]imidazo[4,5-c]quinolin-6-amine (333 mg, 1.00 mmol) dissolved in 10 mL of anhydrous DMF followed by the addition of a solution of N,N-dimethylacrylamide (120 mg, 1.20 mmol) dissolved in 1.0 mL of anhydrous DMF. The mixture was transferred to a glass vessel and the vessel was purged with $N_2$, sealed and heated to 120° C. for 18 hours. The reaction mixture was cooled and concentrated to dryness under reduced pressure to give a golden solid. The solid was treated with $CH_2Cl_2$ and saturated aqueous $K_2CO_3$ solution and the layers were separated. The organic layer was concentrated to dryness to give a light-brown solid. Chromatography ($SiO_2$, 0-15% CMA/$CHCl_3$) gave a white solid that was crystallized from acetonitrile to give 210 mg of the (2E)-3-[(11S)-6-amino-11-methyl-10,11-dihydro-8H-[1,4]oxazino[4',3':1,2]imidazo[4,5-c]quinolin-3-yl]-N,N-dimethylprop-2-enamide as off-white crystals, mp>250° C.

MS (APCI) m/z 352 (M+H)+.

Part B

A 250-mL, glass Parr bottle was charged with palladium on carbon (10%, 0.05 g) and 2 mL of ethanol. A solution of (2E)-3-[(11S)-6-amino-11-methyl-10,11-dihydro-8H-[1,4]oxazino[4',3':1,2]imidazo[4,5-c]quinolin-3-yl]-N,N-dimethylprop-2-enamide (210 mg, 0.60 mmol) dissolved in 50 mL of ethanol was then added. The reaction mixture was placed on Parr apparatus and shaken under H2 at 50 PSI ($3.4 \times 10^5$ Pa) overnight at ambient temperature. The reaction mixture was treated with additional palladium on carbon (10%, 0.05 g) and shaken under H2 at 50 PSI ($3.4 \times 10^5$ Pa) for 24 hours. The reaction mixture was then filtered through a pad of CELITE filter agent. The pad was rinsed with methanol and the combined filtrates were concentrated under reduced pressure to give a white solid. Chromatography ($SiO_2$, 0-15% CMA/$CHCl_3$) gave a white solid that was crystallized from acetonitrile to give 120 mg of 3-[(11S)-6-amino-11-methyl-10,11-dihydro-8H-[1,4]oxazino[4',3':1,2]imidazo[4,5-c]quinolin-3-yl]-N,N-dimethylpropanamide as white crystals, mp 235-237° C.

MS (APCI) m/z 354 (M+H)+. Anal. calcd for $C_{19}H_{23}N_5O_2 \cdot 0.5H_2O$: C, 62.97; H, 6.67; N, 19.32. Found: C, 62.65; H, 6.68; N, 19.01.

Examples 65-73

A solution of (11S)-3-bromo-11-methyl-10,11-dihydro-8H-[1,4]oxazino[4',3':1,2]imidazo[4,5-c]quinolin-6-amine (16 mg, 0.10 mmol) in 7:3 volume:volume (v:v) chloroform:methanol (2 mL) was added to a test tube, and the solvent was removed by vacuum centrifugation. The boronic acid (0.11 mmol) indicated in the table below and n-propanol (1.6 mL) were sequentially added. The test tube was purged with nitrogen. Palladium (II) acetate (150 µL of a 4 mg/mL solution in toluene, 0.0026 mmol), 2 M aqueous sodium carbonate solution (600 µL), deionized water (113 µL), and a solution of 0.15 mol % triphenylphosphine in n-propanol (53 µL, 0.0078 mmol) were sequentially added. The test tube was purged with nitrogen, capped, and then heated at 80° C. overnight in a sand bath. For Example 73, glacial acetic acid (500 µL), tetrahydrofuran (500 µL), and deionized water (500 µL) were added to the test tube. The reaction was heated for 4 hours at 60° C.

The contents of each test tube were passed through a Waters Oasis Sample Extractions Cartridge MCX (6 cc) according to the following procedure. Hydrochloric acid (3 mL of 1 N) was added to adjust each example to pH <5, and the resulting solution was passed through the cartridge optionally using light nitrogen pressure. The cartridge was washed with methanol (5 mL) optionally using light nitrogen pressure and transferred to a clean test tube. A solution of 1N ammonia in methanol (2×5 mL) was then passed through the cartridge optionally using light nitrogen pressure, and the eluent was collected and concentrated by vacuum centrifugation.

The compounds were purified by preparative high performance liquid chromatography using a Waters FractionLynx automated purification system. The fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. The fractions were collected by mass-selective triggering. The table below shows the reagent used for each example, the structure of the resulting compound, and the observed accurate mass for the isolated trifluoroacetate salt.

| Example | Reagent | R | Measured Mass (M + H) |
|---------|---------|---|------------------------|
| 65 | Phenylboronic acid | phenyl | 331.1588 |
| 66 | Pyridine-3-boronic acid | pyridin-3-yl | 332.1479 |
| 67 | 3-Methylphenylboronic acid | 3-methylphenyl | 345.1736 |
| 68 | 3-Chlorophenylboronic acid | 3-chlorophenyl | 365.1198 |
| 69 | 3-Ethoxyphenylboronic acid | 3-ethoxyphenyl | 375.1798 |
| 70 | 3-(N-Isopropylaminocarbonyl)phenylboronic acid | 3-(N-isopropylaminocarbonyl)phenyl | 416.2074 |
| 71 | 3-(Pyrrolidine-1-carbonyl)phenylboronic acid | 3-(pyrrolidine-1-carbonyl)phenyl | 428.2053 |

-continued

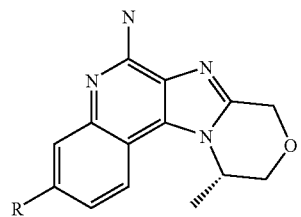

| Example | Reagent | R | Measured Mass (M + H) |
|---|---|---|---|
| 72 | 3-(Piperidine-1-carbonyl)phenylboronic acid | (3-methylphenyl piperidine carbonyl) | 442.2257 |
| 73 | 5-(tert-butyldimethylsilanyloxy-methyl)pyridine-3-boronic acid | (5-hydroxymethylpyridin-3-yl) | 362.1602 |

Examples 74-85

The compounds in the table below were prepared and purified according to the methods of Examples 65-73 except that 3-bromo-12-methyl-11,12-dihydro-8H,10H-[1,4]oxazepino[4′,3′:1,2]imidazo[4,5-c]quinolin-6-amine was used in lieu of (11S)-3-bromo-11-methyl-10,11-dihydro-8H-[1,4]oxazino[4′,3′:1,2]imidazo[4,5-c]quinolin-6-amine. Example 85 was prepared according to the method used for Example 73. The table below shows the reagent used for each example, the structure of the resulting compound, and the observed accurate mass for the isolated trifluoroacetate salt.

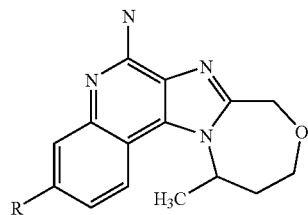

| Example | Reagent | R | Measured Mass (M + H) |
|---|---|---|---|
| 74 | Phenylboronic acid | phenyl | 345.1737 |
| 75 | Pyridine-3-boronic acid | pyridin-3-yl | 346.1703 |
| 76 | (2-Hydroxyphenyl)boronic acid | 2-hydroxyphenyl | 361.1657 |

-continued

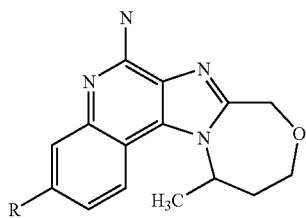

| Example | Reagent | R | Measured Mass (M + H) |
|---|---|---|---|
| 77 | (2-Hydroxymethylphenyl)boronic acid dehydrate | 2-(hydroxymethyl)phenyl | 375.1823 |
| 78 | 3-Chlorophenylboronic acid | 3-chlorophenyl | 379.1333 |
| 79 | [3-(Hydroxypropyl)phenyl]boronic acid | 3-(3-hydroxypropyl)phenyl | 403.2138 |
| 80 | 3-(N,N-Dimethylaminocarbonyl)phenylboronic acid | 3-(N,N-dimethylcarbamoyl)phenyl | 416.2076 |
| 81 | 3-(Methanesulfonyl)phenylboronic acid | 3-(methanesulfonamido)phenyl | 438.1592 |
| 82 | 3-(Pyrrolidine-1-carbonyl)phenylboronic acid | 3-(pyrrolidine-1-carbonyl)phenyl | 442.2242 |

-continued
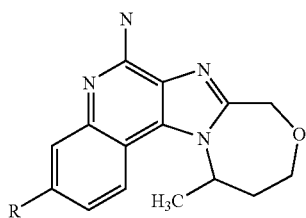
| Example | Reagent | R | Measured Mass (M + H) |
|---|---|---|---|
| 83 | 3-(Morpholine-4-carbonyl)phenylboronic acid | | 458.2185 |
| 84 | 4-(Morpholine-4-carbonyl)phenylboronic acid | | 458.2190 |
| 85 | 5-(tert-butyldimethylsilanyloxymethyl)pyridine-3-boronic acid | | 376.1790 |

Exemplary Compounds

Certain exemplary compounds, including some of those described above in the Examples, have the following Formulas (IIIa, Va, or VIIa) and the following $R_{1b}$ substituents, wherein each line of the table is matched with Formula IIIa, Va, or VIIa to represent a specific embodiment of the invention.

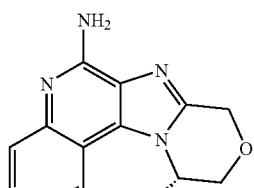

IIIa

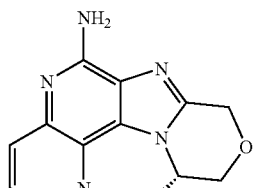

Va

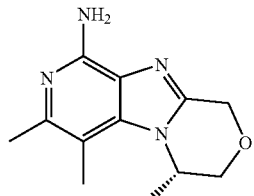

VIIa

| $R_{1b}$ |
| --- |
| methyl |
| isopropyl |
| 1-fluoro-1-methylethyl |
| 1-hydroxy-1-methylethyl |
| phenyl |
| benzyl |
| 1-hydroxyethyl |
| tetrahydro-2H-pyran-4-yl |

Certain exemplary compounds, including some of those described above in the Examples, have the following Formulas (IVb or VIb) and the following $R_{1c}$ substituents, wherein each line of the table is matched with Formula IVb or VIb to represent a specific embodiment of the invention.

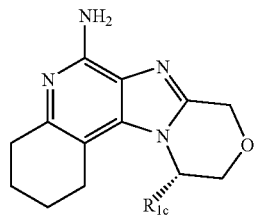

IVb

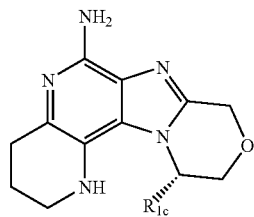

VIb

| $R_{1c}$ |
| --- |
| methyl |
| isopropyl |
| 1-fluoro-1-methylethyl |
| 1-hydroxy-1-methylethyl |
| 1-hydroxyethyl |
| tetrahydro-2H-pyran-4-yl |

Certain exemplary compounds, including some of those described above in the Examples, have the following Formulas (IIIb or IIIc) and the following $R_{1c}$ and $R_{3c}$ substituents, wherein each line of the table is matched with Formula IIIb or IIIc to represent a specific embodiment of the invention.

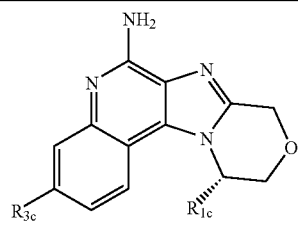

IIIb

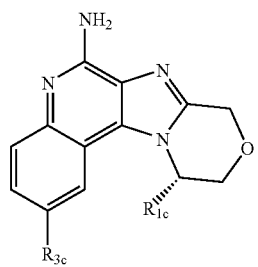

IIIc

| $R_{1c}$ | $R_{3c}$ |
| --- | --- |
| methyl | 2-cyanoethyl |
| methyl | 2-(aminocarbonyl)ethyl |
| methyl | 3-aminopropyl |
| methyl | 3-(acetylamino)propyl |
| methyl | 3-[(methylsulfonyl)amino]propyl |

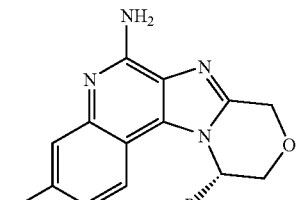

IIIb

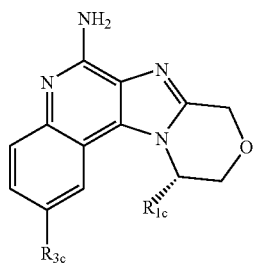

IIIc

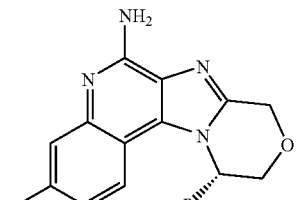

IIIb

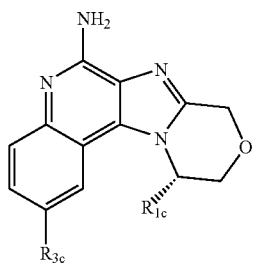

IIIc

| $R_{1c}$ | $R_{3c}$ |
|---|---|
| methyl | 3-{[(isopropylamino)carbonyl]amino}propyl |
| methyl | 2-aminoethyl |
| methyl | 2-(acetylamino)ethyl |
| methyl | 2-[(methylsulfonyl)amino]ethyl |
| methyl | 2-{[(isopropylamino)carbonyl]amino}ethyl |
| methyl | 3-ethoxy-3-oxopropyl |
| methyl | 2-carboxyethyl |
| methyl | ethenyl |
| methyl | ethyl |
| methyl | 2-oxopyrrolidin-1-yl |
| methyl | 2-oxo-1,3-oxazolidin-3-yl |
| methyl | (cyclopropylmethyl)amino |
| methyl | 2-(pyridin-3-yl)ethyl |
| methyl | (1-methyl-1H-imidazol-2-yl)methoxy |
| methyl | (1,3-thiazol-4-yl)methoxy |
| methyl | (pyridin-3-yl)methoxy |
| methyl | 3-(pyridin-3-yl)propoxy |
| methyl | (1-acetylpiperidin-4-yl)oxy |
| methyl | {1-[(isopropylamino)carbonyl]piperidin-4-yl}oxy |
| methyl | [1-(methylsulfonyl)piperidin-4-yl]oxy |
| methyl | 2-(methylsulfonyl)ethoxy |
| methyl | 2-[(methylsulfonyl)amino]ethoxy |
| isopropyl | 2-cyanoethyl |
| isopropyl | 2-(aminocarbonyl)ethyl |
| isopropyl | 3-aminopropyl |
| isopropyl | 3-(acetylamino)propyl |
| isopropyl | 3-[(methylsulfonyl)amino]propyl |
| isopropyl | 3-{[(isopropylamino)carbonyl]amino}propyl |
| isopropyl | 2-aminoethyl |
| isopropyl | 2-(acetylamino)ethyl |
| isopropyl | 2-[(methylsulfonyl)amino]ethyl |
| isopropyl | 2-{[(isopropylamino)carbonyl]amino}ethyl |
| isopropyl | 3-ethoxy-3-oxopropyl |
| isopropyl | 2-carboxyethyl |
| isopropyl | ethenyl |
| isopropyl | ethyl |
| isopropyl | 2-oxopyrrolidin-1-yl |
| isopropyl | 2-oxo-1,3-oxazolidin-3-yl |
| isopropyl | (cyclopropylmethyl)amino |
| isopropyl | 2-(pyridin-3-yl)ethyl |
| isopropyl | (1-methyl-1H-imidazol-2-yl)methoxy |
| isopropyl | (1,3-thiazol-4-yl)methoxy |
| isopropyl | (pyridin-3-yl)methoxy |
| isopropyl | 3-(pyridin-3-yl)propoxy |
| isopropyl | (1-acetylpiperidin-4-yl)oxy |
| isopropyl | {1-[(isopropylamino)carbonyl]piperidin-4-yl}oxy |
| isopropyl | [1-(methylsulfonyl)piperidin-4-yl]oxy |
| isopropyl | 2-(methylsulfonyl)ethoxy |
| isopropyl | 2-[(methylsulfonyl)amino]ethoxy |
| 1-fluoro-1-methylethyl | 2-cyanoethyl |
| 1-fluoro-1-methylethyl | 2-(aminocarbonyl)ethyl |
| 1-fluoro-1-methylethyl | 3-aminopropyl |
| 1-fluoro-1-methylethyl | 3-(acetylamino)propyl |
| 1-fluoro-1-methylethyl | 3-[(methylsulfonyl)amino]propyl |
| 1-fluoro-1-methylethyl | 3-{[(isopropylamino)carbonyl]amino}propyl |
| 1-fluoro-1-methylethyl | 2-aminoethyl |
| 1-fluoro-1-methylethyl | 2-(acetylamino)ethyl |
| 1-fluoro-1-methylethyl | 2-[(methylsulfonyl)amino]ethyl |
| 1-fluoro-1-methylethyl | 2-{[(isopropylamino)carbonyl]amino}ethyl |
| 1-fluoro-1-methylethyl | 3-ethoxy-3-oxopropyl |
| 1-fluoro-1-methylethyl | 2-carboxyethyl |
| 1-fluoro-1-methylethyl | ethenyl |
| 1-fluoro-1-methylethyl | ethyl |
| 1-fluoro-1-methylethyl | 2-oxopyrrolidin-1-yl |
| 1-fluoro-1-methylethyl | 2-oxo-1,3-oxazolidin-3-yl |
| 1-fluoro-1-methylethyl | (cyclopropylmethyl)amino |
| 1-fluoro-1-methylethyl | 2-(pyridin-3-yl)ethyl |
| 1-fluoro-1-methylethyl | (1-methyl-1H-imidazol-2-yl)methoxy |
| 1-fluoro-1-methylethyl | (1,3-thiazol-4-yl)methoxy |
| 1-fluoro-1-methylethyl | (pyridin-3-yl)methoxy |
| 1-fluoro-1-methylethyl | 3-(pyridin-3-yl)propoxy |
| 1-fluoro-1-methylethyl | (1-acetylpiperidin-4-yl)oxy |
| 1-fluoro-1-methylethyl | 3-(pyridin-3-yl)propoxy |
| 1-fluoro-1-methylethyl | {1-[(isopropylamino)carbonyl]piperidin-4-yl}oxy |
| 1-fluoro-1-methylethyl | [1-(methylsulfonyl)piperidin-4-yl]oxy |
| 1-fluoro-1-methylethyl | 2-(methylsulfonyl)ethoxy |
| 1-fluoro-1-methylethyl | 2-[(methylsulfonyl)amino]ethoxy |
| 1-hydroxy-1-methylethyl | 2-cyanoethyl |
| 1-hydroxy-1-methylethyl | 2-(aminocarbonyl)ethyl |
| 1-hydroxy-1-methylethyl | 3-aminopropyl |
| 1-hydroxy-1-methylethyl | 3-(acetylamino)propyl |
| 1-hydroxy-1-methylethyl | 3-[(methylsulfonyl)amino]propyl |
| 1-hydroxy-1-methylethyl | 3-{[(isopropylamino)carbonyl]amino}propyl |
| 1-hydroxy-1-methylethyl | 2-aminoethyl |
| 1-hydroxy-1-methylethyl | 2-(acetylamino)ethyl |
| 1-hydroxy-1-methylethyl | 2-[(methylsulfonyl)amino]ethyl |
| 1-hydroxy-1-methylethyl | 2-{[(isopropylamino)carbonyl]amino}ethyl |
| 1-hydroxy-1-methylethyl | 3-ethoxy-3-oxopropyl |
| 1-hydroxy-1-methylethyl | 2-carboxyethyl |
| 1-hydroxy-1-methylethyl | ethenyl |
| 1-hydroxy-1-methylethyl | ethyl |
| 1-hydroxy-1-methylethyl | 2-oxopyrrolidin-1-yl |
| 1-hydroxy-1-methylethyl | 2-oxo-1,3-oxazolidin-3-yl |
| 1-hydroxy-1-methylethyl | (cyclopropylmethyl)amino |
| 1-hydroxy-1-methylethyl | 2-(pyridin-3-yl) ethyl |

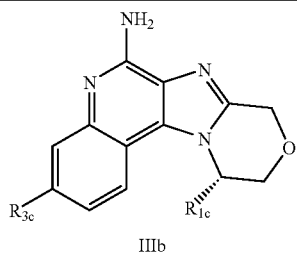

IIIb

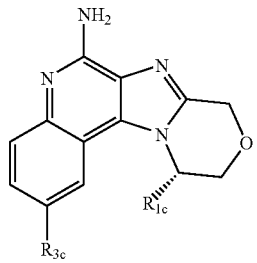

IIIc

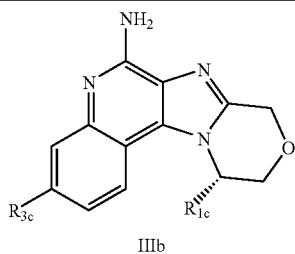

IIIb

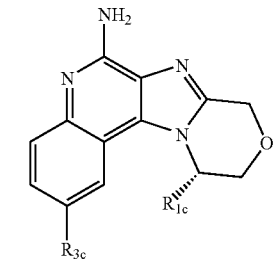

IIIc

| $R_{1c}$ | $R_{3c}$ |
|---|---|
| 1-hydroxy-1-methylethyl | (1-methyl-1H-imidazol-2-yl)methoxy |
| 1-hydroxy-1-methylethyl | (1,3-thiazol-4-yl)methoxy |
| 1-hydroxy-1-methylethyl | (pyridin-3-yl)methoxy |
| 1-hydroxy-1-methylethyl | 3-(pyridin-3-yl)propoxy |
| 1-hydroxy-1-methylethyl | (1-acetylpiperidin-4-yl)oxy |
| 1-hydroxy-1-methylethyl | {1-[(isopropylamino)carbonyl]piperidin-4-yl}oxy |
| 1-hydroxy-1-methylethyl | [1-(methylsulfonyl)piperidin-4-yl]oxy |
| 1-hydroxy-1-methylethyl | 2-(methylsulfonyl)ethoxy |
| 1-hydroxy-1-methylethyl | 2-[(methylsulfonyl)amino]ethoxy |
| 1-hydroxyethyl | 2-cyanoethyl |
| 1-hydroxyethyl | 2-(aminocarbonyl)ethyl |
| 1-hydroxyethyl | 3-aminopropyl |
| 1-hydroxyethyl | 3-(acetylamino)propyl |
| 1-hydroxyethyl | 3-[(methylsulfonyl)amino]propyl |
| 1-hydroxyethyl | 3-{[(isopropylamino)carbonyl]amino}propyl |
| 1-hydroxyethyl | 2-aminoethyl |
| 1-hydroxyethyl | 2-(acetylamino)ethyl |
| 1-hydroxyethyl | 2-[(methylsulfonyl)amino]ethyl |
| 1-hydroxyethyl | 2-{[(isopropylamino)carbonyl]amino}ethyl |
| 1-hydroxyethyl | 3-ethoxy-3-oxopropyl |
| 1-hydroxyethyl | 2-carboxyethyl |
| 1-hydroxyethyl | ethenyl |
| 1-hydroxyethyl | ethyl |
| 1-hydroxyethyl | 2-oxopyrrolidin-1-yl |
| 1-hydroxyethyl | 2-oxo-1,3-oxazolidin-3-yl |
| 1-hydroxyethyl | (cyclopropylmethyl)amino |
| 1-hydroxyethyl | 2-(pyridin-3-yl)ethyl |
| 1-hydroxyethyl | (1-methyl-1H-imidazol-2-yl)methoxy |
| 1-hydroxyethyl | (1,3-thiazol-4-yl)methoxy |
| 1-hydroxyethyl | (pyridin-3-yl)methoxy |
| 1-hydroxyethyl | 3-(pyridin-3-yl)propoxy |
| 1-hydroxyethyl | (1-acetylpiperidin-4-yl)oxy |
| 1-hydroxyethyl | {1-[(isopropylamino)carbonyl]piperidin-4-yl}oxy |
| 1-hydroxyethyl | [1-(methylsulfonyl)piperidin-4-yl]oxy |
| 1-hydroxyethyl | 2-(methylsulfonyl)ethoxy |
| 1-hydroxyethyl | 2-[(methylsulfonyl)amino]ethoxy |
| tetrahydro-2H-pyran-4-yl | 2-cyanoethyl |
| tetrahydro-2H-pyran-4-yl | 2-(aminocarbonyl) ethyl |
| tetrahydro-2H-pyran-4-yl | 3-aminopropyl |
| tetrahydro-2H-pyran-4-yl | 3-(acetylamino)propyl |
| tetrahydro-2H-pyran-4-yl | 3-[(methylsulfonyl)amino]propyl |
| tetrahydro-2H-pyran-4-yl | 3-{[(isopropylamino)carbonyl]amino}propyl |
| tetrahydro-2H-pyran-4-yl | 2-aminoethyl |
| tetrahydro-2H-pyran-4-yl | 2-(acetylamino)ethyl |
| tetrahydro-2H-pyran-4-yl | 2-[(methylsulfonyl)amino]ethyl |
| tetrahydro-2H-pyran-4-yl | 2-{[(isopropylamino)carbonyl]amino}ethyl |
| tetrahydro-2H-pyran-4-yl | 3-ethoxy-3-oxopropyl |
| tetrahydro-2H-pyran-4-yl | 2-carboxyethyl |

| $R_{1c}$ | $R_{3c}$ |
|---|---|
| tetrahydro-2H-pyran-4-yl | ethenyl |
| tetrahydro-2H-pyran-4-yl | ethyl |
| tetrahydro-2H-pyran-4-yl | 2-oxopyrrolidin-1-yl |
| tetrahydro-2H-pyran-4-yl | 2-oxo-1,3-oxazolidin-3-yl |
| tetrahydro-2H-pyran-4-yl | (cyclopropylmethyl)amino |
| tetrahydro-2H-pyran-4-yl | 2-(pyridin-3-yl)ethyl |
| tetrahydro-2H-pyran-4-yl | (1-methyl-1H-imidazol-2-yl)methoxy |
| tetrahydro-2H-pyran-4-yl | (1,3-thiazol-4-yl)methoxy |
| tetrahydro-2H-pyran-4-yl | (pyridin-3-yl)methoxy |
| tetrahydro-2H-pyran-4-yl | 3-(pyridin-3-yl)propoxy |
| tetrahydro-2H-pyran-4-yl | (1-acetylpiperidin-4-yl)oxy |
| tetrahydro-2H-pyran-4-yl | {1-[(isopropylamino)carbonyl]piperidin-4-yl}oxy |
| tetrahydro-2H-pyran-4-yl | [1-(methylsulfonyl)piperidin-4-yl]oxy |
| tetrahydro-2H-pyran-4-yl | 2-(methylsulfonyl)ethoxy |
| tetrahydro-2H-pyran-4-yl | 2-[(methylsulfonyl)amino]ethoxy |

Cytokine Induction in Human Cells

Compounds of the invention, particularly compounds of the Formulas II, IIa, III, IV, V, VI, and VII wherein Z is —O—, have been found to induce cytokine biosynthesis when tested using the method described below.

An in vitro human blood cell system is used to assess cytokine induction. Activity is based on the measurement of interferon (α) and tumor necrosis factor (α) (IFN-α and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction in Human Cells

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 μM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 μM) than the final tested concentration range.

Incubation

Compound solution is then added to the wells containing the PBMC suspension bringing the test compound concentrations to the desired range (usually 30-0.014 μM) and the DMSO concentration to 0.4%. The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Certain compounds of the invention, particularly compounds of Formulas I-1, II-1a, III-1, IV-1, V-1, VI-1, and VII-1, or compounds of Formulas II, IIa, III, IV, V, VI, and VII wherein Z is —N(—Y—$R_2$)—, may modulate cytokine biosynthesis by inhibiting production of tumor necrosis factor α (TNF-α) when tested using the method described below.

TNF-α Inhibition in Mouse Cells

The mouse macrophage cell line Raw 264.7 is used to assess the ability of compounds to inhibit tumor necrosis factor-α (TNF-α) production upon stimulation by lipopolysaccharide (LPS).

Single Concentration Assay:
Blood Cell Preparation for Culture

Raw cells (ATCC) are harvested by gentle scraping and then counted. The cell suspension is brought to $3 \times 10^5$ cells/mL in RPMI with 10% fetal bovine serum (FBS). Cell suspension (100 µL) is added to 96-well flat bottom sterile tissues culture plates (Becton Dickinson Labware, Lincoln Park, N.J.). The final concentration of cells is $3 \times 10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 µM. LPS (Lipopolysaccharide from *Salmonella typhimurium*, Sigma-Aldrich) is diluted with colorless RPMI to the $EC_{70}$ concentration as measured by a dose response assay.

Incubation

A solution of test compound (1 µl) is added to each well. The plates are mixed on a microtiter plate shaker for 1 minute and then placed in an incubator. Twenty minutes later the solution of LPS (1 µL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:
Blood Cell Preparation for Culture

Raw cells (ATCC) are harvested by gentle scraping and then counted. The cell suspension is brought to $4 \times 10^5$ cells/mL in RPMI with 10% FBS. Cell suspension (250 µL) is added to 48-well flat bottom sterile tissues culture plates (Costar, Cambridge, Mass.). The final concentration of cells is $1 \times 10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 µM. LPS (Lipopolysaccharide from *Salmonella typhimurium*, Sigma- Aldrich) is diluted with colorless RPMI to the $EC_{70}$ concentration as measured by dose response assay.

Incubation

A solution of test compound (200 μl) is added to each well. The plates are mixed on a microtiter plate shaker for 1 minute and then placed in an incubator. Twenty minutes later the solution of LPS (200 μL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the Formula IIa:

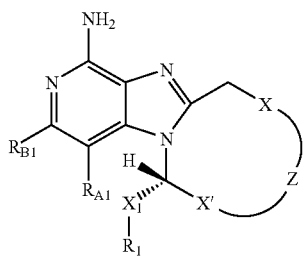

IIa wherein:

X is a bond;
X' is —$CH_2$—;
Z is —O—;
$X_1$ is selected from the group consisting of a bond, alkylene, alkenylene, and alkynylene wherein the alkylene and alkenylene are optionally interrupted by one or more —O— groups, and are optionally substituted by a hydroxy or methoxy group;
$R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of arylalkylenyl, alkylarylenyl, alkoxyarylenyl, haoarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_1$ is heterocyclyl, then the one or more substituents may also be independently selected from the group consisting of arylalkylenyl and aminocarbonyl;

$R_{A1}$ and $R_{B1}$ are each independently selected from the group consisting of:
hydrogen
halogen,
alkyl,
alkenyl,
alkoxy,
alkylthio, and
—$N(R_9)_2$;

or when taken together, $R_{A1}$ and $R_{B1}$ form a fused aryl ring or heteroaryl ring containing one heteroatom selected from the group consisting of N and S, wherein the aryl or heteroaryl ring is unsubstituted or substituted by one or more R groups, or substituted by one $R_3$ group, or substituted by one $R_3$ group and one R group;

or when taken together, $R_{A1}$ and $R_{B1}$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—$N(R_9)_2$;

$R_3$ is selected from the group consisting of:
—Y"—$R_4$,
—Z'—$R_4$,
—Z—X"—$R_4$,
—Z'—X"—Y'—$R_4$,
—Z'—X"—Y' X"—Y'—$R_4$, and
—Z'—X"—$R_5$;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y' is selected from the group consisting of:
—$S(O)_{0-2}$—,
—$S(O)_2$—$N(R_8)$—,
—$C(R_6)$—,
—$C(R_6)$—O—,
O—$C(R_6)$—,
—O—C(O)—O—,
—$N(R_8)$-Q-,
—$C(R_6)$—$N(R_8)$—,
—O—$C(R_6)$—$N(R_8)$—,
—$C(R_6)$—$N(OR_9)$—,

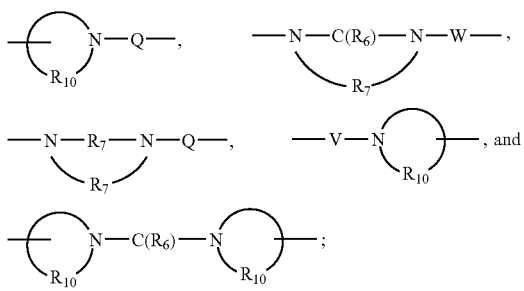

Y" is —O—C(R$_6$)—;
Z' is a bond or —O—;
R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;
R$_5$ is selected from the group consisting of

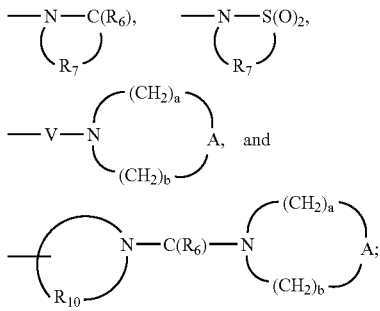

R$_6$ is selected from the group consisting of =O and =S;
R$_7$ is C$_{2-7}$ alkylene;
R$_8$ is selected from the group consisting of hydrogen, C$_{1-10}$alkyl, C$_{2-10}$ alkenyl, C$_{1-10}$alkoxy-C$_{1-10}$alkylenyl, and aryl-C$_{1-10}$alkylenyl;
R$_9$ is selected from the group consisting of hydrogen and alkyl;
R$_{10}$ is C$_{3-8}$ alkylene;
A is selected from the group consisting of —CH$_2$—, —O—, —C(O)—, —S(O)$_{0-2}$—, and N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$);
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and a and b are independently integers from 1 to 6 with the proviso that a+b is ≦7;

or a pharmaceutically acceptable salt thereof.

2. The compound or salt of claim 1 wherein:
X$_1$ is selected from the group consisting of a bond, alkylene, and alkenylene, wherein the alkylene and alkenylene are optionally interrupted by one or more —O— groups;
R$_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when R$_1$ is aryl, arylalkylenyl, heteroaryl, or heteroarylalkylenyl, then the one or more substituents may also be independently selected from the group consisting of alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and
R$_3$ is selected from the group consisting of:
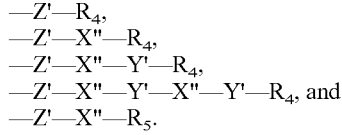

3. A compound of the Formula III:

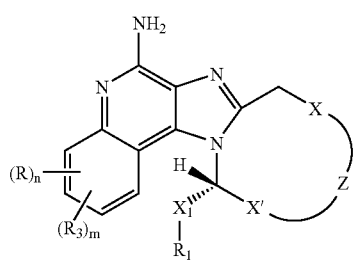

III wherein:
X is a bond;
X' is —CH$_2$—;
Z is —O—;
X$_1$ is selected from the group consisting of a bond, alkylene, alkenylene, and alkynylene wherein the alkylene and alkenylene are optionally interrupted by one or more —O— groups, and are optionally substituted by a hydroxy or methoxy group;
R$_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_1$ is heterocyclyl, then the one or more substituents may also be independently selected from the group consisting of arylalkylenyl and aminocarbonyl;

R is selected from the group consisting of:
 halogen,
 hydroxy,
 alkyl,
 alkenyl,
 haloalkyl,
 alkoxy,
 alkylthio, and
 $-N(R_9)_2$;

n is an integer from 0 to 4;

$R_3$ is selected from the group consisting of:
 $-Y''-R_4$,
 $-Z'-R_4$,
 $-Z'-X''-R_4$,
 $-Z'-X''-Y'-R_4$,
 $-Z'-X''-Y'-X''-Y'R_4$, and
 $-Z'-X''-R_5$;

m is 0 or 1; with the proviso that when m is 1, then n is 0 or 1;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y' is selected from the group consisting of:
 $-S(O)_{0-2}-$,
 $-S(O)_2-N(R_8)-$,
 $-C(R_6)-$,
 $-C(R_6)-O-$,
 $-O-C(R_6)-$,
 $-O-C(O)-O-$,
 $-N(R_8)-Q-$,
 $-C(R_6)-N(R_8)-$,
 $-O-C(R_6)-N(R_8)-$,
 $-C(R_6)-N(OR_9)-$,

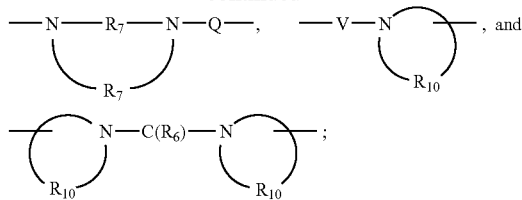

Y" is $-O-C(R_6)-$;

Z' is a bond or $-O-$;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of

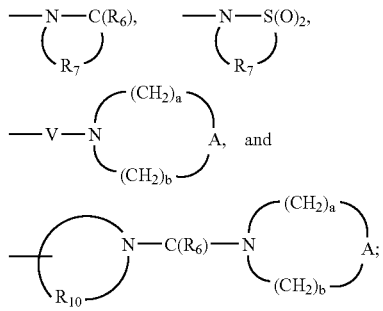

$R_6$ is selected from the group consisting of =O and =S;

$R_7$ is $C_{2-7}$ alkylene;

$R_8$ is selected from the group consisting of hydrogen, $C_{1-10}$alkyl, $C_{2-10}$alkenyl, $C_{1-10}$alkoxy-$C_{1-10}$alkylenyl, and aryl-$C_{1-10}$alkylenyl;

$R_9$ is selected from the group consisting of hydrogen and alkyl;

$R_{10}$ is $C_{3-8}$alkylene;

A is selected from the group consisting of $-CH_2-$, $-O-$, $-C(O)-$, $-S(O)_{0-2}-$, and $-N(R_4)-$;

Q is selected from the group consisting of a bond, $-C(R_6)-$, $-C(R_6)-C(R_6)-$, $-S(O)_2-$, $-C(R_6)-N(R_8)-W-$, $-S(O)_2-N(R_8)-$, $-C(R_6)-O-$, and $-C(R_6)-N(OR_9)$;

V is selected from the group consisting of $-C(R_6)-$, $-O-C(R_6)-$, $-N(R_8)-C(R_6)-$, and $-S(O)_2-$;

W is selected from the group consisting of a bond, $-C(O)-$, and $-S(O)_2-$; and a and b are independently integers from 1 to 6 with the proviso that a+b is ≦7;

or a pharmaceutically acceptable salt thereof.

4. The compound or salt of claim 3 wherein:
$X_1$ is selected from the group consisting of a bond, alkylene, and alkenylene, wherein the alkylene and alkenylene are optionally interrupted by one or more —O— groups;
$R_1$ is selected from the group consisting of alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; cyano; aryl; aryloxy; arylalkyleneoxy; heteroaryl; heteroaryloxy; heteroarylalkyleneoxy; heterocyclyl; and, in the case of heterocyclyl, oxo; with the proviso that when $R_1$ is aryl, arylalkylenyl, heteroaryl, or heteroarylalkylenyl, then the one or more substituents may also be independently selected from the group consisting of alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and
$R_3$ is selected from the group consisting of:
—Z'—$R_4$,
—Z'—X"—$R_4$,
—Z'—X"—Y'—$R_4$,
—Z'—X"—Y'—X"—Y' $R_4$, and
—Z'—X"—$R_5$.

5. The compound or salt of claim 3 wherein n is 0.

6. The compound or salt of claim 3 wherein n and m are 0.

7. The compound or salt of claim 1 wherein $R_3$ is benzyloxy.

8. The compound or salt of claim 1 wherein R is halogen or hydroxy.

9. The compound or salt of claim 1 wherein $R_3$ is —Z'—X"—$R_4$, and wherein X" is $C_{1-3}$alkylene or $C_{1-3}$alkenylene, and $R_4$ is heterocyclyl or heteroaryl wherein heterocyclyl is unsubstituted or substituted by one or more substituents independently selected from alkyl and oxo and wherein heteroaryl is unsubstituted or substituted by one or more substituents independently selected from the group consisting of alkyl, alkoxy, halogen, cyano, and dialkylamino.

10. The compound or salt of claim 1 wherein $R_3$ is —Z'—X"—Y'—$R_4$, wherein X" is selected from the group consisting of $C_{1-3}$alkylene, $C_{1-3}$alkenylene, piperidin-1,4-diyl, and phenylene; Y' is selected from the group consisting of —C($R_6$)—, —C($R_6$)—O—, —C($R_6$)—N($R_8$)—, —N($R_8$)-Q-, and —S(O)$_2$— wherein Q is selected from the group consisting of a bond, —C(O)—, —S(O)$_2$—, - and C($R_6$)—N($R_8$)—, $R_6$ is selected from the group consisting of =O and =S and $R_8$ is selected from the group consisting of hydrogen, $C_{1-4}$alkyl, and $C_{1-4}$alkoxy$C_{1-4}$alkylenyl; and $R_4$ is selected from the group consisting of hydrogen alkyl aryl heteroaryl and heterocyclyl; wherein alkyl is unsubstituted or substituted by one or more substituents independently selected from the group consisting of hydroxy, alkoxy, and aryl, wherein aryl is unsubstituted or substituted by one or more substituents independently selected from the group consisting of alkyl, halogen, cyano, dialkylamino, and alkoxy; and wherein heterocyclyl is unsubstituted or substituted by one or more substituents independently selected from the group consisting of alkyl and oxo.

11. The compound or salt of claim 1 wherein $R_1$ is $C_{1-3}$alkyl optionally substituted by hydroxy or one or more fluorine atoms.

12. The compound or salt of claim 1 wherein $R_1$ is selected from the group consisting of alkyl, alkenyl, alkynyl, aryl, heteroaryl, and heterocyclyl, each of which is unsubstituted or substituted by one or more substituents independently selected from the group consisting of alkyl, alkoxy, hydroxyalkyl, haloalkyl, halogen, hydroxy, aryl, heteroaryl, and heterocyclyl; and wherein when $R_1$ is heteroaryl, then the one or more substituents may also be independently selected from the group consisting of haloarylenyl, alkoxyarylenyl, alkylarylenyl, and arylalkylenyl; and wherein when $R_1$ is heterocyclyl, then the one or more substituents may also be independently selected from the group consisting of arylalkylenyl and aminocarbonyl.

13. The compound or salt of claim 1 wherein $X_1$ is a bond or alkylene.

14. A pharmaceutical composition comprising a therapeutically effective amount of a compound or salt of claim 1 and a pharmaceutically acceptable carrier.

15. A pharmaceutical composition comprising a therapeutically effective amount of a compound or salt of claim 3 and a pharmaceutically acceptable carrier.

* * * * *